(12) United States Patent
Bush et al.

(10) Patent No.: US 7,045,531 B1
(45) Date of Patent: May 16, 2006

(54) COMPOSITION COMPRISING A METAL CHELATOR AND A METHOD OF TREATING AMYLOIDOSIS BY ADMINISTERING THE METAL CHELATOR

(75) Inventors: Ashley I. Bush, Somerville, MA (US); Xudong Huang, Cambridge, MA (US); Craig S. Atwood, Cleveland, OH (US); Rudolph E. Tanzi, Hull, MA (US)

(73) Assignee: The General Hospital Corporation, Boston, MA (US)

( * ) Notice: Subject to any disclaimer, the term of this patent is extended or adjusted under 35 U.S.C. 154(b) by 593 days.

(21) Appl. No.: 09/380,704

(22) PCT Filed: Mar. 11, 1998

(86) PCT No.: PCT/US98/04683

§ 371 (c)(1),
(2), (4) Date: Jun. 6, 2000

(87) PCT Pub. No.: WO98/40071

PCT Pub. Date: Sep. 17, 1998

Related U.S. Application Data

(63) Continuation of application No. 08/816,122, filed on Mar. 11, 1997, now abandoned.

(51) Int. Cl.
A61K 31/47 (2006.01)
A61K 31/53 (2006.01)
A61K 31/40 (2006.01)
A61K 31/105 (2006.01)

(52) U.S. Cl. .................. 514/311; 514/244; 514/420; 514/707

(58) Field of Classification Search ............. 435/4; 514/311, 244, 420, 707, 279
See application file for complete search history.

(56) References Cited

U.S. PATENT DOCUMENTS

| | | | |
|---|---|---|---|
| 5,110,493 A | 5/1992 | Cherng-Chyi et al. | 514/413 |
| 5,242,932 A | 9/1993 | Gandy et al. | 514/313 |
| 5,310,936 A | 5/1994 | Regtop et al. | |
| 5,357,636 A | 10/1994 | Dresdner, Jr. et al. | 2/161.7 |
| 5,373,021 A | 12/1994 | Marangos | 514/483 |
| 5,466,680 A | 11/1995 | Rudy | 514/57 |
| 5,523,295 A | 6/1996 | Fasman | 514/63 |
| 5,688,516 A | 11/1997 | Raad et al. | 424/409 |
| 5,688,651 A | 11/1997 | Solomon | 435/7.1 |
| 5,705,401 A | 1/1998 | Masters et al. | 436/518 |
| 5,707,821 A | 1/1998 | Rydel et al. | 435/18 |
| 5,721,106 A | 2/1998 | Maggio et al. | 435/7.8 |
| 5,927,283 A | 7/1999 | Abraham et al. | 128/898 |
| 5,980,914 A | 11/1999 | Gerolymatos | 424/400 |
| 5,994,323 A | 11/1999 | Gerolymatos | 514/52 |
| 6,001,852 A | 12/1999 | Gerolymatos | 514/311 |
| 6,323,218 B1 * | 11/2001 | Bush et al. | 514/311 |

FOREIGN PATENT DOCUMENTS

| | | |
|---|---|---|
| DE | 40 04 978 A1 | 8/1991 |
| WO | WO 92/18111 | 10/1992 |
| WO | WO 93/10459 | 5/1993 |
| WO | WO 93/24451 | 12/1993 |
| WO | WO 94/04167 | 3/1994 |
| WO | WO 94/27594 A2 | 12/1994 |
| WO | WO 95/31199 | 11/1995 |
| WO | WO 96/07096 | 3/1996 |
| WO | WO 96/12544 | 5/1996 |
| WO | WO 96/28471 | 9/1996 |
| WO | WO 96/39144 A1 | 12/1996 |
| WO | WO 97/01559 A1 | 1/1997 |
| WO | WO 97/04794 | 2/1997 |
| WO | WO 97/09976 | 3/1997 |
| WO | WO 97/36885 | 10/1997 |
| WO | WO 98/06403 | 2/1998 |
| WO | WO 98/40071 | 9/1998 |
| WO | WO 99/09981 | 3/1999 |
| WO | WO 99/18432 | 4/1999 |

OTHER PUBLICATIONS

Cherny et al. Treatment with a copper-zinc chelator markedly and rapidly inhibits beta-amyloid accumulation in Alzheimer's disease transgenic mice. Neuron 30(3):665-676, 2001.*

Cherny et al. Chelation and intercalation: complemetary properties in a compound for the treatment of Alzheimer's disease. J Struct Biol. 130(2-3): 209-216, 2000.*

Kisilevsky et al. A beta amyloidogenesis: unique, or variation on a systemic theme? Crit Rev Biochem Mol Biol. 32(5):361-404, 1997.*

Maury, CP. Molecular pathogenesis of beta-amyloidosis in Alzheimer's disease and other cerebral amyloidoses. Lab Invest 72(2);4-16, 1995.*

Gnjec A, Fonte JA, Atwood C, Martins RN. Transition metal chelator therapy—a potential treatment for Alzheimer's disease? Front Biosci. 7:d1016-23, 2002.*

Fonte et al. Journal of Alzheimer's Disease. 3(2): 209-219, 2001.*

Gillmore et al. Amyloidosis: a review of recent diagnostic and therapeutic developments. Br J Haematol 99(2):245-56, 1997.*

Schnabel, J. New alzheimer's therapy suggested. Science 260: 1719-1720, 1993.*

Sigma Chemical Company. "Bathocuprione", p. 149, catalog #B1000, 1995.*

(Continued)

*Primary Examiner*—Brenda Brumback
*Assistant Examiner*—Bridget E. Bunner
(74) *Attorney, Agent, or Firm*—Sterne, Kessler, Goldstein & Fox P.L.L.C.

(57) ABSTRACT

The invention relates to the identification of pharmacological agents to be used in the treatment of Alzheimer's disease and related pathological conditions. Methods and compositions for treatment of conditions caused by amyloidosis, Aβ-mediated ROS formation, or both, such as Alzheimer's disease, are disclosed.

4 Claims, 56 Drawing Sheets

OTHER PUBLICATIONS

Goodman and Gilman. The Pharmacological Basis of Therapeutics. New York: McGraw-Hill, Inc. 1993, p. 5-6.*

Assaf, S.Y and Chung, S. -H., "Release of endogenous $Zn^{2-}$ from brain tissue during activity," *Nature* 308:734-736 (Apr. 1984).

Atwood, C.S. et al., "Dramatic Aggregation of Alzheimer Aβ by Cu(II) Is Induced by Conditions Representing Physiological Acidosis," *J. Biol. Chem.* 273:12817-12826 (May 1998).

Bacon, P.A. et al., "Rheumatoid Disease, Amyloidosis and its treatment with Penicillamine," *Eur. J. Rheum. Inflamm.* 2:70-74 (1979).

Barrow, C.J., and Zagorski, M.G., "Solution Structures of β Peptide and Its Constituent Fragments: Relation to Amyloid Deposition," *Science* 253:179-182 (Jul. 1991).

Barrow, C.J., et al., "Solution Conformations and Aggregational Properties of Synthetic Amyloid β-Peptides of Alzheimer's Disease," *J. Mol. Biol.* 225:1075-1093 (Jun. 1992).

Basun, H., et al., "Metals and trace elements in plasma and cerebrospinal fluid in normal ageing and Alzheimer's disease," *J. Neural Transm. [P-D Sect.]* 3:231-258 (1991).

Behl, C., et al., "Hydrogen Peroxide Mediates Amyloid β Protein Toxicity," *Cell* 77:817-827 (Jun. 1994).

Biaglow, J.E. and Kachur, A.V., "The Generation of Hydroxyl Radicals in the Reaction of Molecular Oxygen with Polyphosphate Complexes of Ferrous Ion," *Radiation Res.* 148:181-187 (Aug. 1997).

Boado, R.J. et al., "Drug Delivery of Antisense Molecules to the Brain for Treatment of Alzheimer's Disease and Cerebral AIDS," *J. Pharm. Sci.* 87(11):1308-1315 (Nov. 1998).

Borman, S., "Diverse Strategies Emerge For Diagnosing Alzheimer's Disease," *Chem. Eng. News* 272:33-34 (Jun. 1996).

Bruce, A.J. et al., "β-Amyloid toxicity in organotypic hippocampal cultures: Protection by EUK-8, a synthetic catalytic free radical scavenger," *Proc. Natl. Acad. Sci. USA* 93:2312-2316 (Mar. 1996).

Burdick, D., et al., "Assembly and Aggregation Properties of Synthetic Alzheimer's A4/β Amyloid Peptide Analogs," *J. Biol. Chem.* 267:546-554 (Jan. 1992).

Burns, J.A., et al., "Selective Reduction of Disulfides by Tris(2-carboxyethyl)phosphine," *J. Org. Chem.* 56:2648-2650 (Apr. 1991).

Busciglio, J., and Yankner, B.A., "Apoptosis and increased generation of reactive oxygen species in Down's Syndrome neurons in vitro," *nature* 378:776-779 (Dec. 1995).

Bush, A.I., et al., "A Novel Zinc(II) Binding Site Modulates the Function of the βA4 Amyloid Protein Precursor of Alzheimer's Disease," *J. Biol. Chem.* 268:16109-16112 (Aug. 1993).

Bush, A.I., et al., "Modulation of Aβ Adhesiveness and Secretase Site Cleavage by Zinc," *J. Biol. Chem.* 269:12152-12158 (Apr. 1994).

Bush, A. I., et al., "The Amyloid β-Protein Precursor and Its Mammalian Homologues," *J. Biol. Chem.* 269:26618-26621 (Oct. 1994).

Bush, A.I., et al., "Rapid Induction of Alzheimer Aβ Amyloid Formation by Zinc," *Science* 265:1464-1467 (Sep. 1994).

Bush, A.I., et al., Response to "Zinc and Alzheimer's Disease," *Science* 268:1920-1923 (Jun. 1995).

Butterfield, D.A., et al., "β-Amyloid Peptide Free Radical Fragments Initiate Synaptosmal Lipoperoxidation in a Sequence-Specific Fashion: Implications to Alzheimer's Disease," *Biochem. Biophys. res. Commun.* 200:710-715 (Apr. 1994).

Butterfield, D.A., et al., "Aβ(25-35) Peptide Displays $H_2O_2$-Like Reactivity Towards Aqueous $Fe^{2+}$, Nitroxide Spin Probes, and Synaptosomal Membrane Proteins," *Life Sci.* 58:217-228 (1996).

Cherny, R.A. et al., "The Aggregation of Aβ in Human Brain is Mediated by Zinc," *Soc. for Neurosci. Abstracts* 23:534 (Oct. 1997).

Chong, Y.-H., and Suh, Y.-H., "Aggregation of amyloid precursor proteins by alumunum in vitro," *Brain Research* 670:137-141 (Jan. 1995).

Colaco, C.A.L.S., et al., "The role of the Maillard reaction in other pathologies: Alzheimer's disease," *Nephrol. Dial. Transplant.* 11(Suppl. 5):7-12 (1996).

Connor, J.R. et al., "A Histochemical Study of Iron, Transferrin, and Feritin in Alzheimer's Diseased Brains," *J. Neurosci. Res.* 31:75-83 (Jan. 1992).

Connor, J.R. et al., "Ceruloplasmin levels in the human superior temporal gyrus in aging and Alzheimer's disease," *Neursci. Lett.* 159:88-90 (Sep. 1993).

Coyle, J.T., and Puttfarcken, P., "Oxidative Stress, Glutamate, and Neurodegenerative Disorders," *Science* 262:689-695 (Oct. 1993).

Crapper McLachlan, D.R. et al., "Intramuscular desferrioxamine in patients with Alzheimer's disease," *Lancet* 337:1304-1308 (Jun. 1991).

Cuajungco, M.P. and Lees, G.J., "Zinc and Alzheimer's disease: is there a direct link?" *Brain Res. Rev.* 23:219-236 (Apr. 1997).

Dedman, D.J. et al., "Iron and aluminum in relation to brain ferritin in normal individuals and Alzheimer's-disease and chronic renal-dialysis patients," *Biochem J.* 287:509-514 (1992).

Deibel, M.A. et al., "Copper, iron, and zinc imbalances in severely degenerated brain regions in Alzheimer's disease: Possible relation to oxidative stress," *J. Neurol. Sci.* 143:137-142 (Nov. 1996).

Doré, S., et al., "Insulin-like growth factor I protects and rescues hippocampal neurons against β-amyloid- and human amylin-induced toxicity," *Proc. Natl. Acad. Sci. USA* 94:4772-4777 (Apr. 1997).

Dryks, T. et al., "Amyloidogenicity of βA4 and βA4-bearing Amyloid Protein Precursor Fragments by Metal-catalyzed Oxidation," *J. Biol. Chem.* 267:18210-18217 (Sep. 1992).

Ehmann W.D. et al., "Brain Trace Elements in Alzheimer's Disease," *NeuroToxicology* 7:197-206 (1986).

Esler, W.P., et al., "Zinc-Induced Aggregation of Human and Rat β-Amyloid Peptides In Vitro," *J. Neurochem.* 66:723-732 (Feb. 1996).

Esler, W.P., et al., "Aβ deposition inhibitor screen using synthetic amyloid," *Nat. Biotechnol.* 15:258-263 (Mar. 1997).

Fitzgerald, D.J., "Zinc and Alzheimer's Disease," *Science* 268:1920 (Jun. 1995).

Folstein,M. "Nutrition and Alzheimer's Disease," *Nutrition Reviews* 55:23-25 (Jan. 1997).

Fraser, P.E., et al., "ph-dependent structural transitions of Alzheimer amyloid peptides," *Biophys. J.* 60:1190-1201 (Nov. 1991).

Frederiksa, P.H., et al., "Oxidative Stress Increases Production of β-Amyloid Presursor Protein and β-Amyloid (aβ) in Mammalian Lenses, and Aβ Has Toxic Effects on Lens Epithelial Cells," *J. Biol. Chem.* 271:10169-10174 (Apr. 1996).

Frederickson, C.J., "Neurobiology of Zinc and Zinc-Containing Neurons," *Int. Rev. Neurobiol.* 31:145-238 (1989).

Frieden, E., "Ceruloplasmin: A Multi-functional Cuproprotein of vertebrate Plasma," in: *Inflammatory Diseases and Copper*, Sorenson, J.R.J., ed., Clifton, N.J.: Humana Press, pp. 159-169 (1982).

Giampaolo, V., "Copper and Inflammation," in: *Inflammatory Diseases and Copper*, Sorenson, J.R.J., ed., Clifton, W.J.: Humana Press, pp. 329-345 (1982).

Giulian, D. et al., "Specific Domains of β-Amyloid from Alzheimer Plaque Elicit Neuron Killing in Human Microglia," *J. Neurosci.* 16:6021-6037 (Oct. 1996).

Glennner, G.G., and Wong, C.W, "Alzheimer's Disease: Initial Report of the Purification and Characterization of Novel Cerebrovascular Amyloid Protein," *Biochem. Biophys. Res. Commun.* 120:885-890 (May 1984).

Golde, T.E., et al., "Processing of the Amyloid Protein Precursor to Potentially Amyloidogenic Derivatives," *Science* 255:728-730 (Feb. 1992).

Good, P.F. et al., "Selective Accumulation of Aluminum and Iron in the Neurofibrillary Tangles of Alzheimer's Disease: A Laser Microprobe (LAMMA) Study," *Ann. Neurol.* 31:286-292 (Mar. 1992).

Goodman, Y. et al., "Nordihydroguaiaretic acid protects hippocampal neurons against amyloid β-peptide toxicity, and attenuates free radical and calcium accumulation," *Brain Res.* 654:171-176 (Aug. 1994).

Goodman, Y., and Mattson, M.P., "Secreted Forms of β-Amyloid Precursor Protein Protect Hippocampal Neurons against Amyloid β-Peptide-Induced Ixidative Injury," *Exp. Neurol.* 128:1-12 (Jul. 1994).

Gorevic, P.D. et al., "The Biological Significance of Amyloid," *Ann. New York Acad. Sci.* 389:380-394 (1982).

Grundke-Iqbal, I. et al., "Ferritin is a component of the neuritic (sinile) plaque in Alzheimer dementia," *Acta Neuropathol.* 81:105-110 (Dec. 1990).

Gutteridge, J.M.C., and Wilkins, S., "Copper Salt-Dependent Hydroxyl Radical Formation Damage to Proteins Acting as Antioxidants," *Biochim. Biophys, Acta* 759:38-41 (Aug. 1983).

Haass, C. et al., "Amyloid β-peptide is produced by cultured cells during normal metabolism," *Nature* 359:322-325 (Sep. 1992).

Haley, J.V., "Zinc Sulfate and Wound Healing," *J. Surg. Res.* 27:168-174 (Sep. 1979).

Halliwell, B., and Gutteridge, J.M.C., "Oxygen toxicity, oxygen radicals, transition metals and disease," *Biochem. J.* 219:1-14 (Apr. 1984).

Halliwell, B., "Reactive Oxygen Species and the Central Nervous System," *J. Neurochem.* 59:1609-1623 (Nov. 1992).

Han, J., et al., "Quantitation of Hydrogen Peroxide Using Tris(2-carboxyethyl)phosphine," *Anal. Biochem.* 234:107-109 (Feb. 1996).

Han, J.C., and Han, G.Y., "A Procedure for Quantitative Determination of Tris(2-carboxyethyl)phosphine, an Odorless Reducing Agent More Stable and Effective Than Dithiothreitol," *Anal. Biochem,* 220:5-10 (Jul. 1994).

Hanson, M/B., et al., "Re-examination and further development of a precise and rapid dye method for measuring cell growth/cell kill," *J. Immunol. Meth.* 119:203-210 (May 1989).

Harman, D., "Aging: A Theory Based on Free Radical and Radiation Chemistry," *J. Gerentology* 2:298-300 (Jul. 1956).

Harris, M.E., et al., "Direct Evidence of Oxidative Injury Produced by the Alzheimer's β-Amyloid Peptide (1-40) in Cultured Hippocampal Neurons," *Exp. Neurol.* 131:193-202 (Feb. 1995).

Hensley, K et al., "A model for beta-amyloid aggregation and neurotoxicity based on free radical generation by the peptide: Relevance to Alzheimer disease," *Proc. Natl. Acad. Sci. U.S.A.* 91:3270-3274 (Apr. 1994).

Hensley, K et al., "Brain Regional Correspondence Between Alzheimer's Disease Histopathology and Biomarkers of Protein Oxidation," *J. of Neurochem.* 65:2146-2156 (Nov. 1995).

Hensley, K. et al., "Reactive Oxygen Species as Causal Agents in the Neurotoxicity of the Alzheimer's Disease-Associated Amyloid Beta Peptide," *Ann N. Y. Acad. Sci.* 786:120-134 (1996).

Hesse, L., et al., "The βA4 amyloid precursor protein binding to copper," *FEBS Lett.* 349:109-116 (Jul. 1994).

Hilbich, C., et al., "Aggregation and Secondary Structure of Synthetic Amyloid βA4 Peptides of Alzheimer's Disease," *J. Mol. Biol.* 218:149-163 (Mar. 1991).

Hilbich, C. et al., "Substitutions of Hydrophobic Amino Acids Reduce the Amyloidogenicity of Alzheimer's Disease βA4 Peptides," *J. Mol. Biol.* 228:460-473 (Nov. 1992).

Hsu, J.M., et al., "Zinc Deficiency and Incorporation of $^{14}C$-labeled Methionine into Tissue Proteins in Rats," *J. Nutrition* 99:425-432 (Dec. 1969).

Huang, X. et al., "Zinc-induced Alzheimer's Aβ1-40 Aggregation Is Mediated by Conformational Factors," *J. Biol. Chem.* 272:26464-26470 (Oct. 1997).

Ida, N., et al., "Analysis of Heterogeneous βA4 Peptides in Human Cerebrospinal Fluid and Blood by a Newly Developed Sensitive Western Blot Assay," *J. Biol. Chem.* 271:22908-22914 (Sep. 1996).

Jarrett, J.T., et al., "The Carboxy Terminus of the β Amyloid Protein Is Critical for the Seeding of Amyloid Formation: Implications for the Pathogenesis of Alzheimer's Disease," *Biochem.* 32:4693-4697 (May 1993).

Jarrett, J.T., and Lansbury, Jr., P.T., "Amyloid Fibril Formation Requires a Chemically Discriminating Nucleation Event: Studies of an Amyloidogenic Sequence from the Bacterial Protein OsmB," *Biochem.* 31:12345-12352 (Dec. 1992).

Johnstone, E.M. et al. , "Conservation of the sequence of the Alzheimer's disease amyloid peptide in dog, polar bear and five other mammals by cross-species polymerase chain reaction analysis," *Mol. Brain Res.* 10:299-305 (Jul. 1991).

Joshi, J.G., "Iron and Aluminum Homeostasis in Neural Disorders," *Environ. Health Persp.* 102:207-213 (1994).

Kang, J. et al., "The precursor of Alzheimer's disease amyloid A4 protein resembles a cell-surface receptor," *Nature* 325: 733-736 (Feb. 1987).

Kawahara, M. et al., "Alzheimer's Disease Amyloid β-Protein Forms $Zn^{2+}$-Sensitive, Cation-Selective Channels Across Excised Membrane Patches from Hypothalamic Neurons," *Biophys. J.* 73:67-75 (Jul. 1997).

Kennard, M.L. et al., "Serum levels of the iron binding protein p97 are elevated in Alzheimer's disease," *Nat. Med.* 2:1230-1235 (Nov. 1996).

Kidani, Y. et al., "Mass spectrometry of 5-chloro-7-iodo-8-quinolinol metal chelates," *Jpn. Analyst* 23:1375-1378 (1974).

Kirschner, D.A. et al., "Synthetic peptide homologous to β protein from Alzheimer disease forms amyloid-like fibrils *in vitro*," *Proc. Natl. Acad. Sci. USA* 84:6953-6957 (Oct. 1987).

Kirshenbaum, K., and Daggett, V., "pH-Dependent Conformations of the Amyloid β(1-28) Peptide Fragment Explored Using Molecular Dynamics," *Biochem.* 34:7629-7639 (Jun. 1995).

Kisilevsky, R., "Inflammation-Associated Amyloidogenesis," *Mol. Neurobiol.* 8:65-66 (Feb. 1994).

Koh, J.Y., and Choi, D.W., "Quantitative determination of glutamate mediated cortical neuronal injury in cell culture by lactate dehydrogenase efflux assay," *J. Neurosci. Meth.* 20:83-90 (May 1987).

Kotaki, H., et al., "Intestinal Absorption and Metabolism of Clioquinol in the Rat," *J. Pharm. Dyn.* 6:881-887 (Nov. 1983).

Kuo, Y.-M., et al., "Water-soluble Aβ (N-40, N-42) Oligomers in Normal and Alzheimer Disease Brains," *J. Biol. Chem.* 271:4077-4081 (Feb. 1996).

Landers, J.W., and Zak, B., "Determination of Serum Copper and Iron in a Single Small Sample," *Am. J. Clin. Pathol.* 29:590-592 (Jun. 1958).

Lindeman, R.D., et al., "Myocardial zinc metabolism in experimental myocardial infarction," *J. Lab. Clin. Med.* 81:194-204 (Feb. 1973).

Lockhart B.P. et al., "Inhibitors of free radical formation fail to attenuate direct beta-amyloid$_{25-35}$ peptide-mediated neurotoxicity in rat hippocampal cultures," *J. Neurosci. Res.* 39:494-505 (Nov. 1994).

Lohr, J.B., "Oxygen Radicals and Neuropsychiatric Illness," *Arch. Gen. Psychiatry* 48:1097-1106 (Dec. 1991).

Maggio, J.E., et al., "Zinc and Alzheimer's Disease," *Science* 268:1920-1921 (Jun. 1995).

Mantyh, P.W., et al., "Aluminum, Iron, and Zinc Ions Promote Aggregation of Physiological Concentrations of β-Amyloid Peptide," *J. Neurochem.* 61:1171-1174 (Sep. 1993).

Markesbery, W.R., "Oxidative Stress Hypothesis in Alzheimer's Disease," *Free Rad. Biol. Med.* 23:134-147 (1997).

Masters, C.L., et al., "Amyloid plaque core protein in Alzheimer disease and Down syndrome," *Proc. Natl. Acad. Sci. USA* 82:4245-4249 (Jun. 1985).

Masters, C. L. et al., "Neuronal origin of a cerebral amyloid: neurofibrillary tangles of Alzheimer's disease contain the same protein as the amyloid of plaque cores and blood vessels," *EMBO J.* 4:2757-2763 (Nov. 1985).

McGeer, P.L., and McGeer, E.G., "The inflammatory response system of brain: implications for therapy of Alzheimer and other neurodegenerative diseases," *Brain Res. Rev.* 21:195-218 (Sep. 1995).

Mecocci, P., M.D. et al., "Oxidative Damage to Mitochondrial DNA Shows Marked Age-dependent Increases in Human Brain," *Ann. Neurol.* 34:609-616 (Oct. 1993).

Menkin, V., "Studies on Inflammation. X. The Cytological Picture of an Inflammatory Exudate in Relation to its Hydrogen Ion Concentration," *Am. J. Pathol.* 10:193-210 (Mar. 1934).

Michikawa, M., et al., "Oxygen Radical-Induced Neurotoxicity in Spinal Cord Neuron Cultures," *J. Neurosci. Res.* 37:62-70 (Jan 1994).

Milanino, R., et al., "Copper and the Inflammatory Process," *Advances in Inflammation Research* 1:281-191 (1979).

Moir, R.D. et al., "Relative Increase in Alzheimer's Disease of Soluble Forms of Cerebral Aβ Amyloid Protein Precursor Containing the Kunitz Protease Inhibitory Domain," *J. Biol. Chem.* 273:5013-5019 (Feb. 1998).

Mok, S.S., et al., "A Novel Metalloprotease in Rat Brain Cleaves the Amyloid Precursor Protein of Alzheimer's Disease Generating Amyloidogenic Fragments," *Biochemistry* 36:156-163 (Jan. 1997).

Multhaup, G., et al., "Interaction between the zinc(II) and the heparin binding site of the Alzheimer's disease βA4 amyloid precursor protein (APP)," *FEBS Lett.* 355:151-154 (Nov. 1994).

Multhaup, G., et al., "The Amyloid Precursor Protein of Alzheimer's Disease in the Reduction of Copper(II) to Copper(I)," *Science* 271:1406-1409 (Mar. 1996).

Münch, G., et al., "Advanced glycation endproducts in ageing and Alzheimer's disease," *Brain Res. Rev.* 23:134-143 (Feb. 1997).

Okada, H. et al., "Effects of Metal-Containing Drugs Taken Simultaneously with Clioquinol Upon Clinical Features of SMON," *J. Toxicol. Sci.* 9:327-341 (1984).

Owen, C.A., Jr., "Uptake of $^{67}$Cu by Ceruloplasmin *In Vitro* (38878)," *Proc. Soc. Exp. Biol. Med.* 149:681-682 (Jul. 1975).

Padmanabhan, G., et al., "Clioquinol," in:*Analytical Profiles of Drug Substances*, vol. 18, Florey, K., ed. Academic Press, Inc.:San Diego, CA, pp. 57-90 (1989).

Pérez, A.A. et al., "Alzheimer Amyloids Aβ1-40 and Aβ1-42 are Differentially Degraded by Insulin Degrading Enzyme (IDE) From Human Brain," *Soc. Neurosci. Abstracts* 23:821 (Oct. 1997).

Peters, G., and Rodgers, M.A.J., "Single-Electron Transfer from NADH Analoques to Singlet Oxygen," *Biochim. Biophys. Acta* 637:43-52 (Aug. 1981).

Pierce, J.E.S., et al., "Immunohistochemical Characterization of Alterations in the Distribution of Amyloid Precursor Proteins and β-Amyloid Peptide after Experimental Brain Injury in the Rat," *J. Neurosci.* 16:1083-1090 (Feb. 1996).

Potempa, L.A., et al., "Effect of Divalent Metal Ions and pH upon the Binding Reactivity of Human Serum Amyloid P Component, a C-reactive Protein Homologue, for Zymosan," *J. Biol. Chem.*260:12142-12147 (Oct. 1985).

Richardson, J.S., et al., "On the Possible Role of Iron-Induced Free Radical Peroxidation in Neural Degeneration in Alzheimer's Disease," *Ann N.Y. Acad. Sci.* 648:326-327 (1992).

Roberts, G.W., et al., "βA4 amyloid protein deposition in brain after head trauma," *Lancet* 338:1422-1423 (Dec. 1991).

Robinson, S.R. et al., "Most amyloid plaques contain ferritin-rich cells," *Alzheimer's Res.* 1:191-196 (1995).

Rogers, J., et al., "Clinical trail of indomethacin in Alzheimer's disease," *Neurology* 43:1609-1611 (Aug. 1993).

Roher, A.E., et al., "Morphology and Toxicity of Aβ-(1-42) Dimer Derived from Neuritic and Vascular Amyloid Deposits of Alzheimer's Disease," *J. Biol. Chem.* 271:20631-20635 (Aug. 1996).

Rumble, B. et al., "Amyloid A4 Protein and Its Precursor in Down's Syndrome and Alzheimer's Disease," *New Eng. J. of Med. 320*:1446-1452 (Jun. 1989).

Sadowski, M. et al., "Astrocyte and microglia reaction in Alzheimer's disease in the hippocampal formation- a quantitative analysis," *Alzheimer's Res. 1*:71-76 (1995).

Sano, M., et al., "A Controlled Trial of Selegiline, Alpha-Tocopherol, or Both as Treatment for Alzheimer's Disease," *N.Engl. J. Med. 336*:1216-1222 (Apr. 1997).

Sayre, L.M., "Alzheimer's Precursor Protein and the Use of Bathocuproine for Determining Reduction of Copper(II)," *Science 274*:1933-1934 (Dec. 1996).

Schubert, D., and Chevion, M., "The Role of Iron in Beta Amyloid Toxicity," *Biochem. Biophys. Res. Commun. 216*:702-707 (Nov. 1995).

Selkoe, D.J., "Cell Biology of Amyloid B-protein Precursor and the Mechanism of Alzheimer's Disease," *Ann. Rev. Cell Biol. 10*:373-403 (1994).

Seubert, P. et al., "Isolation and quantification of soluble Alzheimer's β-peptide from biological fluids," *Nature 359*:325-327 (Sep. 1992).

Shiraki, H., "Neuropathological aspects of the etiopathogenesis of subacute myelo-optico-neuropathy (SMON)," in *Handbook of Clinical Neurology. Intoxications of the Nervous System Part II*, Vinken, P. J. and Bruyn, G. W., eds., North-Holland Publishing Company, Amsterdam, Holland, pp. 141-198 (1979).

Shivers B.D. et al., "Alzheimer's disease amyloidogenic glycoprotein: expression pattern in rat brain suggests a role in cell contact," *EMBO J. 7*:1365-1370 (1988).

Shoji, M. et al., "Production of the Alzheimer Amyloid β Protein by Normal Proteolytic Processing," *Science 258*:126-129 (Oct. 1992).

Sisodia, S.S. et al., "Cellular and molecular biology of Alzheimer's disease and animal models," *Neurodegenerative Diseases 5*:59-68 (Feb. 1995).

Skinner, M. et al., "Observations on the amyloid-degrading activity of serum and its relationship to human neutrophil elastase," *Chem. Abst. 101*:453, Abstract No. 101:208677n (Dec. 1984).

Smalheiser, N.R., and Swanson, D.R., "Indomethacin and Alzheimer's disease," *Neurology 46*:583 (Feb. 1996).

Smith, C. et al., "The molecular pathology of Alzheimer's disease: are we any closer to understanding the neurodegenerative process?," *Neuropathol. Appl. Neurobiol. 20*:322-38 (Aug. 1994).

Smith, M.A., et al., "Radical AGEing in Alzheimer's disease," *Trends Neurosci. 18*:172-176 (Apr. 1995).

Smith M.A., et al., "Iron accumulation in Alzheimer disease is a source of redox-generated free radicals," *Proc. Natl. Acad. Sci. U.S.A. 94*:9866-9868 (Sep. 1997).

Sobue, I., "Clinical aspects of subacute myelo-optico-neuropathy (SMON)," in *Handbook of Clinical Neurology. Intoxications of the Nerous System Part II*, Vinken, P. J. and Bruyn, G. W., eds., North-Holland Publishing Company, Amsterdam, Holland, pp. 115-139 (1979).

Soto, C. et al., "β-sheet breaker peptides inhibit fibrillogenesis in a rat brain model of amyloidosis: Implications for Alzheimer's therapy," *Nature Med. 4*:822-826 (Jul. 1998).

Soto, C., et al., "Structural Determinants of the Alzheimer's Amyloid β-Peptide," *J. Neurochem. 63*:1191-1198 (Oct. 1994).

Stankovic, A., and Mitrovic, D.R., "Aluminum Salts Stimulate Luminol-Enhanced Chemiluminescence Production by Human Neutrophils," *Free Rad. Res. Comms. 14*:47-55 (1991).

Tanzi, R.E. et al., "The Wilson disease gene is a copper transporting ATPase with homology to the Menkes disease gene," *Nat. Gen. 5*:344-350 (Dec. 1993).

Tanzi, R.E. et al., "Amyloid β Protein Gene: cDNA, mRNA Distribution, and Genetic Linakge Near the Alzheimer Locus," *Science 235*:880-884 (Feb. 1987).

Tamura, Z., "Clinical Chemistry of Clioquinol," *Jpn. J. Med. Sci. Biol. 28*:69-77 (1975).

Tateishi, J. et al., "Strain-differences in dogs for neurotoxicity of clioquinol," *Lancet 1*:1289-1290 (Jun. 1972).

Tateishi, J. et al., "Myeloneuropathy in dogs induces by iodoxyquinoline," *Neurology 22*:702-709 (Jul. 1972).

Tateishi, J. et al., "Autoradiographic Distribution of $^{131}$I-Clioquinol in Canine and Feline," *Folia Phychiatrica et neurologica Japonica 26*:159-164 (1972).

Tateishi, J. et al., "Experimental Myelo-optic Neuropathy by Clioquinol," *Acta neuropath. )Berl.) 24*:304-320 (1973).

Tateishi, J. et al., "Neurotoxicity of Clioquinol in Laboratory Animals," *Lancet 2*:1095 (Nov. 1972).

Teller, J.K., et al., "Presence of soluble amyloid β-peptide precedes amyloid plaque formation in Down's Syndrome," *Nature Med. 2*:93-95 (Jan. 1996).

Terhune, M.W., and Sandstead, H.H., "Decreased RNA Polymerase Activity in Mammalian Zinc Deficiency," *Science 177*:68-69 (Jul. 1972).

Thomas, T., et al., "β-Amyloid-mediated vasoactivity and vascular endothelial damage," *Nature 380*:168-171 (Mar. 1996).

Tomiyama, T., et al., "Rifampicin Prevents the Aggregation and Neurotoxicity of Amyloid β Protein *In Vitro,*" *Biochem. Biophys. Res. Comm. 204*:76-83 (Oct. 1994).

Tomiyama, T., et al., "Inhibition of Amyloid β Protein Aggregation and Neurotoxicity by Rifampicin," *J. Biol. Chem. 271*:6839-6844 (Mar. 1996).

Thompson, C.M. et al., "Regional Brain Trace-Element Studies in Alzheimer's Disease," *NeuroToxicol. 9*:1-8 (1988).

Tomski, S.J., and Murphy, R.M., "Kinetics of Aggregation of Synthetic β-Amyloid Peptide," *Arch. Biochem. Biophys. 294*:630-638 (May 1992).

Treuhaft, P.S., and McCarty, D.J., "Synovial Fluid pH, lactate, Oxygen and Carbon Dioxide Partial Pressure in Various Joint Diseases," *Arth. Rheum. 4*:475-484 (Jul.-Aug. 1971).

Van Nostrand, W.E, "Zinc (II) Selectively Enhances the Inhibition of Coagulation Factor XIa by Protease Nexin-2/Amyloid β-Protein Precursor," *Thrombosis Res. 78*:43-53 (Apr. 1995).

Warren, P.J. et al., "The Distribution of Copper in Human Brain," *Brain. 83*:709-717 (1960).

Weismann, K., and Knudsen, L., "Effects of Penicillamine and Hydroxyquinolone on Adsorption of Orally Ingested $^{65}$Zinc in the Rat," *J. Invest. Dematol. 71*:242-244 (Oct. 1978).

Wood, S.J., et al., "Physical, Morphological and Functional Differences between pH 5.8 and 7.4 Aggregates of the Alzheimer's Amyloid Peptides Aβ," *J. Mol. Biol. 256*:870-877 (Mar. 1996).

Yates, C.M., et al., "Enzyme Activities in Relation to pH and Lactate in Postmortem Brain in Alzheimer-Type and Other Dementias," *J. Neurochem. 55*:1624-1630 (Nov. 1990).

Zagorski, M.G., and Barrow, C.J., "NMR Studies of Amyloid β-Peptides: Proton Assignments, Secondary Structure, and Mechanism of an α-Helix→β-Sheet Conversion for a Homologous, 28-Residue, N-Terminal Fragment," *Biochemistry* 31:5621-5631 (Jun. 1992).

Beal, M. F., "Energy, Oxidative Damage, and Alzheimer's Disease: Clues to the Underlying Puzzle," *Neurobiol. Aging* 15:S171-A174 (1974).

Linert, W. et al., "Dopamine, 6-hydroxdopamine, iron, and dioxygen-their mutual interaction and possible implication in the development of Parkinson's disease," *Biochim. Biophys. Acta*1316:160-168 (Aug. 1996).

Markesbery, W.R. and Ehmann, W.D., "Brain Trace Elements in Alzheimer Disease," Chapter 22 in *Alzheimer Disease*, Terry, R.D. et al., eds., Raven Press, Ltd., New York (1994).

Soto, C. et al., "Inhibition of Alzheimer's Amyloidsis by Peptides That Prevent β-Sheet Conformation," *Biochem. Biophys. Res. Comm.* 226:672-680 (Sep. 1996).

Nakada, T. and I.L. Kwee, "Guanidinoethane sulfate: brain pH alkaline," *NeuroReport* 4:1035-1038 (Aug. 1993)

Schrader-Fischer, G. and P.A. Paganetti, "Effect of alkalizing agents on the processing of the β-amyloid precursor protein," *Brain Research* 716:91-100 (Apr. 1996).

Atwood, C.S. et al., "Copper-Mediated Aggregation And Polymerization of Aβ," *Soc. Neurosci. Abstr.* 23:1883 (Oct. 1997).

Bruijn, L.I., et al., "ALS-Linked S001 Mutant G85R Mediates Damage to Astrocytes and Promotes Rapidly Progressive Disease with S001-Containing Inclusions," *Neuron.* 18:327-338 (Feb. 1997).

Ceballos-Picot, I., et al., "Peripheral Antioxidant Enzyme Activities And Selenium In Elderly Subjects And In Dementia Of Alzheimer's Type—Place Of The Extracellular Glutathione Peroxidase," *Free Radic. Biol. Med.* 20:579-587 (1996).

Chan, C.-W., et al., "Anti-apoptotic action of Alzheimer Aβ," *Alzheimer's Reports* 2:113-119 (Mar. 1999).

Cohen, A.S., "Amyloidosis," *Arthritis and Allied Conditions—A Textbook of Rheumatology*, D.J. McdCarty, ed., Lea and Febiger, Philadelphia, pp. 1273-1293 (1989).

Garzon-Rodriquez, W., et al., "Soluble Amyloid Aβ-(1-40) Exists as a Stable Dimer at Low Concentrations," *J. Biol. Chem.* 272:21037-21044 (Aug. 1997).

Goto, J.J., et al., "Reactions of Hydrogen Peroxide with Familial Amyotrophic Lateral Sclerosis Mutant Human Copper-Zinc Superoxide Dismutases Studied by Pulse Radiolysis," *J. Biol. Chem.* 273:30104-30109 (Nov. 1998).

Huang, X., et al., "The Aβ Peptide of Alzheimer's Disease Directly Produces Hydrogen Peroxide through Metal Ion Reduction," *Biochemistry* 38:7609-7616 (Jun. 1999).

Kisilevsky, R., "Amyloidosis: A Familiar Problem in the Light of Current Pathogenetic Developments," *Lab. Invest.* 49:381-390 (Oct. 1983).

Kuo, Y.-M., et al., "Levels of Circulating Aβ42 Are Sequestered by Plasma Proteins in Alzheimer's Disease," *Biochem. Biophys. Res. Commun.* 257:787-791 (Apr. 1999).

Lovell, M.A., et al., "Copper, iron and zinc in Alzheimer's disease senile plaques," *J. Neurol. Sci.* 158:47-52 (Jun. 1998).

Martins, R.N., et al., "Increased Cerebral Glucose-6-Phosphate Dehydrogenase Activity in Alzheimer's Disease May Reflect Oxidative Stress," *J. Neurochem.* 46:1042-1045 (Apr. 1986).

Kang, J., et al., "The precursor of Alzheimer's disease amyloid A4 protein resembles a cell-surface receptor," *Nature* 325:733-736 (Feb. 1987).

Nunomura, A., et al., "RNA Oxidation Is a Prominent Feature of Vulnerable Neurons in Alzheimer's Disease," *J. Neurosci.* 19 1959-1964 (Mar. 1999).

Pepys, M.B. and Baitz, M.L., "Acute Phase Proteins with Special Reference to C-Reactive Protein and Related Proteins (Pentaxins) and Serum Amyloid A Protein," in *Advances in Immunology*, vol. 34, pp. 141-212 (1983).

Raby, C.A., et al., "Traumatic Brain Injury Increases β-Amyloid Peptide 1-42 in Cerebrospinal Fluid," *J. Neurochem.* 71:2505-2509 (Dec. 1998).

Rosen, D., et al., "Mutations in Cu/Zn superoxide dismutase gene are associated with familial amyotrophic lateral sclerosis," *Nature* 362:59-62 (Mar. 1993).

Smith, M.A., et al., "Oxidative damage in Alzheimer's," *Nature* 382:120-121 (Jul. 1996).

Suzuki, N., et al., "An Increased Percentage of Long Amyloid β-Protein Secreted by Familial Amyloid β-Protein Precursor ($\beta APP_{717}$) Mutants," *Science* 264:1336-1340 (May 1994).

Terry, R.D., et al., "Physical Basis of Cognitive Alterations in Alzheimer's Disease: Synapse Loss Is the Major Correlate of Cognitive Impairment," *Ann. Neurol.* 30:572-580 (Oct. 1991).

Uchida, K. and Kawakishi, S., "Identification of oxidized Histidine Generated at the Active Site of Cu,Zn-Superoxide Dismutase Exposed to $H_2O_2$- Selective Generation Of 2-Oxo-Histidine At The Histidine 118," *J. Biol. Chem.* 269:2405-4210 (Jan. 1994).

Wolozin, B., et al., "Participation of presenilin 2 in Apoptosis: Enhanced Basal Activity Conferred by an Alzheimer Mutation," *Science* 274:1710-1713 (Dec. 1996).

Yankner, B.A., "Neurotrophic and Neurotoxic Effects of Amyloid β Protein: Reversal by Tachykinin Neuropeptides," *Science* 250:279-282 (Oct. 1990).

Yim, M.B., et al., "A gain-of-function of an amyptrophic lateral sclerosis-associated Cu,Zn-superoxide dismutase mutant: An enhancement of free radical formation due to a decrease in $K_n$ for hydrogen peroxide," *Proc. Natl. Sci. USA* 93:5709-5714 (Jun. 1996).

Gutierrez-Corres, J. and A.O.M. Stoppani, Free Rad. Res. 22(3): 239-250 (Mar. 1995) (publisher: Harwood Academic Publishers GmbH).

Lodemann, E., Naturwissenschaften 66(9): 462-466 (Sep. 1979) (publisher: Springer-Verlag).

Sue, Y.-J. et al., Annals of Emergency Medicine 24(4): 709-712 (Oct. 1994) (publisher: American College of Emergency Physicians).

Atwood, C.S. et al., "Role of Free Radicals and Metals Ions in the Pathogenesis of Alzheimer's Disease," in *Metal Ions in Biological Systems*, Sigel, A. and Sigel H., eds., vol. 36, Ch. 10, Marcel Dekker Inc., New York, pp. 309-364 (1999).

McKeon-O'Malley, C., et al., "Potential Therapeutic Targets for Alzheimer's Disease," *Emerging Therapeutic Targets* 2:157-179, Ashley Publications Ltd. (1998).

BIOMOL Product Data for TPEN, Catalog No. AP-300, Lot No. P3707, BIOMOL Research Labratories, Inc. Plymouth Metting, PA (Jul. 2002).

Cardelli, M., et al., "Chelation Therapy. Unproved Modality in the Treatment of Alzheimer-Type Dementia," *J. Am. Geriatr. Soc.* 33:548-551, Blackwell Science (1985).

Ishii, T., and Bannai, S., "The Synergistic Action of the Copper Chelator Bathocuproine Sulphonate and Cysteine in Enhancing Growth of L1210 Cells In Vitro." *J. Cell. Physiol. 125*:151-155, Alan R. Liss, Inc. (1985).

Kruck, T.P.A., et al., "Suppression of deferoxamine mesylate treatment-induced side effects by coadministration of isoniazed in a patients with Alzheimer's disease subject to aluminum removal by ionspecific chelation," *Clin. Pharmacol. Ther. 48*:439-446, Mosby-Year Book (1990).

*The Merck Index: An encyclopedia of chemicals, drugs, and biologicals*, 11th edition, Budavari, S., et al., eds., Merck & Co., Inc., Rahway, N.J., p. 9586 (1989).

Van Reyk, D.M., and Dean, R.T., "The Iron-selective Chelator Desferal Can Reduce Chelated Copper," *Free Radic. Res. 24*:55-60, Harwood Academic Publishers GmbH (Jan. 1996).

* cited by examiner

Age- matched control- (indicative gel)

Young control vs AD, various chelators 5mM

SEQUENCE LISTING

<160> NUMBER OF SEQ ID NOS: 1

<210> SEQ ID NO 1
<211> LENGTH: 48
<212> TYPE: PRT
<213> ORGANISM: Homo sapiens

<400> SEQUENCE: 1

```
Val Lys Met Asp Ala Glu Phe Arg His Asp Ser Gly Tyr Glu Val His
 1               5                  10                  15

His Gln Lys Leu Val Phe Phe Ala Glu Asp Val Gly Ser Asn Lys Gly
            20                  25                  30

Ala Ile Ile Gly Leu Met Val Gly Gly Val Val Ile Ala Thr Val Ile
        35                  40                  45
```

COMPOSITION COMPRISING A METAL CHELATOR AND A METHOD OF TREATING AMYLOIDOSIS BY ADMINISTERING THE METAL CHELATOR

CROSS REFERENCE TO RELATED APPLICATIONS

This application is a 371 of PCT/US98/04683, filed Mar. 11, 1998 and published under PCT Article 21(2) in English on Sep. 17, 1998, which is a continuation of U.S. patent application Ser. No. 08/816,122, filed Mar. 11, 1997, now abandoned.

STATEMENT AS TO RIGHTS TO INVENTIONS MADE UNDER FEDERALLY-SPONSORED RESEARCH AND DEVELOPMENT

Part of the work performed during the development of this invention utilized U.S. Government Funds under Grant No. R29AG12686 from the National Institutes of Health. The government may have certain rights in this invention.

BACKGROUND OF THE INVENTION

1. Field of the Invention

This invention is in the field of medicinal chemistry. In particular, the invention is related to the detection of drugs useful in the treatment of Alzheimer's disease. The invention is also related to compositions for treatment of Alzheimer's disease.

2. Related Art

Polymers of Abeta (Aβ), the 4.3 kD, 39–43 amino acid peptide product of the transmembrane protein, amyloid protein precursor (APP), are the main components extracted from the neuritic and vascular amyloid of Alzheimer's disease (AD) brains. Aβ deposits are usually most concentrated in regions of high neuronal cell death, and may be present in various morphologies, including amorphous deposits, neurophil plaque amyloid, and amyloid congophilic angiopathy (Masters, C. L., et al, *EMBO J.* 4:2757 (1985); Masters, C. L. et al., *Proc. Natl. Acad. Sci. USA* 82: 4245 (1985)). Growing evidence suggests that amyloid deposits are intimately associated with the neuronal demise that leads to dementia in the disorder.

The presence of an enrichment of the 42 residue species of Aβ in these deposits suggests that this species is more pathogenic. The 42 residue form of Aβ ($A\beta_{1-42}$), while a minor component of biological fluids, is highly enriched in amyloid, and genetic studies strongly implicate this protein in the etiopathogenesis of AD. Amyloid deposits are decorated with inflammatory response proteins, but biochemical markers of severe oxidative stress such as peroxidation adducts, advanced glycation end-products, and protein cross-linking are seen in proximity to the lesions. To date, the cause of Aβ deposits is unknown, although it is believed that preventing these deposits may be a means of treating the disorder.

When polymers of Aβ are placed into culture with rat hippocampal neurons, they are neurotoxic (Kuo, Y-M., et al., *J. Biol. Chem.* 271:4077–81 (1996); Roher, A. E., et al., *Journal of Biological Chemistry* 271:20631–20635 (1996)). The mechanism underlying the formation of these neurotoxic polymeric Aβ species remains unresolved. The overexpression of Aβ alone cannot sufficiently explain amyloid formation, since the concentration of Aβ required for precipitation is not physiologically plausible. That alterations in the neurochemical environment are required for amyloid formation is indicated by its solubility in neural phosphate buffer at concentrations of up to 16 mg/ml (Tomski, S. & Murphy, R. M. *Archives of Biochemistry and Biophysics* 294:630 (1992)), biological fluids such as cerebrospinal fluid (CSF) (Shoji, M., et al., *Science* 258:126 (1992); Golde et al. *Science*, 255(5045):728–730 (1992); Seubert, P., et al., *Nature* 359:325 (1992); Haass, C., et al., *Nature* 359:322 (1992)) and in the plaque-free brains of Down's syndrome patients (Teller, J. K., et al., *Nature Medicine* 2:93–95 (1996)).

Studies into the neurochemical vulnerability of Aβ to form amyloid have suggested altered zinc and [$H^+$] homeostasis as the most likely explanations for amyloid deposition. Aβ is rapidly precipitated under mildly acidic conditions in vitro (pH 3.5–6.5) (Barrow, C. J. & Zagorski, M. G., *Science* 253:179–182 (1991); Fraser, P. E., et. al., *Biophys. J.* 60:1190–1201 (1991); Barrow, C. J., et. al., *J. Mol. Biol.* 225:1075–1093 (1992); Burdick, D., *J. Biol. Chem.* 267: 546–554 (1992); Zagorski, M. G. & Barrow, C. J., *Biochemistry* 31:5621–5631 (1992); Kirshenbaum, K. & Daggett, V., *Biochemistry* 34:7629–7639 (1995); Wood, S. J., et al., *J. Mol. Biol.* 256:870–877 (1996)). Recently, it has been shown that the presence of certain biometals, in particular redox inactive $Zn^{2+}$ and, to a lesser extent, redox active $Cu^{2+}$ and $Fe^{3+}$, markedly increases the precipitation of soluble Aβ (Bush, A. I., et al., *J. Biol. Chem.* 268:16109 (1993); Bush, A. I., et al., *J. Biol. Chem.* 269:12152 (1994); Bush, A. I., et al., *Science* 265: 1464 (1994); Bush. A. I., et al., *Science* 268:1921 (1995)). At physiological pH, $A\beta_{1-40}$ specifically and saturably binds $Zn^{2+}$, manifesting high affinity binding ($K_D$=107 nM) with a 1:1 ($Zn^{2+}$:Aβ) stoichiometry, and low affinity binding ($K_D$=5.2 μM) with a 2:1 stoichiometry.

The reduction by APP of copper (II) to copper (I) may lead to irreversible Aβ aggregation and crosslinking. This reaction may promote an environment that would enhance the production of hydroxyl radicals, which may contribute to oxidative stress in AD (Multhaup, G., et al., *Science* 271: 1406–1409 (1996)). A precedence for abnormal Cu metabolism already exists in the neurodegenerative disorders of Wilson's disease, Menkes' syndrome and possibly familial amyotrophic lateral sclerosis (Tanzi, R. E. et al., *Nature Genetics* 5:344 (1993); Bull, P. C., et al., *Nature Genetics* 5:327 (1993); Vulpe, C., et al., *Nature Genetics* 3:7 (1993); Yamaguchi, Y., et al., *Biochem. Biophys. Res. Commun.* 197:271 (1993); Chelly, J., et al., *Nature Genetics* 3:14 (1993); Wang, D. & Munoz, D. G., *J. Neuropathol. Exp. Neurol.* 54:548 (1995); Beckman, J. S., et al., *Nature* 364: 584 (1993); Hartmann, H. A. & Evenson, M. A., *Med. Hypotheses* 38:75 (1992)).

Although much fundamental pathology, genetic susceptibility and biology associated with AD is becoming clearer, a rational chemical and structural basis for developing effective drugs to prevent or cure the disease remains elusive. While the genetics of the disorder indicates that the metabolism of Aβ is intimately associated with the etiopatholgenesis of the disease, drugs for the treatment of AD have so far focused on "cognition enhancers" which do not address the underlying disease processes.

SUMMARY OF THE INVENTION

In one aspect, the invention relates to a method for the identification of an agent to be used in the treatment of AD, wherein the agent is capable of altering the production of $Cu^+$ by Aβ, the method comprising:

(a) adding $Cu^{2+}$ to a first Aβ sample;
(b) allowing the first sample to incubate for an amount of time sufficient to allow said first sample to generate $Cu^+$;
(c) adding $Cu^{2+}$ to a second Aβ sample, the second sample additionally comprising a candidate pharmacological agent;
(d) allowing the second sample to incubate for the same amount of time as the first sample;
(e) determining the amount of $Cu^+$ produced by the first sample and the second sample; and
(f) comparing the amount of $Cu^+$ produced by the first sample to the amount of $Cu^+$ produced by the second sample;

whereby a difference in the amount of $Cu^+$ produced by the first sample as compared to the second sample indicates that the candidate pharmacological agent has altered the production of $Cu^+$ by Aβ.

In a preferred embodiment, the amount of $Cu^+$ present in said first and said second sample is determined by
(a) adding a complexing agent to said first and said second sample, wherein said complexing agent is capable of combining with $Cu^+$ to form a complex compound, wherein said complex compound has an optimal visible absorption wavelength;
(b) measuring the absorbancy of said first and said second sample; and
(c) calculating the concentration of $Cu^+$ in said first and said second sample using the absorbancy obtained in step (b).

In a more preferred embodiment, the complexing agent is bathocuproinedisulfonic (BC) anion. The concentration of $Cu^+$ produced by Aβ may then be calculated on the basis of the absorbance of the sample at about 478 nm to about 488 nm, more preferable about 480 to about 486 nm, and most preferably about 483 nm. In another preferred embodiment, the method is performed in a microtiter plate, and the absorbancy measurement is performed by a plate reader. Most preferably, two or more different test candidate agents are simultaneously evaluated for an ability to alter the production of $Cu^+$ by Aβ. In another preferred embodiment, said Aβ samples of step 1(a) and step 1(c) are biological samples. Most preferably, said biological samples are CSF.

In another aspect, the invention relates to a method for the identification of an agent to be used in the treatment of AD, wherein said agent is capable of altering the production of $Fe^{2+}$ by Aβ, said method comprising:
(a) adding $Fe^{3+}$ to a first Aβ sample;
(b) allowing said first sample to incubate for an amount of time sufficient to allow said first sample to generate $Fe^{2+}$;
(c) adding $Fe^{3+}$ to a second Aβ sample, said second sample additionally comprising a candidate pharmacological agent;
(d) allowing said second sample to incubate for the same amount of time as said first sample;
(e) determining the amount of $Fe^{2+}$ produced by said first sample and said second sample; and
(f) comparing the amount of $Fe^{2+}$ present in said first sample to the amount of $Fe^{2+}$ present in said second sample;

whereby a difference in the amount of $Fe^{2+}$ present in said first sample as compared to said second sample indicates that said candidate pharmacological agent has altered the production of $Fe^{2+}$ by Aβ.

In a preferred embodiment, the amount of $Fe^{2-}$ present is determined by using a spectrophotometric method analogous to that used for the determination of $Cu^+$, above. In this method, the complexing agent is bathophenanthrolinedisulfonic (BP) anion. The concentration of $Fe^{2+}$-BP produced by Aβ may then be calculated on the basis of the absorbance of the sample at about 530 to about 540 nm, more preferably about 533 nm to about 538 nm, and most preferably about 535 nm. In another preferred embodiment, said method is performed in a microtiter plate and the absorbancy measurement is performed by a plate reader. Most preferably, two or more different test candidate agents are simultaneously evaluated for an ability to alter the production of $Fe^{2+}$ by Aβ.

In another preferred embodiment, said AP samples of step 1(a) and step 1(c) are biological samples. Most preferably, the biological sample is CSF.

In yet another aspect, the invention relates to a method for the identification of an agent to be used in the treatment of AD, wherein said agent is capable of altering the production of $H_2O_2$ by Aβ, said method comprising:
(a) adding $Cu^{2-}$ or $Fe^{3+}$ to a first Aβ sample;
(b) allowing said first sample to incubate for an amount of time sufficient to allow said first sample to generate $H_2O_2$;
(c) adding $Cu^{2+}$ or $Fe^{3+}$ to a second Aβ sample, said second sample additionally comprising a candidate pharmacological agent;
(d) allowing said second sample to incubate for the same amount of time as said first sample;
(e) determining the amount of $H_2O_2$ produced by said first sample and said second sample; and
(f) comparing the amount of $H_2O_2$ present in said first sample to the amount of $H_2O_2$ present in said second sample;

whereby a difference in the amount of $H_2O_2$ present in said first sample as compared to said second sample indicates that said candidate pharmacological agent has altered the production of $H_2O_2$ by Aβ. In a preferred embodiment, the determination of the amount of $H_2O_2$ present in said first and said second sample is determined by
(a) adding catalase to a first aliquot of said first sample obtained in step (a) above in an amount sufficient to break down all of the $H_2O_2$ generated by said sample;
(b) adding TCEP, in an amount sufficient to capture all of the $H_2O_2$ present in said samples, to
 (i) said first aliquot
 (ii) a second aliquot of said first sample obtained in step (a) above; and
 (iii) said second sample obtained in step (b) above;
(c) incubating the samples obtained in step (b) for an amount of time sufficient to allow the TCEP to capture all of the $H_2O_2$;
(d) adding DTNB to said samples obtained in step (c);
(e) incubating said samples obtained in step (d) for an amount of time sufficient to generate TMB;
(f) measuring the absorbancy at about 407 to about 417 nm of said samples obtained in step (e); and
(g) calculating the concentration of $H_2O_2$ in said first and said second sample using the absorbancies obtained in step (f). In a preferred embodiment, the absorbancy of TMB is measured at about 412 nm. In preferred embodiment, said method is performed in a microtiter plate, and the absorbancy measurement is performed by a plate reader. Most preferably, two or more different test candidate agents are simultaneously evaluated for an ability to alter the production of $H_2O_2$ by Aβ.

In another aspect, the invention relates to a method for the identification of an agent to be used in the treatment of AD, wherein said agent is capable of decreasing the production of $O_2^-$ by A$\beta$, said method comprising:
 (a) adding A$\beta$ and to a first buffer sample having an $O_2$ tension greater than 0;
 (b) allowing said first sample to incubate for an amount of time sufficient to allow said first sample to generate $O_2^-$;
 (c) adding A$\beta$ and a candidate pharmacological agent to a second buffer sample having an $O_2$ tension greater than 0;
 (d) allowing said second sample to incubate for the same amount of time as said first sample;
 (e) determining the amount of $O_2^-$ produced by said first sample and said second sample; and
 (f) comparing the amount of $O_2^-$ present in said first sample to the amount of $O_2^-$ present in said second sample;

whereby a difference in the amount of $O_{2-}$ present in said first sample as compared to said second sample indicates that said candidate pharmacological agent has altered the production of $O_2^-$ by A$\beta$. In a preferred embodiment, the A$\beta$ used is A$\beta_{1-42}$.

In a preferred embodiment, the determination of the amount of $O_2^-$ present in said samples is accomplished by measuring the absorbancy of the sample at about 250 nm.

Because the ability of A$\beta$ to generate $H_2O_2$ from $O_2^-$ may in many instances be beneficial. Therefore, in a preferred embodiment, the invention also relates to a method for the identification of an agent to be used in the treatment of AD, wherein said agent is capable of interfering with the interaction of $O_2$ and A$\beta$ to produce $O_2^-$, without interfering with the SOD-like activity of A$\beta$, said method comprising:
 (a) identifying an agent capable of decreasing the production of $O_2^-$ by A$\beta$; and
 (b) determining the ability of said agent to alter the SOD-like activity of A$\beta$. In a preferred embodiment, the determination of the ability of said agent to alter the SOD-like activity of A$\beta$ is made by determining whether A$\beta$ is capable of catalytically producing $Cu^+$, $Fe^{2+}$ or $H_2O_2$.

In another aspect the invention relates to a method for the identification of agents useful in the treatment of Alzheimer's disease (AD) because they are capable of reducing the toxicity of A$\beta$.

In one aspect the invention relates to a method for the identification of an agent to be used in the treatment of AD, wherein said agent is capable of reducing the toxicity of A$\beta$, said method comprising:
 (a) adding A$\beta$ to a first cell culture;
 (b) adding A$\beta$ to a second cell culture, said second cell culture additionally containing a candidate pharmacological agent;
 (c) determining the level of neurotoxicity of A$\beta$ in said first and said second samples; and
 (d) comparing the level of neurotoxicity of A$\beta$ in said first and said second samples, whereby a lower neurotoxicity level in said second sample as compared to said first sample indicates that said candidate pharmacological agent has reduced the neurotoxicity of A$\beta$, and is thereby capable of being used to treat AD. In a preferred embodiment, the neurotoxicity of A$\beta$ is determined by using an MTT assay. In another preferred embodiment, the neurotoxicity of A$\beta$ is determined by using an LDH release assay. In still another preferred embodiment, the neurotoxicity of A$\beta$ is determined by using a Live/Dead assay. Preferably said cells utilized in the assays are rat cancer cells. Even more preferably said cells are rat primary frontal neuronal cells.

Yet another aspect of the invention relates to a kit for determining whether an agent is capable of altering the production of $Cu^+$ by A$\beta$ which comprises a carrier means being compartmentalized to receive in close confinement therein one or more container means wherein
 (a) the first container means contains a peptide comprising A$\beta$ peptide;
 (b) a second container means contains a $Cu^{2+}$ salt; and
 (c) a third container means contains BC anion.

Preferably, said A$\beta$ peptide is present as a solution in an aqueous buffer or a physiological solution, at a concentration above about 10 $\mu$M.

In another aspect the invention relates to a kit for determining whether an agent is capable of altering the production of $Fe^{2+}$ by A$\beta$ which comprises a carrier means being compartmentalized to receive in close confinement therein one or more container means wherein
 (a) the first container means contains a peptide comprising A$\beta$ peptide;
 (b) a second container means contains an $Fe^{3+}$ salt; and
 (c) a third container means contains BP anion.

Preferably, said A$\beta$ peptide is present as a solution in an aqueous buffer or a physiological solution, at a concentration above about 10 $\mu$M.

In another aspect, the invention relates to a kit for determining whether an agent is capable of altering the production of $H_2O_2$ by A$\beta$ which comprises a carrier means being compartmentalized to receive in close confinement therein one or more container means wherein
 (a) the first container means contains a peptide comprising A$\beta$ peptide;
 (b) a second container means contains a $Cu^{2+}$ salt;
 (c) a third container means contains TCEP; and
 (d) a fourth container means contains DTNB.

Preferably, said A$\beta$ peptide is present as a solution in an aqueous buffer or a physiological solution, at a concentration above about 10 $\mu$M.

In yet another aspect the invention relates to a method for the identification of an agent to be used in the treatment of AD, wherein said agent is capable of inhibiting redox-reactive metal-mediated polymerization of A$\beta$, said method comprising:
 (a) adding a redox-reactive metal to a first A$\beta$ sample;
 (b) allowing said first sample to incubate for an amount of time sufficient to allow A$\beta$ polymerization;
 (c) adding said redox-reactive metal to a second A$\beta$ sample, said second sample additionally comprising a candidate pharmacological agent;
 (d) allowing said second sample to incubate for the same amount of time as said first sample;
 (e) removing an aliquot from each of said first and said second sample; and
 (f) determining presence or absence of polymerization in said first and second samples, whereby an absence of A$\beta$ polymerization in said second sample as compared to said first sample indicates that said candidate pharmacological agent has inhibited A$\beta$ polymerization. Preferably, at step (f), a western blot analysis is performed to determine the presence or absence of polymerization in the first and the second sample.

Another aspect of the present invention contemplates a method for treating AD in a subject, said method comprising administering to said subject an effective amount of an agent which is capable of inhibiting or otherwise reducing metal-mediated production of free radicals.

The present invention provides a method for treating AD in a subject, said method comprising administering to said subject an effective amount of an agent comprising a metal chelator and/or a metal complexing compound for a time and under conditions sufficient to inhibit or otherwise reduce metal-mediated production of free radicals by Aβ. In one aspect, the free radicals are reactive oxygen species such as $O_2^-$ or OH.. In another aspect, the free radicals include forms of Aβ.

Still another aspect of the present invention relates to a method of treating AD in a subject comprising administering to said subject an agent capable of preventing, reducing or otherwise inhibiting ROS production by Aβ deposits in the brain for a time and under conditions to effect said treatment.

In one aspect, the invention relates to a method of treating amyloidosis in a subject, said method comprising administering to said subject an effective amount of (a) a metal chelator selected from the group consisting of: bathocuproine, bathophenanthroline, penacillamine, TETA, TPEN or hydrophobic derivatives thereof; and (b) one or more pharmaceutically acceptable carriers or diluents; for a time and under conditions to bring about said treatment; and wherein said chelator reduces, inhibits or otherwise interferes with Aβ-mediated production of radical oxygen species. The invention also relates to said method further comprising administering to the subject an effective amount of a compound selected from the group consisting of: rifampicin, disulfiram, and indomethacin, or a pharmaceutically acceptable salt thereof.

In another aspect, the invention relates to a method of treating amyloidosis in a subject, said method comprising administering to said subject a combination of (a) a metal chelator selected from the group consisting of: bathocuproine, bathophenanthroline, DTPA, EDTA, EGTA, penacillamine, TETA, and TPEN, or hydrophobic derivatives thereof; and (b) a supplement selected from the group consisting of: ammonium salt, calcium salt, magnesium salt, and sodium salt, for a time and under conditions to bring about said treatment; and wherein said chelator reduces, inhibits or otherwise interferes with Aβ-mediated production of radical oxygen species. In a preferred embodiment, the metal chelator is EGTA. In another preferred embodiment, the metal chelator is TPEN. In yet another preferred embodiment, the supplement is magnesium salt.

In yet another aspect, the invention relates to said method further comprising administering to the subject an effective amount of a compound selected from the group consisting of: rifampicin, disulfiram, and indomethacin, or a pharmaceutically acceptable salt thereof.

In yet another aspect, the invention relates to a method of treating amyloidosis in a subject, said method comprising administering to said subject an effective amount of a salt of a metal chelator, wherein said chelator is selected from the group consisting of: bathocuproine, bathophenanthroline, DTPA, EDTA, EGTA, penacillamine, TETA, and TPEN, or hydrophobic derivatives thereof; wherein said salt is selected from the group consisting of: ammonium, calcium, magnesium, and sodium; and wherein said salt of a metal chelator reduces, inhibits or otherwise interferes with Aβ-mediated production of radical oxygen species. In a preferred embodiment, the metal chelator is EGTA. In another preferred embodiment, the the metal chelator is TPEN. In yet another preferred embodiment, the salt of a metal chelator is a magnesium salt. In yet another aspect, the invention relates to said method further comprising administering to said subject a compound selected from the group consisting of: rifampicin, disulfiram, and indomethacin, or a pharmaceutically acceptable salt thereof.

In another aspect, the invention relates to a method of treating amyloidosis in a subject, said method comprising administering to said subject an effective amount of a chelator specific for copper; wherein said chelator reduces, inhibits or otherwise interferes with Aβ-mediated production of radical oxygen species. In a preferred embodiment, the chelator specific for copper is specific for the reduced form of copper. Most preferreably, the chelator is bathocuproine or a hydrophobic derivative thereof.

In yet another aspect, the invention relates to a method of treating amyloidosis in a subject, said method comprising administering to said subject an effective amount of an alkalinizing agent, wherein said alkalinizing agent reduces, inhibits or otherwise interferes with Aβ-mediated production of radical oxygen species. In a preferred embodiment, the alkalinizing agent is magnesium citrate. In another preferred embodiment, the alkalinizing agent is calcium citrate.

Still another aspect of the present invention contemplates a method of treating AD in a subject comprising administering to said subject an agent capable of preventing formation of Aβ amyloid, promoting, inducing or otherwise facilitating resolubilization of Aβ deposits in the brain, or both, for a time and under conditions to effect said treatment.

In one aspect, the invention relates to a method of treating amyloidosis in a subject, said method comprising administering to said subject an effective amount of (a) a metal chelator selected from the group consisting of: bathocuproine, bathophenanthroline, penacillamine, TETA, TPEN or hydrophobic derivatives thereof; and (b) one or more pharmaceutically acceptable carriers or diluents; for a time and under conditions to bring about said treatment; and wherein said chelator prevents formation of Aβ amyloid, promotes, induces or otherwise facilitates resolubilization of Aβ deposits, or both. In another aspect, the invention relates to said method further comprising administering to the subject an effective amount of a compound selected from the group consisting of: rifampicin, disulfiram, and indomethacin, or a pharmaceutically acceptable salt thereof.

In yet another aspect, the invention relates to a method of treating amyloidosis in a subject, said method comprising administering to said subject a combination of (a) a metal chelator selected from the following group: bathocuproine, bathophenanthroline, DTPA, EDTA, EGTA, penacillamine, TETA, and TPEN, or hydrophobic derivatives thereof; and (b) a supplement selected from the group consisting of: ammonium salt, calcium salt, magnesium salt, and sodium salt, for a time and under conditions to bring about said treatment; and wherein said combination prevents formation of Aβ amyloid, promotes, induces or otherwise facilitates resolubilization of Aβ deposits, or both.

In a preferred embodiment, the metal chelator is EGTA. In another preferred embodiment, the the metal chelator is TPEN. In yet another preferred embodiment, the supplement is a magnesium salt. In another aspect, the invention relates to said method further comprising administering to the subject an effective amount of a compound selected from the group consisting of: rifampicin, disulfiram, and indomethacin, or a pharmaceutically acceptable salt thereof.

In another aspect, the invention relates to a method of treating amyloidosis in a subject, said method comprising administering to said subject an effective amount of a salt of a metal chelator, wherein said chelator is selected from the group consisting of: bathocuproine, bathophenanthroline, DTPA, EDTA, EGTA, penacillamine, TETA, and TPEN, or hydrophobic derivatives thereof; wherein said salt is selected from the group consisting of: ammonium, calcium, magnesium, and sodium; and wherein said salt of a metal chelator prevents formation of Aβ amyloid, promotes, induces or otherwise facilitates resolubilization of Aβ deposits, or both. In a preferred embodiment, the metal chelator is EGTA. In another preferred embodiment, the the metal chelator is TPEN. In yet another preferred embodiment, the salt of a metal chelator is a magnesium salt. In another aspect, the invention relates to said method further comprising administering to the subject an effective amount of a compound selected from the group consisting of: rifampicin, disulfiram, and indomethacin, or a pharmaceutically acceptable salt thereof.

In another aspect, the invention relates to a method of treating amyloidosis in a subject, said method comprising administering to said subject an effective amount of a chelator specific for copper; wherein said chelator prevents formation of Aβ amyloid, promotes, induces or otherwise facilitates resolubilization of Aβ deposits, or both. In a preferred embodiment, the chelator specific for copper is specific for the reduced form of copper. Most preferably, the chelator is bathocuproine or a hydrophobic derivative thereof.

In yet another aspect, the invention relates to a method of treating amyloidosis in a subject, said method comprising administering to said subject an effective amount of an alkalinizing agent, wherein said alkalinizing agent prevents formation of Aβ amyloid, promotes, induces or otherwise facilitates resolubilization of Aβ deposits, or both. In a preferred embodiment, the alkalinizing agent is magnesium citrate. In another preferred embodiment, the alkalinizing agent is calcium citrate.

Still another aspect contemplates pharmaceutical compositions for the prevention, reduction or inhibition of ROS production by Aβ deposits, or the prevention of formation of Aβ amyloid, promoting, inducing or otherwise facilitating the resolubilization of Aβ deposits, or both, in the brain.

In one aspect, the invention relates to a pharmaceutical composition for treatment of conditions caused by amyloidosis, Aβ-mediated ROS formation, or both, comprising: (a) a metal chelator selected from the group consisting of: bathocuproine, bathophenanthroline, DTPA, EDTA, EGTA, penacillamine, TETA, and TPEN, or hydrophobic derivatives thereof; and (b) a supplement selected from the group consisting of: ammonium salt, calcium salt, magnesium salt, and sodium salt, together with one or more pharmaceutically acceptable carriers or diluents.

In a preferred embodiment, the metal chelator is EGTA. In another preferred embodiment, the metal chelator is TPEN. In yet another preferred embodiment, the supplement is a magnesium salt.

In another aspect, the invention relates to a pharmaceutical composition for treatment of conditions caused by amyloidosis, Aβ-mediated ROS formation, or both, comprising a salt of a metal chelator selected from the group consisting of: bathocuproine, bathophenanthroline, DTPA, EDTA, EGTA, penacillamine, TETA, and TPEN, or hydrophobic derivatives thereof; and wherein said salt is selected from the group consisting of: ammonium, calcium, magnesium, and sodium, together with one or more pharmaceutically acceptable carriers or diluents. In a preferred embodiment, the metal chelator is EGTA. In another preferred embodiment, the the metal chelator is TPEN. In yet another preferred embodiment, the salt of a metal chelator is a magnesium salt.

In yet another aspect, the invention relates to pharmaceutical composition for treatment of conditions caused by amyloidosis, Aβ-mediated ROS formation, or both, comprising a chelator specific for copper, with one or more pharmaceutically acceptable carriers or diluents. In a preferred embodiment, the chelator is specific for the reduced form of copper. Most preferably, the chelator specific for the reduced form of copper is bathocuproine.

In another aspect, the invention relates to a pharmaceutical composition for treatment of conditions caused by amyloidosis, Aβ-mediated ROS formation, or both, comprising an alkalinizing agent, with one or more pharmaceutically acceptable carriers or diluents. In a preferred embodiment, the alkalinizing agent is magnesium citrate. In another preferred embodiment, the alkalinizing agent is calcium citrate.

In yet another aspect, the invention relates to a composition of matter comprising: (a) a metal chelator selected from the group consisting of: bathocuproine, bathophenanthroline, penacillamine, TETA, and TPEN, or hydrophobic derivatives thereof; and (b) a compound selected from the group consisting of: rifampicin, disulfiram, and indomethacin.

In still another aspect, the invention relates to a composition of matter comprising: (a) a metal chelator selected from the group consisting of: bathocuproine, bathophenanthroline, DTPA, EDTA, EGTA, penacillamine, TETA, and TPEN, or hydrophobic derivatives thereof; and (b) a supplement selected from the group consisting of: ammonium salt, calcium salt, magnesium salt, and sodium salt. In a preferred embodiment, the metal chelator is EGTA. In another preferred embodiment, the metal chelator is TPEN. In yet another preferred embodiment, the supplement is a magnesium salt.

Still another aspect, the invention relates to a method for determining which metal chelators used in the treatment of amyloidosis, should be supplemented with ammonium, calcium, magnesium, or sodium salts, comprising:
(a) contacting Aβ aggregates with solutions containing a range of concentrations of said metal chelators;
(b) preparing a dilution curve from data obtained in step (a);
(c) selecting chelators which solubilize less Aβ aggregates at higher concentrations than at lower or intermiate concentrations;
(d) contacting Aβ aggregates with chelators selected in step (c), in the presence of an ammonium, calcium, magnesium or sodium salt; and
(e) determining if resolubilization is increased in the presence of said salt; thereby determining whether a metal chelator used in the treatment of amyloidosis should be supplemented with ammonium, calcium, magnesium, or sodium salts.

BRIEF DESCRIPTION OF THE FIGURES

FIG. 2A is a graph showing the proportion of soluble $A\beta_{1-40}$ remaining in the supernatant after incubation with various metal ions. FIG. 2B is a graph showing a turbidometric analysis of pH effect on metal ion-induced $A\beta_{1-40}$ aggregation. FIG. 2C is a graph showing the proportion of soluble $A\beta_{1-40}$ remaining in the supernatant after incubation with various metal ions, where high metal ion concentrations were used.

FIG. 4A is a graph showing the proportion of soluble $A\beta_{1-40}$ remaining in the supernatant following incubation at various pHs in PBS±$Zn^{2+}$ or $Cu^{2+}$. FIG. 4B is a graph showing the proportion of soluble $A\beta_{1-40}$ remaining in the supernatant following incubation at various pHs with different $Cu^{2+}$ concentrations. FIG. 4C is a graph showing the relative aggregation of nM concentrations of $A\beta_{1-40}$ at pH 7.4 and 6.6 with different $Cu^{2+}$ concentrations.

FIG. 5A is a graph showing a turbidometric analysis of $Cu^{2+}$-induced $A\beta_{1-40}$ aggregation at pH 7.4 reversed by successive cycles of chelator. FIG. 5B is a graph showing a turbidometric analysis of the reversibility of $Cu^{2+}$-induced $A\beta_{1-40}$ aggregation as the pH cycles between 7.4 and 6.6.

FIG. 13A illustrates the reducing capacity of $A\beta$ species (10 µM), compared to Vitamin C and insulin (Sigma) (all 10 µM) towards $Fe^{3+}$ or $Cu^{2+}$ (10 µM) in PBS, pH 7.4, after 1 hour co-incubation, 37° C. Data indicate concentration of reduced metal ions generated. FIG. 13B shows the effect of oxygen tension and chelation upon $A\beta_{1-42}$ metal reduction. $A\beta_{1-42}$ was incubated as in FIG. 13A under various buffer gas conditions. "Ambient"=no efforts were made to adjust the gas tension in the bench preparations of the buffer vehicle, "$O_2$"=100% $O_2$ was continuously bubbled through the PBS vehicle for 2 hours (at 20° C.), before the remainder of the incubation components were added, "Ar"=100% Ar was continuously bubbled through the PBS vehicle for 2 hours (at 20° C.), before the remainder of the incubation components were added. "+DFO or TETA"=Desferrioxamine (DFO, Sigma, 200 µM) was added to the $A\beta_{1-42}$ incubation in the presence of $Fe^{3+}$ 10 µM, or triethylenetetramine dihydrochloride (TETA, Sigma, 200 µM) was added to the $A\beta_{1-42}$ incubation in the presence of $Cu^{2+}$ +10 µM, under ambient oxygen conditions. All data points are means±SD, n=3.

FIG. 14A shows $H_2O_2$ produced by $A\beta_{1-42}$ (in PBS, pH 7.4, under ambient gas conditions, 1 hour, 37° C.) following co-incubation with various concentrations of catalase in the presence of 1 µM $Fe^{3+}$. FIG. 14B shows a comparison of $H_2O_2$ generation by variant $A\beta$ species: $A\beta_{1-42}$, $A\beta_{1-40}$, rat $A\beta_{1-40}$, $A\beta_{40-1}$, and $A\beta_{1-28}$ (vehicle conditions as in FIG. 14A). FIG. 14C shows the effect of metal chelators (200 µM) on $H_2O_2$ production from $A\beta_{1-42}$ when incubated in the presence of $Fe^{3+}$ or $Cu^{2+}$ (1 µM) (vehicle conditions as in FIG. 14A). BC=Bathocuproinedisulfonate, BP=Bathophenanthrolinedisulfonate. The effects of DFO were assessed in the presence of $Fe^{3+}$, and TETA was assessed in the presence of $Cu^{2+}$, as indicated. FIG. 14D shows $H_2O_2$ produced by $A\beta_{1-42}$, $A\beta_{1-40}$, and Vitamin C in the presence of $Fe^{3+}$ (1 µM) (in PBS, pH 7.4 buffer, 1 hr, 37° C.) under various dissolved gas conditions (described in FIG. 13B): ambient air, $O_2$ enrichment, and anaerobic (Ar) conditions, as indicated. FIG. 14E shows $H_2O_2$ produced by $A\beta_{1-42}$, $A\beta_{1-40}$, and Vitamin C in the presence of $Cu^{2+}$ (1 µM) (in PBS, pH 7.4 buffer, 1 hr, 37° C.) under various dissolved gas conditions (as in FIG. 14D). All data points are means±SD, n=3.

FIG. 15A shows the spectrophotometric absorbance at 250 nm (after subtracting buffer blanks) for $A\beta_{1-42}$ (10 µM, in PBS, pH 7.4, with 1 µM $Fe^{3+}$, incubated 1 hr, 37° C.) under ambient air (+100 U/mL superoxide dismutase, SOD), $O_2$ enrichment, and anaerobic (Ar) buffer gas conditions (described in FIG. 13B). FIG. 15B shows the spectrophotometric absorbance at 250 nm (after subtracting buffer blanks) for variant $A\beta$ peptides: $A\beta_{1-42}$, $A\beta_{1-40}$, rat $A\beta_{1-40}$, $A\beta_{40-1}$, and $A\beta_{1-28}$ (10 µM in PBS, pH 7.4, with 1 µM $Fe^{3+}$, incubated 1 hr, 37° C., under ambient buffer gas conditions). All data points are means±SD, n=3.

FIG. 16A shows the signal from the TBARS assay of OH. produced from Vitamin C (100 µM) and variant $A\beta$ species (10 µM): $A\beta_{1-42}$, $A\beta_{1-40}$, rat $A\beta_{1-40}$, $A\beta_{40-1}$, and $A\beta_{1-28}$ (in PBS, pH 7.4, with 1 µM $Fe^{3+}$ or $Cu^{2+}$ as indicated, incubated 1 hr, 37° C., under ambient buffer gas conditions). FIG. 16B illustrates the effect of OH.-specific scavengers upon OH. generation by Vitamin C and $A\beta_{1-42}$. Mannitol (5 mM, Sigma) or dimethyl sulfoxide (DMSO, 5 mM, Sigma), was co-incubated with Vitamin C (10 µM+500 µM $H_2O_2$) or $A\beta_{1-42}$ (10 µM) (conditions as for FIG. 16A). All data points are means±SD, n=3.

FIGS. 19A–19F show that metal chelators promote the solubilization of $A\beta$ from human brain sample homogenates.

FIG. 20B shows a western blot comparing extracted $A\beta$ from an AD brain (AD) to that of sedimentable deposits from healthy brain tissue (young control—C). In the experiments of FIG. 20B, TBS buffer was used rather than PBS.

FIG. 24B shows that Aβ solubility in metal-depleted tissue is restored by the addition of magnesium.

Upper panel: representative blot from AD specimen.

Lower panel: representative blot from aged non-AD tissue bearing a similar total Aβ load.

Figure 25A:
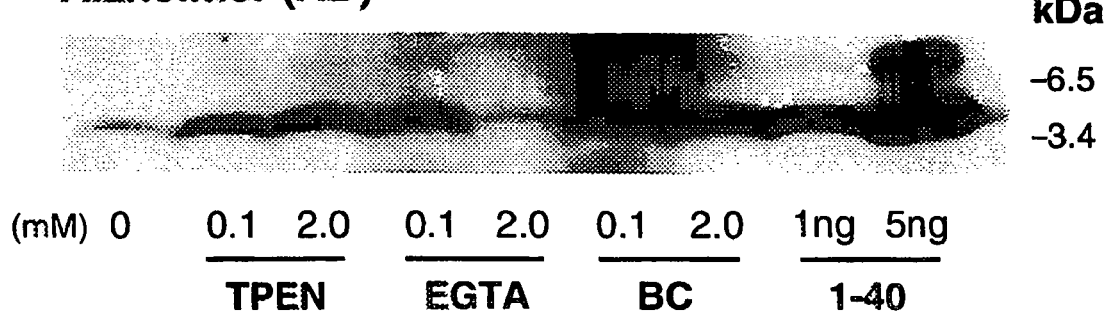
FIGS. 25A and 25B—FIG. 25A shows that patterns of chelator-promoted solubilization of Aβ differ in AD and aged-matched, non-AD tissue.
Figure 25A:
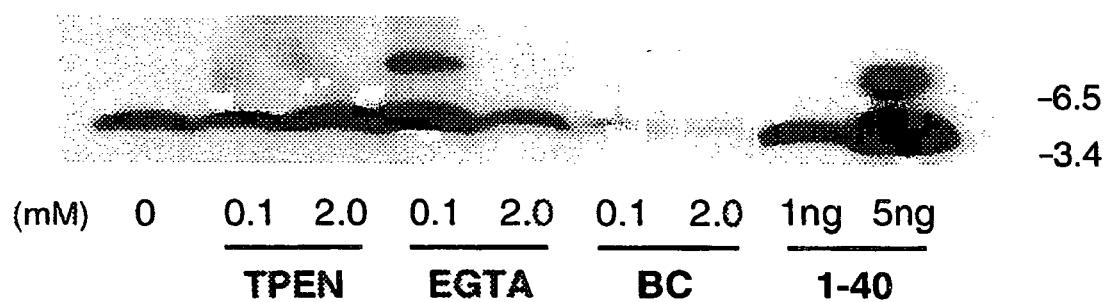
Figure 25B:
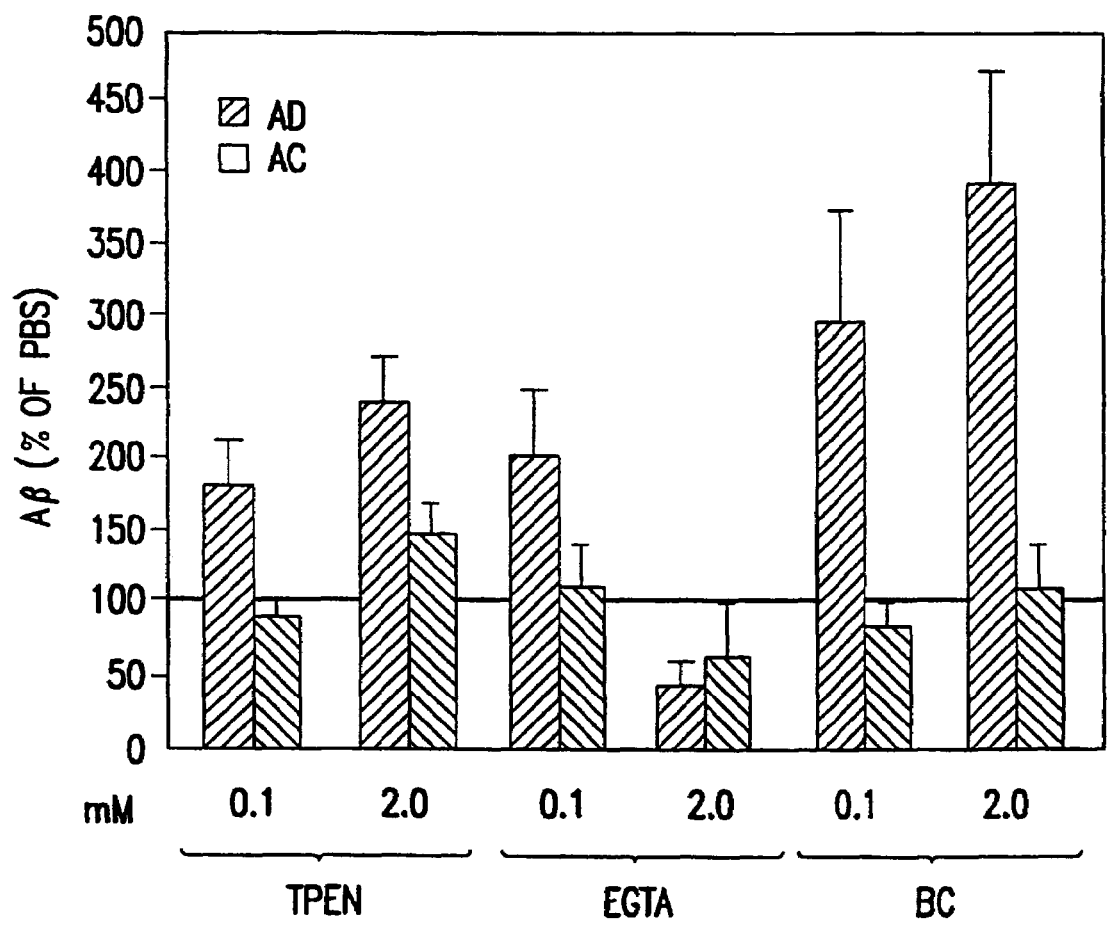

FIG. 25B shows soluble Aβ resulting from chelation treatment for AD and aged-matched, non-AD tissue, expressed as a percentage of the PBS-only treatment group.

Figures 26A, 26B:
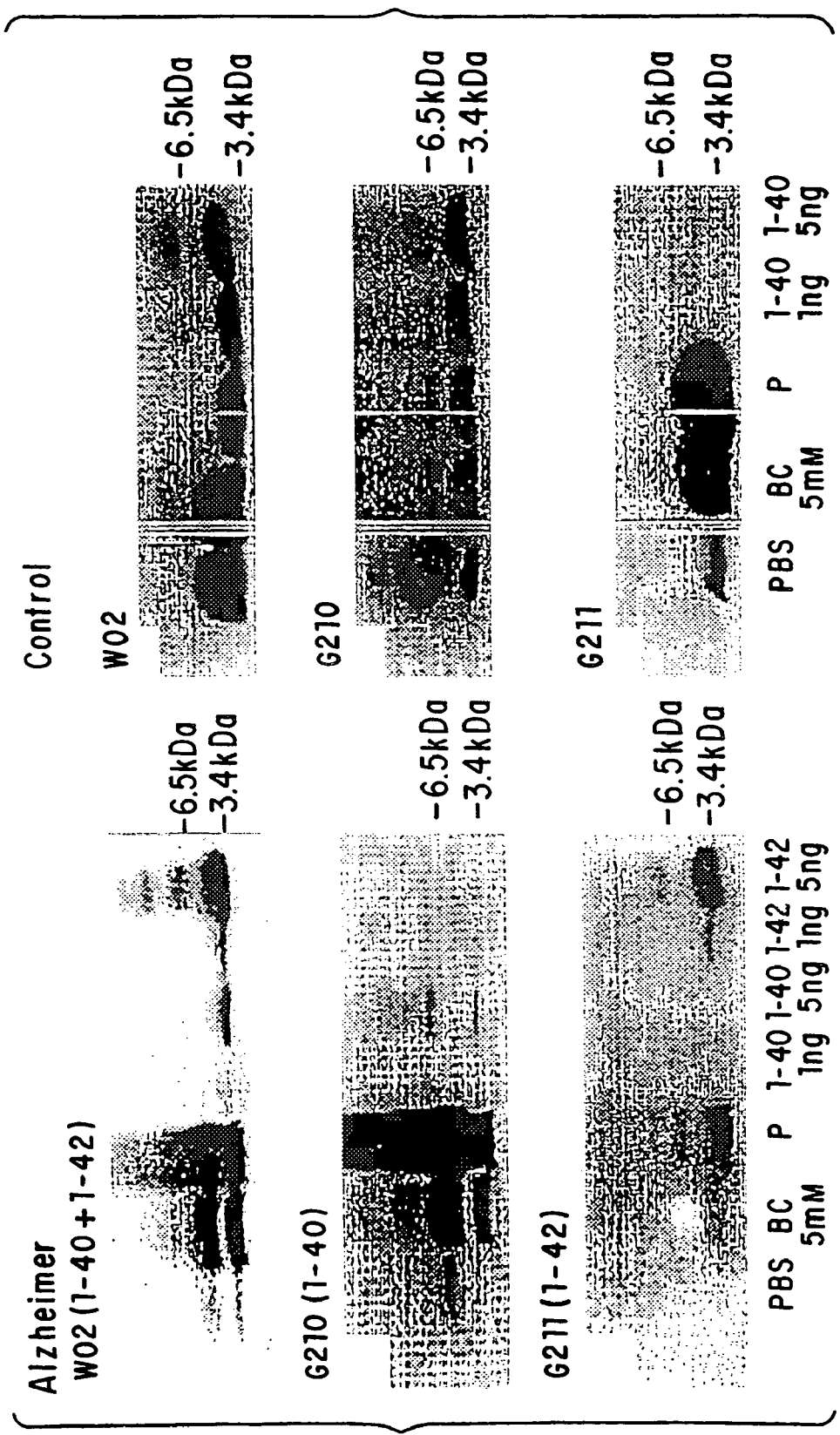

FIGS. 26A and 26B show that chelation promotes the solubilization of $A\beta_{1-40}$ and $A\beta_{1-42}$ from AD and non-AD tissue. Representative AD (FIG. 26A) and aged-matched control specimens (FIG. 26B) were prepared as described in PBS or 5 mM BC. Identical gels were run and Western blots were probed with mAbs WO2 (raised against residues 5–16, recognizes $A\beta_{1-40}$ and $A\beta_{1-42}$) G210 (raised against residues 35–40, recognizes $A\beta_{1-40}$) or G211 (raised against residues 35–42, recognizes $A\beta_{1-42}$) (See Ida, N. et al., *J. Biol. Chem.* 271:22908 1996).

Figure 27A:
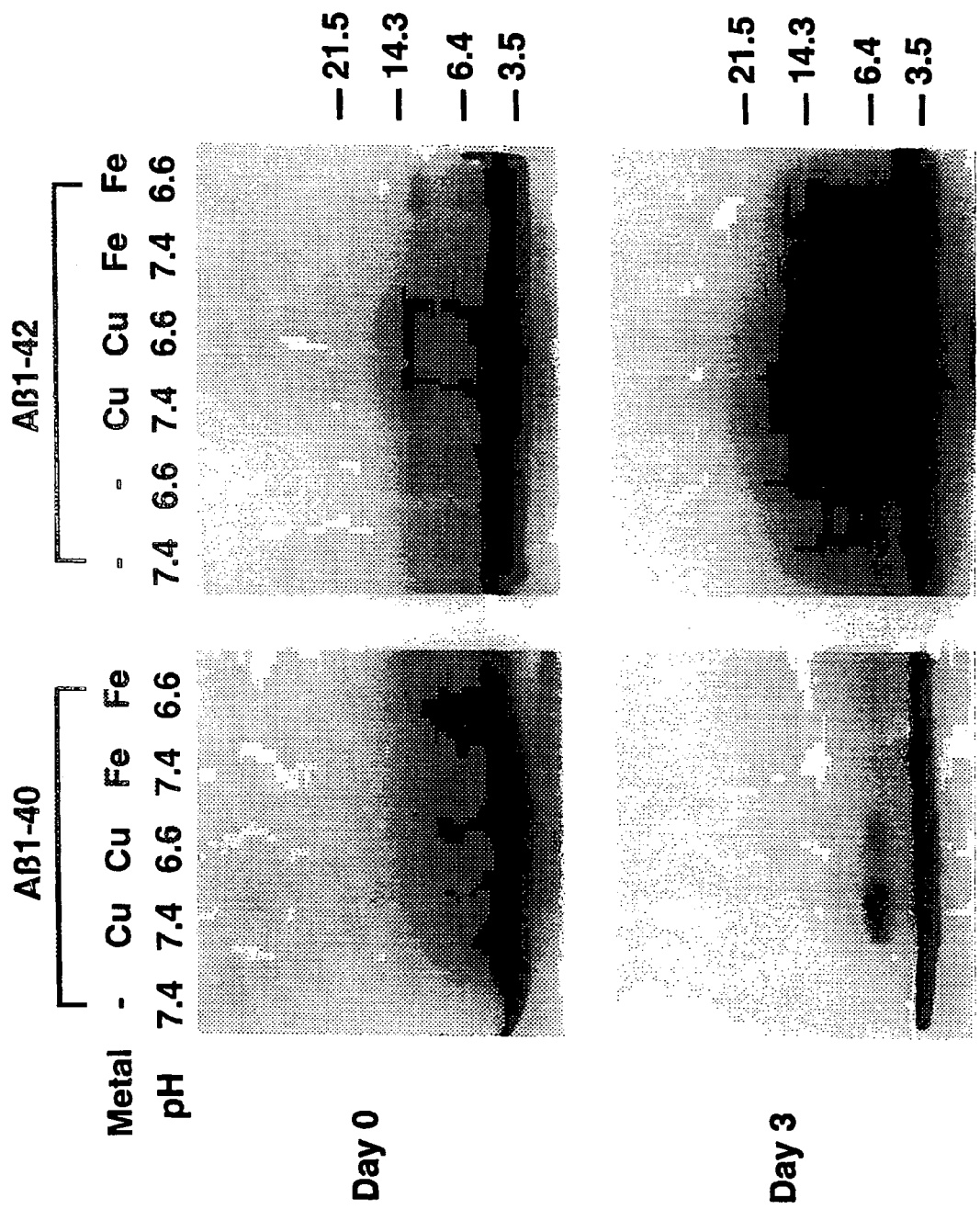
Figure 27B:
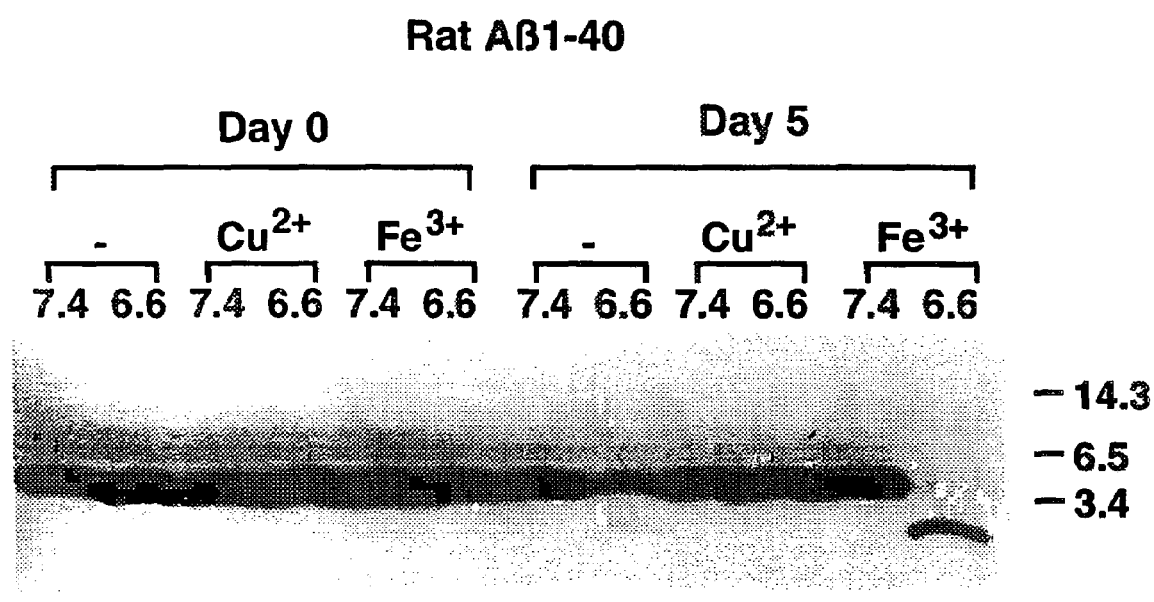

FIGS. 27A and 27B—FIG. 27A shows SDS-resistant polymerization of human $A\beta_{1-40}$ versus human $A\beta_{1-42}$ with $Cu^{2+}$ or $Fe^{3+}$. FIG. 27B shows SDS-resistant polymerization of rat $A\beta^{1-40}$ with $Cu^{2+}$ or $Fe^{3+}$.

Figure 28A:
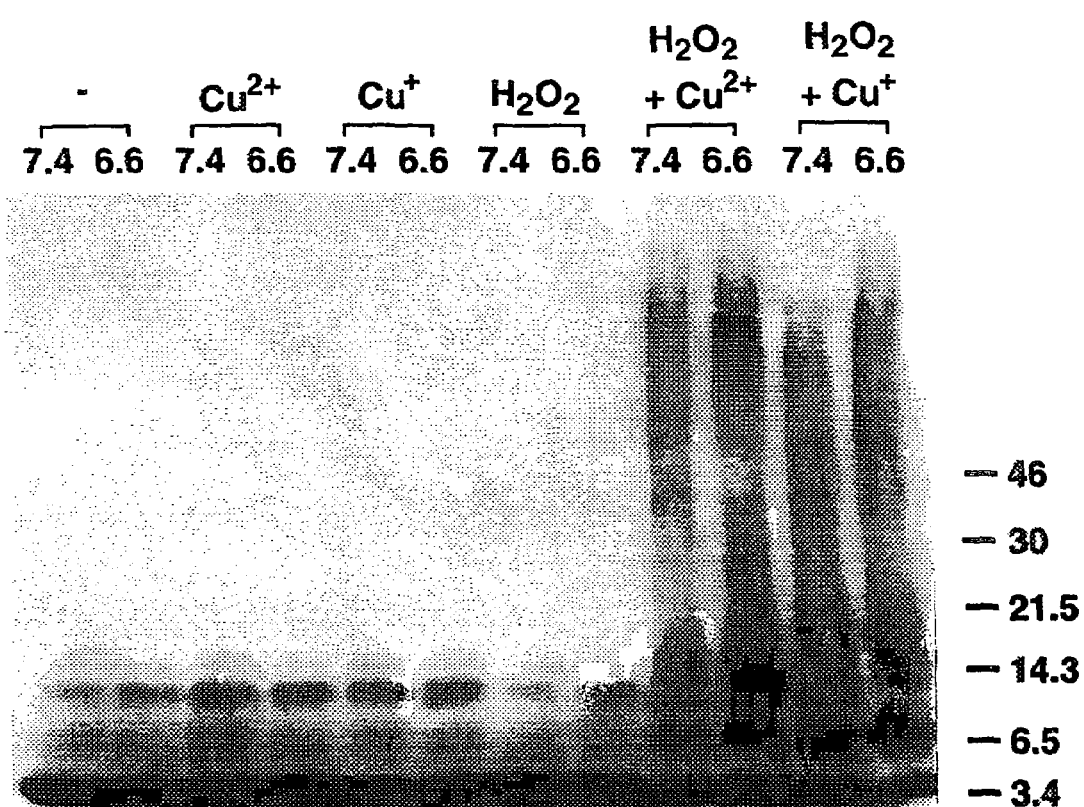
Figure 28B:
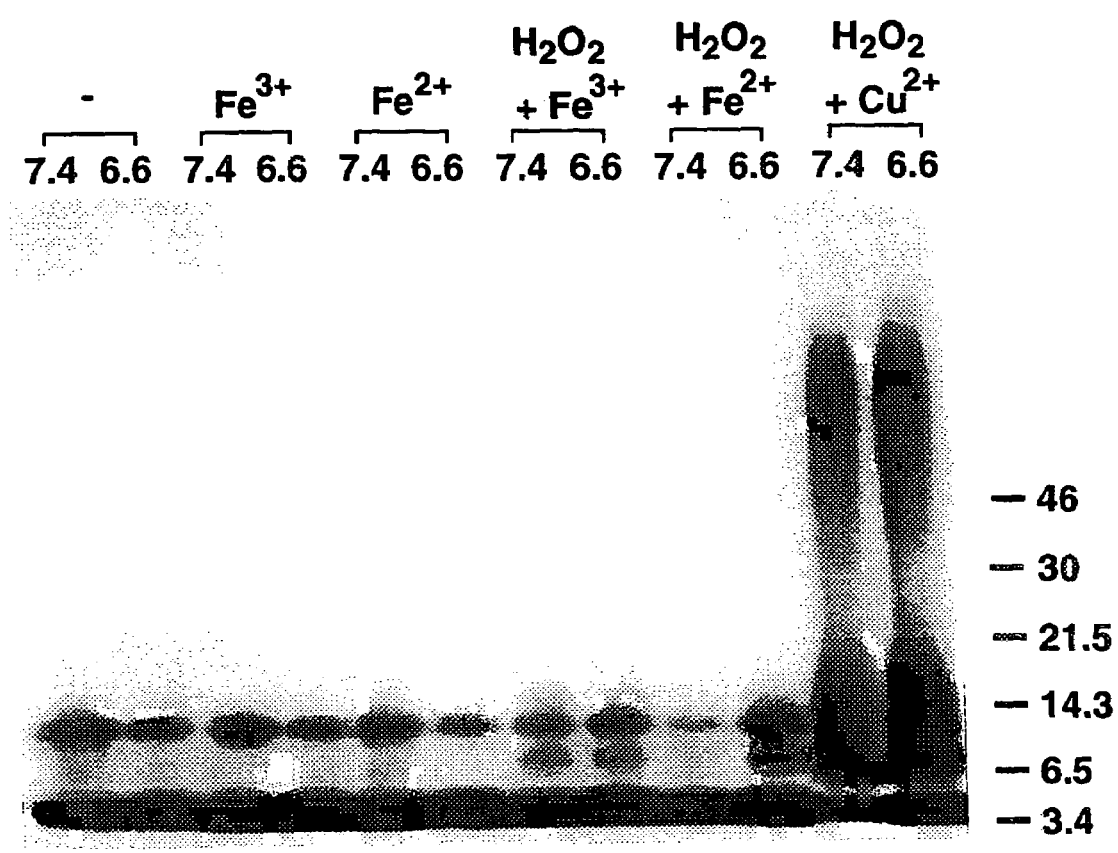
Figure 28C:
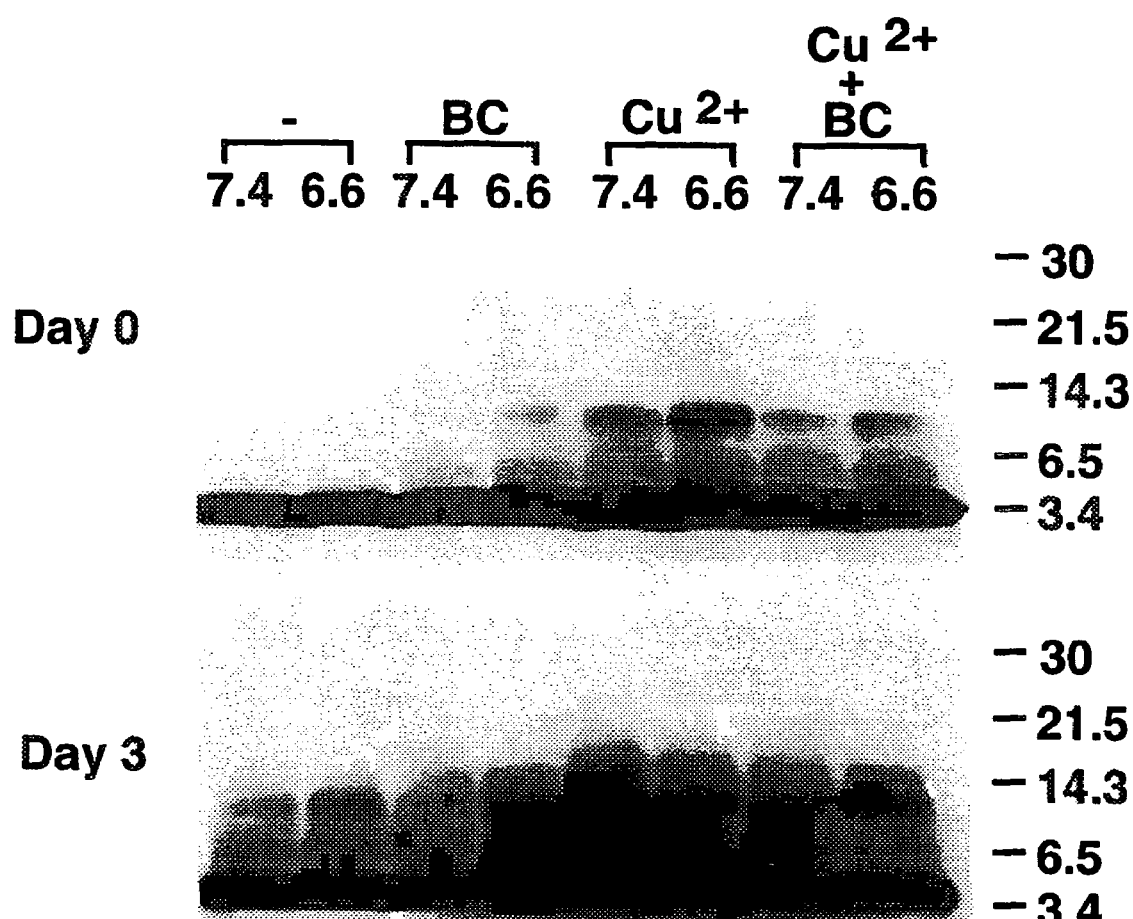

FIGS. 28A–28C—FIG. 28A shows $H_2O_2/Cu$ induced SDS-resistant polymerization of $A\beta_{1-42}$ (2.5 μM). FIG. 28B shows $H_2O_2/Fe$ induced SDS-resistant polymerization of $A\beta_{1-42}$ (2.5 μM). FIG. 28C shows that BC attenuates SDS-resistant polymerization of $A\beta_{1-42}$ (2.5 μM).

Figure 29A:
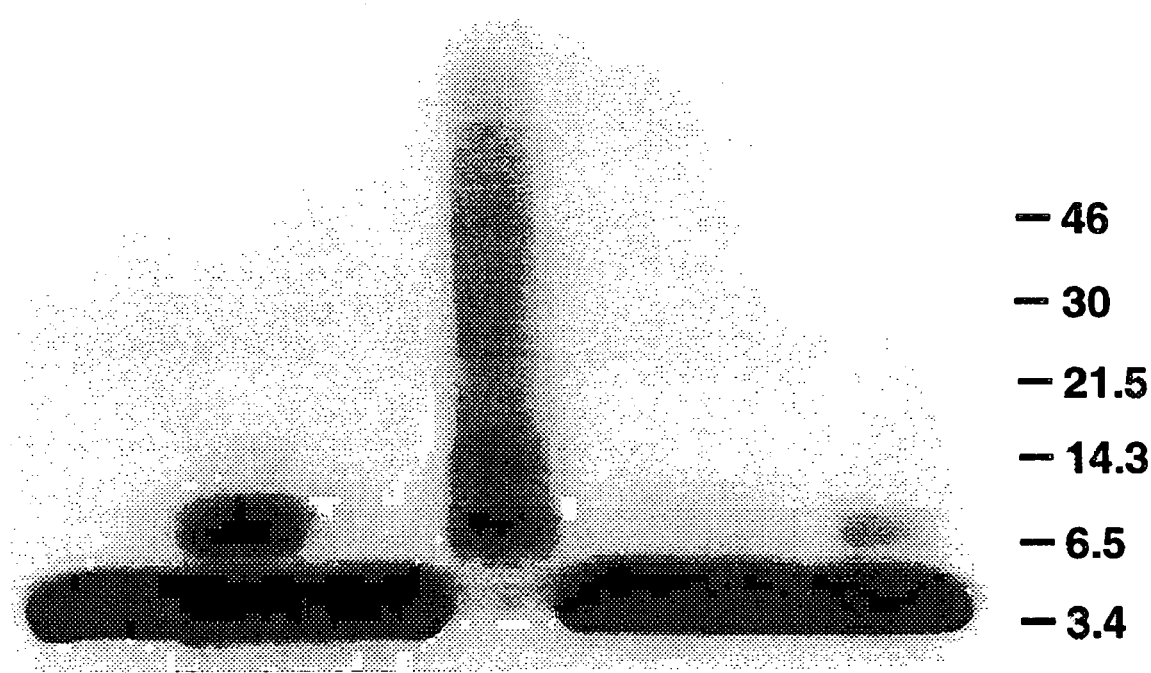
Figure 29B:
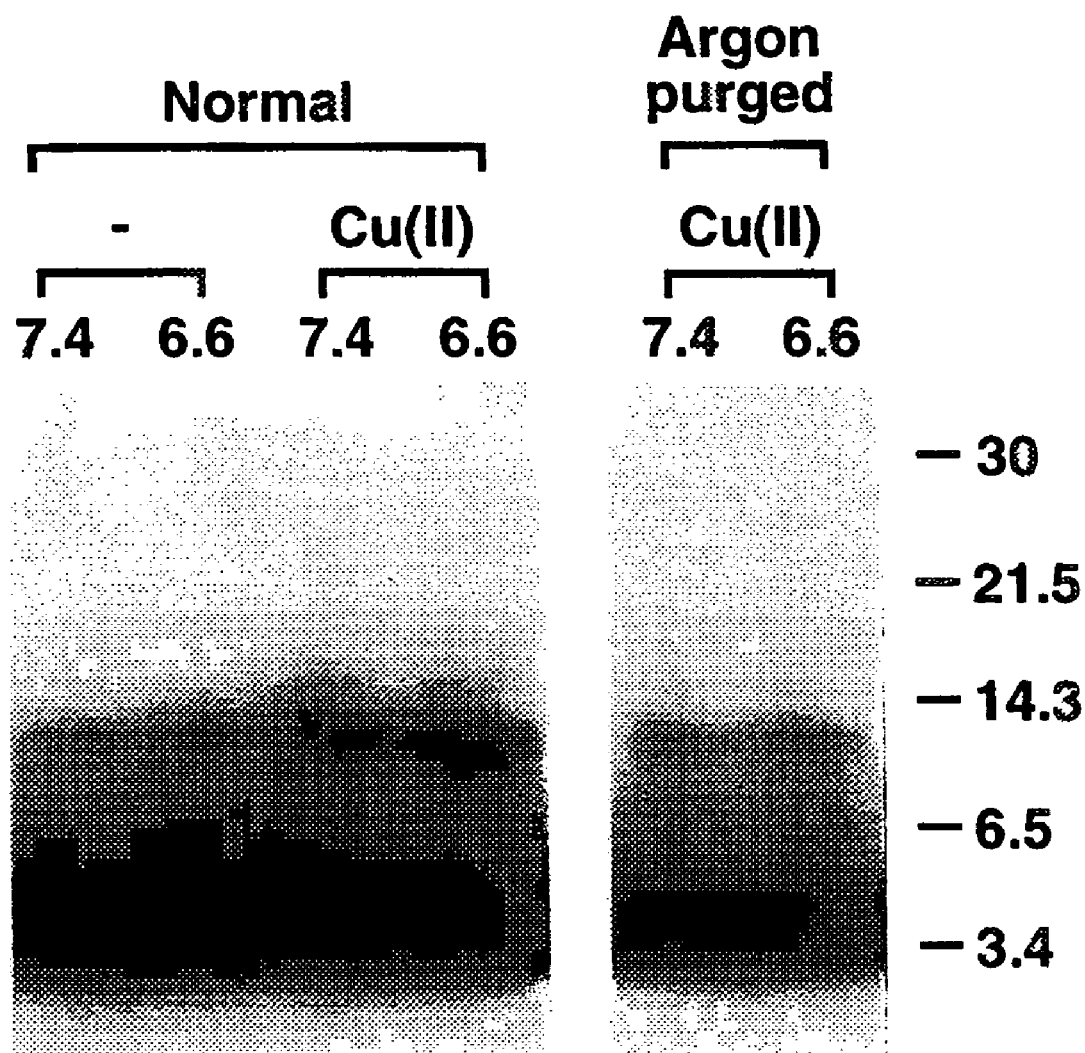

FIGS. 29A and 29B show that $H_2O_2$ generation is required for SDS-resistant polymerization of human $A\beta_{1-42}$. Solution concentrations of metal ion and $H_2O_2$ were 30 μM and 100 μM, respectively. FIG. 29A shows that TCEP (Tris(2-Carboxyethyl)-Phosphine Hydrochloride) attenuates SDS-resistant $A\beta_{1-42}$ polymerization. $A\beta_{1-42}$ (2.5 μM), $H_2O_2$ (100 μM), ascorbic acid (100 μM), TCEP (100 μM). FIG. 29B shows that anoxic conditions prevent SDS-resistant Aβ polymerization. $A\beta_{1-42}$ (2.5 μM) was incubated with no metal or $Cu^{2+}$ at either pH 7.4 or 6.6 and incubated for 60 min. at 25° C. under normal or argon purged conditions. Argon was continuously bubbled through the buffer for 2 h (at 20° C.) before the remainder of the incubation components were added.

Figure 1:
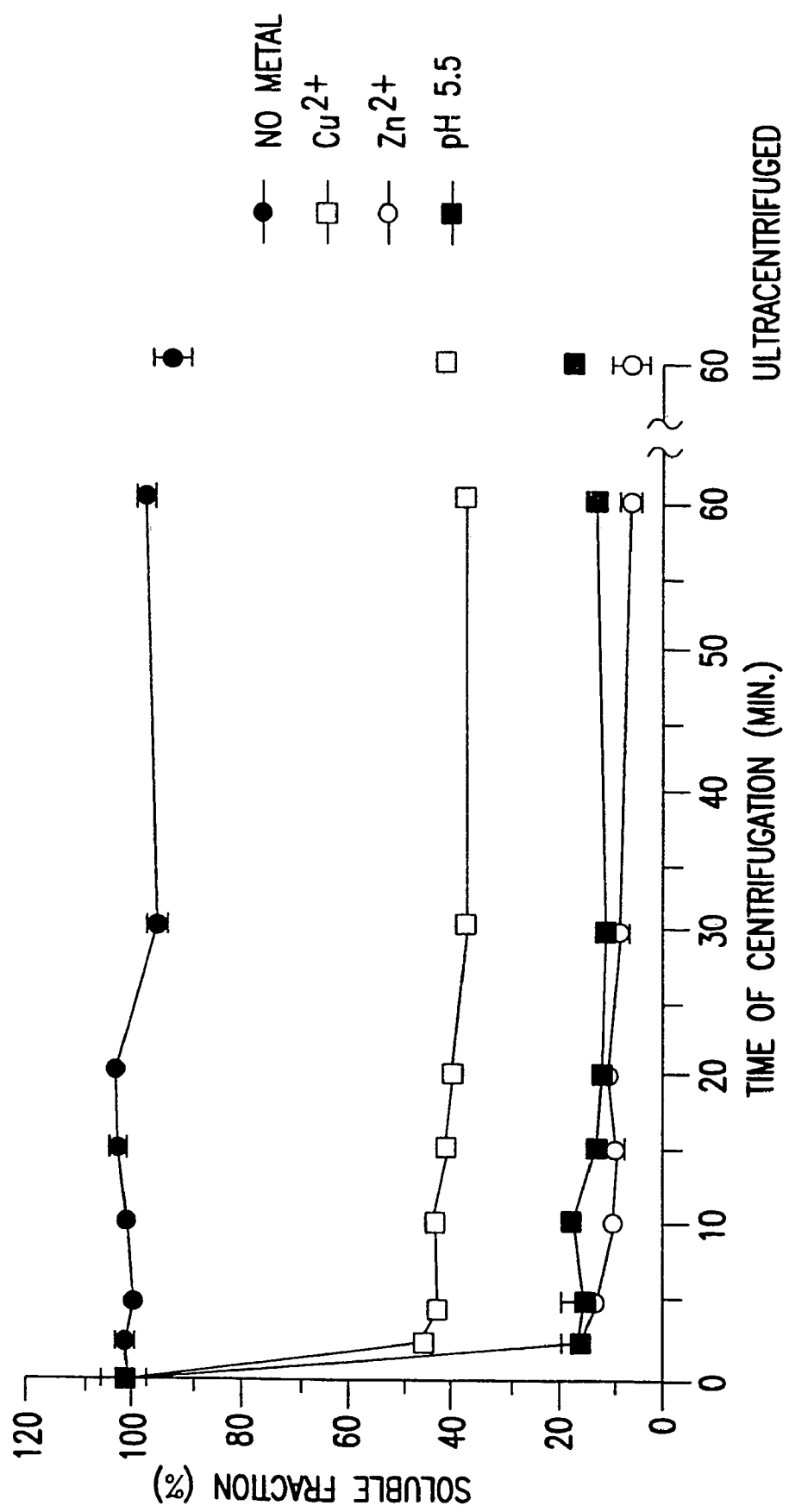
FIG. 1 is a graph showing the proportion of soluble $A\beta_{1-40}$ remaining following centrifugation of reaction mixtures.
Figures 1, 30A:
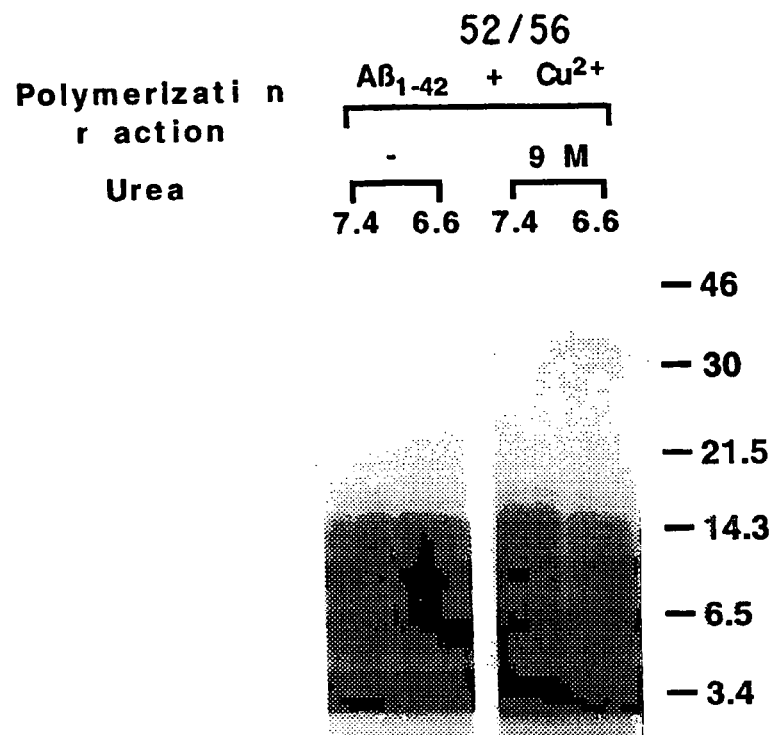
Figures 2, 30A:
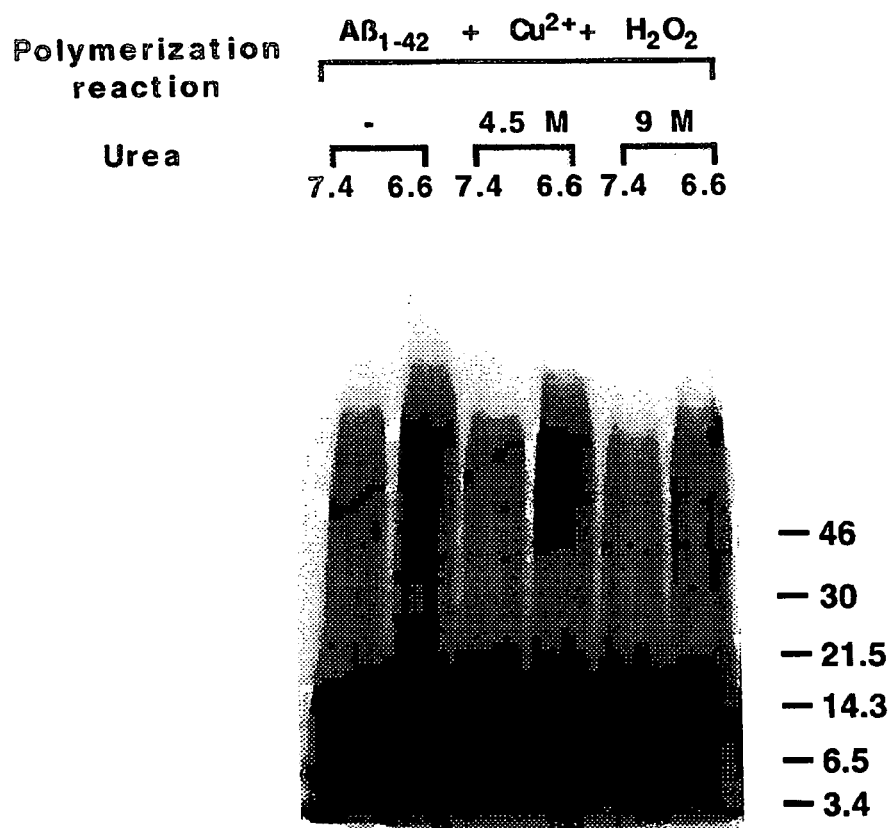
Figure 30B:
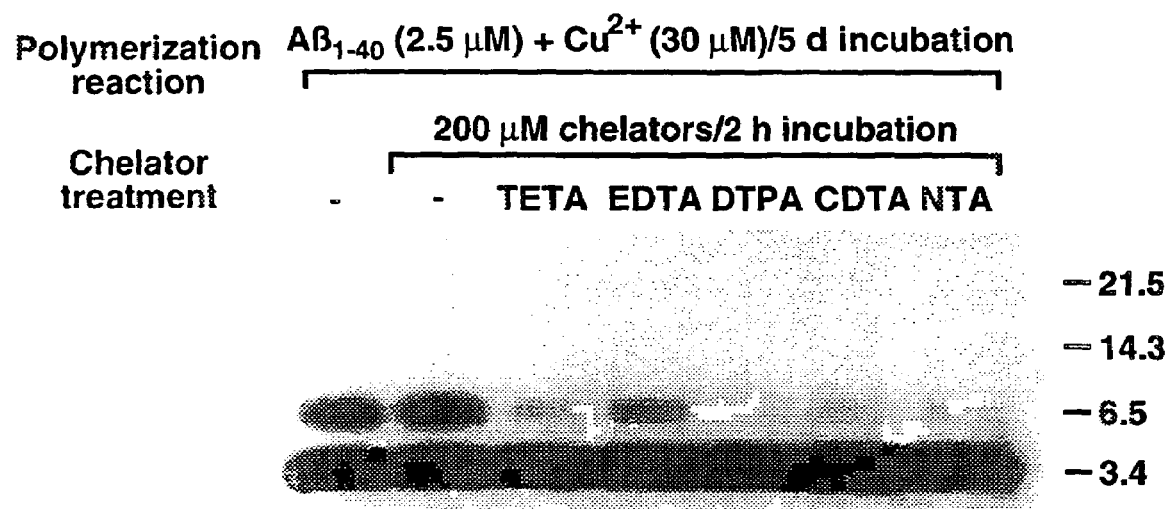
Figure 30C:
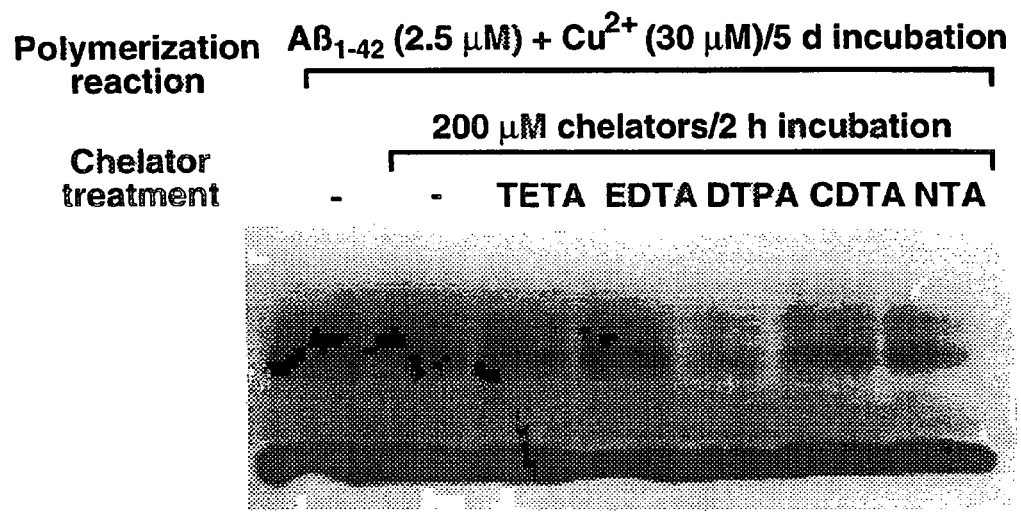
Figure 30D:
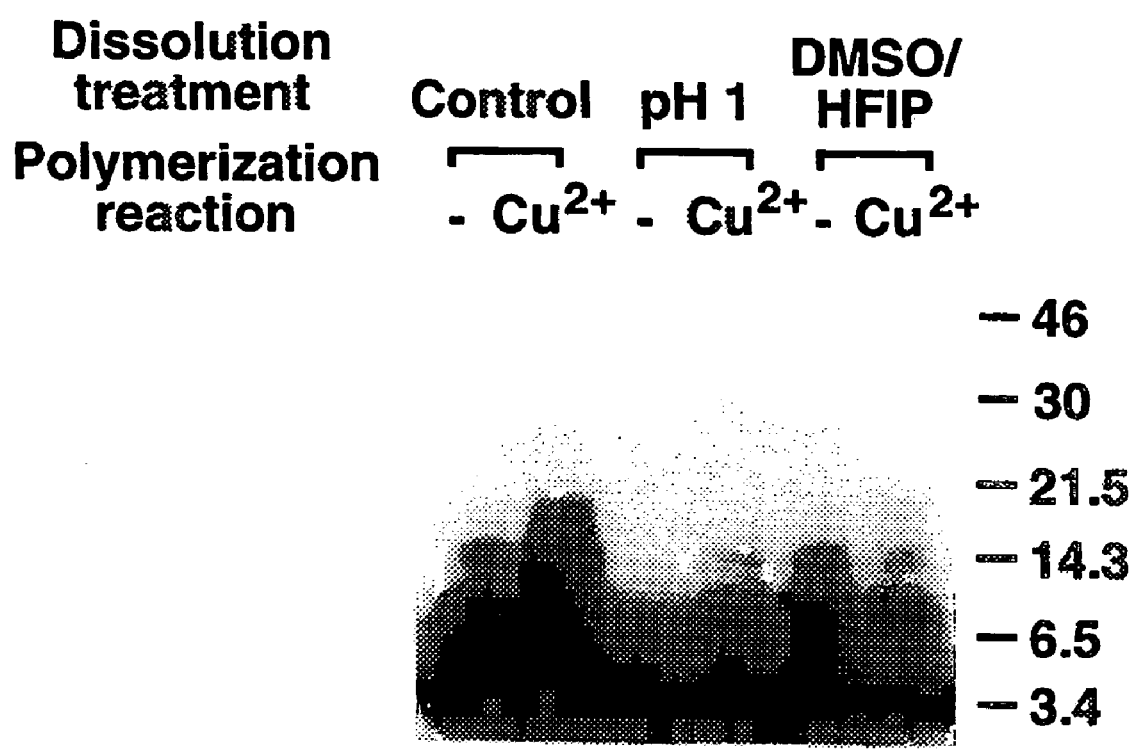
Figure 30E:
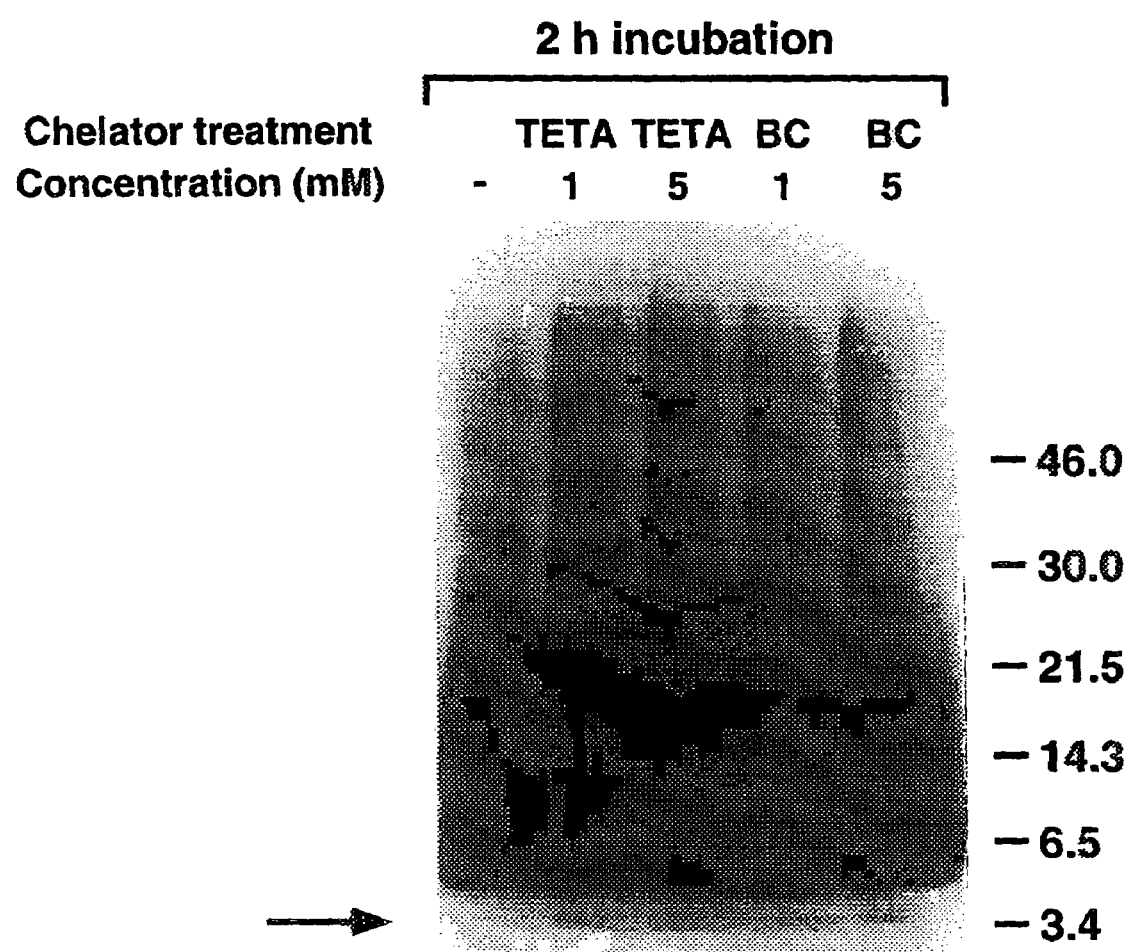

FIGS. 30A–30E show dissolution of SDS-resistant Aβ polymers. FIGS. 30A-1 and 30A-2 show that chaotrophic agents are unable to disrupt polymerization. FIG. 30B shows that metal ion chelators disrupt SDS-resistant $A\beta_{1-40}$ polymers. FIG. 30C shows that metal ion chelators disrupt SDS-resistant $A\beta_{1-42}$ polymers. The chelators, their log stability constant, and their molecular weight, respectively, are as follows: TETA (tetraethylenediamine), 20.4, 146; EDTA (ethylenediaminetetra acetic acid), 18.1, 292; DTPA (diethylenetriaminopenta acetic acid), 21.1, 393; CDTA (trans-1,2-diaminocyclohexanetetra acetic acid), 22.0, 346; and NTA (nitrilotriacetic acid), 13.1, 191. FIG. 30D shows that α-helical promoting solvents and low pH disrupt polymers. Aliquots of $A\beta_{1-42}$ were incubated at pH 1 or with DMSO/HFIP (75%:25%) for 2 h (30 min., 37° C.). FIG. 30E shows that metal ion chelators disrupt SDS-resistant Aβ polymers extracted from AD brains. Aliquots of SDS-resistant Aβ polymers extracted from AD brains were incubated with no chelator, TETA (1 mM or 5 mM) or BC (1 mM or 5 mM) for 2 h (30 min., 37° C.) and aliquots collected for analysis. Monomer $A\beta_{1-40}$ is indicated.

DETAILED DESCRIPTION OF THE PREFERRED EMBODIMENTS

Definitions

In the description that follows, a number of terms are utilized extensively. In order to provide a clear and consistent understanding of the specification and claims, including the scope to be given such terms, the following definitions are provided.

Aβ peptide is also known in the art as Aβ, β protein, β-A4 and A4. In the present invention, the Aβ peptide may be comprised of peptides $A\beta_{1-39}$ $A\beta_{1-40}$, $A\beta_{1-41}$, $A\beta_{1-42}$, and $A\beta_{1-43}$. The most preferred embodiment of the invention makes use of $A\beta_{1-40}$. However, any of the Aβ peptides may be employed according to the present invention. The sequence of Aβ peptide is found in Hilbich, C., et al., *J. Mol. Biol.* 228:460–473 (1992).

Amyloid as is commonly known in the art, and as is intended in the present specification, is a form of aggregated protein.

Amyloidosis is any disease characterized by the extracellular accumulation of amyloid in various organs and tissues of the body.

Aβ Amyloid is an aggregated Aβ peptide. It is found in the brains of patients afflicted with AD and DS and may accumulate following head injuries.

Biological fluid means fluid obtained from a person or animal which is produced by said person or animal. Examples of biological fluids include but are not limited to cerebrospinal fluid (CSF), blood, serum, and plasma. In the present invention, biological fluid includes whole or any fraction of such fluids derived by purification by any means, e.g., by ultrafiltration or chromatography.

Copper(II), unless otherwise indicated, means salts of $Cu^{2+}$, i.e., $Cu^{2+}$ in any form, soluble or insoluble.

Copper(I), unless otherwise indicated, means salts of $Cu^+$, i.e., $Cu^+$ in any form, soluble or insoluble.

Metal chelators include metal-binding molecules characterized by two or more polar groups which participate in forming a complex with a metal ion, and are generally well-known in the art for their ability to bind metals competitively.

Physiological solution as used in the present specification means a solution which comprises compounds at physiological pH, about 7.4, which 5 closely represents a bodily or biological fluid, such as CSF, blood, plasma, et cetera.

Treatment: delay or prevention of onset, slowing down or stopping the progression, aggravation, or deterioration of the symptoms and signs of Alzheimer's disease, as well as amelioration of the symptoms and signs, or curing the disease by reversing the physiological and anatomical damage.

Zinc, unless otherwise indicated, means salts of zinc, i.e., $Zn^{2+}$ in any form, soluble or insoluble.

Methods for Identifying Agents Useful in the Treatment of AD

The aim of the present invention is to clarify both the factors which contribute to the neurotoxicity of Aβ polymers and the mechanism which underlies their formation. These findings can then be used to (i) identify agents that can be used to decrease the neurotoxicity of Aβ, as well as the formation of Aβ polymers, and (ii) utilize such agents to develop methods of preventing, treating or alleviating the symptoms of AD and related disorders.

The present invention relates to the unexpected discovery that Aβ peptides directly produce oxidative stress through the generation of abundant reactive oxygen species (ROS), which include hydroxyl radical (OH.) and hydrogen peroxide ($H_2O_2$). The production of ROS occurs by a metal (Cu, Fe) dependant, pH mediated mechanism, wherein the reduction of $Cu^{2+}$ to $Cu^+$, or $Fe^{3+}$ to $Fe^{2+}$, is catalyzed by Aβ. Aβ is highly efficient at reducing $Cu^{2+}$ and $Fe^{3+}$.

All the redox properties of $Aβ_{1-40}$ (the most abundant form of soluble Aβ) are exaggerated in $Aβ_{1-42}$. Additionally, $Aβ_{1-42}$, but not $Aβ_{1-40}$, recruits $O_2$ into spontaneous generation of another ROS, $O_2^-$, which also occurs in a metal-dependent manner. The exaggerated redox activity of $Aβ_{1-42}$ and its enhanced ability to generate ROS are likely to be the explanation for its neurotoxic properties. Interestingly, the rat homologue of Aβ, which has 3 substitutions that have been shown to attenuate zinc binding and zinc-mediated precipitation, also exhibits less redox activity than its human counterpart. This may explain why the rat is exceptional in that it is the only mammal that does not exhibit amyloid pathology with age. All other mammals analyzed to date possess the human Aβ sequence.

The sequence of ROS generation by Aβ follows the pathway of superoxide-dismutation, which leads to hydrogen peroxide production in a Cu/Fe-dependent manner. After forming $H_2O_2$, the hydroxyl radical (OH.) is rapidly formed by a Fenton reaction with the Fe or Cu that is present, even when these metals are only at trace concentrations. The OH. radical is very reactive and rapidly attacks the Aβ peptide, causing it to cross-link and polymerize. This is very likely to be the chemical mechanism that causes the covalent cross-linking that is seen in mature plaque amyloid. Importantly, the redox activity of Aβ is not attenuated by precipitation of the peptide, suggesting that, in vivo, amyloid deposits could be capable of generating ROS in situ on an enduring basis. This suggests that the major source of the oxidative stress in an AD-affected brain are amyloid deposits.

Figure 12:
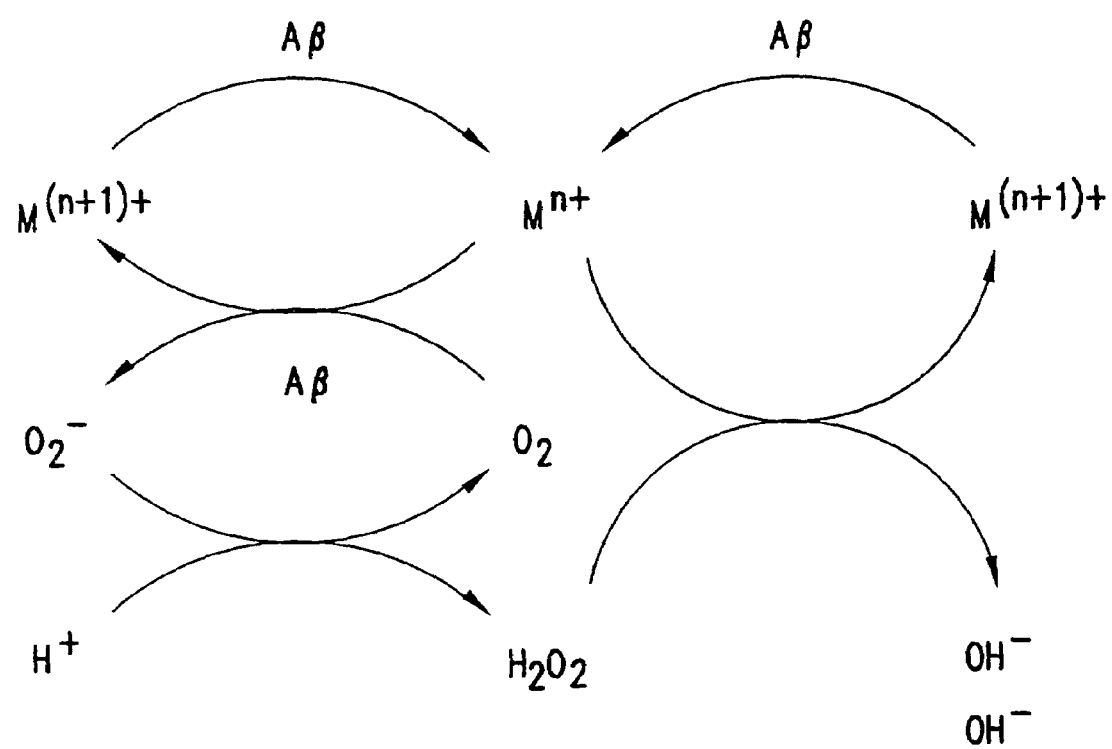
FIG. 12 is a graphical representation showing a model for the generation of reduced metal ions, $O_2^-$, $H_2O_2$, and OH. by $A\beta$ peptides. Note that $A\beta$ facilitates two consecutive steps in the pathway: the reduction of metal ions, and the reaction of $O_2$ with reduced metal ions. The peptide does not appear to be consumed or modified in a one hour time frame by participation in these reactions.

A model for free radical and amyloid formation in AD is shown in FIG. 12. The proposed mechanism is explained as follows.

(1) Soluble and precipitated Aβ species possess superoxide dismutase (SOD)-like activity. Superoxide ($O_{2-}$), the substrate for the dismutation, is generated both by spillover from mitochondrial respiratory metabolism, and by $Aβ_{1-42}$ itself. Aβ-mediated dismutation produces hydrogen peroxide ($H_2O_2$)(see FIG. 11), requiring $Cu^{2+}$ or $Fe^{3+}$, which are reduced during the reaction. Since $H^+$ is required for $H_2O_2$ production, an acidotic environment will increase the reaction.

(2) $H_2O_2$ is relatively stable, and freely permeable across cell membranes. Normally, it will be broken down by intercellular catalase or glutathione peroxidase.

(3) In aging and AD, levels of $H_2O_2$ are high, and catalase and peroxidase activities are low. If $H_2O_2$ is not completely catalyzed, it will react with reduced $Cu^+$ and $Fe^{2+}$ in the vicinity of Aβ to generate the highly reactive hydroxyl radical (OH.) by Fenton chemistry.

(4) OH. engenders a non-specific stress and inflammatory response in local tissue. Among the neurochemicals that are released from microglia and possibly neurons in the response are $Zn^{2+}$, $Cu^{2+}$ and soluble Aβ. Familial AD increases the likelihood that $Aβ_{1-42}$ will be released at this point. Local acidosis is also part of the stress/inflammatory response. These factors combine to make Aβ precipitate and accumulate, presumably so that it may function in situ as an SOD, since these factors induce reversible aggregation. Hence, more soluble Aβ species decorate the perimeter of the accumulating plaque deposits.

(5) If Aβ encounters OH., it will covalently cross-link during the oligomerization process, making it a more difficult accumulation to resolubilize, and leading to the formation of SDS-resistant oligomers characteristic of plaque amyloid.

(6) If $Aβ_{1-42}$ accumulates, it has the property of recruiting $O_2$ as a substrate for the abundant production of $O_2^-$ by a process that is still not understood. Since $O_2$ is abundant in the brain, $Aβ_{1-42}$ is responsible for setting off a vicious cycle in which the accumulation of covalently linked Aβ is a product of the unusual ability of Aβ to reduce $O_2$, and feed an abundant substrate ($O_2^-$) to itself for dismutation, leading to OH. formation. The production of abundant free radicals by the accumulating amyloid may further damage many systems including metal regulatory proteins, thus compounding the problem. This suggests that the major source of the oxidative stress in an AD-affected brain are amyloid deposits.

The metal-dependent chemistry of Aβ-mediated superoxide dismutation is reminiscent of the activity of superoxide dismutase (SOD). Interestingly, mutations of SOD cause amyotrophic lateral sclerosis, another neurodegenerative disorder. SOD is predominantly intracellular, whereas Aβ is constitutively found in the extracellular spaces where it accumulates. Investigation of Aβ by laser flash photolysis confirmed the peptide's SOD-like activity, suggesting that Aβ may be an anti-oxidant under physiological circumstances. Since $H_2O_2$ has been shown to induce the production of Aβ, the accumulation of Aβ in AD may reflect a response to an oxidant stress paradoxically caused by Aβ excess. This may cause and, in turn, be compounded by, damage to the biometal homeostatic mechanisms in the brain environment.

Thus, it has recently been discovered (i) that much of the Aβ aggregate in AD-affected brain is held together by zinc and copper, (ii) that Aβ peptides exhibit Fe/Cu-dependent redox activity similar to that of SOD, (iii) that $Aβ_{1-42}$ is especially redox reactive and has the unusual property of reducing $O_2$ to $O_2$, and (iv) that deregulation of Aβ redox reactivity causes the peptide to conveniently polymerize. Since these reactions must be strongly implicated in the pathogenetic events of AD, they offer promising targets for therapeutic drug design.

The discovery that Aβ can generate $H_2O_2$ and $Cu^+$, both of which are associated with neurotoxic effects, offers an explanation for the neurotoxicity of Aβ polymers. These findings suggest that it may be possible to lessen the neurotoxicity of Aβ by controlling factors which alter the concentrations of $Cu^+$ and ROS, including hydrogen peroxide, being generated by accumulated and soluble Aβ. It has been discovered that manipulation of factors such as zinc, copper, and pH can result in altered $Cu^+$ and $H_2O_2$ production by Aβ. Therefore, agents identified as being useful for the adjustment of the pH and levels of zinc and copper of the brain interstitium can be used to adjust the concentration of $Cu^+$ and $H_2O_2$, and can therefore be used to reduce the neurotoxic burden. Such agents will thus be a means of treating Alzheimer's disease.

Thus, one object of the present invention is to provide a method for the identification of agents to be used in the treatment of AD. As may be understood by reference to the Examples below, agents to be used in the treatment of AD include:
- (a) agents that reduce the amount of $Cu^+$ or $Fe^{2+}$ produced by Aβ;
- (b) agents that promote or inhibit the production of hydrogen peroxide by Aβ;
- (c) agents that inhibit the production of $O_2^-$ by Aβ;
- (d) agents that inhibit the production of OH..

Of course, as aggregation and especially crosslinking of Aβ contributes to the neurotoxic burden, agents which have been identified to have the activities listed above may then also be subjected to tests which determine if an agent is capable of inhibiting Aβ plaque deposition or facilitating plaque resolubilization (see Example 1).

Agents identified as having the above-listed activities may then be tested for their ability to reduce the neurotoxicity of both soluble and crosslinked Aβ.

Thus, in one aspect, the invention relates to a method for the identification of an agent to be used in the treatment of AD, wherein the agent is capable of altering, and preferably decreasing, the production of $Cu^+$ by Aβ, the method comprising:
- (a) adding $Cu^{2+}$ to a first Aβ sample;
- (b) allowing the first sample to incubate for an amount of time sufficient to allow said first sample to generate $Cu^+$;
- (c) adding $Cu^{2+}$ to a second Aβ sample, the second sample additionally comprising a candidate pharmacological agent;
- (d) allowing the second sample to incubate for the same amount of time as the first sample;
- (e) determining the amount of $Cu^+$ produced by the first sample and the second sample; and
- (f) comparing the amount of $Cu^+$ produced by the first sample to the amount of $Cu^+$ produced by the second sample;

whereby a difference in the amount of $Cu^+$ produced by the first sample as compared to the second sample indicates that the candidate pharmacological agent has altered the production of $Cu^+$ by Aβ. Of course, where the amount of $Cu^+$ is lower in the second sample then in the first sample, this will indicate that the agent has decreased $Cu^+$ production.

In a preferred embodiment, the amount of $Cu^+$ present in said first and said second sample is determined by
- (a) adding a complexing agent to said first and said second sample, wherein said complexing agent is capable of combining with $Cu^+$ to form a complex compound, wherein said complex compound has an optimal visible absorption wavelength;
- (b) measuring the absorbancy of said first and said second sample; and
- (c) calculating the concentration of $Cu^+$ in said first and said second sample using the absorbancy obtained in step (b).

In a more preferred embodiment, the complexing agent is bathocuproinedisulfonic (BC) anion. The concentration of $Cu^+$ produced by Aβ may then be calculated on the basis of the absorbance of the sample at about 478 nm to about 488 nm, more preferable about 480 to about 486 nm, and most preferably about 483 nm.

In an even more preferred embodiment, the above-described method may be performed in a microtiter plate, and the absorbancy measurement is performed by a plate reader, thus allowing large numbers of candidate pharmacological compounds to be tested simultaneously.

In another aspect, the invention relates to a method for the identification of an agent to be used in the treatment of AD, wherein said agent is capable of altering, and preferably decreasing, the production of $Fe^{2+}$ by Aβ, said method comprising:
- (a) adding $Fe^{3+}$ to a first Aβ sample;
- (b) allowing said first sample to incubate for an amount of time sufficient to allow said first sample to generate $Cu^+$;
- (c) adding $Fe^{3+}$ to a second Aβ sample, said second sample additionally comprising a candidate pharmacological agent;
- (d) allowing said second sample to incubate for the same amount of time as said first sample;
- (e) determining the amount of $Fe^{2+}$ produced by said first sample and said second sample; and
- (f) comparing the amount of $Fe^{2+}$ present in said first sample to the amount of $Fe^{2+}$ present in said second sample;

whereby a difference in the amount of $Fe^{2+}$ present in said first sample as compared to said second sample indicates that said candidate pharmacological agent has altered the production of $Fe^{2+}$ by Aβ. Of course, where the amount of $Fe^{2+}$ is lower in the second sample than in the first sample, this will indicate that the agent has decreased $Fe^{2+}$ production.

In a preferred embodiment, the amount of $Fe^{2+}$ present is determined by using a spectrophotometric method analogous to that used for the determination of Cu, above. In this method, the complexing agent is bathophenanthrolinedisulfonic (BP) anion. The concentration of $Fe^{2+}$-BP produced by Aβ may then be calculated on the basis of the absorbance of the sample at about 530 to about 540 nm, more preferably about 533 nm to about 538 nm, and most preferably about 535 nm.

In an even more preferred embodiment, the above-described method may be performed in a microtiter plate, and the absorbancy measurement is performed by a plate reader, thus allowing large numbers of candidate pharmacological compounds to be tested simultaneously.

In yet another aspect, the invention relates to a method for the identification of an agent to be used in the treatment of AD, wherein said agent is capable of altering the production of $H_2O_2$ by Aβ, said method comprising:
- (a) adding $Cu^{2+}$, or $Fe^{3+}$ to a first Aβ sample;
- (b) allowing said first sample to incubate for an amount of time sufficient to allow said first sample to generate $H_2O_2$;
- (c) adding $Cu^{2+}$ or $Fe^{3+}$ to a second Aβ sample, said second sample additionally comprising a candidate pharmacological agent;
- (d) allowing said second sample to incubate for the same amount of time as said first sample;
- (e) determining the amount of $H_2O_2$ produced by said first sample and said second sample; and
- (f) comparing the amount of $H_2O_2$ present in said first sample to the amount of $H_2O_2$ present in said second sample;

whereby a difference in the amount of $H_2O_2$ present in said first sample as compared to said second sample indicates that said candidate pharmacological agent has altered the production of $H_2O_2$ by Aβ. As will be understood by one of ordinary skill in the art, this method may be used to detect agents which decrease the amount of $H_2O_2$ produced (in which case the amount of $H_2O_2$ will be lower in the second sample than in the first sample), or to increase the amount of $H_2O_2$ produced (in which case the amount of $H_2O_2$ will be lower in the first sample than in the second sample).

In a preferred embodiment, the determination of the amount of $H_2O_2$ present in said first and said second sample is determined by
- (a) adding catalase to a first aliquot of said first sample obtained in step (a) of claim 1 in an amount sufficient to break down all of the $H_2O_2$ generated by said sample;
- (b) adding TCEP, in an amount sufficient to capture all of the $H_2O_2$ generated by said samples, to
    - (i) said first aliquot
    - (ii) a second aliquot of said first sample obtained in step (a) of claim 1; and
    - (iii) said second sample obtained in step (b) of claim 1;
- (c) incubating the samples obtained in step (b) for an amount of time sufficient to allow the TCEP to capture all of the $H_2O_2$;
- (d) adding DTNB to said samples obtained in step (c);
- (e) incubating said samples obtained in step (d) for an amount of time sufficient to generate TMB;
- (f) measuring the absorbancy at about 407 to about 417 nm of said samples obtained in step (e); and
- (g) calculating the concentration of $H_2O_2$ in said first and said second sample using the absorbancies obtained in step (f).

In a preferred embodiment, the absorbancy of TMB is measured at about 412 nm.

In a preferred embodiment, the above-described method is performed in a microtiter plate, and the absorbancy measurement is performed by a plate reader, thus making it possible to screen large numbers of candidate pharmacological agent simultaneously.

In another embodiment, the invention provides a method for the identification of an agent to be used in the treatment of AD, wherein said agent is capable of decreasing the production of $O_2^-$ by Aβ, said method comprising:
- (a) adding Aβ and to a first buffer sample having an $O_2$ tension greater than 0;
- (b) allowing said first sample to incubate for an amount of time sufficient to allow said first sample to generate $O_2^-$;
- (c) adding Aβ and a candidate pharmacological agent to a second buffer sample having an $O_2$ tension greater than 0;
- (d) allowing said second sample to incubate for the same amount of time as said first sample;
- (e) determining the amount of $O_2^-$ produced by said first sample and said second sample; and
- (f) comparing the amount of $O_2^-$ present in said first sample to the amount of $O_2^-$ present in said second sample;

whereby a difference in the amount of $O_2^-$ present in said first sample as compared said second sample indicates that said candidate pharmacological agent has altered the production of $O_2^-$ by Aβ. In a preferred embodiment, the Aβ used is $Aβ_{1-42}$.

Of course, the amount of $O_2^-$ produced by Aβ may be measured by any method known to those of ordinary skill in the art. In a preferred embodiment, the determination of the amount of $O_2^-$ present in said samples is accomplished by measuring the absorbancy of the sample at about 250 nm.

Because the ability of Aβ to generate $H_2O_2$ from $O_2^-$ may in many instances be beneficial, in a preferred embodiment, the invention also relates to a method for the identification of an agent to be used in the treatment of AD, wherein said agent is capable of interfering with the interaction of $O_2$ and Aβ to produce $O_2^-$, without interfering with the SOD-like activity of Aβ, said method comprising:
- (a) identifying an agent capable of decreasing the production of $O_2^-$ by Aβ; and
- (b) determining the ability of said agent to alter the SOD-like activity of Aβ. In a preferred embodiment, the determination of the ability of said agent to alter the SOD-like activity of Aβ is made by determining whether Aβ is capable of catalytically producing $Cu^+$, $Fe^{2+}$ or $H_2O_2$. Methods, besides those which are disclosed elsewhere in this application, for determining if Aβ is capable of catalytically producing $Cu^+$, $Fe^{2+}$ or $H_2O_2$ are well known to those of ordinary skill in the art. In particular, the catalytic production of $H_2O_2$ may be determined by using laser flash photolysis or pulse radiolysis (Peters, G. & Rodgers, M. A. *J., Biochim. Biophys. Acta* 637:43–52 (1981).

In another aspect, candidate pharmacological agents which have been identified by one or more of the above screening assays can undergo further screening to determine if the agents are capable of altering, and preferably reducing or eliminating, Aβ-mediated toxicity in cell culture. Such assays include the MTT assay, which measures the reduction of 3-(4,5-dimethylthiazol- 2-yl)-2,5, diphenyl tetrazolium bromide (MTT) to a colored formazon (Hansen et al., *J Immunol Methods,* 119:203–210 (1989)). Although alternatives have not been ruled out (see Burdon et al., *Free Radic Res Commun.,* 18(6):369–380 (1993)), the major site of MTT reduction is thought to be at two stages of electron transport, the cytochrome oxidase and ubiquinone of mitochondria (Slater et al., 1963). A second cytotoxic assay is the release of lactic dehydrogenase (LDH) from cells, a measurement routinely used to quantitate cytotoxicity in cultured CNS cells (Koh, J. Y. and D. W. Choi, *J. Neurosci. Meth.* 20:83–90 (1987). While MTT measures primarily early redox changes within the cell reflecting the integrity of the electron transport chain, the release of LDH is thought to be through cell lysis. A third assay is visual counting in conjunction with trypan blue exclusion. Other commercially available assays for neurotoxicity, including the Live-Dead assay, may also be used to determine if a candidate compound which alters $Cu^+$, $Fe^{2+}$, $H_2O_2$, OH., and $O_2^-$ production, or alters copper-induced, pH dependent aggregation and crosslinking of Aβ, is also capable of reducing the neurotoxicity of Aβ.

Thus, in another preferred embodiment, the invention relates to a method for the identification of an agent to be used in the treatment of AD, wherein said agent is capable of reducing the toxicity of Aβ, said method comprising:
- (a) adding Aβ to a first cell culture;
- (b) adding Aβ to a second cell culture, said second cell culture additionally containing a candidate pharmacological agent;
- (c) determining the level of neurotoxicity of Aβ in said first and said second samples; and
- (d) comparing the level of neurotoxicity of Aβ in said first and said second samples, whereby a lower neurotoxicity level in said second sample as compared to said first sample indicates that said candidate pharmacological agent has reduced the neurotoxicity of Aβ, and is thereby capable of being used to treat AD.

Assays which can be used to determine the neurotoxicity of a candidate agent include, but are not limited to, the MTT assay and the LDH release assay, as described in Behl et al., *Cell* 77:817–827 (1994), and the Live/Dead EukoLight Viability/Cytotoxicity Assay, commercially available from Molecular Probes, Inc. (Eugene, Oreg.).

Cells types which may be used for these neurotoxicity assays include both cancer cells and primary cells, such as rat primary frontal neuronal cells.

Candidate pharmacological agents to be tested in any of the above-described methods will be broad-ranging but can be classified as follows: Candidate pharmacological agents for the alteration of the SOD-like activity of Aβ will be broad-ranging but can be classified as follows:

Agents which Modify the Availability of Zn or Cu for Interaction with Aβ

They include chelating agents such as desferrioxamine, but also include amino acids histidine and cysteine which bind free zinc, and are thought to be involved in bringing zinc from the plasma across the blood-brain barrier (BBB). These agents include all classes of specific zinc chelating agents, and combinations of non-specific chelating agents capable of chelating zinc such as EDTA (Edetic acid, N,N'-1,2-Ethane diylbis[N-(carboxymethyl)glycine] or (ethylenedinitrilo)tetraacetic acid, entry 3490 in Merck Index 10th edition) and all salts of EDTA, and/or phytic acid [myo-Inositol hexakis(dihydrogen phosphate), entry 7269 in the Merck Index 10th edition] and phytate salts. Preferred candidate agents within this class include bathocuproine and bathophenanthroline.

Miscellaneous

Because there is no precedent for an effective anti-amyloidotic pharmaceutical, it is reasonable to serendipitously try out compounds which may have access to the brain compartment for their ability to inhibit either $Cu^+$ or $H_2O_2$ production by Aβ. These compounds include dye compounds, heparin, heparin sulfate, and anti-oxidants, e.g., ascorbate, trolox and tocopherols.

In the present invention, the Aβ used may be any form of Aβ. In a preferred embodiment, the Aβ used is selected from the group consisting of $A\beta_{1-39}$, $A\beta_{1-40}$, $A\beta_{1-41}$, $A\beta_{1-42}$, and $A\beta_{1-43}$. Even more preferably, the Aβ used is $A\beta_{1-40}$ or $A\beta_{1-42}$. The most preferred embodiment of the invention makes use of $A\beta_{1-40}$. The sequence of Aβ peptide is found in Hilbich, C., et al., *J. Mol. Biol.* 228:460–473 (1992).

The pH of the various reaction mixtures are preferably close to neutral (about 7.4). The pH, therefore, may range from about 6.6 to about 8, preferably from about 6.6 to about 7.8, and most preferably about 7.4.

Buffers which can be used in the methods of the present invention include, but are not limited to, PBS, Tris-chloride and Tris-base, MOPS, HEPES, bicarbonate, Krebs, and Tyrode's. The concentration of the buffers may be between about 10 mM and about 500 mM. Because of the nature of the assays which are included in the methods of the claimed invention, when choosing a buffer, it must be borne in mind that spontaneous free radical production within a given buffer might interfere with the reactions. For this reason, PBS is the preferred buffer for use in the methods of the invention, although other buffers may be used provided that proper controls are used to correct for the above-mentioned free radical formation of a given buffer.

$Cu^{2+}$ must be present in the reaction mixture for Aβ to produce $Cu^+$. Any salt of $Cu^{2+}$ may be used to satisfy this requirement, including, but not limited to, $CuCl_2$, $Cu(NO_3)_2$, etc. Concentrations of copper from at least about 1 μM may be used; most preferable, a copper concentration of about 10 μM is to be included in the reaction mixture.

Similarly, a redox active metal such as $Cu^{2+}$ or $Fe^{3+}$ must be present in the reaction mixture for Aβ to catalytically produce $H_2O_2$. Any salt of $Cu^{2+}$ may be used to satisfy this requirement, including, but not limited to, $CuCl_2$, $Cu(NO_3)_2$, etc. Similarly, and salt of $Fe^{3+}$ may be used in accordance with the invention, such as $FeCl_3$. Concentrations of copper or iron from at least about 1 μM may be used; most preferably, a copper or iron concentration of about 10 μM is to be included in the reaction mixture.

The present invention may be practiced at temperatures ranging from about 25° C. to about 40° C. The preferred temperature range is from about 30° C. to about 40° C. The most preferred temperature for the practice of the present invention is about 37° C., i.e., human body temperature.

The production of $Cu^+$ and $H_2O_2$ by Aβ peptide occurs at near-instantaneous rate. Hence, the measurement of the concentration of $Cu^+$ or $H_2O_2$ produced may be performed by the present methods substantially immediately after the addition of $Cu^2$ to the Aβ peptide. However, if desired, the reaction may be allowed to proceed longer. In a preferred embodiment of the invention, the reaction is carried out for about 30 minutes.

The invention may also be carried out in the presence of biological fluids, such as the preferred biological fluid, CSF, to closely simulate actual physiological conditions. Of course, such fluids will already contain Aβ, so that where the methods of the invention are to be carried out utilizing a biological fluid such as CSF, no further Aβ peptide will be added to the sample. The biological fluid may be used directly or diluted from about 1:1,000 to about 1:5 fold.

The amount of $H_2O_2$, $Cu^+$ or $Fe^{2+}$ produced by a sample may be measured by any standard assay for $H_2O_2$, $Cu^+$ or $Fe^{2+}$. For example, the PeroXOquant Quantitative Peroxide Assay (Pierce, Rockford, Ill.) may be used to determine the amount of $H_2O_2$ produced. $Fe^{2+}$ may be determined using the spectrophotometric method of Linert et al., *Biochim. Biophys. Acta* 1316:160–168 (1996). Other such methods will be readily apparent to those of ordinary skill in the art.

In a preferred embodiment, the $H_2O_2$ or $Cu^+$ produced by the sample is complexed with a complexing agent having an optimal visible absorption wavelength. The amount of $H_2O_2$ or $Cu^+$ produced by a sample is then detected using optical spectrophotometry (see Example 2).

In a preferred embodiment, the complexing agent to be used for the determination of the amount of $Cu^+$ produced is bathocuproinedisulfonic anion (BC), (see Example 2); the complex $Cu^+$-BC has an optimal visible absorption wavelength of about 483 nm. As is mentioned above, Aβ will produce $H_2O_2$ and $Cu^+$ almost immediately following the addition of $Cu^{2+}$ and $Zn^{2+}$ to the reaction mixture. Thus, BC may be added to the reaction immediately following the addition of $Cu^{2+}$ and $Zn^{2+}$ to the Aβ samples. The concentration of BC to be achieved in a sample is between about 10 μM to about 400 μM, more preferably about 75 μM to about 300 μM, and still more preferably about 150 μM to about 275 μM. In the most preferred embodiment, the concentration of BC to be achieved in a sample is about 200 μM. Of course, one of ordinary skill in the art can easily optimize the concentration of BC to be added with no more than routine experimentation.

Where the amount of $Fe^{2+}$ produced is to be determined, the complexing agent to be used for the determination of the amount of $Fe^{2+}$ produced is bathophenanthrolinedisulfonic (BP) anion, (see Example 2); the complex $Fe^{2+}$-BP has an optimal visible absorption wavelength of about 535 nm. As is mentioned above, Aβ will produce $H_2O_2$ and $Fe^{2+}$ almost immediately following the addition of $Fe^{3+}$ and $Zn^{2+}$ to the reaction mixture. Thus, BP may be added to the reaction immediately following the addition of $Fe^{3+}$ and $Zn^{2+}$ to the Aβ samples. The concentration of BP to be achieved in a sample is between about 10 μM to about 400 μM, more preferably about 75 μM to about 300 μM, and still more preferably about 150 μM to about 275 μM. In the most preferred embodiment, the concentration of BP to be achieved in a sample is about 200 μM. Of course, one of ordinary skill in the art can easily optimize the concentration of BP to be added with no more than routine experimentation.

The above-described spectrophotometric assays may be used to determine the concentration of $Cu^+$ or $Fe^{2+}$, as is described in Example 2.

Each of the assays of the present invention is ideally suited for the preparation of a kit. Such a kit may comprise a carrier means being compartmentalized to receive in close confinement therein one or more container means, such as vials, tubes, and the like, each of said container means comprising one of the separate elements of the assay to be used in the method. For example, there may be provided a container means containing standard solutions of the Aβ peptide or lyophilized Aβ peptide and a container means containing a standard solution or varying amounts of a salt of redox active metal, such as $Cu^{2+}$ or $Fe^{3+}$, in any form, i.e., in solution or dried, soluble or insoluble, in addition to further carrier means containing varying amounts and/or concentrations of reagents used in the present methods. For example, solutions to be used for the determination of $Cu^+$ or $Fe^{2+}$ as described in Example 2 will include BC anion and BP anion, respectively. Similarly, solutions to be used for the determination of $H_2O_2$ as described in Example 2 include TCEP and DTNB, as well as catalase (10 U/ml). Standard solutions of Aβ peptide preferably have concentrations above about 10 μM, more preferably from about 10 to about 25 μM or if the peptide is provided in its lyophilized form, it is provided in an amount which can be solubilized to said concentrations by adding an aqueous buffer or physiological solution. The standard solutions of analytes may be used to prepare control and test reaction mixtures for comparison, according to the methods of the present invention.

Agents Useful in the Treatment of AD

A further aspect of the present invention is predicted in part on the elucidation of mechanisms of neurotoxicity in the brain in AD subjects. One mechanism involves a novel $O_2^-$ and biometal-dependent pathway of free radical generation by Aβ peptides. The radicals of this aspect of the present invention may comprise reactive oxygen species (ROS) such as but not limited to $O_2^-$ and OH as well as radicalized Aβ peptides. It is proposed, according to the present invention, that by interfering in the radical generating pathway, the neurotoxicity of the Aβ peptides is reduced.

Accordingly, one aspect of the present invention contemplates a method for treating Alzheimer's disease (AD) in a subject, said method comprising administering to said subject an effective amount of an agent which is capable of inhibiting or otherwise reducing metal-mediated production of free radicals.

The preferred agents according to this aspect are metal chelators, metal complexing compounds, antioxidants and compounds capable of reducing radical formation of Aβ peptides or mediated by Aβ peptides. Particularly preferred metal chelators and metal complexors are capable of interacting with metals (M) having either a reduced charge state $(M^{n+1})$ or an oxidized state of $(M^{n-1})+$. Even more particularly, M is Fe and/or Cu.

It is proposed that interactions of Aβ with Fe and Cu are of significance to the genesis of the oxidation insults that are observed in the AD-affected brain. This is due to redox-active metal ions being concentrated in brain neurons and participating in the generation of ROS or other radicals by transferring electrons in their reduced state and described in the following reactions:

Reduced Fe/Cu reacts with molecular oxygen to generate the superoxide anion.

$$M^{n+}+O_2 \rightarrow M^{(n+1)+}+O_2^-$$ Reaction (1)

The $O_2^-$ generated undergoes dismutation to $H_2O_2$ either catalyzed by SOD or spontaneously.

$$O_2^-+O_2^-+2H^+ \rightarrow H_2O_2+O_2$$ Reaction (2)

The reaction of reduced metals with $H_2O_2$ generates the highly reactive hydroxyl radical by the Fenton reaction.

$$M^{n+}+H_2O_2 \rightarrow M^{(n+1)+}+OH+OH^-$$ Reaction (3)

Additionally, the Haber-Weiss reaction can form OH in a reaction catalyzed by $M^{(n+1)+}/M^{n+}$ (Miller et al., 1990).

$$O_2^-+H_2O_2 \rightarrow OH+OH^-+O_2$$ Reaction (4)

Still more preferably, the agent comprises one or more of bathocuproine and/or bathophenanthroline or compounds related thereto at the structural and/or functional levels. Reference to compounds such as bathocuproine and bathophenanthroline include functional derivatives, homologues and analogues thereof.

Accordingly, another aspect of the present invention provides a method for treating AD in a subject said method comprising administering to said subject an effective amount of an agent comprising at least one metal chelator and/or metal complexing compound for a time and under conditions sufficient to inhibit or otherwise reduce metal-mediated production of free radicals.

In one aspect, the free radicals are reactive oxygen species such as $O_2^-$ or OH.. In another aspect, the free radicals include forms of Aβ. In another aspect, the free radicals include forms of Aβ. However, in a broader sense, it has been found that the metal-mediated Aβ reactions in the brain of AD patients results in the generation of reduced metals and hydrogen peroxide, as well as superoxide and hydroxyl radicals. Furthermore, formation of any other radical or reactive oxygen species by interaction of any of these products with any other metabolic substrate (e.g., superoxide+nitric acid=peroxynitrite) contributes to the pathology observed in AD and Down's syndrome patients. $Cu^{2+}$ reaction with Aβ generates $Cu^+$, Aβ., $O_2^-$, $H_2O_2$, and OH., all of which not only directly damage the cells, but also react with biochemical substrates like nitric oxide.

Yet a further aspect of the present invention is directed to a method for treating AD in a subject, said method comprising administering to said subject an effective amount of an agent, said agent comprising a metal chelator, metal complexing compound or a compound capable of interfering with metal mediated free radical formation mediated by Aβ peptides for a time and under conditions sufficient to inhibit or otherwise reduce production of radicals.

The preferred metals according to these aspects of the present invention include Cu and Fe and their various oxidation states. Most preferred are reduced forms of copper ($Cu^+$) and iron ($Fe^{2+}$).

Another mechanism elucidated in accordance with the present invention concerns the formation of aggregates of Aβ, as in conditions involving amyloidosis. In a preferred embodiment, the aggregates are those of amyloid plaques occurring in the brains of AD-affected subjects.

The aggregates according to this aspect of the present invention are non-fibrillary and fibrillary aggregates and are held together by the presence of a metal such as zinc and copper. A method of treatment involves resolubilizing these Aβ aggregates.

The data indicate that Zn-induced Aβ$_{1-40}$ aggregation is completely reversible in the presence of divalent metal ion chelating agents. This suggests that zinc binding may be a reversible, normal function of Aβ and implicates other neurochemical mechanisms in the formation of amyloid. A process involving irreversible Aβ aggregation, such as the polymerization of Aβ monomers, in the formation of polymeric species of Aβ that are present in amyloid plaques is thus a more plausible explanation for the formation of neurotoxic polymeric Aβ species.

According to this aspect of the present invention, there is provided a method of treating AD in a subject comprising administering to said subject an agent capable of promoting, inducing or otherwise facilitating resolubilization of amyloid deposits for a time and under conditions to effect said treatment.

With respect to this aspect of the present invention, it is proposed that a metal chelator or metal complexing agent be administered. Aβ deposits which are composed of fibrillary and non-fibrillary aggregates may be resolubilized by the metal chelating or metal complexing agents, according to this aspect. While fibrile aggregations per se, may not be fully disassociated by administration of such agents, overall deposit resolubilization approaches 70%.

In addition, the agent of this aspect of the present invention may comprise a metal chelator or metal complexing agent alone or in combination with another active ingredient such as but not limited to rifampicin, disulfiram, indomethacin or related compounds. Preferred metal chelators are bathocuproine, bathophenanthroline, DTPA, EDTA, EGTA, penacillamine, TETA, and TPEN, or hydrophobic derivatives thereof.

A "related" compound according to these and other aspects of the present invention are compounds related to the levels of structure or function and include derivatives, homologues and analogues thereof.

Accordingly, the present invention contemplates compositions such as pharmaceutical compositions comprising an active agent and one or more pharmaceutically, acceptable carriers and/or diluents. The active agent may be a single compound such as a metal chelator or metal complexing agent or may be a combination of compounds such as a metal chelating or complexing compound and another compound. Preferred active agents include, for reducing radical formation and for promoting resolubilization, bathocuproine, bathophenanthroline, DTPA, EDTA, EGTA, penacillamine, TETA, and TPEN, or hydrophobic derivatives thereof, or any combination thereof.

It has been found that for some chelators there is an optimal concentration "window" within which the Aβ aggregates are dissolved (see Example 5 below). Increasing the concentration of chelators above the concentration window may not only be toxic to the patient, but also can sharply decrease the dissolution effect of chelators on the Aβ amyloid. Similarly, amounts below the optimal concentration window are too small to result in significant dissolution.

Although the data indicate that higher concentrations of chelators may be effective in dissolution of Aβ aggregates when supplemented by certain substances which favor dissolution, e.g. magnesium, it is expected that there will still be an optimally effective window of chelator concentration. Within the optimal dissolution window, it will be important to balance optimal dissolution against possible side effects or toxicity inherent in the use of chelators as pharmaceutical compositions.

Therefore, for each given patient, the attending physician need be mindful of the window effect and attend to varying the dosages of chelator compsositions so that during the course of administration, chelator concentrations will be varied frequently to randomly allow achieving the most effective concentration for dissolving Aβ amyloid deposits in the given patient.

It is, therefore, desired that the plasma levels of chelators not be steady state, but be kept fluctuating, so that transiently optimal concentrations occur in the patient. The best way to dose the patient is no more often than every three hours, preferably every six hours or eight hours, but as infrequently as once every day or once every two days are expected to be therapeutic.

For the treatment of moderately affected or severely affected patients, where risking the neurological side effects is less of a concern since the quality of their life is very poor, the patient may be put on a program of treatment consisting of high dose chelator compositions for 1 to 21 days, but preferably no more than 14 days, followed by a period of low dose therapy for seven days to three months. A convenient schedule would be two weeks of high dose therapy followed by two weeks of low dose therapy, oscillating between high and low dose periods for up to 12 months. If after 12 months the patient has made no clinical gains on high/low chelator therapy, the treatment should be discontinued.

Another typical case would be the treatment of a mildly affected individual. Such a patient would be treated with low dose chelators for up to 12 months. If after 6 months no clinical gains have been made, the patient could then be placed on the high/low alternation regimen for up to another 12 months.

Accordingly, the present invention contemplates compositions such as pharmaceutical compositions comprising an active agent and one or more pharmaceutically, acceptable carriers and/or diluents. The active agent may be a metal chelator or a combination of a metal chelator and another active agent, e.g. an antioxidant or an alkalinizing agent.

Most preferably, the invention involves the co-administration hydrophobic and hydrophillic derivatives of chelators. Also most preferably, the invention involves the co-administration of chelators of oxidized metals and chelators of reduced metals. Various permutations of both classes of chelators may be administered to achieve optimal results.

The pharmaceutical forms containing the active agents may be administered in any convenient manner either orally or parenteraly, such as by intravenous, intraperitoneal, subcutaneous, rectal, implant, transdermal, slow release, intrabuccal, intracerebral or intranasal administration. Generally, the active agents need to pass the blood brain barrier and may have to be chemically modified, e.g. made hydrophobic, to facilitate this or be administered directly to the brain or via other suitable routes. For injectable use, sterile aqueous solutions (where water soluble) are generally used or alternatively sterile powders for the extemporaneous preparation of sterile injectable solutions may be used. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active agents in the required amount in the appropriate solvent with various of the other ingredients enumerated above, as required, followed by sterilization by, for example, filtration or irradiation. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof. Preferred compositions or preparations according to the present invention are prepared so that an injectable dosage unit contains between about 0.25 µg and 500 mg of active compound.

When the active agents are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 1 µg and 2000 mg of active compound.

The tablets, troches, pills, capsules and the like may also contain other components such as listed hereafter: A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 µg to about 2000 mg. Alternatively, amounts ranging from 200 ng/kg/body weight to above 10 mg/kg/body weight may be administered. The amounts may be for individual active agents or for the combined total of active agents.

Compositions of the present invention include all compositions wherein the compounds of the present invention are contained in an amount which is effective to achieve their intended purpose. They may be administered by any means that achieve their intended purpose. The dosage administered will depend on the age, health, and weight of the recipient, kind of concurrent treatment, if any, frequency of the treatment, and the nature of the effect desired. The dosage of the various compositions can be modified by comparing the relative in vivo potencies of the drugs and the bioavailability using no more than routine experimentation.

The pharmaceutical compositions of the invention may be administered to any animal which may experience the beneficial effects of the compounds of the invention. Foremost among such animals are mammals, e.g., humans, although the invention is not intended to be so limited.

The following examples are provided by way of illustration to further describe certain preferred embodiments of the invention, and are not intended to be limiting of the present invention, unless specified.

EXAMPLES

Example 1

Copper-Induced, pH Dependent Aggregation of Aβ

Materials and Methods a) Preparation of Aβ Stock

Human $A\beta_{1-40}$ peptide was synthesized, purified and characterized by HPLC analysis, amino acid analysis and mass spectroscopy by W. M. Keck Foundation Biotechnology Resource Laboratory (Yale University, New Haven, Conn.). Synthetic Aβ peptide solutions were dissolved in trifluoroethanol (30% in Milli-Q water (Millipore Corporation, Milford, Mass.)) or 20 mM HEPES (pH 8.5) at a concentration of 0.5–1.0 g/ml, centrifuged for 20 min. at 10,000g and the supernatant (stock $A\beta_{1-40}$) used for subsequent aggregation assays on the day of the experiment. The concentration of stock $A\beta_{1-40}$ was determined by UV spectroscopy at 214 nm or by Micro BCA protein assay (Pierce, Rockford, Ill.). The Micro BCA assay was performed by adding 10 μl of stock $A\beta_{1-40}$ (or bovine serum albumin standard) to 140 μl of distilled water, and then adding an equal volume of supernatant (150 μl) to a 96-well plate and measuring the absorbance at 562 nm. The concentration of $A\beta_{1-40}$ was determined from the BSA standard curve. Prior to use all buffers and stock solutions of metal ions were filtered though a 0.22 μm filter (Gelan Sciences, Ann Arbor, Mich.) to remove any particulate matter. All metal ions were the chloride salt, except lead nitrate.

b) Aggregation Assays $A\beta_{1-40}$ stock was diluted to 2.5 μM in 150 mM NaCl and 20 mM glycine (pH 3–4.5), MES (pH 5–6.2) or HEPES (pH 6.4–8.8), with or without metal ions, incubated (30 min., 37° C.), centrifuged (20 min., 10,000 g). The amount of protein in the supernatant was determined by the Micro BCA protein assay as described above.

c) Turbidometric Assays

Turbidity measurements were performed as described by Huang, X., et al., *J. Biol. Chem.* 272:26464–26470 (1997), except $A\beta_{1-40}$ stock was brought to 10 μM (300 μl) in 20 mM HEPES buffer, 150 mM NaCl (pH 6.6, 6.8 or 7.4) with or without metal ions prior to incubation (30 min., 37° C.). To investigate the pH reversibility of $Cu^{2+}$-induced $A\beta$ aggregation, 25 μM $A\beta_{1-40}$ and 25 μM $Cu^{2+}$ were mixed in 67 mM phosphate buffer, 150 mM NaCl (pH 7.4) and turbidity measurements were taken at four 1 min. intervals. Subsequently, 20 μl aliquots of 10 mM EDTA or 10 mM $Cu^{2+}$ were added into the wells alternatively, and, following a 2 min. delay, a further four readings were taken at 1 min. intervals. After the final EDTA addition and turbidity reading, the mixtures were incubated for an additional 30 min. before taking final readings. To investigate the reversibility of pH mediated $Cu^{2+}$-induced $A\beta_{1-40}$ aggregation, 10 μM $A\beta_{1-40}$ and 30 μM $Cu^{2+}$ were mixed in 67 mM phosphate buffer, 150 mM NaCl (pH 7.4) and an initial turbidity measurement taken. Subsequently, the pH of the solution was successively decreased to 6.6 and then increased back to 7.5. The pH of the reaction was monitored with a microprobe (Lazar Research Laboratories Inc., Los Angeles, Calif.) and the turbidity read at 5 min. intervals for up to 30 min. This cycle was repeated three times.

d) Immunofiltration Detection of Low Concentrations of $A\beta_{1-40}$ Aggregate Physiological concentrations of $A\beta_{1-40}$ (8 nM) were brought to 150 mM NaCl, 20 mM HEPES (pH 6.6 or 7.4), 100 nM BSA with $CuCl_2$ (0, 0.1, 0.2, 0.5 and 2 μM) and incubated (30 min., 37° C.). The reaction mixtures (200 μl) were then placed into the 96-well Easy-Titer ELIFA system (Pierce, Rockford, Ill.) and filtered through a 0.22 μm cellulose acetate filter (MSI, Westboro, Mass.). Aggregated particles were fixed to the membrane (0.1% glutaraldehyde, 15 min.), washed thoroughly and then probed with the anti-$A\beta$ mAB 6E10 (Senetek, Maryland Heights, Mich.). Blots were washed and exposed to film in the presence of ECL chemiluminescence reagents (Amersham, Buckinghamshire, England). Immunoreactivity was quantified by transmitance analysis of ECL film from the immunoblots.

e) $A\beta$ Metal-Capture ELISA $A\beta_{1-40}$ (1.5 ng/well) was incubated (37° C., 2 hr) in the wells of $Cu^{2+}$ coated microtiter plates (Xenopore, Hawthorne, N.J.) with increasing concentrations of $Cu^{2+}$ (1–100 nM) as described by Moir et al., *Journal of Biological Chemistry* (submitted). Remaining ligand binding sites on well surfaces were blocked with 2% gelatin in tris-buffered saline (TBS) (3 hr at 37° C.) prior to overnight incubation at room temperature with the anti-$A\beta$ mAb 6E10 (Senetek, Maryland Heights, Mich.). Anti-mouse IgG coupled to horseradish peroxidase was then added to each well and incubated for 3 hr at 37° C. Bound antibodies were detected by a 30 minute incubation with stable peroxidase substrate buffer/3,3',5,5'-Tetramethyl benzidine (SPSB/TMB) buffer, followed by the addition of 2 M sulfuric acid and measurement of the increase in absorbance at 450 nm.

f) Extraction of $A\beta$ from Post-Mortem Brain Tissue

Figure 8:
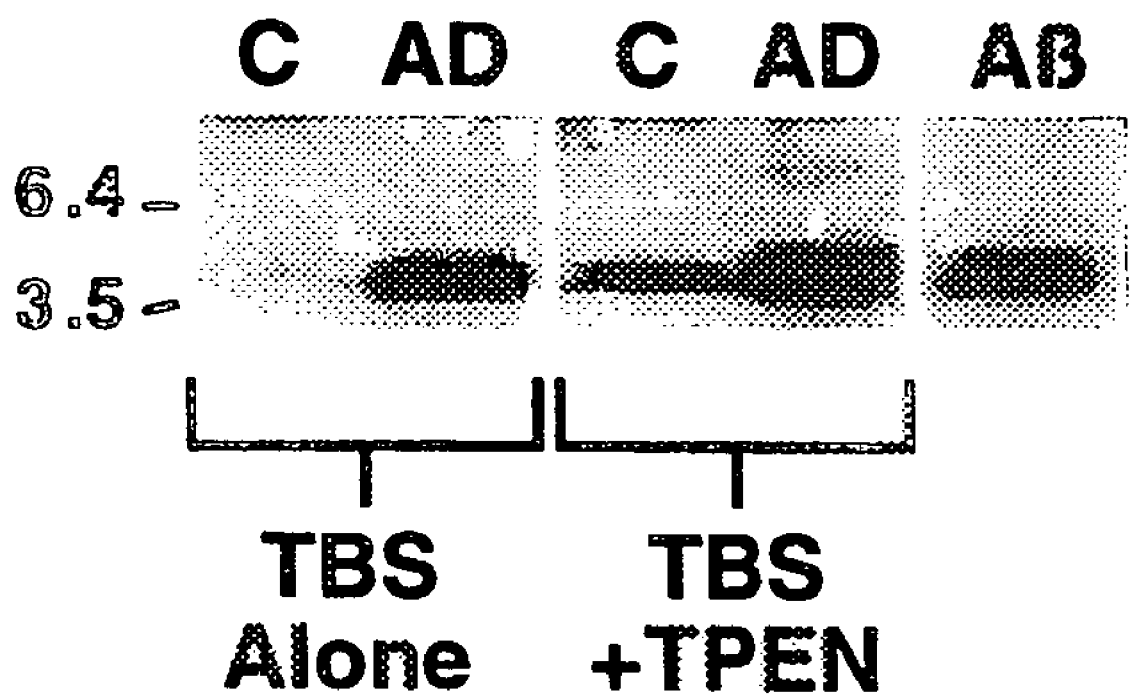
FIG. 8 is a western blot showing the extraction of $A\beta$ from post-mortem brain tissue.
Figure 9:
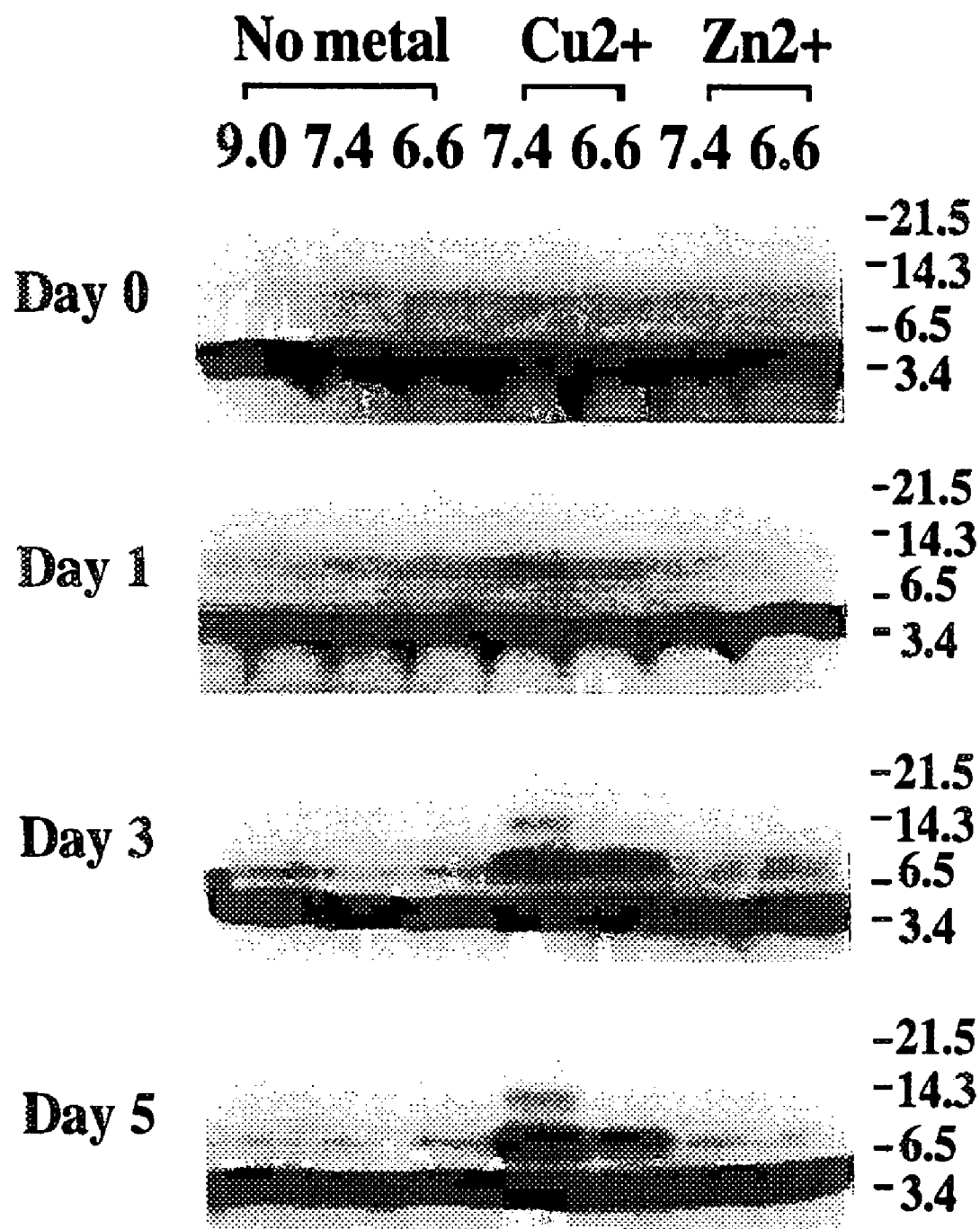
FIG. 9 is a western blot showing $A\beta$ SDS-resistant polymerization by copper.

Identical regions of frontal cortex (0.5 g) from post-mortem brains of individuals with AD, as well as non-AD conditions, were homogenized in TBS, pH 4.7±metal chelators. The homogenate was centrifuged and samples of the soluble supernatant as well as the pellet were extracted into SDS sample buffer and assayed for $A\beta$ content by western blotting using monoclonal antibody (mAb) WO2. The data shows a typical (of n=12 comparisons) result comparing the amount of $A\beta$ extracted into the supernatant phase in AD compared to control (young adult) samples. N,N,N',N'-tetrakis [2-pyridyl-methyl]ethylenediamine (TPEN) (5 μM) allows the visualization of a population of pelletable $A\beta$ that had not previously been recognized in unaffected brain samples (FIG. 8).

g) $A\beta$ Cross-Linking by Copper $Cu^{2+}$-induced SDS-resistant oligomerization of $A\beta$: $A\beta_{1-40}$ (2.5 μM), 150 mM NaCl, 20 mM hepes (pH 6.6, 7.4, 9) with or without $ZnCl_2$ or $CuCl_2$. Following incubation (37° C.), aliquots of each reaction (2 ng peptide) were collected at 0 d, 1 d, 3 d and 5 d and western blotted using anti-$A\beta$ monoclonal antibody 8E10 (FIG. 9). Migration of the molecular size markers are indicated (kDa). The dimer formed under these conditions has been found to be SDS-resistant. $Cu^{2+}$ (2–30 μM) induced SDS-resistant polymerization of peptide. Co-incubation with similar concentrations of $Zn^{2-}$ accelerates the polymerization, but zinc alone has no effect. The antioxidant sodium metabisulfite moderately attenuates the reaction, while ascorbic acid dramatically accelerates $A\beta$ polymerization. This suggests reduction of $Cu^{2+}$ to $Cu^+$ with the latter mediating SDS-resistant polymerization of $A\beta$. Mannitol also abolishes the polymerization, suggesting that the bridging is mediated by the generation of the hydroxyl radical by a Fenton reaction that recruits $Cu^+$. It should be noted that other means of visualizing and/or determining the presence or absence of polymerization other than western blot analysis may be used. Such other means include but are not limited to density sedimentation by centrifugation of the samples.

Results

It has previously been reported that $Zn^{2+}$ induces rapid precipitation of $A\beta$ in vitro (Bush, A. I., et al., *J. Biol. Chem.* 269:12152 (1994)). This metal has an abnormal metabolism in AD and is highly concentrated in brain regions where $A\beta$ precipitates. The present data indicate that under very slightly acidic conditions, such as in the lactic acidotic AD brain, $Cu^{2+}$ strikingly induces the precipitation of $A\beta$ through an unknown conformational shift. pH alone dramatically affects $A\beta$ solubility, inducing precipitation when the pH of the incubation approaches the pH of the peptide (pH 5–6). Zinc induces 40–50% of the peptide to precipitate at pH>6.2, below pH 6.2 the precipitating effects of $Zn^{2+}$ and acid are not summative. At pH≦5, $Zn^{2+}$ has little effect upon Aβ solubility. $Cu^{2+}$ is more effective than $Zn^{2+}$ in precipitating Aβ and even induces precipitation at the physiologically relevant pH 6–7. Copper-induced precipitation of Aβ occurs as the pH falls below 7.0, comparable with conditions of acidosis (Yates, C. M., et al., *J. Neurochem.* 55:1624 (1990)) in the AD brain. Investigation of the precipitating effects of a host or other metal ions in this system indicated that metal ion precipitation of Aβ was limited to copper and zinc, as illustrated, although $Fe^{2+}$ possesses a partial capacity to induce precipitation (Bush, A. I., et al., *Science* 268:1921 (1995)).

On the basis these in vitro findings, the possibility that Aβ deposits in the AD-affected brain may be held in assembly by zinc and copper ions was investigated. Roher and colleagues have recently shown that much of the Aβ that deposits in AD-affected cortex can be solubilized in water (Roher, A. E, et al., *J. Biol. Chem.* 271:20631 (1996)). Supporting the clinical relevance of in vitro findings, it has recently been demonstrated that metal chelators increase the amount of Aβ extracted by Roher's technique (in neutral saline buffer), and that the extraction of Aβ is increased as the chelator employed has a higher affinity for zinc or copper. Hence TPEN is highly efficient in extracting Aβ, as are TETA, and bathocuproine, EGTA and EDTA are less efficient, requiring higher concentrations 91 mm) to achieve the same level of recovery as say, TPEN (5 μM). Zinc and copper ions (5–50 μM) added back to the extracting solution abolish the recovery of Aβ (which is subsequently extracted by the SDS sample buffer in the pellet fraction of the centrifuged brain homogenate suspension), but $Ca^{2+}$ and $Mg^{2+}$ added back to the chelator-mediated extracts of Aβ cannot abolish Aβ resolubilization from AD-affected tissue even when these metal ions are present in millimolar concentrations.

Importantly, atomic absorption spectrophotometry assays of the metal content of the chelator-mediated extracts confirms that Cu and Zn are co-released with Aβ by the chelators, along with lower concentrations of Fe. These data strongly indicate that Aβ deposits (probably of the amorphous type) are held together by Cu and Zn and may also contain Fe. Interestingly, Aβ is not extractable from control brain without the use of chelators. This suggests that metal-assembled Aβ deposits may be the earliest step in the evolution of Aβ plaque pathology.

These findings propelled further inquiries into chemistry of metal ion-Aβ interaction. The precipitating effects upon Aβ of $Zn^{2+}$ and $Cu^{2+}$ were found to be qualitatively different. Zn-mediated aggregation is reversible with chelation and is not associated with neurotoxicity in primary neuronal cell cultures, whereas Cu-mediated aggregation is accompanied by the slow formation of covalently-bonded SDS-resistant dimers and induction of neurotoxicity. These neurotoxic SDS-resistant dimers are similar to those described by Roher (Roher, A. E, et al., *J. Biol. Chem.* 271:20631 (1996)).

To accurately quantitate the effects of different metals and pH on Aβ solubility, synthetic human $Aβ_{1-40}$ (2.5 μM) was incubated (37° C.) in the presence of metal ions at various pH for 30 min. The resultant aggregated particles were sedimented by centrifugation to permit determination of soluble $Aβ_{1-40}$ in the supernatant. To determine the centrifugation time required to completely sediment the aggregated particles generated under these conditions, $Aβ_{1-40}$ was incubated for 30 min at 37° C. with no metal, $Zn^{2+}$ (100 μM), $Cu^{2+}$ (100 μM) and pH (5.5). Reaction mixtures were centrifuged at 10 000 g for different times, or ultracentrifuged at 100 000 g for 1 h. (FIG. 1). FIG. 1 shows the proportion of soluble $Aβ_{1-40}$ remaining following centrifugation of reaction mixtures. $Aβ_{1-40}$ was incubated (30 min., 37° C.) with no metal, under acidic conditions (pH 5.5), $Zn^{2+}$ (100 μM) or $Cu^{2+}$ (100 μM), and centrifuged at 10 000 g for different time intervals, or at 100,000 g (ultracentrifuged) for 1 h for comparison. All data points are means±SD, n=3.

Figure 2A:
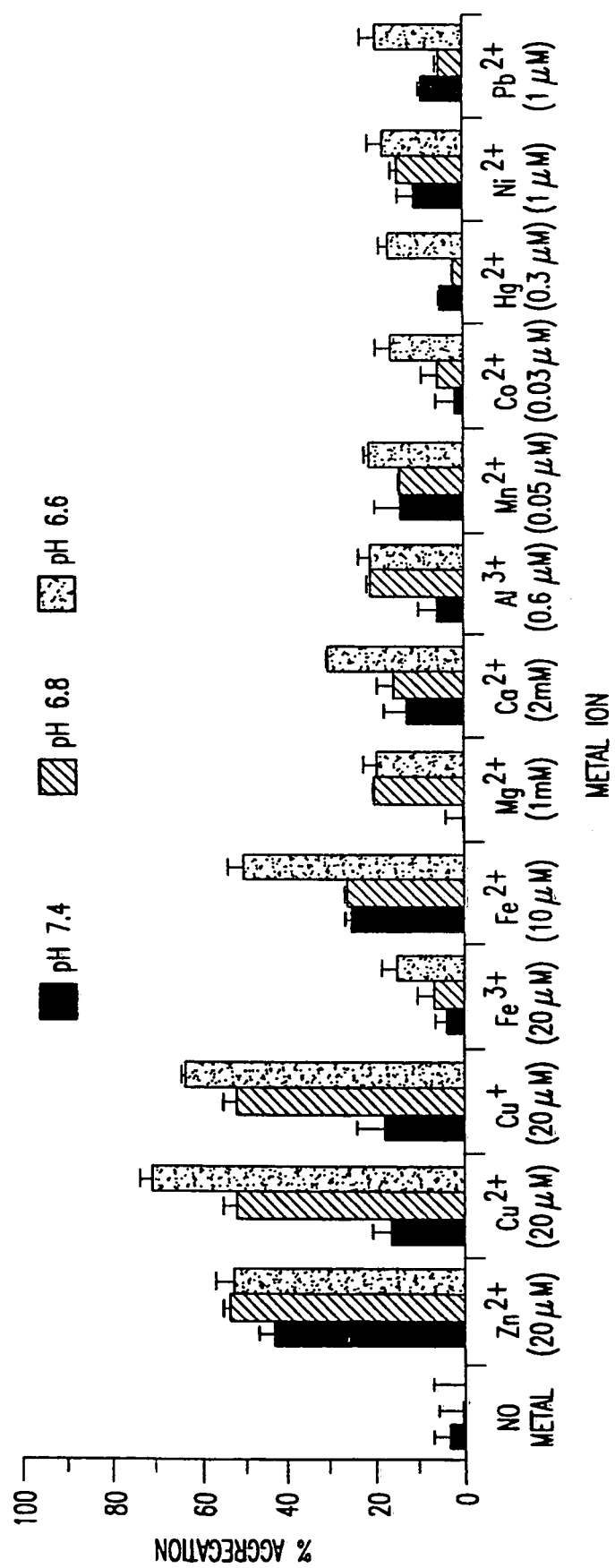
FIGS. 2A–2C.

Given that conformational changes within the N-terminal domain of Aβ are induced by modulating $[H^+]$ (Soto, C., et al., *J. Neurochem.* 63:1191–1198 (1994)), and that there is a metal ($Zn^{2+}$) binding domain in the same region, experiments were designed to determine whether there was a synergistic effect of pH on metal ion-induced Aβ aggregation. $Aβ_{1-40}$ was incubated with different bioessential metal ions at pH 6.6, 6.8 and 7.4. The results are show in FIG. 2A, where "all metals" indicates incubation with a combination containing each metal ion at the nominated concentrations, concurrently. FIG. 2A shows the proportion of soluble $Aβ_{1-40}$ remaining in the supernatant after incubation (30 min., 37° C.) with various metals ions at pH 6.6, 6.8 or 7.4 after centrifugation (10,000 g, 20 min.).

The $[H^+]$ chosen represented the most extreme, yet physiologically plausible $[H^+]$ that $Aβ_{1-40}$ would be likely to encounter in vivo. The ability of different bioessential metal ions to aggregate $Aβ_{1-40}$ at increasing $H^+$ concentrations fell into two groups; $Mg^{2+}$ $Ca^{2+}$, $Al^{3+}$ $Co^{2+}$, $Hg^{2+}$, $Fe^{3+}$, $Pb^{2+}$ and $Cu^{2+}$ showed increasing sensitivity to induce $Aβ_{1-40}$ aggregation, while $Fe^{2+}$, $Mn^{2+}$, $Ni^{2+}$, and $Zn^{2+}$ were insensitive to alterations in $[H^+]$ in their ability to aggregate $Aβ_{1-40}$. $Cu^{2+}$ and $Hg^{2+}$ induced most aggregation as the $[H^+]$ increased, although the $[H^+]$ insensitive $Zn^{2+}$-induced aggregation produced a similar amount of aggregation. $Fe^{2+}$, but not $Fe^{3+}$, also induced considerable aggregation as the $[H^+]$ increased, possibly reflecting increased aggregation as a result of increased crosslinking of the peptide.

Figure 2B:
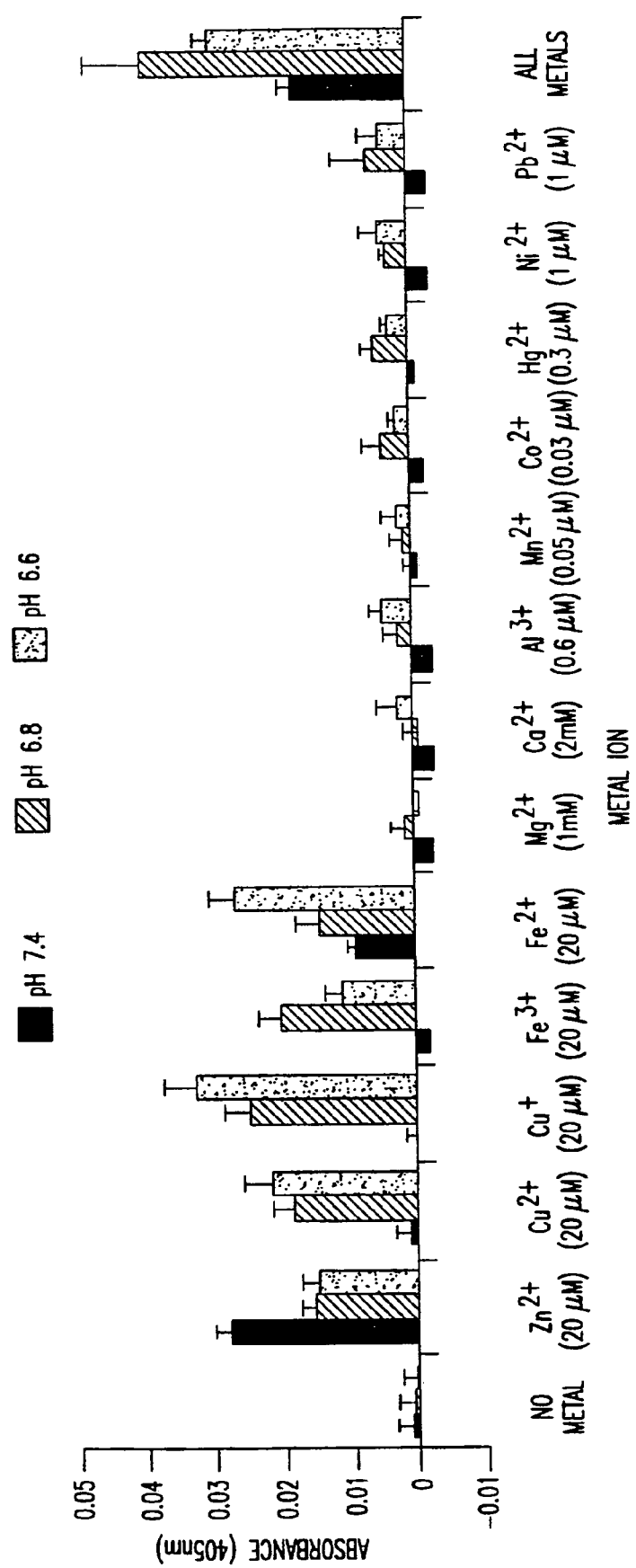
Figure 2C:
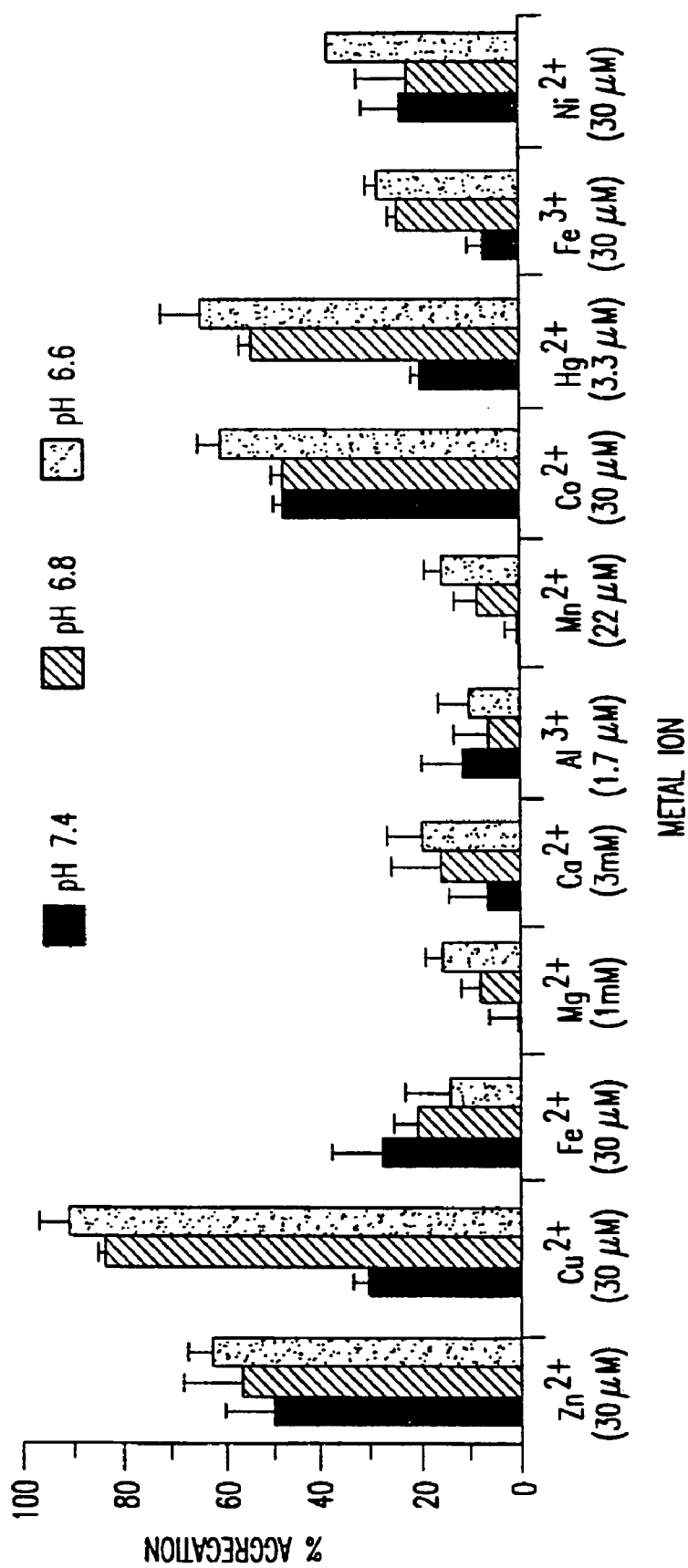

Similar results were obtained when these experiments were repeated using turbidometry as an index of aggregation (FIG. 2B). The data indicate the absorbance changes between reaction mixtures with and without metal ions at pH 6.6, 6.8 or 7.4. Thus, $Aβ_{1-40}$ has both a pH insensitive and a pH sensitive metal binding site. At higher concentrations of metal ions this pattern was repeated, except $Co^{2+}$ and $Al^{3+}$-induced Aβ aggregation became pH insensitive, and Mn became sensitive (FIG. 2C).

Figure 3:
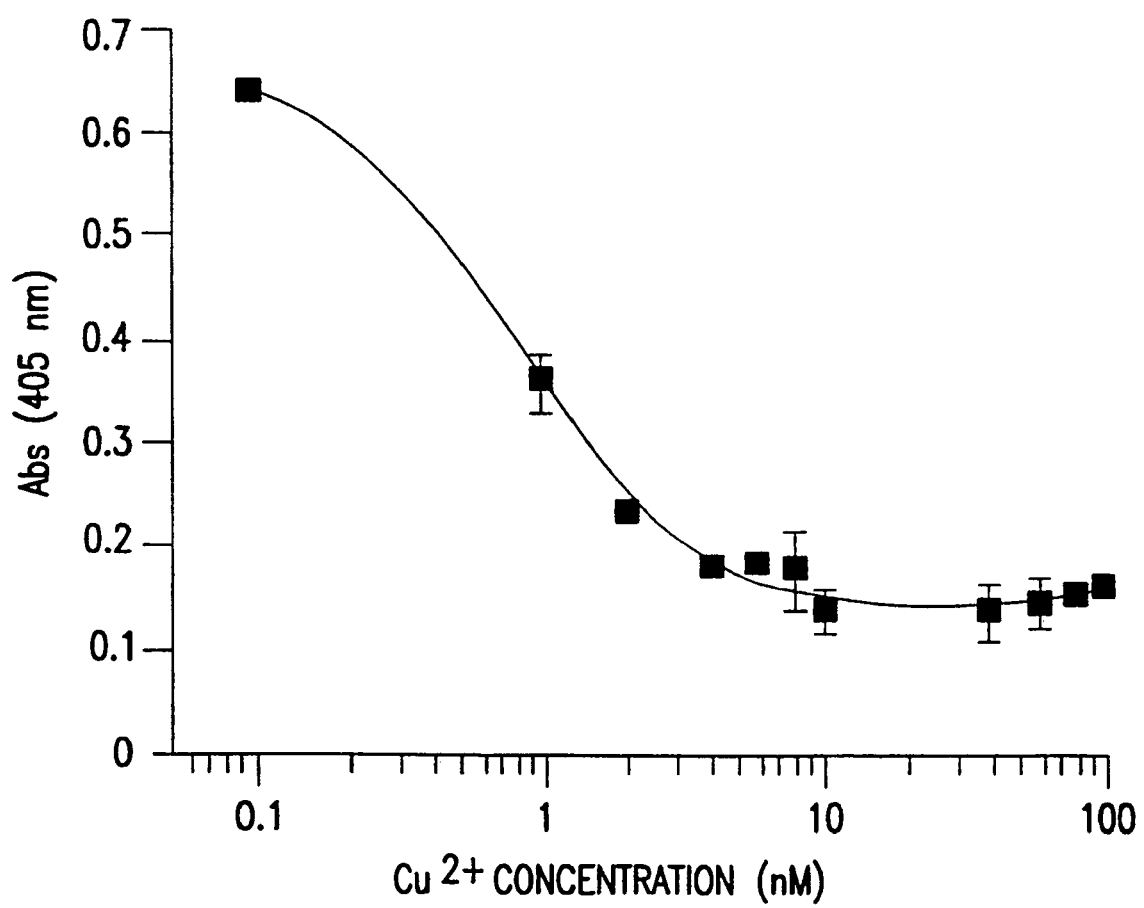
FIG. 3 is a graph showing a competition analysis of $A\beta_{1-40}$ binding to $Cu^{2+}$.

Since $^{64}Cu$ is impractically short-lived (t½=13 h), a novel metal-capture ELISA assay was used to perform competition analysis of $Aβ_{1-40}$ binding to a microtiter plate impregnated with $Cu^{2+}$, as described in Materials and Methods. Results are shown in FIG. 3. All assays were performed in triplicate and are means±SD, n=3. Competition analysis revealed that $Aβ_{1-40}$ has at least one high affinity, saturable $Cu^{2+}$ binding site with a Kd=900 pM at pH 7.4 (FIG. 3). The affinity of Aβ for $Cu^{2+}$ is higher than that for $Zn^{2+}$ (Bush, A. I., et al., *J. Biol. Chem.* 269: 12152 (1994)). Since $Cu^{2+}$ does not decrease $Zn^{2+}$-induced aggregation (Bush, A. I. et al., *J. Biol. Chem.* 269:12152 (1994)), indicating $Cu^{2+}$ does not displace bound $Zn^{2+}$, there are likely to be two separate metal binding sites. This is supported by the fact that there is both a pH sensitive and insensitive interaction with different metal ions.

Figure 4A:
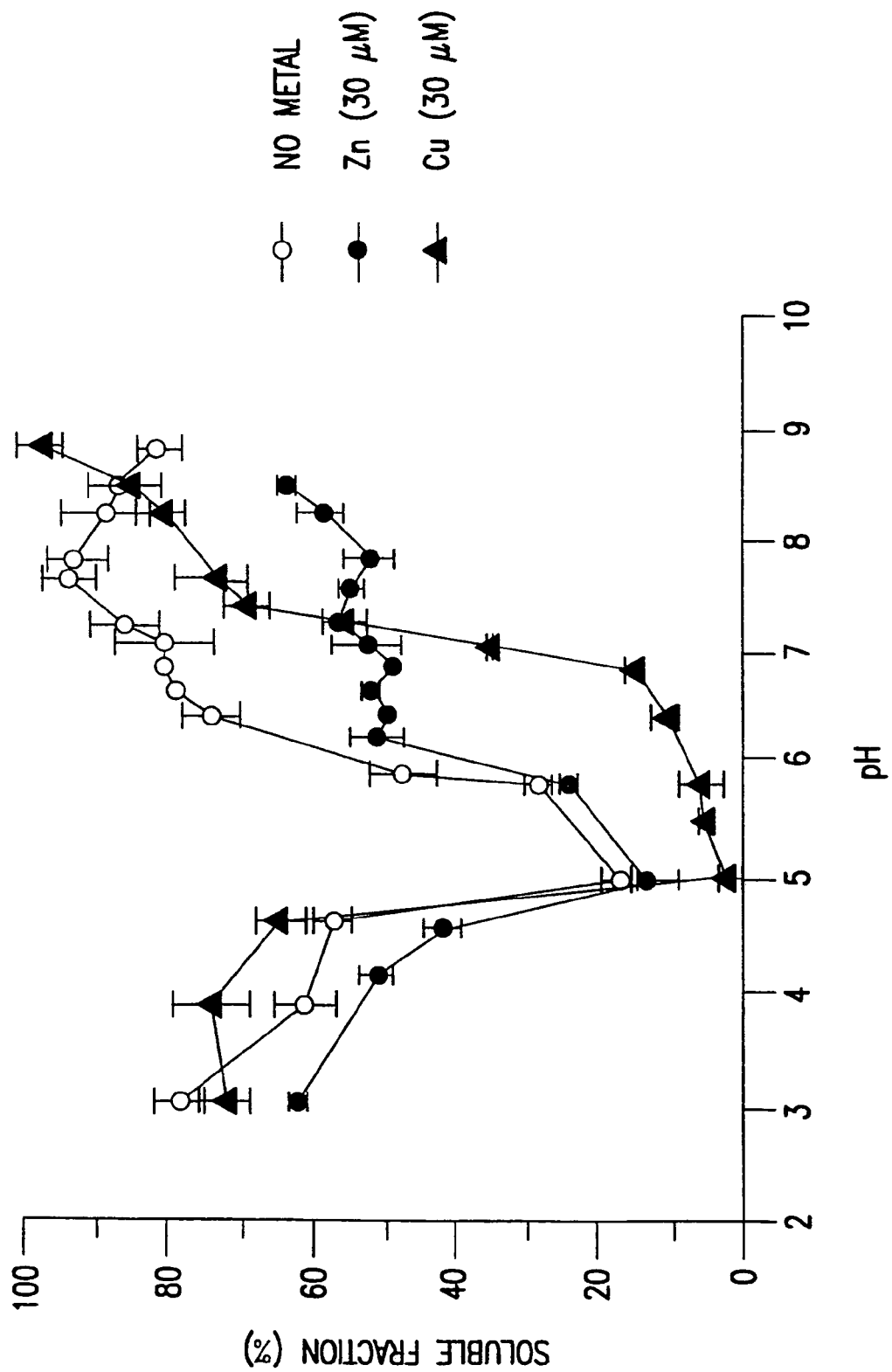
FIGS. 4A–4C.
Figure 4B:
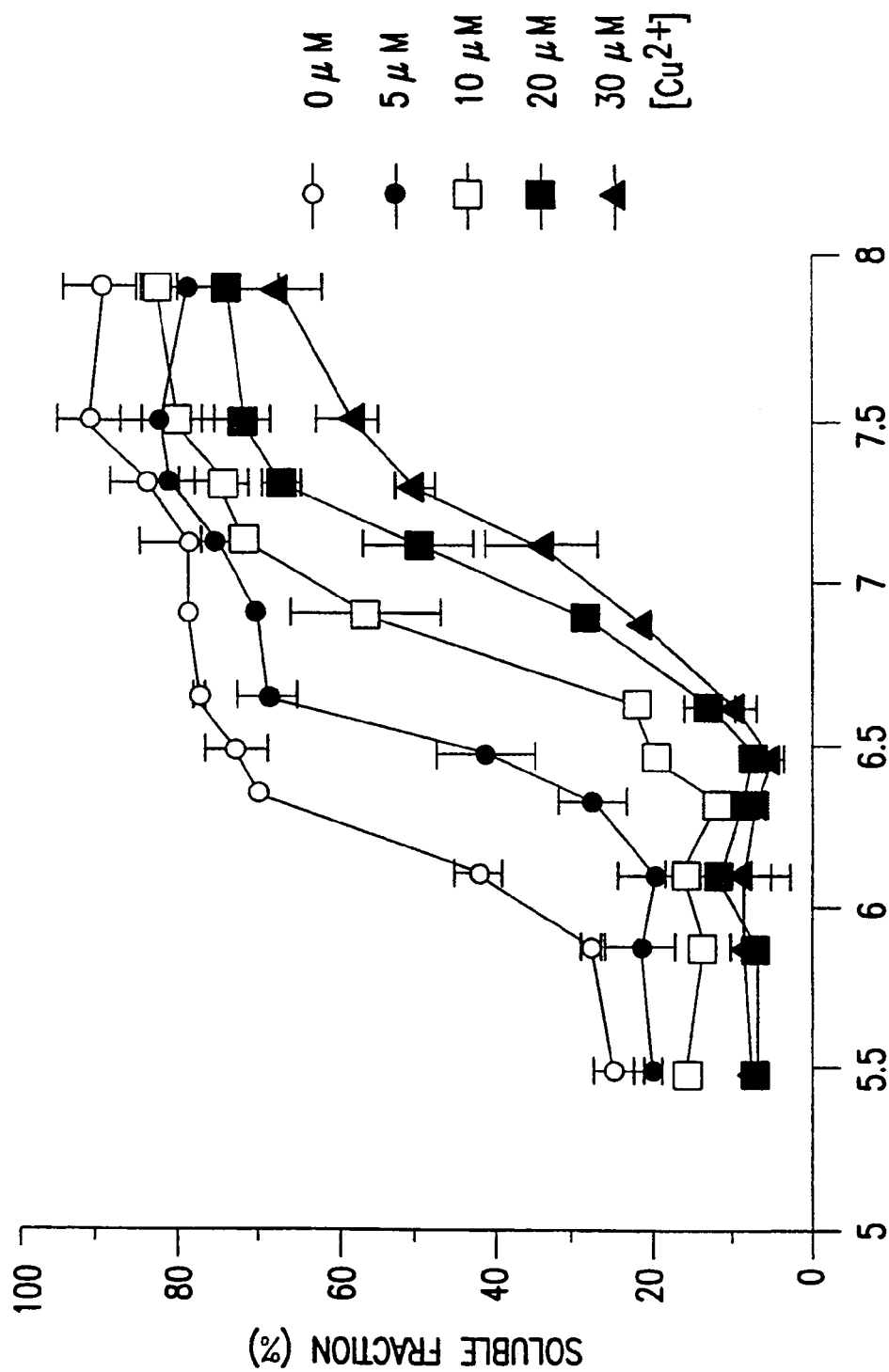
Figure 4C:
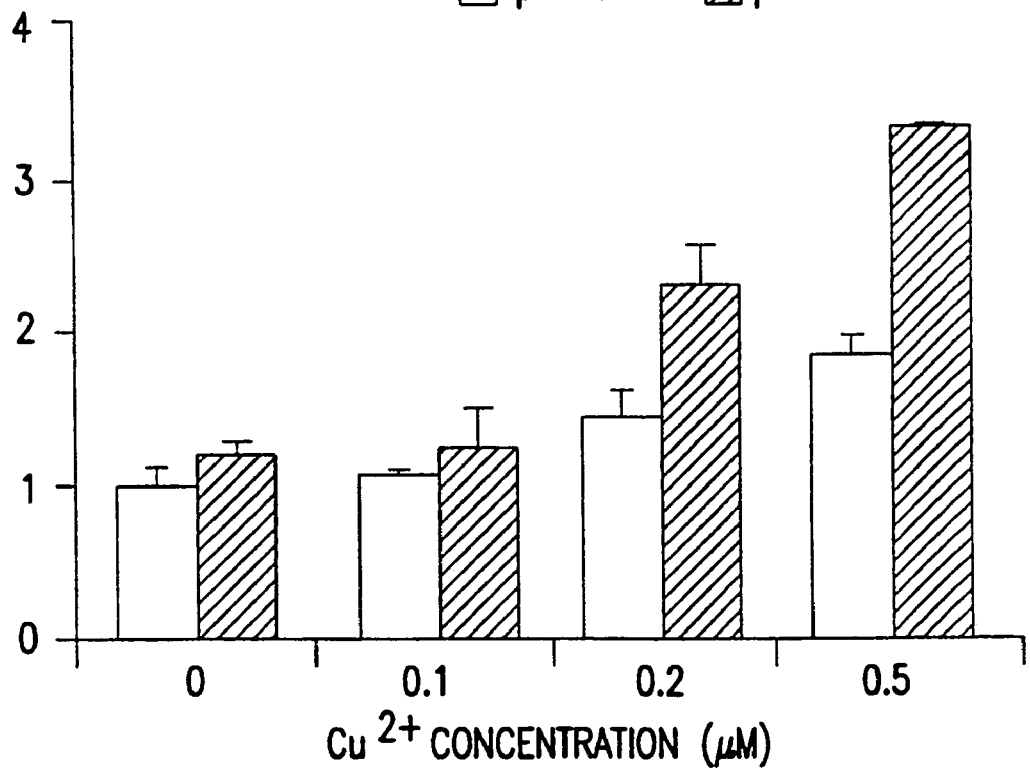

Since the conformational state and solubility of Aβ is altered at different pH (Soto, C. et al., *J. Neurochem.* 63:1191–1198 (1994)), the effects of $[H^+]$ on $Zn^{2+}$- and Cu$^+$-induced Aβ$_{1-40}$ aggregation were studied. Results are shown in FIGS. 4A, 4B and 4C. FIG. 4A shows the proportion of soluble Aβ$_{1-40}$ remaining in the supernatant following incubation (30 min., 37° C.) at pH 3.0–8.8 in buffered saline±Zn$^{2+}$ (30 μM) or Cu$^{2+}$ (30 μM) and centrifugation (10 000 g, 20 min.), expressed as a percentage of starting peptide. All data points are means=SD, n=3. [H$^+$] alone precipitates Aβ$_{1-40}$ (2.5 μM) as the solution is lowered below pH 7.4, and dramatically once the pH falls below 6.3 (FIG. 4A). At pH 5.0, 80% of the peptide is precipitated, but the peptide is not aggregated by acidic environments below pH 5, confirming and extending earlier reports on the effect of pH on Aβ solubility (Burdick, D., *J. Biol. Chem.* 267: 546–554 (1992)). Zn$^{2+}$ (30 μM) induced a constant level (~50%) of aggregation between pH 6.2–8.5, while below pH 6.0, aggregation could be explained solely by the effect of [H$^+$].

In the presence of Cu$^{2+}$ (30 μM), a decrease in pH from 8.8 to 7.4 induced a marked drop in Aβ$_{1-40}$ solubility, while a slight decrease below pH 7.4 strikingly potentiated the effect of Cu$^{2+}$ on the peptide's aggregation. Surprisingly, Cu$^{2+}$ caused >85% of the available peptide to aggregate by pH 6.8, a pH which plausibly represents a mildly acidic environment. Thus, conformational changes in Aβ brought about by small increases in [H$^+$] result in the unmasking of a second metal binding site that leads to its rapid self-aggregation. Below pH 5.0, the ability of both Zn$^{2+}$ and Cu$^{2+}$ to aggregate Aβ was diminished, consistent with the fact that Zn binding to Aβ is abolished below pH 6.0 (Bush, A. I., et al., *J. Biol. Chem.* 269:12152 (1994)), probably due to protonation of histidine residues.

The relationship between pH and Cu$^{2+}$ on Aβ$_{1-40}$ solubility was then further defined by the following experiments (FIG. 4B). The proportion of soluble Aβ$_{1-40}$ remaining in the supernatant after incubation (30 min., 37° C.) at pH 5.4–7.8 with different Cu$^{2+}$ concentrations (0, 5, 10, 20, 30 μM), and centrifugation (10,000 g, 20 min.), was measured and expressed as a percentage of starting peptide. All data points are means±SD, n=3. At pH 7.4, Cu$^{2+}$-induced Aβ aggregation was 50% less than that induced by Zn$^{2+}$ over the same concentration range, consistent with earlier reports (Bush, A. I., et al., *J. Biol. Chem.* 269:12152 (1994)). There was a potentiating relationship between [H$^+$] and [Cu$^{2+}$] in producing Aβ aggregation; as the pH fell, less Cu$^{2+}$ was required to induce the same level of aggregation, suggesting that [H$^+$] is controlling Cu$^{2+}$ induced Aβ$_{1-40}$ aggregation.

To confirm that this reaction occurs at physiological concentrations of Aβ$_{1-40}$ and Cu$^{2+}$, a novel filtration immunodetection system was employed. This technique enabled the determination of the relative amount of Aβ$_{1-40}$ aggregation in the presence of different concentrations of H$^+$ and Cu$^{2+}$ (FIG. 4C). The relative aggregation of nM concentrations of Aβ$_{1-40}$ at pH 7.4 and pH 6.6 in the presence of different Cu$^{2+}$ concentrations (0, 0.1, 0.2, 0.5 μM) were determined by this method. Data represent mean reflectance values of immunoblot densitometry expressed as a ratio of the signal obtained when the peptide is treated in the absence of Cu$^{2+}$. All data points are means±SD, n=2.

This sensitive technique confirmed that physiological concentrations of Aβ$_{1-40}$ are aggregated under mildly acidic conditions and that aggregation was greatly enhanced by the presence of Cu$^{2+}$ at concentrations as low as 200 nM. Furthermore, as previously observed at higher Aβ$_{1-40}$ concentrations, a decrease in pH from 7.4 to 6.6 potentiated the effect of Cu$^{2+}$ on aggregation of physiological concentrations of Aβ$_{1-40}$. Thus, Aβ$_{1-40}$ aggregation is concentration independent down to 8 nM where Cu$^{2+}$ is available.

It has recently been shown that Zn$^{2+}$ mediated Aβ$_{1-40}$ aggregation is reversible whereas Aβ$_{1-40}$ aggregation induced by pH 5.5 was irreversible. Therefore, experiments were performed to determine whether Cu$^{2+}$/pH-mediated Aβ$_{1-40}$ aggregation was reversible. Cu$^{2+}$-induced Aβ$_{1-40}$ aggregation at pH 7.4 was reversible following EDTA chelation, although for each new aggregation cycle, complete resolubilization of the aggregates required a longer incubation. This result suggested that a more complex aggregate is formed during each subsequent aggregation cycle, preventing the chelator access to remove Cu$^{2+}$ from the peptide. This is supported by the fact that complete resolubilization occurs with time, and indicates that the peptide is not adopting a structural conformation that is insensitive to Cu$^{2+}$-induced aggregation/EDTA-resolubilization.

Figure 5A:
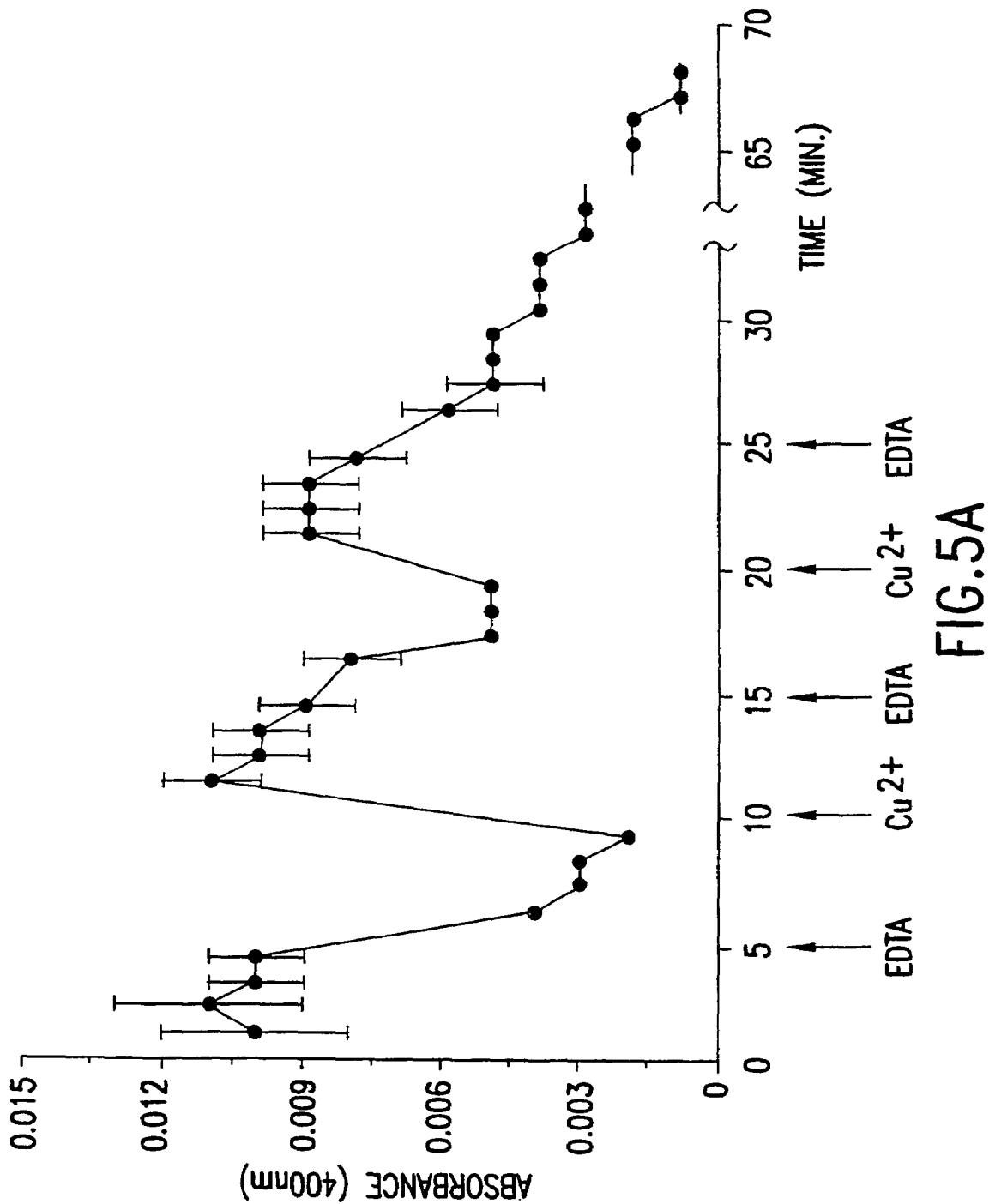
FIGS. 5A and 5B.
Figure 5B:
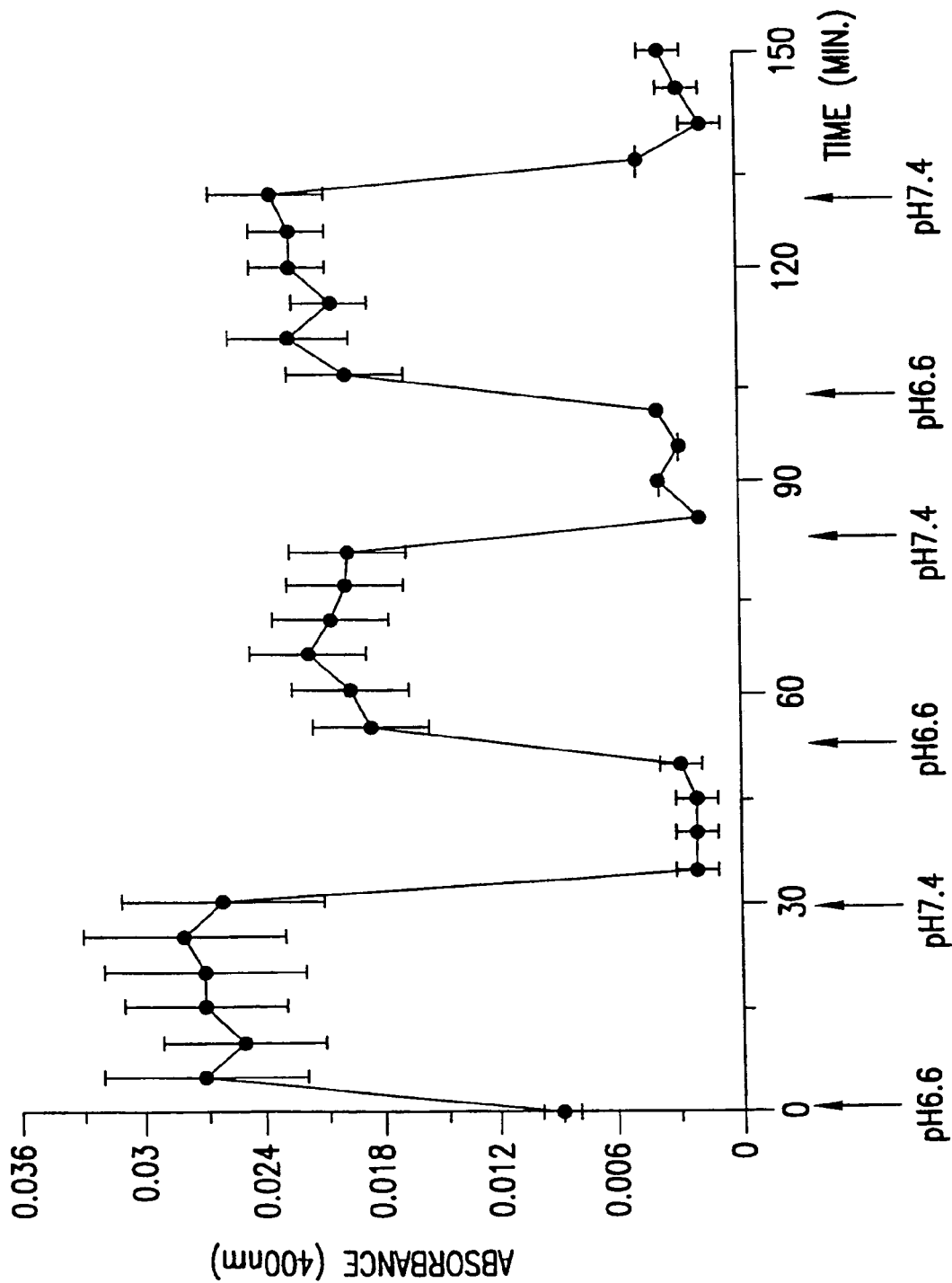

The reversibility of pH potentiated Cu$^{2+}$-induced Aβ$_{1-40}$ aggregation was studied by turbidometry between pH 7.5 to 6.6, representing H$^+$ concentration extremes that might be found in vivo (FIGS. 5A and 5B). Unlike the irreversible aggregation of Aβ$_{1-40}$ observed at pH 5.5. Cu$^{2+}$-induced Aβ$_{1-40}$ aggregation was fully reversible as the pH oscillated between pH 7.4 and 6.6. FIG. 5A shows the turbidometric analysis of Cu$^{2+}$-induced Aβ$_{1-40}$ aggregation at pH 7.4 reversed by successive cycles of chelator (EDTA), as indicated. FIG. 5B shows turbidometric analysis of the reversibility of Cu$^{2+}$-induced Aβ$_{1-40}$ as the pH cycles between 7.4 and 6.6. Thus, subtle conformational changes within the peptide induced by changing [H$^+$] within a narrow pH window, that corresponds to physiologically plausible [H$^+$], allows the aggregation or resolubilization of the peptide in the presence of Cu$^{2+}$.

Discussion

These results suggest that subtle conformational changes in Aβ induced by [H$^+$] promote the interaction of Aβ$_{1-40}$ with metal ions, in particular Cu$^{2+}$ and Hg$^{2+}$ allowing self-aggregate or resolubilize depending on the [H$^+$] (FIGS. 2A–2C, 4A–4C). A decrease in pH below 7.0 increases the β-sheet conformation (Soto, C., et al., *J. Neurochem.* 63:1191–1198 (1994)), and this may allow the binding of Cu$^{2+}$ to soluble Aβ that could further alter the conformation of the peptide allowing for self aggregation, or simply help coordinate adjacent Aβ molecules in the assembly of the peptides into aggregates. Conversely, increasing pH above 7.0 promotes the α-helical conformation (Soto, C., et al. *J. Neurochem.* 63:1191–1198 (1994)), which may alter the conformational state of the dimeric aggregated peptide, releasing Cu and thereby destabilizing the aggregate with the resultant release of Aβ into solution. Thus, in the presence of Cu$^{2+}$, Aβ$_{1-40}$ oscillates between an aggregated and soluble state dependent upon the [H$^+$].

Aβ$_{1-40}$ aggregation by Co$^{2+}$, like Zn$^{2+}$, was pH insensitive and per mole induced a similar level of aggregation. Unlike Zn$^{2+}$, Aβ$_{1-40}$ binding of Co$^{2+}$ may be employed for the structural determination of the pH insensitive binding site given its nuclear magnetic capabilities (See FIG. 2C).

The biphasic relationship of Aβ solubility with pH mirrors the conformational changes previously observed by CD spectra within the N-terminal fragment (residues 1–28) of Aβ (reviewed in (Soto, C., et al., *J. Neurochem.* 63:1191–1198 (1994)); α-helical between pH 1–4 and >7, but β-sheet between pH 4–7. The irreversible aggregates of Aβ formed at pH 5.5 supports the hypothesis that the β-sheet conformation is a pathway for Aβ aggregation into amyloid fibrils. Since aggregates produced by Zn$^{2+}$ and Cu$^{2+}$ under mildly acidic conditions (FIGS. 5A and 5B) are chelator/pH reversible, their conformation may be the higher energy α-helical conformation.

These results now indicate that there are three physiologically plausible conditions which could aggregate Aβ: pH (FIGS. 1, 4A–4C; Fraser, P. E., et al., *Biophys. J.* 60:1190–1201 (1991); Barrow, C. J. and Zagorski, M. G., *Science* 253:179–182 (1991); Burdick, D., *J. Biol. Chem.* 267:546–554 (1992); Barrow, C. J., et al., *J. Mol. Biol.* 225:1075–1093 (1992); Zagorski, M. G. and Barrow, C. J., *Biochemistry* 31:5621–5631 (1992); Kirshenbaum, K. and Daggett, V., *Biochemistry* 34:7629–7639 (1995); Wood, S. J., et al., *J. Mol. Biol.* 256:870–877 (1996), [$Zn^{2-}$] (FIGS. 1, 2A and 2B, 4A–4C; Bush, A. I., et al. *J. Biol. Chem.* 269:12152 (1994); Bush, A. I. et al., *Science* 265:1464 (1994); Bush, A. I., et al., *Science* 268:1921 (1995); Wood, S. J., et al., *J. Mol. Biol.* 256:870–877 (1996)) and under mildly acidic conditions, [$Cu^{2+}$] (FIGS. 2A, 4A–4C, 5B). Interestingly, changes in metal ion concentrations and pH are common features of the a inflammatory response to injury. Therefore, the binding of $Cu^{2+}$ and $Zn^{2-}$ to Aβ may be of particular importance during inflammatory processes, since local sites of inflammation can become acidic (Trehauf, P. S. & McCarty, D. J. *Arthr. Rheum.* 14:475–484 (1971); Menkin, V., *Am. J. Pathol.* 10:193–210(1934)) and both $Zn^{2+}$ and $Cu^{2+}$ are rapidly mobilized in response to inflammation (Lindeman, R. D., et al., *J. Lab. Clin. Med.* 81:194–204 (1973); Terhune, M. W. & Sandstead, H. H., *Science* 177:68–69 (1972); Hsu, J. M., et al., *J. Nutrition* 99:425–432 (1969); Haley, J. V., *J. Surg. Res.* 27:168–174 (1979); Milaninio, R. et al., *Advances in Inflammation Research* 1:281–291 (1979); Frieden, E., in *Inflammatory Diseases and Copper*, Sorenson, J. R. J., ed, Humana Press, New Jersey (1980), pp. 159–169).

Serum copper levels increase during inflammation, associated with increases in ceruloplasmin, a $Cu^{2+}$ transporting protein that may donate $Cu^{2+}$ to enzymes active in processes of basic metabolism and wound healing such as cytochrome oxidase and lysyl oxidase (Giampaolo, V., et al., in *Inflammatory Diseases and Copper*, Sorenson, J. R. J., ed, Humana Press, New Jersey (1980), pp. 329–345; Peacock, E. E. and vanWinkle, W., in *Wound Repair*, W.B. Saunders Co., Philadelphia, pp. 145–155) (1976)). Since the release of $Cu^{2+}$ from ceruloplasmin is greatly facilitated by acidic environments where the cupric ion is reduced to its cuprous form (Owen, C. A., Jr., *Proc. Soc. Exp. Biol. Med.* 149:681–682 (1975)), periods of mild acidosis may promote an environment of increased free $Cu^{2+}$. Similarily, aggregation of another amyloid protein, the acute phase reactant serum amyloid P component (SAP) to the cell wall polysaccharide, zymosan, has been observed with $Cu^{2-}$ at acidic pH (Potempa, L. A., et al., *Journal of Biological Chemistry* 260:12142–12147 (1985)). Thus, exchange of $Cu^{2+}$ to $Aβ_{1-40}$ during times of decreased pH may provide a mechanism for altering the biochemical reactivity of the protein required by the cell under mildly acidic conditions. Such a function may involve alterations in the aggregation/adhesive properties (FIGS. 1–5B) or oxidative functions of Aβ at local sites of inflammation.

While the pathogenic nature of $Aβ_{1-42}$ in AD is well described (Maury, C. P. J., *Lab. Investig.* 72:4–16 (1995); Multhaup, G., et al., *Nature* 325:733–736 (1987)), the function of the smaller $Aβ_{1-40}$ remains unclear. The present data suggest that $Cu^{2+}$-binding and aggregation of Aβ will occur when the pH of the microenvironment rises. This conclusion can be based on the finding that the reaction is [$H^+$] and [$Cu^{2+}$] dependent and reversible within a narrow, physiologically plausible, pH window. This is further supported by the specificity and high affinity of $Cu^{2+}$ binding under mildly acidic conditions compared to the constant $Zn^{2+}$-induced aggregation (and binding) of $Aβ_{1-40}$ over a wide pH range (6.2–8.5). The brain contains high levels of both $Zn^{2+}$ (~150 μM; Frederickson, C. J. *International Review of Neurobiology* 31:145–237 (1989)) and Cu2– (~100 μM; Warren, P. J., et al., *Brain* 83:709–717 (1960); Owen, C. A., *Physiological Aspects of Copper*, Noyes Publications, Park Ridge, New Jersey (1982), pp 160–191). Intracellular concentrations are approximately 1000 and 100 fold higher than extracellular concentrations. This large gradient between intracellular and extracellular compartments suggests a highly energy dependent mechanism is required in order to sequester these metals within neurons. Therefore, any alterations in energy metabolism, or injury, may affect the reuptake of these metal ions and promote their release into the extracellular space, and together with the synergistic affects of decreased pH (see above) induce membrane bound $Aβ_{1-40}$ to aggregate. Since increased concentrations of $Zn^{2+}$ and $Cu^{2+}$, and decreased pH, are common features of all forms of cellular insult, the initiation of $Aβ_{1-40}$ function likely occurs in a coordinated fashion to alter adhesive and/or oxidative properties of this membrane protein essential for maintaining cell integrity and viability. That $Aβ_{1-40}$ has such a high affinity for these metal ions, indicates a protein that has evolved to respond to slight changes in the concentration of extracellular metal ions. This is supported by the fact that aggregation in the presence of Cu is approx. 30% at pH 7.1, the pH of the brain (Yates, C. M., et al., *J. Neurochem.* 55:1624–1630 (1990)), but 85% at pH 6.8. Taken together, our present results indicate that $Aβ_{1-40}$ may have evolved to respond to biochemical changes associated with neuronal damage as part of the locally mediated response to inflammation or cell injury. Thus, it is possible that $Cu^{2+}$ mediated $Aβ_{1-40}$ binding and aggregation might be a purposive cellular response to an environment of mild acidosis.

The deposition of amyloid systemically is usually associated with an inflammatory response (Pepys, M. B. & Baltz, M. L., *Adv. Immunol.* 34:141–212 (1983); Cohen, A. S., in *Arthritis and Allied Conditions*, D. J. McCarty, ed., Lea and Febiger, Philadelphia, pp. 1273–1293 (1989); Kisilevsky, R., *Lab. Investig.* 49:381–390 (1983)). For example, serum amyloid A, one of the major acute phase reactant proteins that is elevated during inflammation, is the precursor of amyloid A protein that is deposited in various tissues during chronic inflammation, leading to secondary amyloidosis (Gorevic, P. D., et al., *Ann. NY Acad. Sci* 380:393 (1982)). An involvement of inflammatory mechanisms has been suggested as contributing to plaque formation in AD (Kisilevsky, R., *Mol. Neurobiol.* 49:65–66 (1994)). Acute-phase proteins such as alpha 1-antichymotrypsin and c-reactive protein, elements of the complement system and activated microglial and astroglial cells are consistently found in AD brains.

The rapid appearance, within days of Aβ deposits and APP immunoreactivity following head injury (Roberts, G. W., et al., *Lancet.* 338:1422–1423 (1991); Pierce, J. E. S., et al., *Journal of Neuroscience* 16:1083–1090 (1996)), rather than the more gradual accumulation of Aβ into more dense core amyloid plaques over months or years in AD may be compatible with the release of $Zn^{2+}$, $Cu^{2+}$ and mild acidosis in this time frame. Thus, pH/metal ion mediated aggregation may form the basis for the amorphous Aβ deposits observed in the aging brain and following head injury, allowing the maintenance of endothelial and neuronal integrity while limiting the oxidative stress associated with injury that may lead to a diminishment of structural function.

Since decreased cerebral pH is a complication of aging (Yates, C. M., et al., *J. Neurochem.* 55:1624–1630 (1990)), these data indicate that Cu and Zn mediated Aβ aggregation may be a normal cellular response to an environment of mild acidosis. However, prolonged exposure of Aβ to an environment of lowered cerebral pH may promote increased concentrations of free metal ions and reactive oxygen species, and the inappropriate interaction of $A\beta_{1-42}$ over time promoting the formation of irreversible Aβ oligomers and it's subsequent deposition as amyloid in AD. The reversibility of this pH mediated $Cu^{2+}$ aggregation does however present the potential for therapeutic intervention. Thus, cerebral alkalinization may be explored as a therapeutic modality for the reversibility of amyloid deposition in vivo.

Example 2

Free Radical Formation and SOD-Like Activity of Alzheimer's Aβ Peptides

Materials and Methods a) Determination of $Cu^+$ and $Fe^{2+}$

This method is modified from a protocol assaying serum copper and iron (Landers, J. W., et al., *Amer. J. Clin. Path.* 29:590 (1958)). It is based on the fact that there are optimal visible absorption wavelengths of 483 nm and 535 nm for $Cu^+$ complexed with bathocuproinedisulfonic (BC) anion and $Fe^{2+}$ coordinated by bathophenanthrolinedisulfonic (BP) anion, respectively.

Determination of molar absorption of these two complexes was accomplished essentially as follows. An aliquot of 500 μl of each complex (500 μM, in PBS pH 7.4, with ligands in excess) was pipetted into 1 cm-pathlength quartz cuvette, and their absorbances were measured. Their molar absorbancy was determined based on Beer-Lambert's Law. $Cu^+$-BC has a molar absorbancy of 2762 $M^{-1}$ $cm^{-1}$, while $Fe^{2+}$-BP has a molar absorbancy of 7124 $M^{-1}$ $cm^{-1}$.

Determination of the equivalent vertical pathlength for $Cu^+$-BC and $Fe^{2+}$-BP in a 96-well plate was carried out essentially as follows. Absorbances of the two complexes with a 500 μM, 100 μM, 50 μM, and 10 μM concentration of relevant metal ions ($Cu^+$, $Fe^{2+}$) were determined both by 96-well plate readers (300 μL) and UV-vis spectrometer (500 μL), with PBS, pH 7.4, as the control blank. The resulting absorbancies from the plate reader regress against absorbancies by a UV-vis spectrometer. The slope k from the linear regression line is equivalent to the vertical pathlength if the measurement is carried out on a plate. The results are:

|  | k(cm) | $r^2$ |
|---|---|---|
| $Cu^+$—BC | 1.049 | 0.998 |
| $Fe^{2+}$—BP | 0.856 | 0.999 |

With molar absorbancy and equivalent vertical pathlength in hand, the concentrations (μM) of $Cu^+$ or $Fe^{2+}$ can be deduced based on Beer-Lambert's Law, using proper buffers as controls.

for $Fe^{2+}$: $[Fe^{2+}] (\mu M) = \frac{\Delta A(535 \text{ nm})}{(7124 \times 0.856)} \times 10^6$ for $Cu^+$: $[Cu^+] (\mu M) = \frac{\Delta A(483 \text{ nm})}{(2762 \times 1.049)} \times 10^6$ where ΔA is absorbancy difference between sample and control blank.

b) Determination of $H_2O_2$

This method is modified from a $H_2O_2$ assay reported recently (Han, J. C., et al., *Anal. Biochem.* 234:107 (1996)). The advantages of this modified $H_2O_2$ assay on 96-well plate include high throughput, excellent sensitivity (~1 μM), and the elimination of the need for a standard curve of $H_2O_2$, which is problematic due to the labile chemical property of $H_2O_2$.

Aβ peptides were co-incubated with a $H_2O_2$-trapping reagent (Tris(2-carboxyethyl)-phosphine hydrochloride, TCEP, 100 μM) in PBS (pH 7.4 or 7.0) at 37° C. for 30 mins. Then 5,5'-dithio-bis(2-nitrobenzoic acid) (DBTNB, 100 μM) was added to react with remaining TCEP. The product of this reaction has a characteristic absorbance maximum of 412 nm [18]. The assay was adapted to a 96-well format using a standard absorbance range (see FIG. 11).

The chemical scheme for this novel method is:

Scheme I:

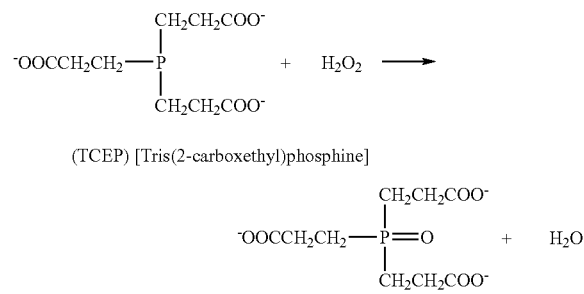

(TCEP) [Tris(2-carboxyethyl)phosphine]

Scheme II:

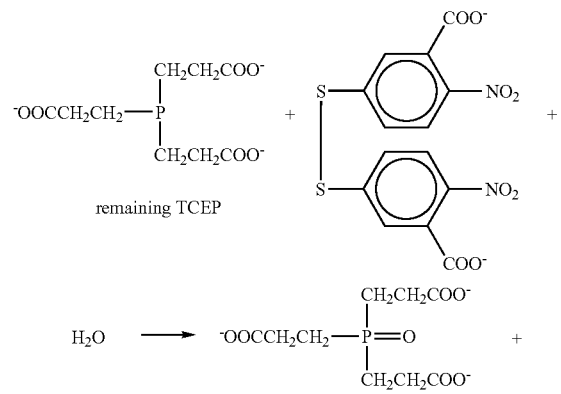

remaining TCEP

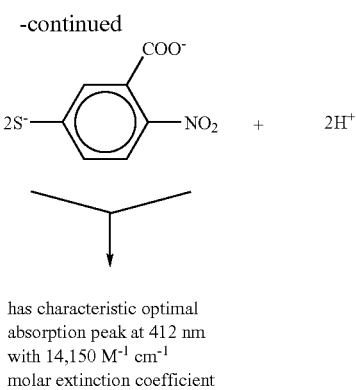

has characteristic optimal absorption peak at 412 nm with 14,150 M$^{-1}$ cm$^{-1}$ molar extinction coefficient TCEP.HCl was synthesized by hydrolyzing tris (2-cynoethyl)phosphine (purchased from Johnson-Mathey (Waydhill, Mass.)), in refluxing aqueous HCl (Burns, J. A. et al., J. Org. Chem. 56:2648 (1991)) as shown below.

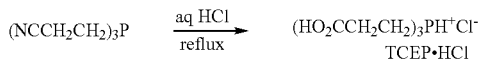

In order to carry out the above-described assay in a 96-well plate, it was necessary to calculate the equivalent vertical pathlength of 2-nitro-5-thiobenzoic acid (TMB) in a 96-well plate. This determination was carried out essentially as described for Cu$^+$-BC and Fe$^{2+}$-BP in Example 2. The resulting absorbancies from the plate reader regress against absorbancies by a UV-vis spectrometer. The slope k from the linear regression line is equivalent to the vertical pathlength if the measurement is carried out on a plate. The results are:

| k | r$^2$ |
|---|---|
| 0.875 | 1.00 |

The concentration of H$_2$O$_2$ can then be deduced from the difference in absorbance between the sample and the control (sample plus 1000 U/µl catalase)

$$[H_2O_2] \ (\mu M) = \frac{\Delta A(412 \ nm)}{(2 \times 0.875 \times 14150)}$$

c) Determination of OH.

Determination of OH. was performed as described in Gutteridge et al. Biochim. Biophys. Acta 759: 38–41 (1983).

d) Cu$^+$ Generation by Aβ: Influence of Zn$^{2+}$ and pH

Aβ (10 µM in PBS, pH 7.4 or 6.8, as shown) was incubated for 30 minutes (37° C.) in the presence of Cu$^{2+}$ 10 µM±Zn$^{2+}$ 10 µM). Cu$^+$ levels (n=3, ±SD) were assayed against a standard curve. These data indicate that the presence of Zn$^{2+}$ can mediate the reduction of Cu$^{2+}$ in a mildly acidic environment. The effects of zinc upon these reactions are strongly in evidence but complex. Since the presence of 10 µM zinc will precipitate the peptide, it is clear that the peptide possesses redox activity even when it is not in the soluble phase, suggesting that cortical Aβ deposits will not be inert in terms of generating these highly reactive products. Cerebral zinc metabolism is deregulated in AD, and therefore levels of interstitial zinc may play an important role in adjusting the Cu$^+$ and H$_2$O$_2$ production generated by Aβ. The rat homologue of Aβ$_{1-40}$ does not manifest the redox reactivity of the human equivalent. Insulin, a histidine-containing peptide that can bind copper and zinc, exhibits no Cu$^{2+}$ reduction.

e) Hydrogen Peroxide Production by Aβ Species

Aβ$_{1-42}$ (10 µM) was incubated for 1 hr at 37° C., pH 7.4 in ambient air (first bar), continuous argon purging (Ar), continuous oxygen enrichment (O$_2$) at pH 7.0 (7.0), or in the presence of the iron chelator desferioxamine (220 µM; DFO). Variant Aβ species (10 µM) were tested: Aβ$_{1-40}$ (Aβ$_{1-40}$), rat Aβ$_{1-40}$ (rAβ$_{1-40}$), and scrambled Aβ$_{1-40}$ (sAβ$_{1-40}$) were incubated for 1 hr at 37° C., pH 7.4 in ambient air. Values (mean±SD, n=3) represent triplicate samples minus values derived from control samples run under identical conditions in the presence of catalase (10 U/ml). The details of the experiment are as follows: Aβ peptides were co-incubated with a H$_2$O$_2$-trapping reagent (Tris(2-carboxyethyl)-phosphine hydrochloride, TCEP, 100 µM) in PBS (pH 7.4 or 7.0) at 37° C. for 30 mins. Then 5,5'-dithio-bis(2-nitrobenzoic acid) (DTNB, 100 µM) was added to react with remaining TCEP, the product has a characteristic absorbance maximum of 412 nm. The assay was adapted to a 96-well format using a standard absorbance range.

Results and Discussion

Aβ Exhibits Metal-Dependent and Independent Redox Activity

Figure 10:
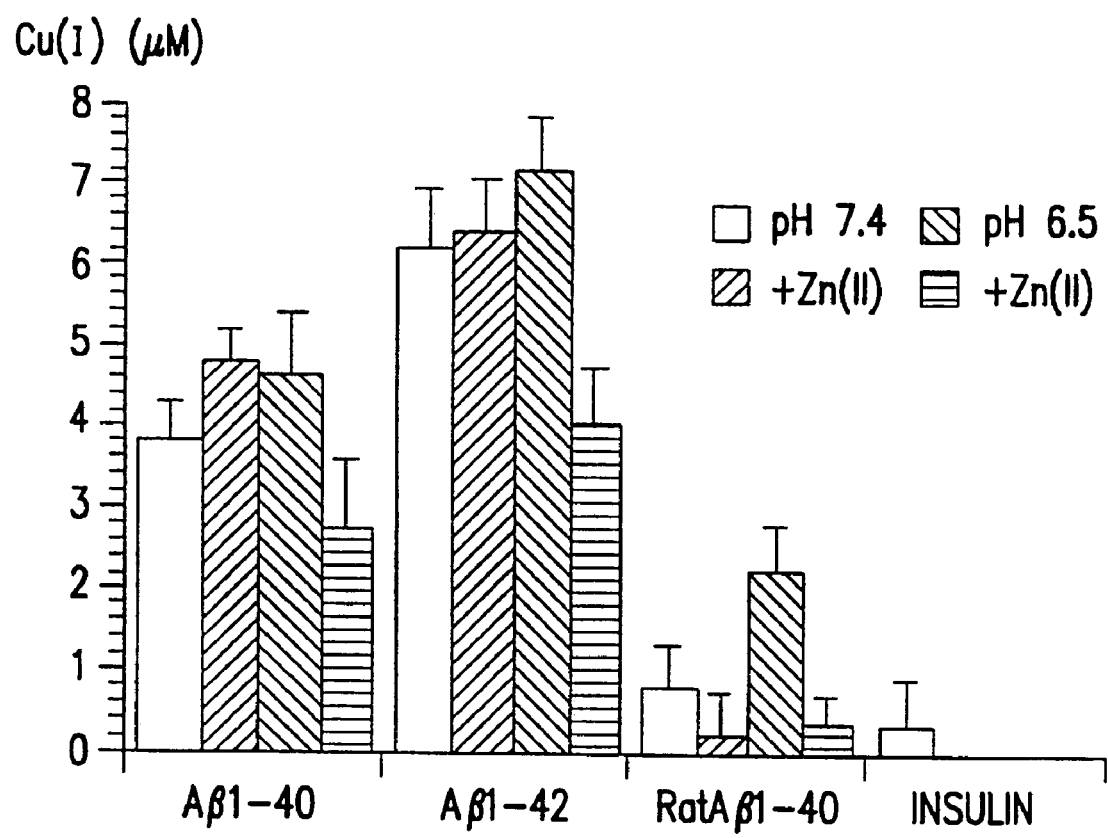
FIG. 10 is a graph showing $Cu^+$ generation by $A\beta$.
Figure 11:
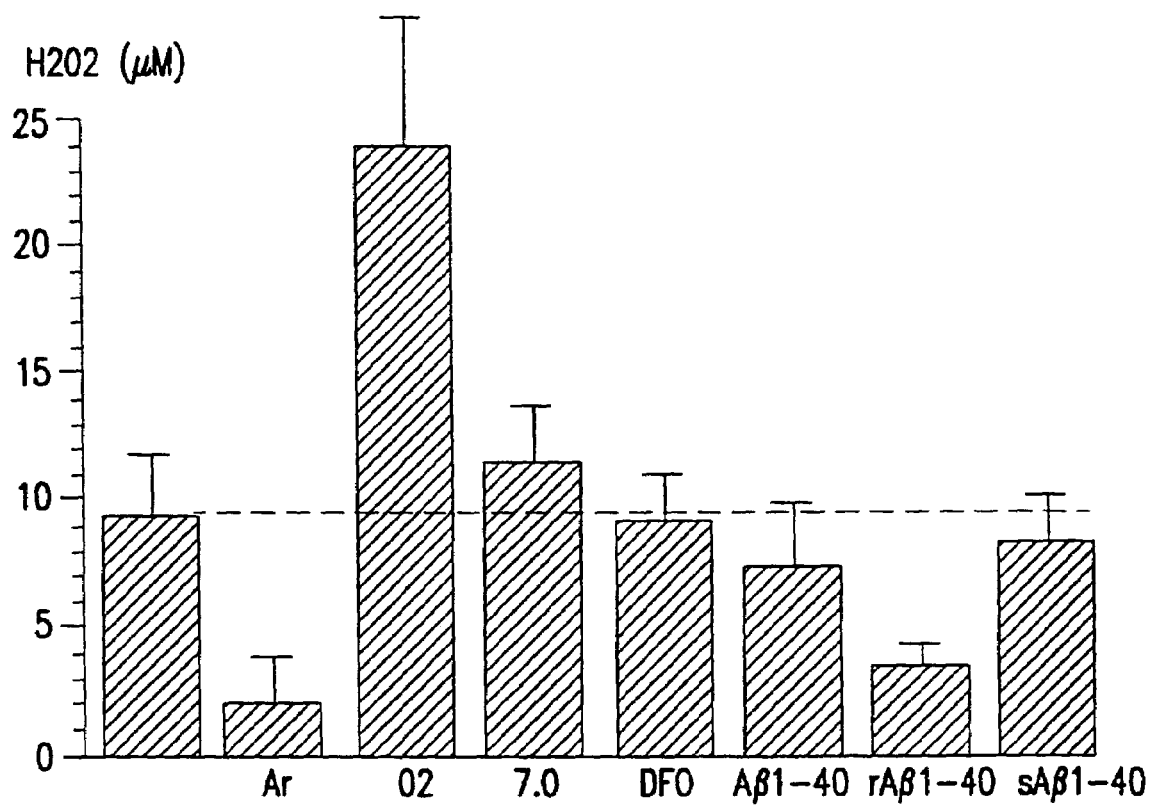
FIG. 11 is a graph showing $H_2O_2$ production by $A\beta$.

Because Aβ was observed to be covalently linked by Cu, the ability of the peptide to reduce metals and generate hydroxyl radicals was studied. The bathocuproine and bathophenanthroline reduced metal assay technique employed by Multhaup et al. was used in order to determine that APP itself possesses a Cu$^{2+}$ reducing site on its ectodomain (Multhaup, G., et al., Science 271:1406 (1996)). It has been discovered that Aβ possesses a striking ability to reduce both Fe$^{3+}$ to Fe$^{2+}$, and Cu$^{2+}$ to Cu$^+$, modulated by Zn$^{2+}$ and pH (6.6–7.4) (See FIG. 10). It is of great interest that the relative redox activity of the peptides studied correlates so well with their relative pathogenicity viz Aβ$_{1-42}$>Aβ$_{1-40}$>ratAβ in all redox assays studied. Since one of the caveats in using the reduced metals assay is that the detection agents can exaggerate the oxidation potential of Cu$^{2+}$ or Fe (III), other redox products were explored by assays where no metal ion indicators were necessary. It was discovered that hydrogen peroxide was rapidly formed by Aβ species (FIG. 11). Thus, Aβ produces both H$_2$O$_2$ and reduced metals whilst also binding zinc. Structurally, this is difficult to envisage for a small peptide, but we have recently shown that Aβ is dimeric in physiological buffers. Since H$_2$O$_2$ and reduced metal species are produced in the same vicinity, these reaction products are liable to produce the highly toxic hydroxyl radical by Fenton chemistry, and the formation of hydroxyl radicals from these peptides has now been shown with the thiobarbituric acid assay. The formation of hydroxyl radicals correlates with the covalent polymerization of the peptide (FIG. 9) and can be blocked by hydroxyl scavengers. Thus the concentrations of Fe, Cu, Zn & H$^+$ in the brain interstitial milieu could be important in facilitating precipitation and neurotoxicity for Aβ by direct (dimer formation) and indirect (Fe$^{2+}$/Cu$^+$ and H$_2$O$_2$ formation) mechanisms.

Figure 6:
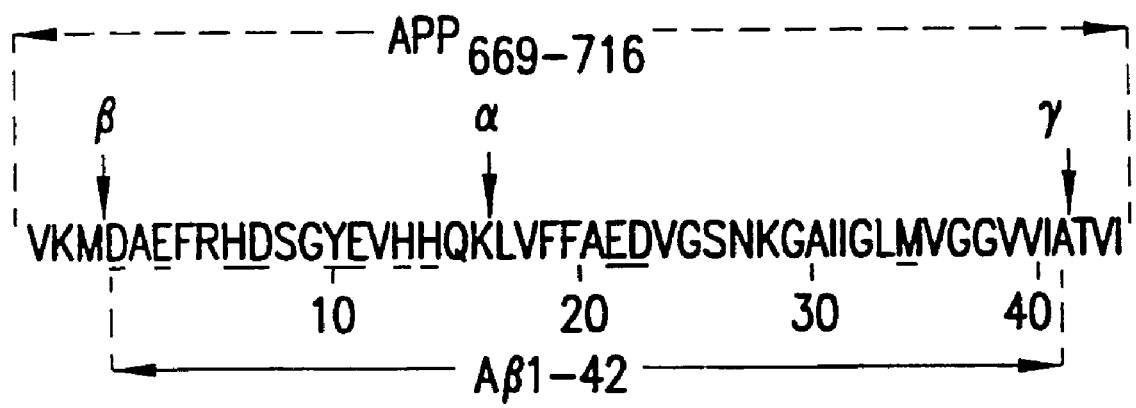
FIG. 6 shows the amino acid sequence of $APP_{669-716}$ near $A\beta_{1-42}$ (SEQ ID NO:1). Rat $A\beta$ is mutated (R5G, Y10F, H13R; bold). Possible metal-binding residues are underlined.
Figure 7:
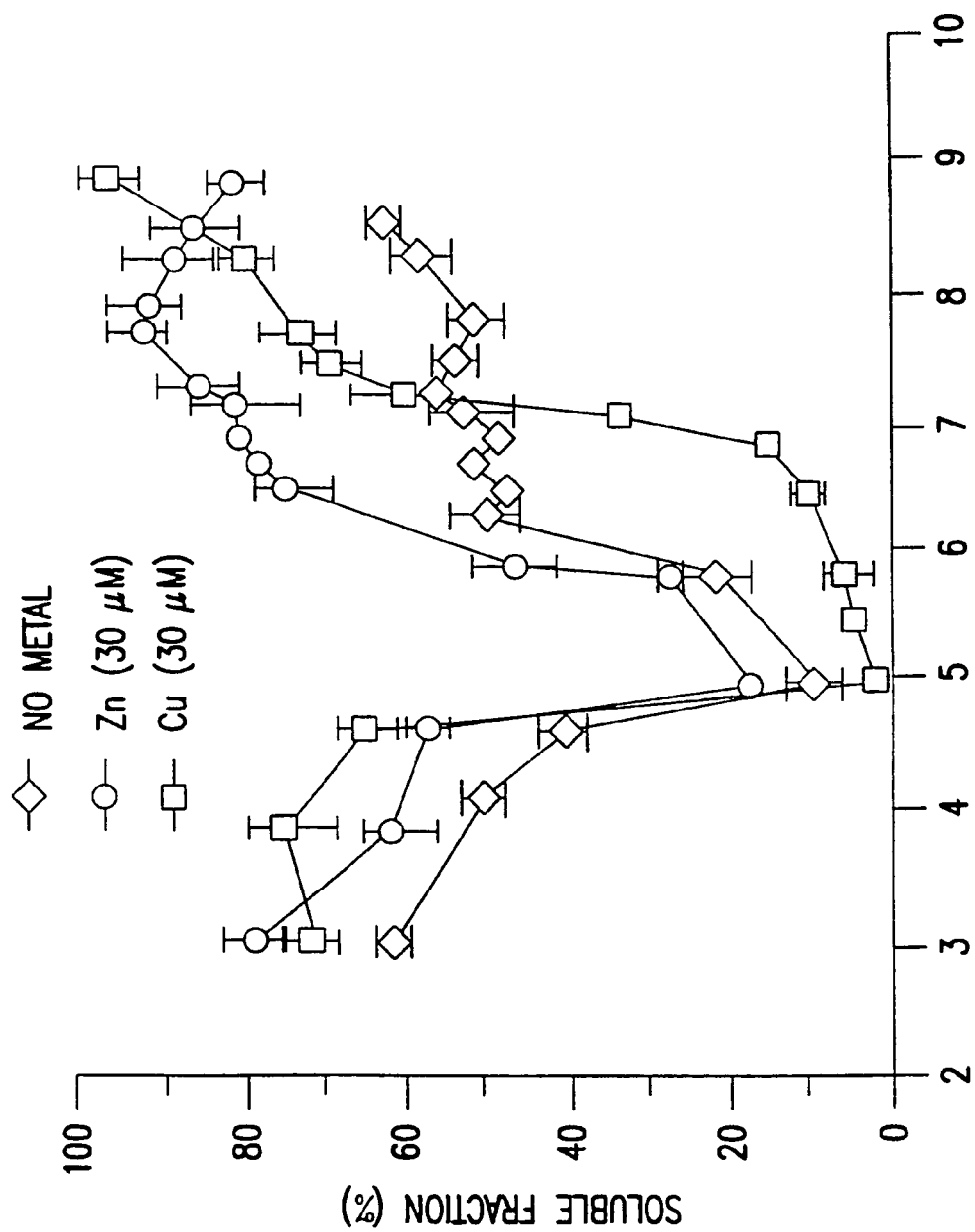
FIG. 7 is a graph showing the effects of pH, $Zn^{2+}$ or $Cu^{2+}$ upon $A\beta$ deposit formation.

H$_2$O$_2$ production by Aβ explains the mechanism by which H$_2$O$_2$ has been described to mediate neurotoxicity (Behl, C.

et al., Cell 77:827 (1994)), previously thought to be the product of cellular overproduction alone. Interestingly, the scrambled Aβ peptide (same size and residue content as FIG. 6) produces appreciable $H_2O_2$ but no hydroxyl radicals. This is because the scrambled Aβ peptide is unable to reduce metal ions. This leads to the conclusion that what makes Aβ such a potent neurotoxin is its capacity to produce both reduced metals and $H_2O_2$ at the same time. This "double whammy" can then produce hydroxyl radicals by the Fenton reaction, especially if the $H_2O_2$ is not rapidly removed from the vicinity of the peptide. Catalase and glutathione peroxidase are the principal means of catabolizing $H_2O_2$, and their levels are low in the brain, especially in AD, perhaps explaining the propensity of Aβ to accumulate in brain tissue.

FIG. 11 shows that the production of $H_2O_2$ is oxygen dependent, and further investigation has indicated that Aβ can spontaneously produce the superoxide radical ($O_2^-$) in the absence of metal ions. This property of Aβ is particularly exaggerated in the case of $Aβ_{1-42}$, probably explaining why this peptide is more neurotoxic and more enriched than $Aβ_{1-40}$ in amyloid. $O_2^-$ generation will be subject to spontaneous dismutation to generate $H_2O_2$, however, this is a relatively slow reaction, although it may account for the majority of the $H_2O_2$ detected in our Aβ assays. $O_2^-$ is reactive, and the function of superoxide dismutase (SOD) is to accelerate the dismutation to produce $H_2O_2$ which is then catabolized by catalase and peroxidases into oxygen and water. The most abundant form of SOD is Cu/Zn SOD, mutations of which cause another neurodegenerative disease, amyotrophic lateral sclerosis (Rosen, D., et al., *Nature* 364:362 (1993)). Since Aβ, like Cu/Zn SOD, is a dimeric protein that binds Cu and Zn and reduces $Cu^{2+}$ and $Fe^{3+}$, we studied the $O_2^-$ dismutation behavior of Aβ in the µsec time-scale using laser pulse photolysis. These experiments have shown that Aβ exhibits Fe/Cu-dependent SOD-like activity with rate constants of dismutation at $≈10^8 M^{-1} sec^{-1}$, which are strikingly similar to SOD. Hence, Aβ appears to be a good candidate to possess the same function as SOD, and therefore may function as an antioxidant. This may explain why oxidative stresses cause it to be released by cells (Frederikse, P. H., et al., *Journal of Biological Chemistry* 271: 10169 (1996)). However, if $Aβ_{1-42}$ is involved in the reaction to oxidative stress, or if the $H_2O_2$ clearance is compromised at the cellular level, Aβ will accumulate, recruiting more $O_2$ and producing more $O_2^-$ leading to a vicious cycle and localizing tissue peroxidation damage and protein cross-linking.

Example 3

Cell Culture and Cytotoxic Assays

Several different assays may be utilized to determine whether a candidate pharmacological agent identified by any of the above-summarized assays is capable of altering the neurotoxicity of Aβ. The first is the MTT assay, which measures the reduction of 3-(4,5-dimethylthiazol-2-yl)-2,5, diphenyl tetrazolium bromide (MTT) to a colored formazon (Hansen et al., *J Immunol Methods,* 119:203–210 (1989)). A second cytotoxic assay is the release of lactic dehydrogenase (LD11) from cells, a measurement routinely used to quantitate cytotoxicity, in cultured CNS cells (Koh, J. Y. and D. W. Choi, *J. Neurosci. Meth.* 20:83–90 (1987). While MTT measures primarily early redox changes within the cell reflecting the integrity of the electron transport chain, the release of LDH is thought to be through cell lysis. A third assay is visual counting in conjunction with trypan blue exclusion. Yet another assay is the Live/Dead EukoLight Viability/Cytotoxicity Assay (Molecular Probes, Inc., Eugene, Oreg.).

Example 4

Therapeutic Agents for Inhibition of Metal-Mediated Production of Reactive Oxygen Species Materials and Methods a) Synthesis of Peptides Synthetic Aβ peptides $Aβ_{1-40}$ and $Aβ_{1-42}$ were synthesized by the W. Keck Laboratory, Yale, Conn. In order to verify the reproducibility of the data obtained with these peptides, confirmatory data were obtained by reproducing experiments with these Aβ peptides synthesized and obtained from other sources: Glabe laboratory, University of California, Irvine, Calif. Multhaup Laboratory, University of Heidelberg, U.S. Peptides, Bachem, and Sigma. Rat Aβ was synthesized and characterized by the Multhaup Laboratory, University of Heidelberg. $Aβ_{1-28}$ was purchased from U.S. Peptides, Bachem, and Sigma. Aβ peptide stock solutions were prepared in chelex-100 resin (BioRad) treated water and quantified.

b) Metal Reduction Assay

The metal reduction assay was performed using a 96-well microtiter plate (Costar) based upon a modification of established protocols (Landers, J. W., et al., Amer. Clin. Path. 29:590 (1958); Landers. J. W. et al., *Clinica Chimica Acta* 3:329 (1958)). Polypeptides (10 µM) or Vitamin C (100 µM), metal ions (10 µM, $Fe(NO_3)_3$ or $Cu(NO_3)_2$), and reduced metal ion indicators, bathophenanthrolinedisulfonic acid (BP, for $Fe^{2+}$, Sigma, 200 µM) or bathocuproinedisulfonic acid (BC, for $Cu^+$, Sigma, 200 RM), were coincubated in phosphate buffered saline (PBS), pH 7.4, for 1 hr at 37° C. The metal ion solutions were prepared by direct dilution in the buffer from their aqueous stocks purchased from National Institute of Standards and Technology (NIST). Absorbances were then measured at 536 nm ($Fe^{2+}$-BP complex) and 483 nm ($Cu^+$-BC complex), respectively, using a 96-well plate reader (SPECTRAmax 250, Molecular Devices, Calif.). In control samples, both metal ion and indicator were present to determine the background buffer signal. As a further control, both metal ion and peptide were present in the absence of indicator to estimate the contribution of light scattering due to turbidity to the absorbance reading at these wavelengths. The net absorbances (ΔA) at 536 nm or 483 nm were obtained by deducting the absorbances from these controls from the absorbances generated by the peptide and metal in the presence of the respective indicator.

The concentrations of reduced metal ions ($Fe^{2+}$ or $Cu^+$) were quantified based on the formula: $Fe^{2+}$ or $Cu^+$ (~M) $=A*10^6/(L*M)$, where L is the measured equivalent vertical pathlength for a well of 300 µL volume as described in the instrument's specifications manual (0.856 cm for $Fe^{2+}$; 1.049 cm for $Cu^+$); M is the known molecular absorbance ($M^{-1} cm^{-1}$) which is 7124 (for $Fe^{2+}$-BP complex) or 2762 (for $Cu^+$-BC complex).

c) $H_2O_2$ Assay

The $H_2O_2$ assay was performed in a UV-transparent 96-well microtiter plate (Molecular Devices, CA), according to a modification of an existing protocol (Han, J. C., et al., *Anal. Biochem.* 234:107 (1996); Han et al., *Anal. Biochem.*

220: 5–10 (1994)). Polypeptides (10 µM) or Vitamin C (10 µM), Fe$^{3+}$ or Cu$^{2+}$ (1 µM) and a H$_2$O$_2$ trapping agent—Tris (2-Carboxyethyl)Phosphine Hydrochloride (TCEP, Pierce, 50 µLM)—were co-incubated in PBS buffer (300 µL), pH 7.4, for 1 hour at 37° C. Under identical conditions, catalase (Sigma, 100 U/mL) was substituted for the polypeptides, to serve as a control signal representing 0 µM H$_2$O$_2$. Following incubation, the unreacted TCEP was detected by 5,5-Dithiobis(2-Nitrobenzoic acid) (DTNB, Sigma, 50 KLM) which generates 2 moles of the coloured product. The reactions are:

TCEP+H$_2$O$_2$→TCEP=O+H$_2$O, then the remaining TCEP is reacted with DTNB:

TCEP+DTNB+H$_2$O→TCEP=O+2NTB (2-nitro-5-thiobenzoate).

The amount of H$_2$O$_2$ produced was quantified based on the formula: H$_2$O$_2$ (µM)=hA*106/(2*L*M), where hA is the absolute absorbance difference between a sample and catalase-only control at 412 nm wavelength; L=0.875 cm, the equivalent vertical pathlength obtained from the platereader manufacturer's specifications; M is the molecular absorbance for NTB (14150 M$^{-1}$ cm$^{-1}$ at 412 nm).

TCEP is a strong reducing agent, and, hence, will artifactually react with polypeptides that contain disulfide bonds. This was determined not to be a source of artifact for the measurement of H$_2$O$_2$ generation from Aβ, which does not possess a disulfide bond.

d) Estimation of O$_2^-$

The spectrophotometric absorption peak for O$_2^-$ is 250 nm where its extinction coefficient is much greater than that of H$_2$O$_2$ (Bielski et al., *Philos Trans R Soc Lond B Biol Sci.* 311: 473–482 (1985)). The production of O$_2^-$ was estimated by measuring the spectrophotometric absorption of polypeptides (10 µM, 300 µL) after incubation for one hour in PBS, pH 7.4, at 37° C., using a 96-well plate reader. The corresponding blank was the signal from PBS alone. An absolute baseline for the signal generated by the peptide was not achievable in this assay since the absorption peak for tyrosine (residue 10 of Aβ) is close (254 nm) to the absorption peak for O$_2^-$. However, attenuation of the absorbance by co-incubation with superoxide dismutase (100 U/mL) indicated that the majority of the absorbance signal was due to the presence of O$_2^-$.

e) Thiobarbituric Acid Reaction Substance (TBARS) Assay—OH.

The Thiobarbituric Acid-Reactive Substance (TBARS) assay for incubation mixtures with Fe$^{3+}$ or Cu$^{2+}$ was performed in a 96-well microtiter format modified from established protocols (Gutteridge et al. *Biochim. Biophys. Acta* 759: 38–41 (1983)). Aβ peptide species (10 µM) or Vitamin C (100 µM), were incubated with Fe$^{3+}$ or Cu$^{2+}$ (1 µM) and deoxyribose (7.5 mM, Sigma) in PBS, pH 7.4. Following incubation (37° C., 1 hour), glacial (17 M) acetic acid and 2-thiobarbuic acid (1%, w/v in 0.05 M NaOH, Sigma) were added and heated (100° C., 10 min). The final mixtures were placed on ice for 1–3 minutes before absorbances at 532 nm were measured. The net absorbance change for each sample were obtained by deducting the absorbance from a control sample consisting of identical chemical components except for the Vitamin C or Aβ peptides.

Results and Discussion

Oxygen radical involvement in human aging, the predominant risk factor for Alzheimer's disease (AD), was first proposed by Harman in 1956 (Harman, D., *J Gerontol.* 11:298 (1956)) and increasing evidence has implicated oxidative stress in the pathogenesis of AD. Apart from metabolic signs of oxidative stress in AD-affected neocortex such as increased glucose-6-phosphate dehydrogenase activity (Martins, R. N., et al., *J. Neurochem.* 46:1042–1045 (1986)) and increased heme oxygenase-1 levels (Smith, M. A., et al., *Am. J. Pathol.* 145:42 (1994)), there are also numerous signs of oxygen radical-mediated chemical attack such as increased protein and free carbonyls (Smith, C. D., et al., *Proc. Natl. Acad. Sci. USA* 88:10540 (1991); Hensley, K., et al., *J. Neurochem.* 65:2146 (1995); Smith, M. A., et al., *Nature* 382:120 (1996)), lipid peroxidation adducts (Palmer, A. M. & Burns, M. A., *Brain Res.* 645:338 (1994); Sayre, L. M. et al., *J. Neurochem.* 68:2092 (1997)), peroxynitrite-mediated protein nitration (Good, P. F., et al., *Am. J. Pathol.* 149:21 (1996)); Smith, M. A., et al., *Proc. Natl. Acad. Sci. USA* 94:9866 (1997)), and mitochondrial and nuclear DNA oxidation adducts (Mecocci, P., et al., *Ann. Neurol.,* 34:609–616 (1993); Mecocci, P., et al., *Ann. Neurol.,* 36:747–751 (1994)). Recently, treatment of individuals with the antioxidant vitamin E has been reported to delay the progression of clinical AD (Sano, M. et al., *N. Engl. J. Med.* 336:1216 (1997)).

A relationship seems likely to exist between the signs of oxidative stress and the characteristic Aβ collections (Glenner, G. G. & Wong, C., *Biochem. Biophys. Res. Commun.* 120:885 (1984)) found in the cortical interstitium and cerebrovascular intima media in AD. The brain regional variation of oxidation biomarkers corresponds with amyloid plaque density (Hensley, K., et al., *J. Neurochem.* 65:2146 (1995)). Indeed, neurons cultured from subjects with Down's syndrome, a condition complicated by the invariable premature deposition of cerebral Aβ (Rumble, B., et al., *N. Engl. J. Med.* 320:1446 (1989)) and the overexpression of soluble Aβ1-42 in early life (Teller, J. K., et al., *Nature Medicine* 2:93 (1996)), exhibit lipid peroxidation and apoptotic cell death caused by increased generation of hydrogen peroxide (Busciglio, J. & Yankner, B. A., *Nature* 378:776 (1995)). Synthetic Aβ peptides have been shown to induce lipid peroxidation of synaptosomes (Butterfield, D. A., et al., *Biochem. Biophys. Res. Commun.* 200:710 (1994)), and to exert neurotoxicity (Behl, C., et al., *Cell* 77:817 (1994); Mattson, M. P., et al., *J. Neurochem.* 65:1740 (1995)) or vascular endothelial toxicity through a mechanism that involves the generation of cellular superoxide/hydrogen peroxide (O$_2^-$/H$_2$O$_2$) and is abolished by the presence of SOD (Thomas, T., et al., *Nature* 380:168 (1996) or catalytic synthetic O$_2^-$/H$_2$O$_2$ scavengers (Bruce, A. J., et al., *Proc. Natl. Acad. Sci. USA* 93:2312 (1996)). Antioxidant vitamin E and the spin-trap compound PBN have been shown to protect against Aβ-mediated neurotoxicity in vitro (Goodman, Y., & Mattson, M. P., *Exp. Neurol.* 128:1 (1994); Harris, M. E., et al., *Exp. Neurol.* 131:193 (1995)).

Aβ, a 39–43 amino acid peptide, is produced (Haass, C., et al., *Nature* 359:322 (1992); Seubert, P., et al., *Nature* 359:325 (1992); Shoji, M., et al., *Science* 258:126 (1992)) by constitutive cleavage of the amyloid protein precursor (APP) (Kang, J., et al., *Nature* 325:733 (1987); Tanzi, R. E., et al., *Nature Genet* (1993)) as a mixture of polypeptides manifesting carboxyl-terminal heterogeneity. Aβ-40 is the major soluble Aβ species in biological fluids (Vigo-Pelfrey, C., et al., *J. Neurochem.* 61:1965 (1993)) and Aβ$_{1-42}$ is a minor soluble species, but is heavily enriched in interstitial plaque amyloid (Masters, C. L., et al., *Proc. Natl. Acad. Sci: USA* 82:4245 (1985); Kang, J. et al., *Nature* 325:733 (1987); Prelli, F., et al., *J. Neurochem.* 51:648 (1988); Roher et al., *J. Cell Biol.* 107:2703–2716 (1988); Roher et al. *J. Neuro-* chem. 61:1916–1926 (1993); Miller, D. L., et al., *Arch. Biochem. Biophys.* 301:41 (1993)). The discovery of pathogenic mutations of APP close to or within the Aβ domain (van Broeckhoven, C., et al., *Science* 248:1120 (1990); Levy, E., et al., *Science* 248:1124 (1990); Goate, A., et al., *Nature* 349:704 (1991); Murrell, J., et al., *Science* 254:94 (1991); Mullan, M., et al., *Nature Genet* 1:345 (1992)) indicates that the metabolism of Aβ is involved with the pathophysiology of this predominantly sporadic disease. Familial AD-linked mutations of APP, presenilin-1 and presenilin-2 correlate with increased cortical amyloid burden and appear to induce an increase in the ratio of $A\beta_{1-42}$ as part of their common pathogenic mechanism (Suzuki, N., et al., *Science* 264:1336 (1994); Scheuner et al., *Nat Med.,* 2(8):864–870 (1996); Citron, M., et al., *Nature Medicine* 3:67 (1997)). However, the mechanism by which $A\beta_{1-42}$ exerts more neurotoxicity than $A\beta_{1-40}$ and other Aβ peptides (Doré, S., et al., *Proc. Natl. Acad. Sci. USA* 94:4772 (1997)) remains unclear.

One of the models proposed for Aβ neurotoxicity is based on a series of observations of Aβ-generated oxyradicals generated by a putative Aβ peptide fragmentation mechanism which is $O_2$-dependent, metal-independent and involves the sulfoxation of the methionine at Aβ residue 35 (Butterfield, D. A., et al., *Biochem. Biophys. Res. Commun.* 200:710 (1994); Hensley, K., et al., *Proc. Natl. Acad. Sci. USA* 91:3270 (1994); Hensley, K., et al., *Ann N Y Acad Sci.,* 786: 120–134 (1996). $A\beta_{25-35}$ peptide has been reported to exhibit $H_2O_2$-like reactivity towards aqueous $Fe^{2+}$, nitroxide spin probes, and synaptosomal membrane proteins (Butterfield, D. A., et al., *Life Sci.* 58:217 (1996)), and $A\beta_{1-40}$ has also been reported to generate the hydroxyl radical by mechanisms that are unclear (Tomiyama, T., et al., *J. Biol. Chem.* 271:6839 (1996)). However, there has been no quantitative appraisal of the ROS-generating capacity of $A\beta_{1-42}$ versus that of $A\beta_{1-40}$ and other Aβ variants, to date.

Aβ is a metal binding protein which saturably binds zinc via a histidine-mediated specific high affinity site ($K_D$=107 nM) as well as by low affinity binding ($K_D$=5.2 μM). The high-affinity zinc binding site was mapped to a stretch of contiguous residues between positions 6–28 of the Aβ sequence (Bush, A. I., et al., *J. Biol. Chem.* 269:12152 (1994)). Concentrations of zinc÷1 μM rapidly induce aggregation of human $A\beta_{1-40}$ solutions (Bush, A. I., et al., *Science* 265:1464 (1994)), in reversible manner which is dependent upon the dimerization of peptide in solution, its alpha-helical content, and the concentration of NaCl (Huang, X. et al., *J. Biol. Chem.* 272:26464–26470 (1997)). Rat/mouse $A\beta_{1-40}$ ("rat Aβ" with substitutions o $R_5\rightarrow G$, $Y_{10}f\rightarrow F$, and $H_{13}\rightarrow R$, as compared to human Aβ) binds zinc less avidly (a single binding site, $K_A$=3.8 μM) and, unlike the human peptide, is not precipitated by zinc at concentrations ≤25 μM. Since zinc is concentrated in the neocortex, we hypothesized that the differential solubility of the rat/mouse Aβ peptide in the presence of zinc may explain the scarcity with which these animals form cerebral Aβ deposits (Johnstone, E. M., et al., *Mol. Brain Res.* 10:299 (1991); Shivers, B. D., et al., *EMBO J.* 7:1365 (1988)).

We have also observed interactions of Aβ with $Cu^{2+}$, which stabilizes dimerization of $A\beta_{1-40}$ on gel chromatography (Bush, A. I., et al., *J. Biol. Chem.* 269:12152 (1994)), and which binds to the peptide with an affinity estimated to be in the low picomolar range. $Fe^{2+}$ has been observed to induce partial aggregation of Aβ (Bush, A. I., et al., *Science* 268:1921 (1995)), and to induce SDS-resistant polymerization of the peptide (Dyrks, T., et al., *J. Biol. Chem.* 267: 18210–18217 (1992)). We hypothesized that the interactions of Aβ with Fe and Cu may contribute to the genesis of the oxidation insults that are observed in the AD-affected brain. This is because $Fe^{3+}$ and $Cu^{2+}$ are redox-active metal ions that are concentrated in brain neurons, and may participate in the generation of ROS by transferring electrons in their reduced state (reviewed in Markesbery, 1997).

The levels of Cu and Fe, and their binding proteins, are dysregulated in AD (Diebel, M. A., et al., *J Neurol. Sci.* 143:137 (1996); Good, P. F., et al., *Ann. Neurol.* 31:286 (1992); Robinson, S. R., et al., *Alzheimer's Research* 1:191 (1995); Thompson, C. M., et al., *Neurotoxicology* 9:1 (1988); Kennard, M. L., et al., *Nature Medicine* 2:1230 (1996); Connor, J. R., et al., *Neurosci. Lett.* 159:88 (1993)) and may therefore lead to conditions that could promote ROS production. While a direct role for Aβ in metal-dependent ROS generation has not been described, the peptide's physiochemical interation with transition metals, the presence of ferritin (Grudke-Iqbal, I., et al., *Acta Neuropathol.* 81:105 (1990)) and redox reactive iron (Smith, M. A., et al., *Proc. Natl. Acad. Sci. USA* 94:9866 (1997)) in amyloid lesions, and the facilitation of $A\beta_{1-40}$ neurotoxicity in cell culture by nanomolar concentrations of iron (Schubert, D. & Chevion., M., Biochem. Biophys. Res. Commun. 216:702 (1995)), collectively support such a possibility.

We report the simultaneous production of $H_2O_2$ and reduced metal ions by Ab, with the consequent generation of the hydroxyl radical. The amounts of reduced metal and ROS were both greatest when generated by $A\beta_{1-42}>A\beta_{1-40}>>$rat $A\beta_{1-40}$, $A\beta_{40-1}$ and $A\beta_{1-28}$, a chemical relationship that correlates with the relative neurotoxicity of these peptides. These data describe a novel, $O_2^-$ and biometal-dependent pathway of ROS generation by Alzheimer Aβ peptides which may explain the occurrence of oxidative stress in AD brain.

a) Metal Ion Reduction by Aβ Peptides

Figure 13A:
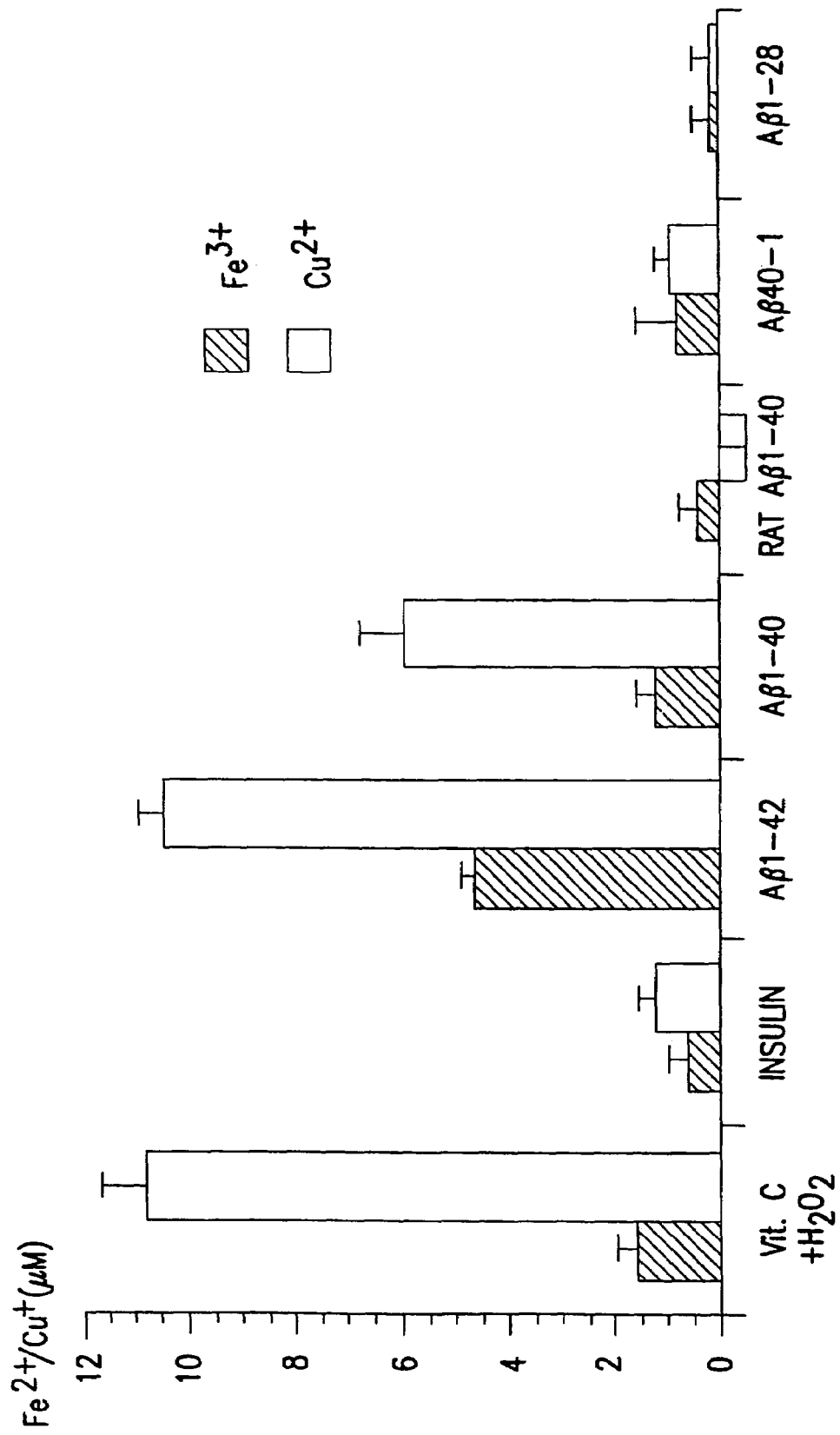
FIGS. 13A and 13B are graphical representations showing $Fe^{3+}$ or $Cu^{2+}$ reduction by $A\beta$ peptides.

To determine whether Aβ peptides possess metal-reducing properties, the ability of Aβ peptides (Example 1) to reduce $Fe^{3+}$ and $Cu^{2+}$, compared to Vitamin C and other polypeptides (Example 2) was measured. Vitamin C, serving as a positive control, reduced $Cu^{2+}$ efficiently (FIG. 13A). However, the reduction of $Cu^{2+}$ by $A\beta_{1-42}$ was as efficient, reducing all of the available $Cu^{2+}$ during the incubation period. $A\beta_{1-40}$ reduced 60% of the available $Cu^{2+}$, whereas rat $A\beta_{1-40}$ and $A\beta_{1-28}$ reduced no $Cu^{2+}$. The reduction of $Cu^{2+}$ by BSA (25%) and insulin (10%) was less efficient than that by the human Aβ peptides, and was not unexpected since these polypeptides possess cysteine residues and reduce $Cu^{2+}$ in the process of forming disulfide bonds.

$Fe^{3+}/Fe^{2+}$ has lower standard reduction potential (0.11 V) than $Cu^{2+}/Cu^+$ (0.15 V) does under our experimental conditions (Miller, D. M., et al., *Free Radical Biology & Medicine* 8:95 (1990)), and, in general, $Fe^{3+}$ was reduced with less efficiency by Vitamin C and the polypeptides that reduced $Cu^{2+}$. Vitamin C reduced 15% of the available $Fe^{3+}$, however $A\beta_{1-42}$ was the most efficient (50%) of the agents tested for $Fe^{3+}$ reduction, reducing more $Fe^{3+}$ in the incubation period than Vitamin C (15%), $A\beta_{1-40}$ (12%) and BSA (8%). Rat $A\beta_{1-40}$, $A\beta_{1-28}$ and insulin did not significantly facilitate the reduction of $Fe^{3+}$. Analysis of $A\beta_{1-42}$ and $A\beta_{1-40}$, after incubation with $Cu^{2+}$ and $Fe^{3+}$ under these conditions revealed that there was no apparent mass modification of the peptides on mass spectrometry, and no change in its migration pattern on sodium dodecyl sulfate polyacrylamide gel electrophoresis (SDS PAGE), nor evidence for increased aggregation of the peptides by turbidometry or sedimentation analysis, suggesting that the peptides were not consumed or modified during the reduction reaction. Under these conditions, the complete kinetics of the peptide-mediated reactions cannot be appreciated (the presence of $A\beta_{1-42}$ induced the total consumption of the $Cu^{2+}$ substrate within the incubation period), but a striking relationship exists between the relative efficiencies of the various $A\beta$ peptides to reduce $Cu^{2+}/Fe^{3+}$ in this system and their respective participation in amyloid neuropathology.

Figure 13B:
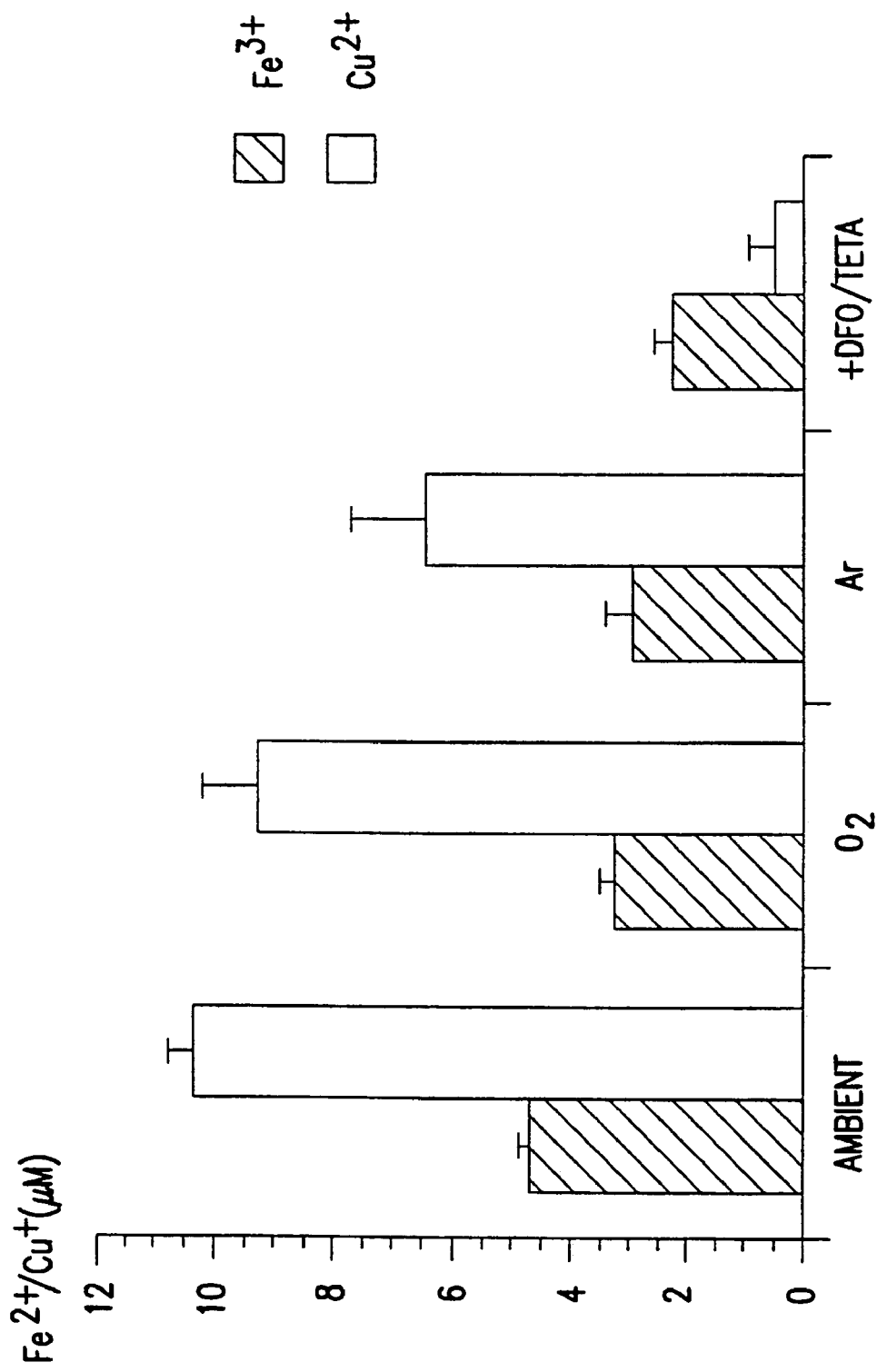

Since the dissolved $O_2$ in the buffer vehicle may be expected to react with the reduced metals being generated [Reaction (1)], the effect of modulating the $O_2$ tension in the buffer upon the generation of reduced metals by the $A\beta$ peptides (FIG. 13B) was examined. Prior to the addition of Vitamin C or polypeptide, the buffer vehicle was continuously bubbled for 2 hours at 20° C. with 100% $O_2$ to create conditions of increased $O_2$ tension, or Argon to create anaerobic conditions. Increasing the $O_2$ tension slightly reduced the levels of reduced metals being detected, probably due to the diversion of a fraction of the $Fe^{2+}/Cu^+$ being generated to Reaction (1), and, if $H_2O_2$ is being produced as a product of Reaction (2), the recruitment of $Fe^{2+}/Cu^+$ into the Fenton reaction [Reaction (3)]. However, performing the reaction under anaerobic (Argon purged) conditions also slightly reduced the levels of reduced metals being detected. This may be because some of the reduction of $Fe^{3+}/Cu^{2+}$ is due to reaction with $O_2^-$:

$$M^{(n+1)+} + O_2^- \rightarrow M^{n+} + O_2 \quad \text{Reaction (5)}$$

To determine whether the reduction of metal ions in the presence of $A\beta$ was due to the action of the peptide or the generation of $O_2^-$ by the peptide, the effects of metal ion chelators on the generation of reduced metal ions (FIG. 13B) was studied. It was found that coincubation of $A\beta_{1-42}$ with the relatively $Fe^{3+}$-specific chelator desferrioxamine (DFO) under ambient oxygenation conditions nearly halved the production of $Fe^{2+}$. Coincubation of $A\beta_{1-42}$ with the high-affinity $Cu^{2+}$ chelator TETA abolished 95% of the $Cu^+$ generated by the peptide under ambient oxygenation conditions. These data indicate that the majority of the $Cu^+$ and a significant amount of the $Fe^{2+}$ produced by $A\beta_{1-42}$ are due to the direct action of the peptide and not indirectly due to the production of $O_2^-$.

The inhibitory effects of chelation upon $A\beta$-mediated reduction of metal ions indicates that $A\beta$ probably directly coordinates $Fe^{3+}$ and $Cu^{2+}$, and also that these chelating agents are not potentiating the redox potential of the metals ions, suggested to be an artifactual mechanism for the generation of reduced metal species (Sayre, L. M. et al., Science 274:1933 (1996)). The reasons for DFO being less effective than TETA in attenuating metal reduction may relate to the respective (unknown) binding affinities for $Fe^{3+}$ and $Cu^{2+}$ to the $A\beta$ peptide, the stereochemistry of the coordination of the metal ions by the peptide, and the abilities of the chelating agents to affect electron transfer after coordinating the metal ion.

The reduction of metal ions by $A\beta$ must leave the peptide, at least transiently, radicalized, in agreement with the electron paramagnetic resonance (EPR) findings of Hensley et al., Proc. Natl. Acad. Sci. 91:3270 (1994). In their report, DFO, EDTA or Chelex 100 could not abolish the EPR signal generated by $A\beta_{25-35}$ in PBS, leading these investigators to conclude that the radicalization of $A\beta$ was metal-independent. However, the inventors have found that after treatment with Chelex 100 the concentrations of Fe and Cu in PBS are still as high as ≈0.5 μM (8), which could be sufficient to induce the radicalization of the peptide after metal reduction. Since DFO does not abolish the reduction of $Fe^{3+}$ by $A\beta_{1-42}$ (FIG. 13B), and since EDTA has been observed to potentiate Fe-mediated Fenton chemistry (Samuni et al., Eur. J. Biochem. 13 7:119–124(1983)), it is suspected that Hensley and colleagues may have inadvertently overlooked the contribution of metal reduction to $A\beta$-mediated radical formation.

Rat $A\beta_{1-40}$ did not reduce metal ions, and has been shown to have attenuated binding of $Zn^{2+}$ (Bush et al., Science, 265:1464 (1994)). A similar attenuation of $Cu^{2+}$ and $Fe^{3+}$ binding by rat $A\beta_{1-40}$ compared to human $A\beta_{1-40}$ is anticipated. These data also indicate that the rat $A\beta$ substitutions in human $A\beta$'s zinc binding domain towards the peptide's amino terminus (Bush et al., J. Biol. Chem., 269:12152 (1994)) involve residues that mediate the metal-reducing properties of the peptide. However, the hydrophobic carboxyl-terminal residues were also critical to the reduction properties of $A\beta$. That $A\beta_{1-28}$ did not reduce metal ions indicates that an intact $Zn^{2+}$-binding site (Bush et al., J. Biol. Chem. 269:12152 (1994)) is insufficient to facilitate the metal reduction reaction. The mechanism by which the two additional hydrophobic residues (Ile and Ala) on $A\beta_{1-42}$ so substantially enhance the peptide's redox activity compared to $A\beta_{1-40}$ is still unclear.

It has been observed that sulfoxation of the methionine residue at $A\beta$ position 35 accompanies the EPR changes seen during the incubation of $A\beta_{25-35}$ for 3 hours in PBS at 37° C. (Hensley, K., et al., Ann N Y Acad Sci., 786:120–134 (1996)), however, no evidence was found for a modification of $A\beta_{1-40}$ and $A\beta_{1-42}$ after mass spectrophotometric examination of the peptides incubated under conditions as described. Therefore, $A\beta$-mediated metal reduction, and the subsequent $A\beta$-mediated redox reactions described below, appear to be achieved by a mechanism that differs from that previously reported.

b) Production of $H_2O_2$ by $A\beta$ Peptides

Figure 14A:
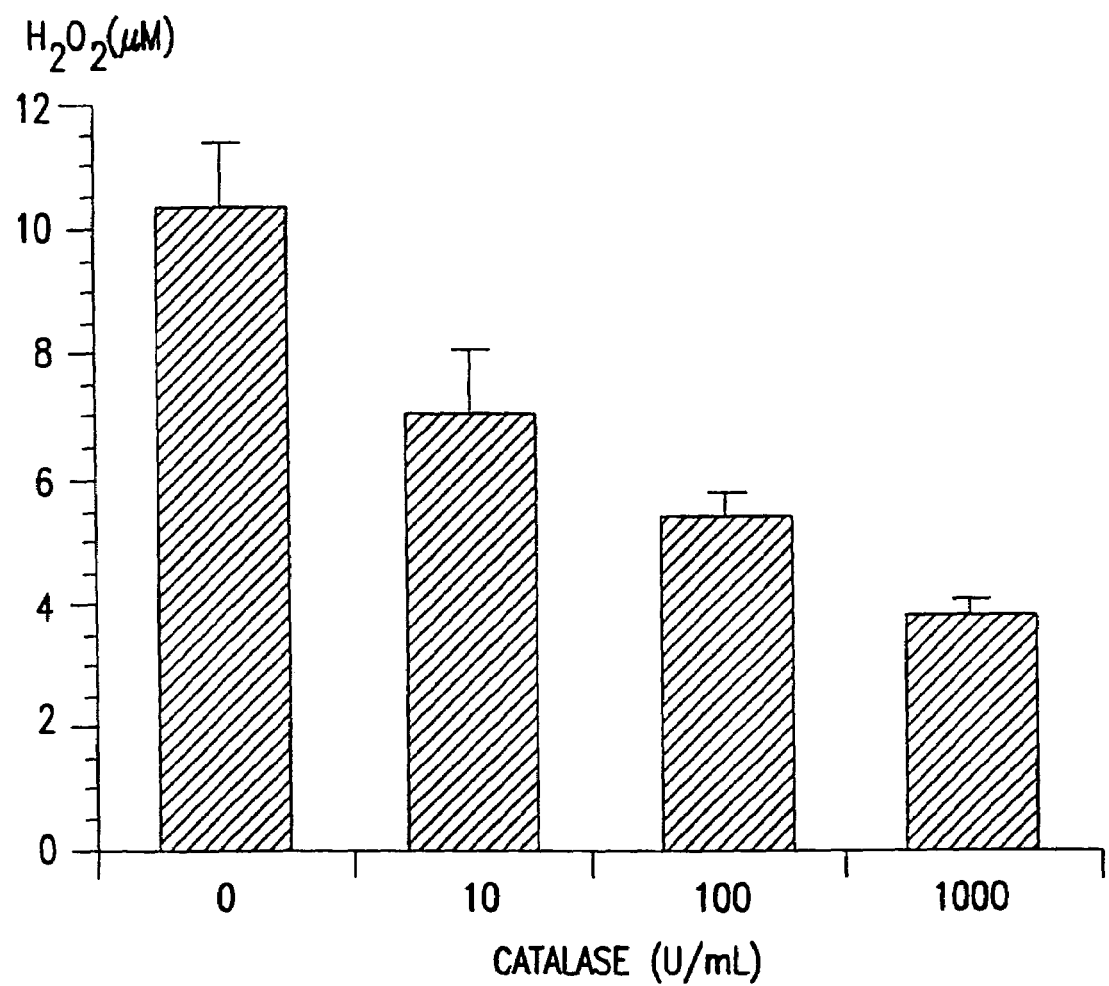
FIGS. 14A–14E are graphical representations showing production of $H_2O_2$ from the incubation of $A\beta$ in the presence of substoichiometric amounts of $Fe^{3+}$ or $Cu^{2+}$.
Figure 14B:
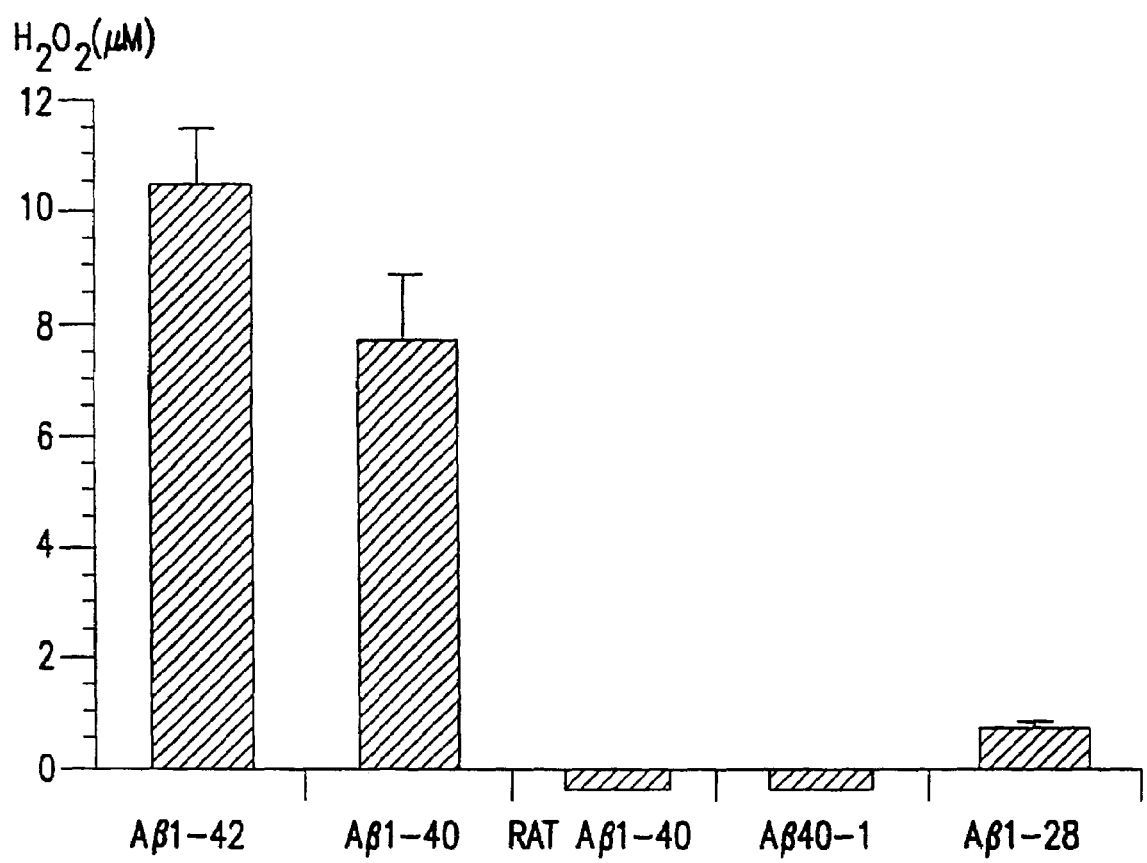

The reduced metal ions produced by $A\beta$ were expected to generate $O_2^-$ and $H_2O_2$ by Reactions (1) and (2). To study this, a novel assay was developed (Example 2) which detected the generation of 10 μM $H_2O_2$ by $A\beta_{1-42}$ in the presence of 1 μM $Fe^{3+}$ under ambient $O_2$ conditions (FIG. 14A). To validate the assay, coincubation with catalase was observed to abolish the $H_2O_2$ signal in a dose dependent manner. The amount of $H_2O_2$ produced by the various $A\beta$ peptides was studied, and observed that the order of the production of $H_2O_2$ by the $A\beta$ variants was $A\beta_{1-42} > A\beta_{1-40} >>$ rat $A\beta_{1-40} – A\beta_{1-28}$ (FIG. 14B), paralleling the amounts of metal reduction by the same peptides (FIG. 13A).

Figure 14C:
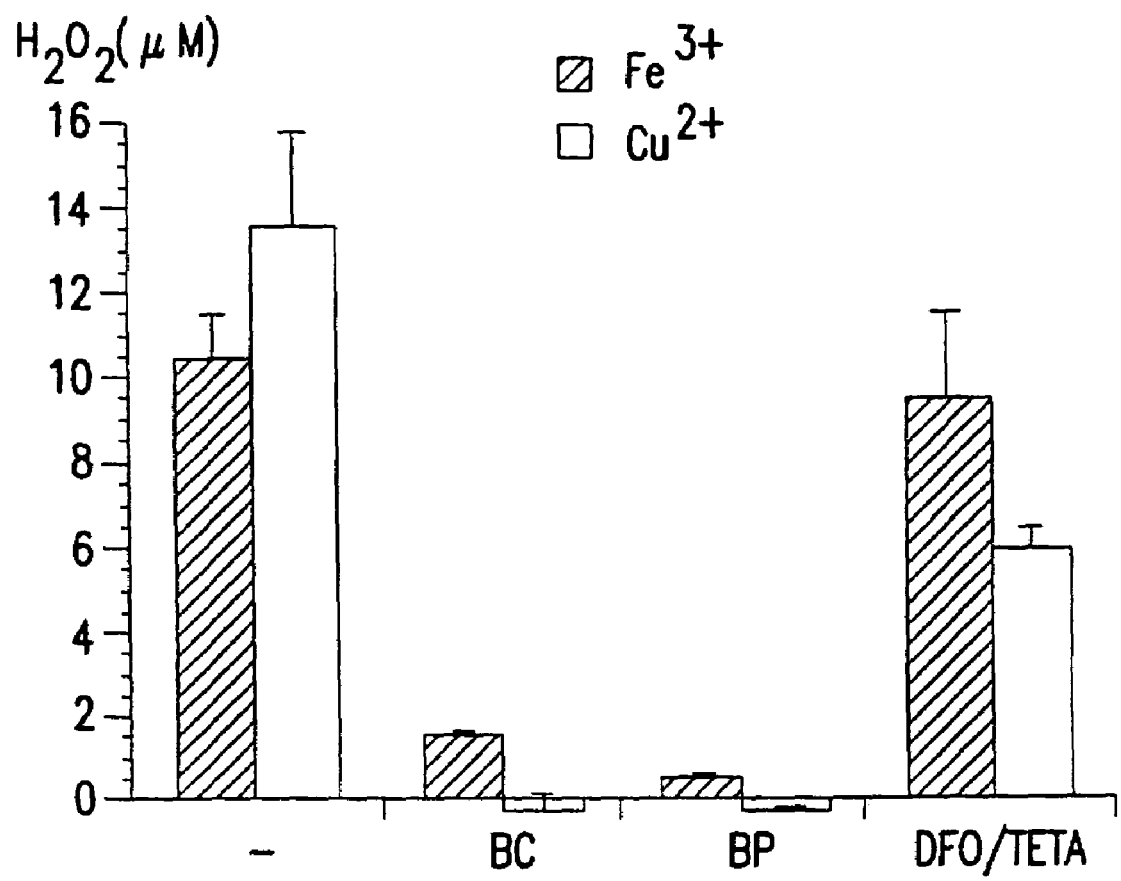

$H_2O_2$ formation is likely to be mediated first by $O_2$-dependent $O_2^-$ formation [Reaction (1)], followed by dismutation [Reaction (2)]. To appraise the contribution of Reaction (1) to $H_2O_2$ formation, $H_2O_2$ formation by $A\beta_{1-42}$ in the presence of chelators was measured (FIG. 14C). The amount of $H_2O_2$ formed in the presence of 1 μM $Cu^{2+}$ was 25% greater than the amount formed in the presence of 1 μM $Fe^{3+}$. Coincubation with DFO had no effect on $H_2O_2$ formation in the presence of 1 μM $Fe^{3+}$. However, TETA, and the $Cu^+$-specific indicator BC, both substantially inhibited the formation of $H_2O_2$ in the presence of 1 μM $Cu^{2-}$. The reasons why DFO partially inhibited $Fe^{3+}$ reduction, but was unable to inhibit $H_2O_2$ formation are unclear. These data indicate that the formation of $H_2O_2$ by $A\beta$ is dependent upon the presence of substoichiometric amounts of $Cu^+/(II)$. The possibility that formation of $H_2O_2$ in the presence of $Fe^{3+}$ was due to the presence of trace quantities of $Cu^{2+}$ cannot be excluded.

BC and BP, agents that specifically complex reduced metal ions, were far more effective than DFO and TETA at inhibiting $H_2O_2$ formation by A$\beta$ (FIG. 14C) but the reasons for this are not clear. The relatively $Fe^{2+}$-specific complexing agent, BP, inhibited $H_2O_2$ formation in the presence of $Cu^{2+}$, and the relatively $Cu^+$-specific complexing agent, BC, inhibited $H_2O_2$ formation in the present of $Fe^{3+}$, suggesting that these agents are not totally specific in their metal ion affinities. The formation of $H_2O_2$ by A$\beta$ in the absence of BC or BP confirms that the reduction of metals is not contingent upon the artifactual enhancement of the metal ions' redox potentials (Sayre, L. M., *Science* 274:1933 (1996)).

Figure 14D:
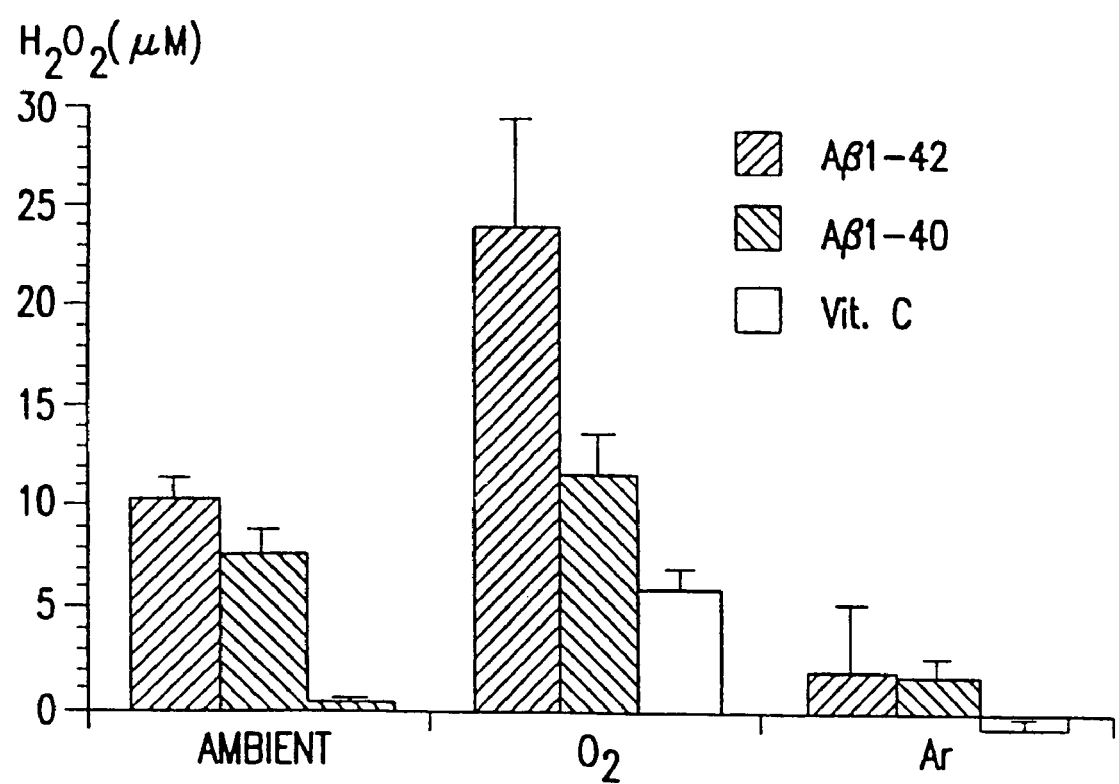
Figure 14E:
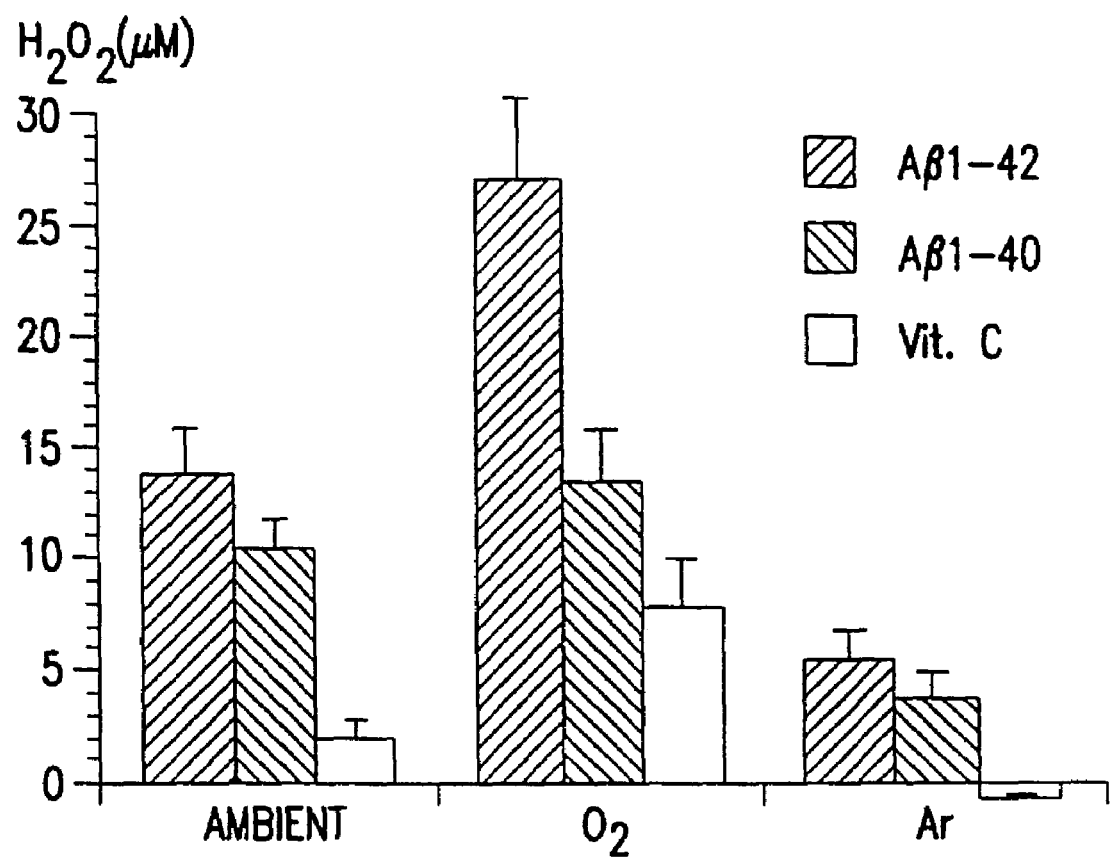

To determine whether the formation of $O_2^-/H_2O_2$ by A$\beta$ is merely due to the reduction of metal ions, or whether A$\beta$ also facilitates the recruitment of the substrates in Reaction (1), the generation of $H_2O_2$ by A$\beta_{1-42}$, A$\beta_{1-40}$ and Vitamin C under different $O_2$ tensions in the presence of 1 $\mu$M $Fe^{3+}$ (FIG. 14D) or 1 $\mu$M $Cu^{2+}$ (FIG. 14E) was studied. The presence of Vitamin C was used as a control measure to determine the amount $H_2O_2$ that is generated by the presence of reduced metals alone. In the presence of either metal ion, there was a significant increase in the amount of $H_2O_2$ produced under higher $O_2$ tensions. The presence of either A$\beta_{1-42}$ and A$\beta_{1-40}$ generated more $H_2O_2$ (A$\beta_{1-42}$>A$\beta_{1-40}$) than Vitamin C under any $O_2$ tension studied, and generated $H_2O_2$ under conditions where Vitamin C produced none, even though reduced metal ions must be present due to the activity of Vitamin C. Therefore, under these ambient and argon-purged conditions, the reduction of metal ions is insufficient to produce $H_2O_2$. These data indicate that A$\beta$ indeed facilitates the recruitment of $O_2$ into Reaction (1) more than would be expected by the interaction of the metals reduced by A$\beta$ with the passively dissolved $O_2$. Under relatively anaerobic conditions, the A$\beta$ peptides were observed to still produce $H_2O_2$ in the presence of $Cu^{2+}$ (FIG. 14E). This is probably due to the ability of A$\beta$ to recruit $O_2$ into Reaction (1) under conditions of very low $O_2$ tension. Since $O_2$ is preferentially dissolved in hydrophobic environments (Halliwell and Gutteridge, *Biochem. J.*, 219:1–14 (1984)), it seems that the hydrophobic carboxyl-terminus of A$\beta$ could attract $O_2$, serving as a reservoir for the substrate.

c) Evidence of the Superoxide Anion Formed by the A$\beta$-Metal Complex

Figure 15A:
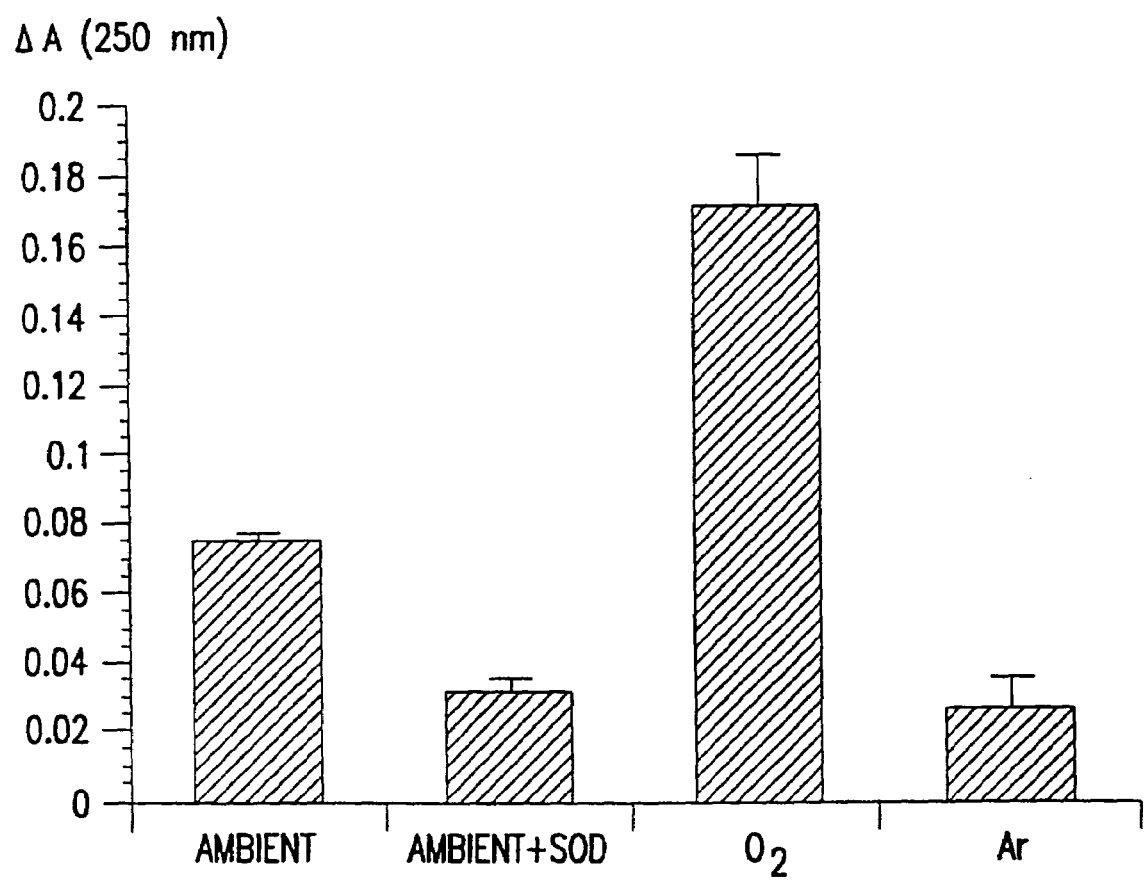
FIGS. 15A and 15B are graphical representations showing superoxide anion detection.

To confirm the production of $O_2^-$ by A$\beta$, the absorbance of the peptide in solution at 250 nm, the absorbance peak of $O_2^-$ (FIG. 15A) was measured. The absorbance generated by A$\beta_{1-42}$ in the presence of 1 $\mu$M $Fe^{3+}$ was 60% reduced when co-incubated with SOD, increased in the presence of high $O_2$ tension and abolished under anaerobic conditions. These data support the likelihood that A$\beta$ generates $H_2O_2$ by first generating $O_2^-$.

Figure 15B:
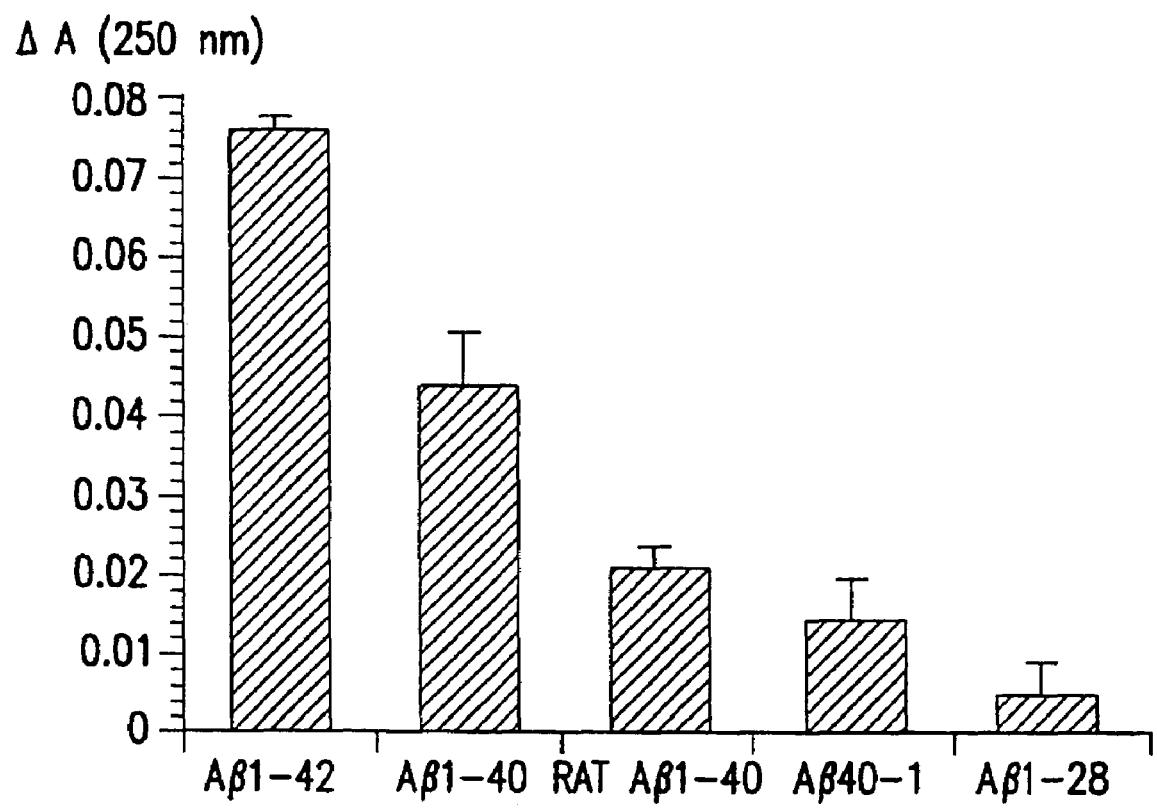

The absorbance changes at 250 nm for the various A$\beta$ peptides in PBS (FIG. 15B) paralleled the production of $H_2O_2$ from the same peptides (FIG. 14B), but the reason for the $A_{250}$ being much greater for A$\beta_{1-42}$ compared to A$\beta_{1-40}$ is unclear. It is likely that a fraction of the total $H_2O_2$ generated by A$\beta$ is decomposed by the Fenton reaction [Reaction (3)]. Therefore, the amount of $H_2O_2$ detected may be an attenuated reflection of the amount of $O_2^-$ detected.

d) Detection of Hydroxyl Radicals Generated from the A$\beta$-Metal Complex

Figure 16A:
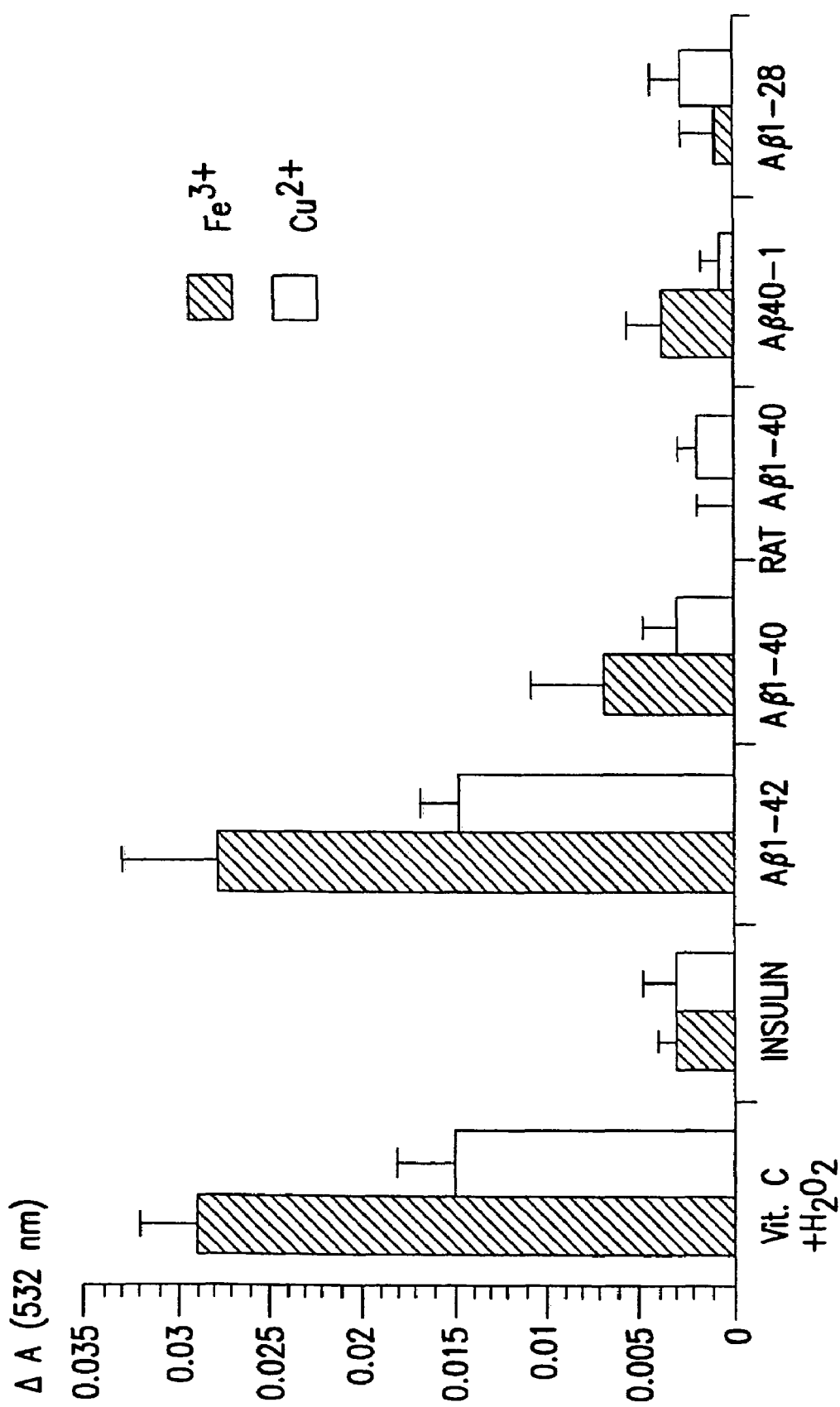
FIGS. 16A and 16B are graphical representations showing production of the hydroxyl radical (OH.) from the incubation of $A\beta$ in the presence of substoichiometric amounts of $Fe^{3+}$ or $Cu^{2+}$.

Having demonstrated that human A$\beta$ peptides simultaneously produce $H_2O_2$ and reduced metals, we proceeded to determine whether the hydroxyl radical was formed by the Fenton or Haber-Weiss reactions [Reactions (3) and (4)]. A modified TBARS assay was employed to detect OH. released from co-incubation mixtures of A$\beta$ peptides and 1 $\mu$M $Fe^{3+}$ or $Cu^{2+}$. As expected, A$\beta_{1-42}$ produced more OH. than A$\beta_{1-40}$, and rat A$\beta$ did not generate OH. (FIG. 16A). In contrast to the amount of $Fe^{2+}$ and $Cu^+$ produced (FIG. 13A), A$\beta$ generated more OH. in the presence of $Fe^{3+}$ than in the presence of $Cu^{2+}$. This may be because $Fe^{2+}$ is more stable than $Cu^+$, which may be more rapidly oxidized by Reaction (1). Therefore, the $Fe^{2+}$ generated by A$\beta$ may have a greater opportunity than the $Cu^+$ generated to react with $H_2O_2$. It is also possible that the contribution of the Haber-Weiss reaction to the production of OH. [Reaction (5)] is greater in the presence of $Fe^{3+}$ than in the presence of $Cu^{2+}$.

Figure 16B:
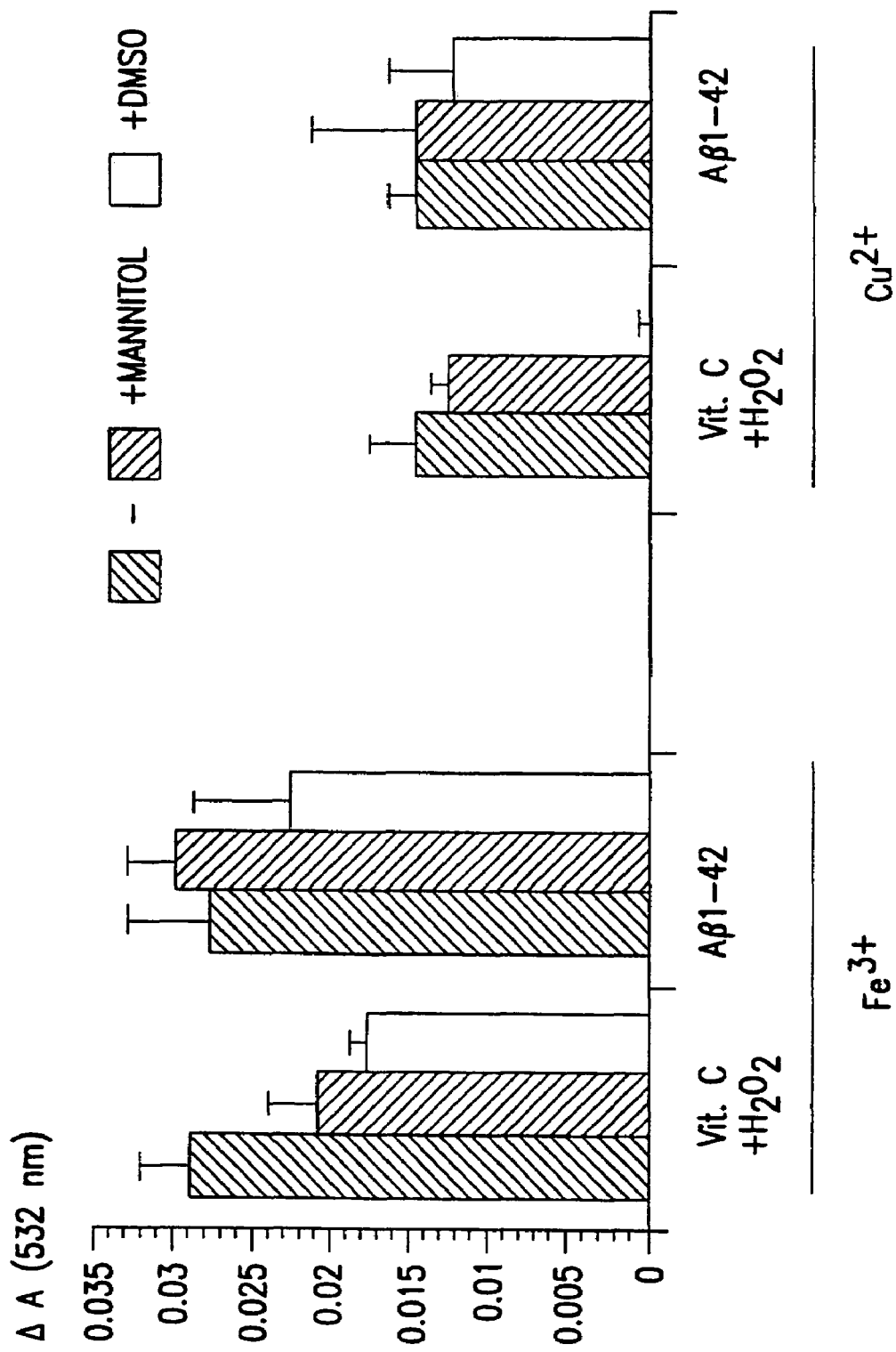
Figure 17:
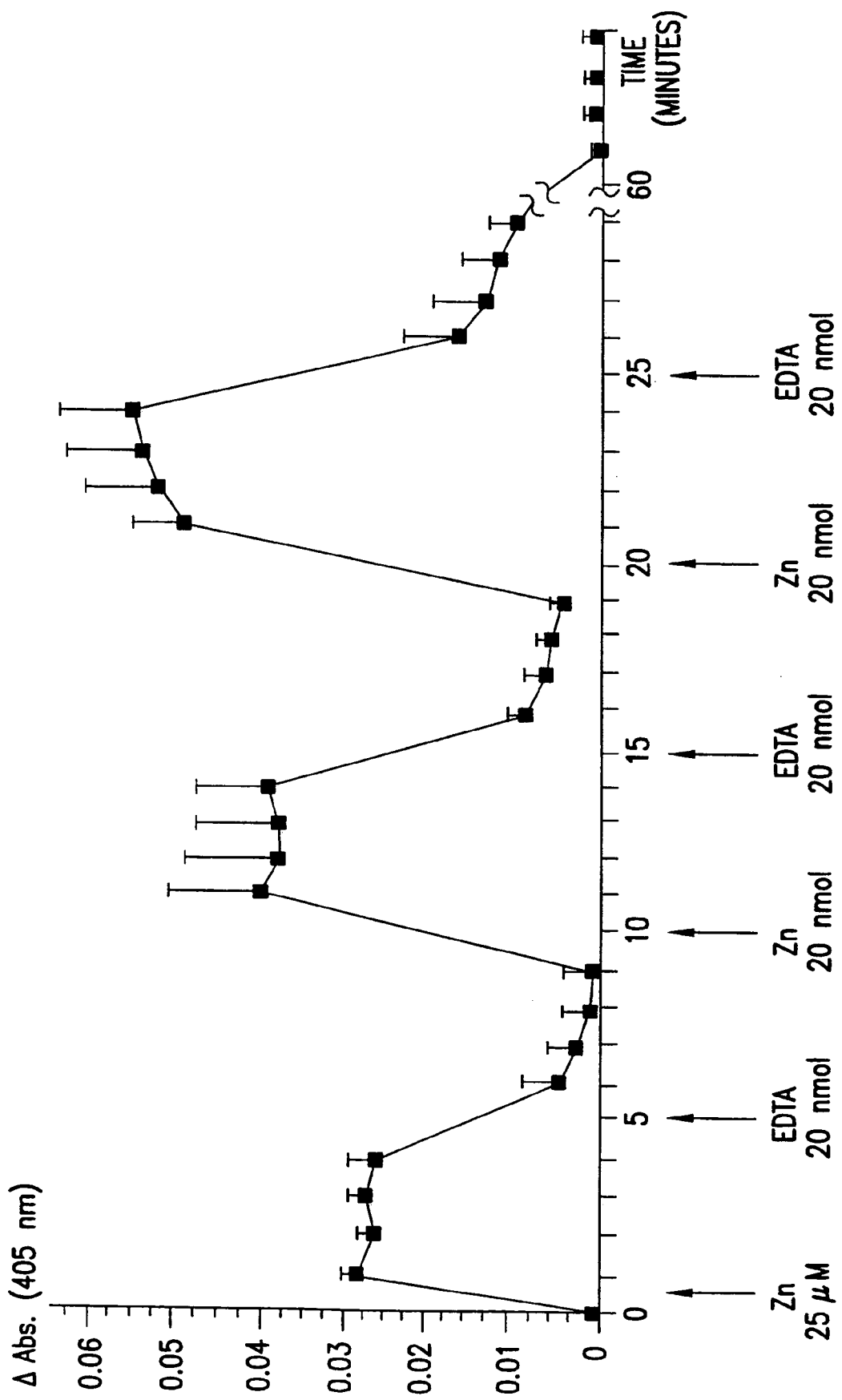
FIG. 17 shows the reversibility of zinc-induced $A\beta_{1-40}$ aggregation with EDTA. Aggregation induced by pH 5.5 was not reversable in the same manner (data not shown).
Figure 18:
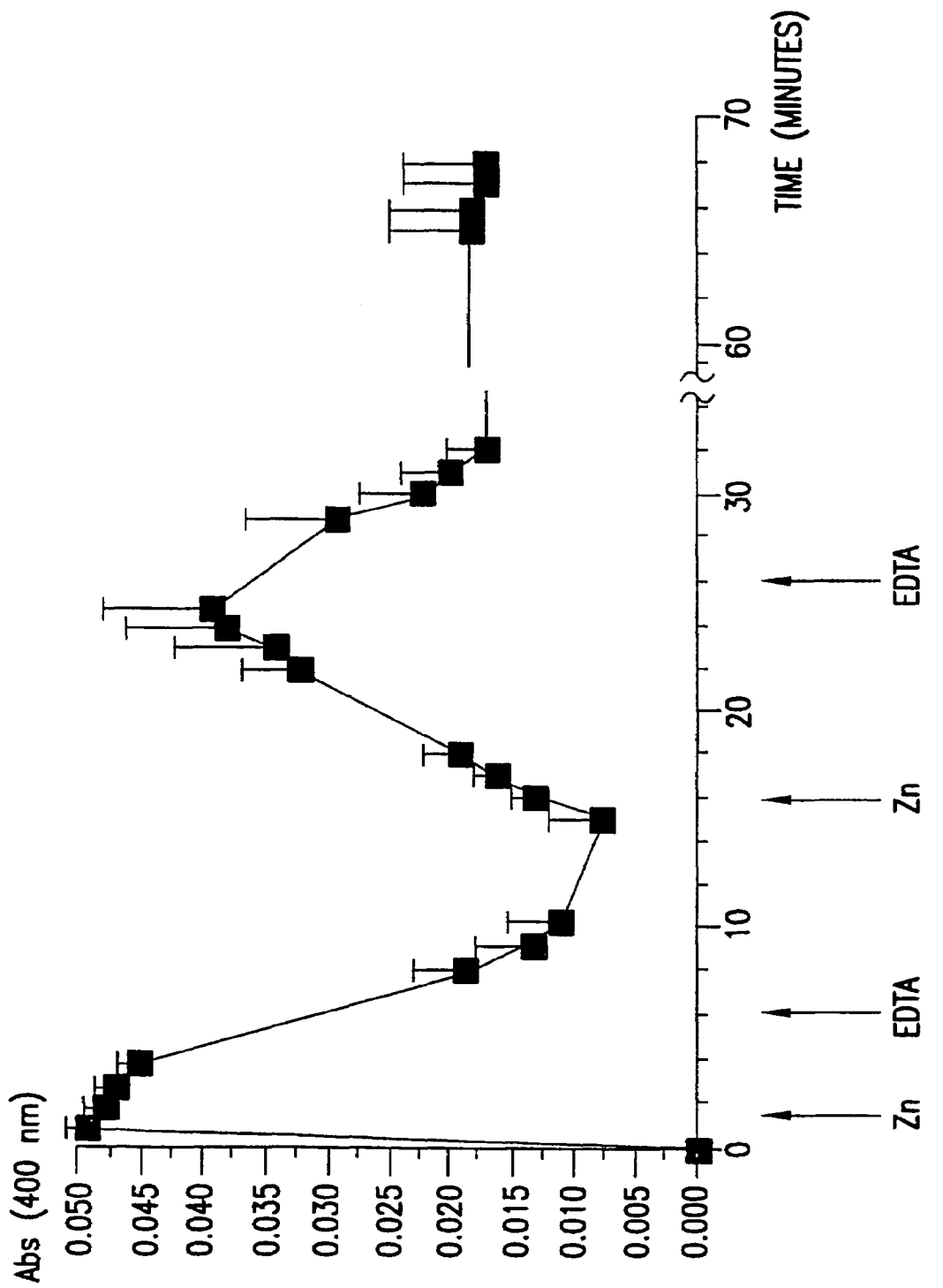
FIG. 18 shows the reversibility of zinc-induced aggregation of $A\beta_{1-40}$ mixed with 5% $A\beta_{1-42}$.

The effects of the OH. scavengers, dimethyl sulfoxide (DMSO) and mannitol, upon A$\beta_{1-42}$-mediated OH. generation were studied. Whereas these agents suppressed the generation of OH. by Vitamin C in the presence of $Fe^{3+}$, and DMSO suppressed the generation of OH. by Vitamin C in the presence of $Cu^{2+}$, neither were able to quench the generation of OH. by A$\beta_{1-42}$, whether in the presence of $Fe^{3+}$ or $Cu^{2+}$ (FIG. 16B). This suggests that these scavengers cannot encounter the OH. generated by A$\beta$ before the TBARS reagent does.

e) Similarity Between Bleomycin-Fe and A$\beta$-Fe/Cu Complexes

The present Examples provide evidence for a model by which Fe/Cu and $O_2$ are mediators and substrates for the production of OH. by A$\beta$ (FIGS. 16A and 16B) in a manner that depends upon the presence and length of the peptide's carboxyl terminus. The brain neocortex is an environment that is rich in both $O_2$ and Fe/Cu, which may explain why this organ is predisposed to A$\beta$-mediated neurotoxicity, if this mechanism is confirmed in vivo. The transport of Fe, Cu and Zn in the brain is largely energy-dependent. For example, the copper-transporting gene for Wilson's disease is an ATPase (Tanzi, R. E. et al., *Nature Genetics* 5:344 (1993)), and the re-uptake of zinc following neurotransmission is highly energy-dependent (Assaf, S. Y. & S. H. Chung, *Nature*, 308:734–736 (1984); Howell et al., *Nature*, 308: 736–738 (1984)).

There is increasing evidence for lesions of brain energy metabolism in aging and AD (Parker et al., *Neurology*, 40:1302–1303 (1990); (Mecocci et al., *Ann. Neurol.* 34:609–616 (1993); Beal, M. F. *Neurobiol. Aging* 15 (*Suppl* 2):S171–S174 (1994)). Therefore, damage to energy-dependent brain metal homeostasis may be an upstream lesion for the genesis of A$\beta$ deposition in AD. Most brain biometals are bound to proteins or other ligands, however, according to our findings, only A$\beta$ small fraction of the available metals needs to be derailed to the A$\beta$-containing compartment to precipitate the peptide and to activate its ROS-generating activities. The generation of ROS described herein depends upon the sub-stoichiometric amounts of $Fe^{3+}/Cu^{2+}$ (1:10, metal:A$\beta$), and it was estimated that 1% of the zinc that is released during neurotransmission would be sufficient to precipitate soluble A$\beta$ in the synaptic vicinity (Huang, X. et al., *J. Biol. Chem.* 272:26464–26470 (1997)).

A polypeptide which generates both substrates of the Fenton reaction in sufficient quantities to form significant amounts of the OH. radical is unusual. Therefore, A$\beta$ collections in the AD-affected brain are likely to be a major source of the oxidation stress seen in the effected tissue. One recent report describes that A$\beta$ is released by the treatment of the mammalian lens in culture with $H_2O_2$ (Frederikse, P. H. et al., *J. Biol. Chem.* 271:10169 (1996)). If a similar response mechanism to $H_2O_2$ stress exists in neocortex, then the increasing $H_2O_2$ concentration generated by the accumulating Aβ mass in the AD-affected brain may induce the production of even more Aβ leading to a vicious cycle of Aβ accumulation and ROS stress.

The simultaneous production of Fenton substrates by Aβ is a chemical property that is brought into therapeutic application in the oxidation mechanism of the bleomycin-iron complex. Bleomycin is a glycopeptide antibiotic produced by *Streptomyces verticillus* and is a potent antitumor agent. It acts by complexing $Fe^{3+}$ and then binding to tumor nuclear DNA which is degraded in situ by the generation of OH. (Sugiura, Y., et al., *Biochem. Biophys. Res. Commun.* 105:1511 (1997)). Similar to Aβ-$Fe^{3+}$/$Cu^{2+}$ complexes, incubation of bleomycin in aqueous solution also engenders the production of $O_2^-$, $H_2O_2$, and OH. in an $Fe^{3+}$-dependent manner. DFO could not inhibit $H_2O_2$ production from the Aβ-$Fe^{3+}$/$Cu^{2+}$ complex, and similarly, DFO does not inhibit the OH. mediated DNA damage caused by the bleomycin-$Fe^{3+}$ complex. Also, low-molecular-mass OH. scavengers mannitol and DMSO were unable to inhibit the generation of OH. by Aβ-$Fe^{3+}$/$Cu^{2+}$, and are similarly unable to inhibit OH. production from bleomycin-$Fe^{3+}$.

It is proposed herein that inhibition of Aβ-mediated OH. provides means of treatment, e.g. therapy, by compounds that are Fe or Cu chelators. The clinical administration of DFO was reported as being effective in preventing the progression of AD (Crapper-McLachlan, D. R. et al., *Lancet* 337:1304 (1991)); however, since DFO chelates $Zn^{2+}$ as well as $Fe^{3+}$ and Al(III), the effect, if verifiable, may not have been due to the abolition of the redox activity of Aβ, but may have been due to the disaggregation of $Zn^{2+}$-mediated Aβ deposits (Cherny, R. A. et al., *Soc. Neurosci. Abstr.* 23:(abstract)(1997)) which may have reduced cortical Aβ burden and, consequently, oxidation stress.

j) Oxidative Stress and Alzheimer's Disease Pathology

Autopsy tissue from AD subjects has been reported to exhibit higher basal TBARS formation than control material (Subbarao, K. V. et al. *J. Neurochem.* 55:342 (1990); Balazs, L. and M. Leon, *Neurochem. Res.* 19:1131 (1994); Lovell et al., *Neurology* 45:1594 (1995)). These observations could be explained, on the basis of the present findings, as being due to the reactivity of the Aβ content within the tissue. $Aβ_{1-40}$ recently has been shown to generate TBARS in a dose-dependent manner when incubated in cell culture, however TBARS reactivity was reduced by pre-treating the cells with trypsin which also abolished the binding of the peptide to the RAGE receptor (Yan et al., *Nature* 382:685 (1996)). One possibility for this result is that the RAGE receptor tethers an Aβ microaggregate sufficiently close to the cell to permit increased penetration of the cell by $H_2O_2$ which may then combine with reduced metals within the cell to generate the Fenton reaction. Alternatively, Aβ may generate the Fenton chemistry at the RAGE receptor. The resulting attack of the cell surface by the highly reactive OH. radical, which reacts within nanometers of its generation, may have been the source of the positive TBARS assay.

APP also reduces $Cu^{2+}$, but not $Fe^{3+}$, at a site in its amino terminus (Multhaup, G., et al., *Science* 271:1406–1409 (1996)), adjacent to a functional and specific $Zn^{2+}$-binding site that modulates heparin binding and protease inhibition (Bush et al., 1993; Van Nostrand, 1995). Therefore, the amino terminus of APP reiterates an association with transition metal ions that is found in the Aβ domain. This intriguing theme of tandem Cu/Zn interaction and associated redox activity found in two soluble fragments of the parent protein may indicate that the function and metabolism of APP could be related to biometal homeostasis and associated redox environments.

The present findings indicate that the manipulation of the brain biometal environment with specific agents acting directly (e.g. chelators and antioxidants) or indirectly (e.g. by improving cerebral energy metabolism) holds promise as a means for therapeutic intervention in the prevention and treatment of Alzheimer's disease.

Example 5

Resolubilization of Aβ

Considerable evidence now indicates that the accumulation of Aβ in the brain cortex is very closely related to the cause of Alzheimer's disease. Aβ is a normal component of biological fluids whose function is unknown. Aβ accumulates in a number of morphologies varying from highly insoluble amyloid to deposits that can be extracted from post-mortem tissue in aqueous buffer. The factors behind the accumulation are unknown, but the inventors have systematically appraised the solubility of synthetic Aβ peptide in order to get some clues as to what kind of pathological environment could induce the peptide to precipitate.

It was found that Aβ has three principal vulnerabilities: zinc, copper and low pH. The precipitation of Aβ by copper is dramatically exaggerated under mildly acidic conditions (e.g., pH 6.9), suggesting that the cerebral lactic acidosis that complicates Alzheimer's disease could contribute to the precipitation of Aβ were this event to be mediated by copper. A consideration of the involvement of zinc and copper in plaque pathology is contemplatable since the regulation of these metals in the brain has been shown to be abnormal in AD.

Recently direct evidence has been obtained indicating that these metals are integral components of the Aβ deposits in the brain in AD. It was found that zinc- and copper-specific chelators dramatically redissolve a significant proportion (up to 70%) of Aβ extracted from post-mortem AD affected brain tissue, compared to the amount extracted from the tissue by buffer in the absence of chelators.

These data support a strategy of redissolving Aβ deposits in vivo by chelation. Interestingly, a reported success in attempting to slow down the progression of Alzheimer's disease used a chelation strategy with desferrioxamine. The authors (Crapper-McLachlan, D. R., et al., 337:1304 (1991), thought that they were chelating aluminum, but desferrioxamine is also a chelator of copper and zinc. Treatment with desferrioxamine is impractical because the therapy requires twice daily deep intramuscular injections which are very painful, and also causes side effects such as anaemia due to iron chelation.

Aβ Extraction from Human Brain Post-Mortem Samples

The inventors have recently characterized zinc-mediated Aβ deposits in human brain (Cherny, R. A., et al., *Soc. Neurosci Abstr.* 23:(Abstract) (1997)). It was recently reported that there is a population of water-extractable Aβ deposit in the AD-affected brain (Kuo, Y-M., et al., *J. Biol. Chem.* 271:4077–81 (1996)). The inventors hypothesized that homogenization of brain tissue in water may dilute the metal content in the tissue, so lowering the putative zinc concentration in Aβ collections, and liberating soluble Aβ subunits by freeing Aβ complexed with zinc [$Zn^{2+}$].

To test this hypothesis, the brain tissue preparation protocol of Kuo and colleagues was replicated, but phosphate-buffered saline pH 7.4 (PBS) was substituted as the extraction buffer, achieving similar results. Highly sensitive and specific anti-Aβ monoclonal antibodies (Ida, N. et al., *J. Biol. Chem.* 271:22908 1996) were used to assay Aβ extraction by western blot. Next, the extraction of the same material was repeated with PBS in the presence of chelators of varying specificities (Table 1), and it was determined that the presence of a chelator increased the amount of Aβ in the soluble extract several-fold (FIGS. 19A–19C, 20A and 20B, 25A; Table 2).

The amount of Aβ detected in the pellet fraction of each sample is correspondingly lower (data not shown), indicating that the effect of the chelator is upon the disassembly of the Aβ aggregate, and not by inhibition of an Aβ-cleaving metalloprotease (such as insulin degrading enzyme cleavage of Aβ reported recently by Dennis Selkoe at the 27$^{th}$ Annual Meeting for the Society for Neuroscience, New Orleans). The extraction of sedimentable Aβ into the soluble phase correlated only with the extraction of zinc from the pellet, and not with any other metal assayed (Table 3). Examination of the total amount of protein released by the treatments revealed that chelation was not merely liberating more proteins in a non-specific manner.

TABLE 1

Dissociation Constants for Metal Ions of Various Chelators Used to Extract Human Brain Aβ.

| CHELATOR | Ca | Cu | Mg | Fe | Zn | Al | Co |
|---|---|---|---|---|---|---|---|
| EGTA | 10.9 | 17.6 | 5.3 | 11.8 | 12.6 | 13.9 | 12.4 |
| EDTA | 10.7 | 18.8 | 8.9 | 14.3 | 16.5 | 16.5 | 16.5 |
| Penicillamine | 0 | 18.2 | 0 | 0 | 10.2 | 0 | 0 |
| TPEN | 3.0 | 20.2 | 0 | 14.4 | 15.4 | 0 | 0 |
| Bathophenanthroline | 0 | 8.8 | 0 | 5.6 | 6.9 | 0 | 0 |
| Bathocuproine (BC) | 0 | 19.1 (Cu$^+$) | 0 | 0 | 4.1 | 0 | 4.2 |

LogK is illustrated for the chelators, where K=[ML]/[M][L]. Different chelators have greatly differing affinities for metal ions, as shown. TPEN is relatively specific for Zn and Cu, and has no affinity for Ca and Mg (which are far more abundant metal ions in tissues). Bathocuproine (BC) has high affinity for zinc and for cuprous ions. Whereas all the chelators examined have a significant affinity for zinc. EGTA and EDTA have significant affinities for Ca and Mg.

The ability of chelators to extract Aβ from post-mortem brain tissue was studied in over 40 cases (25 AD, 15 age-matched and young adult controls, all confirmed by histopathology). While there is a lot of variation between samples as to what is the best concentration of given chelator for the optimum extraction of Aβ, there are no cases where a chelator does not, at some concentration, extract far more Aβ than PBS alone.

FIG. 19 shows that metal chelators promote the solubilization of Aβ from human brain sample homogenates. Representative curves for three chelators (TPEN, EGTA, Bathocuproine) used in extracting the same representative AD brain sample are shown. 0.5 g of prefrontal cortex was dissected and homogenized in PBS±chelator as indicated. The homogenate was then centrifuged (100,000 g) and the supernatant removed, and a sample taken for western blot assay using anti-Aβ specific antibodies after Tricine PAGE. Densitometry was performed against synthetic peptide standards. The blots shown here represent typical results. Similar results were achieved whether or not protease inhibitors were included in the PBS (extraction was at 4° C.). Furthermore, similar results were achieved when the brain sample was homogenized in PBS and then pelleted before treated with PBS±chelator.

Figure 19A:
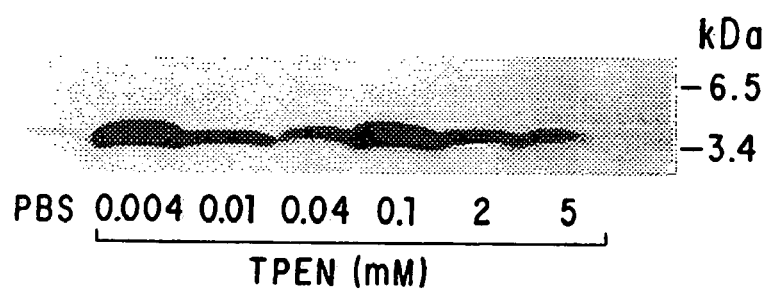
FIGS. 19A, 19C and 19E show the results of Western blot analysis of 6 AD brain samples homogenized in the presence of chelators as indicated.
Figure 19C:
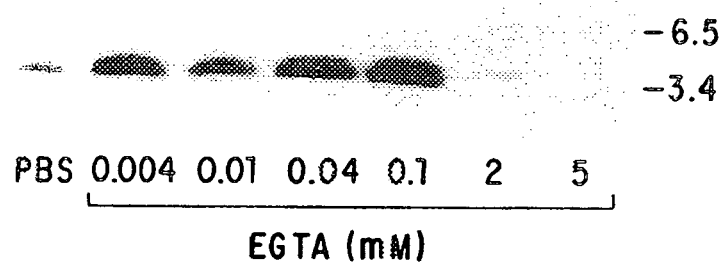
Figure 19E:
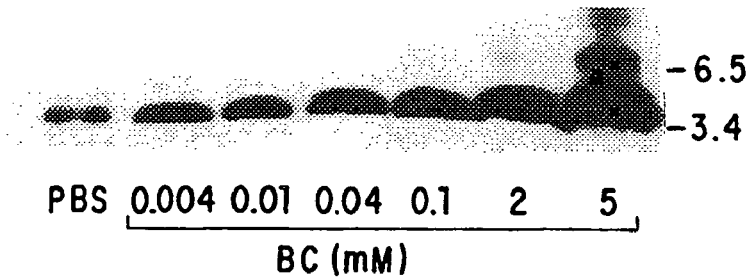
Figure 19B:
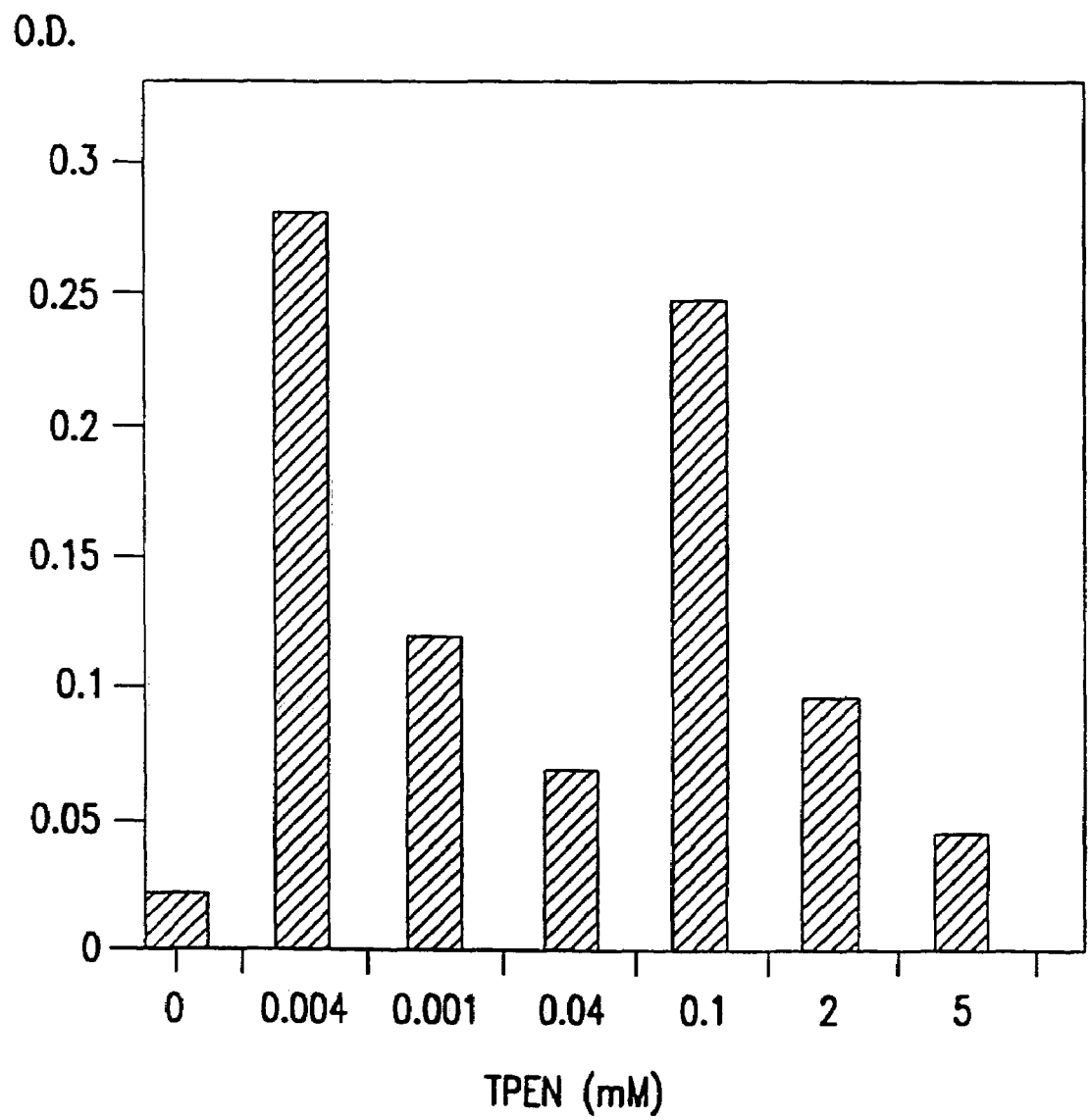
FIGS. 19B, 19D and 19F show the results of densitometry analysis of the Western blots of FIGS. 19A, 19C and 19E, respectively.
Figure 19D:
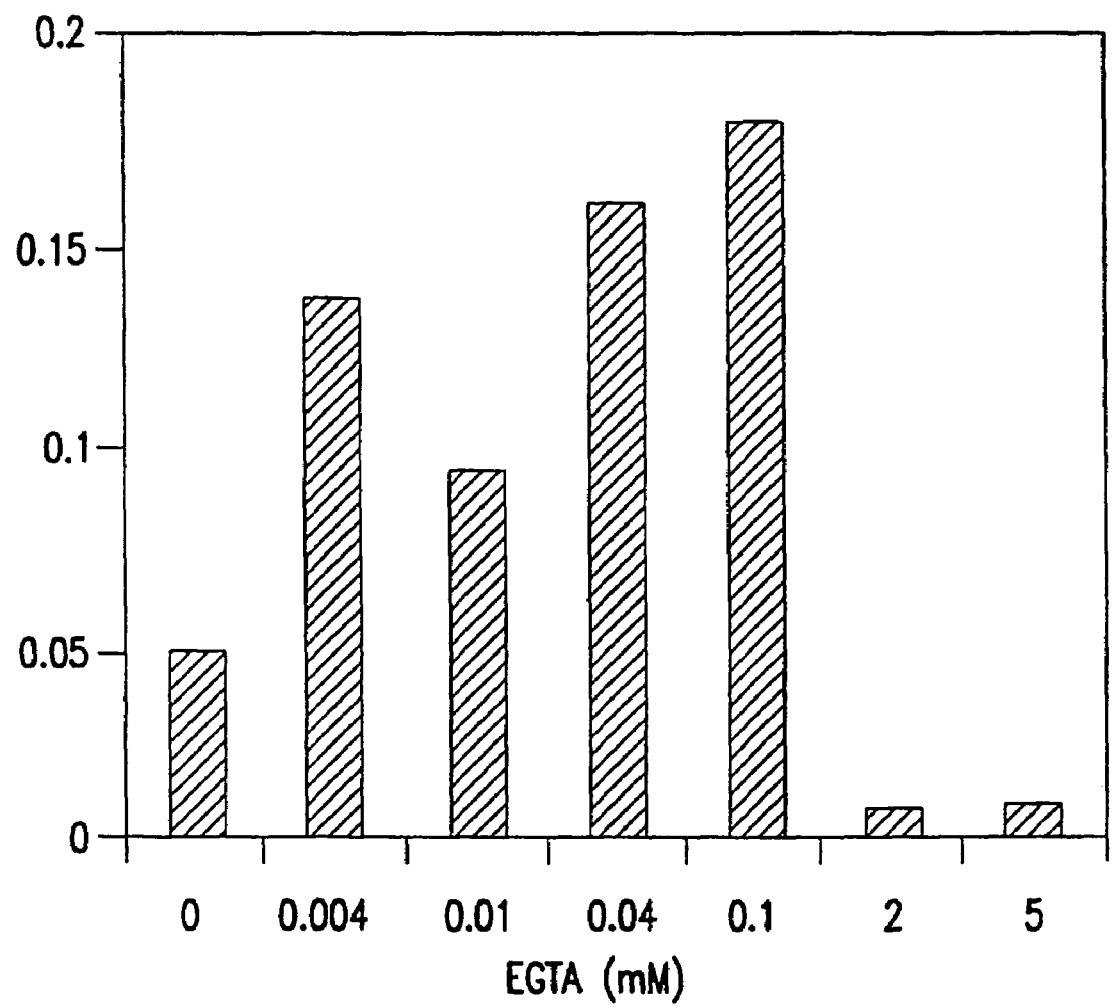
Figure 19F:
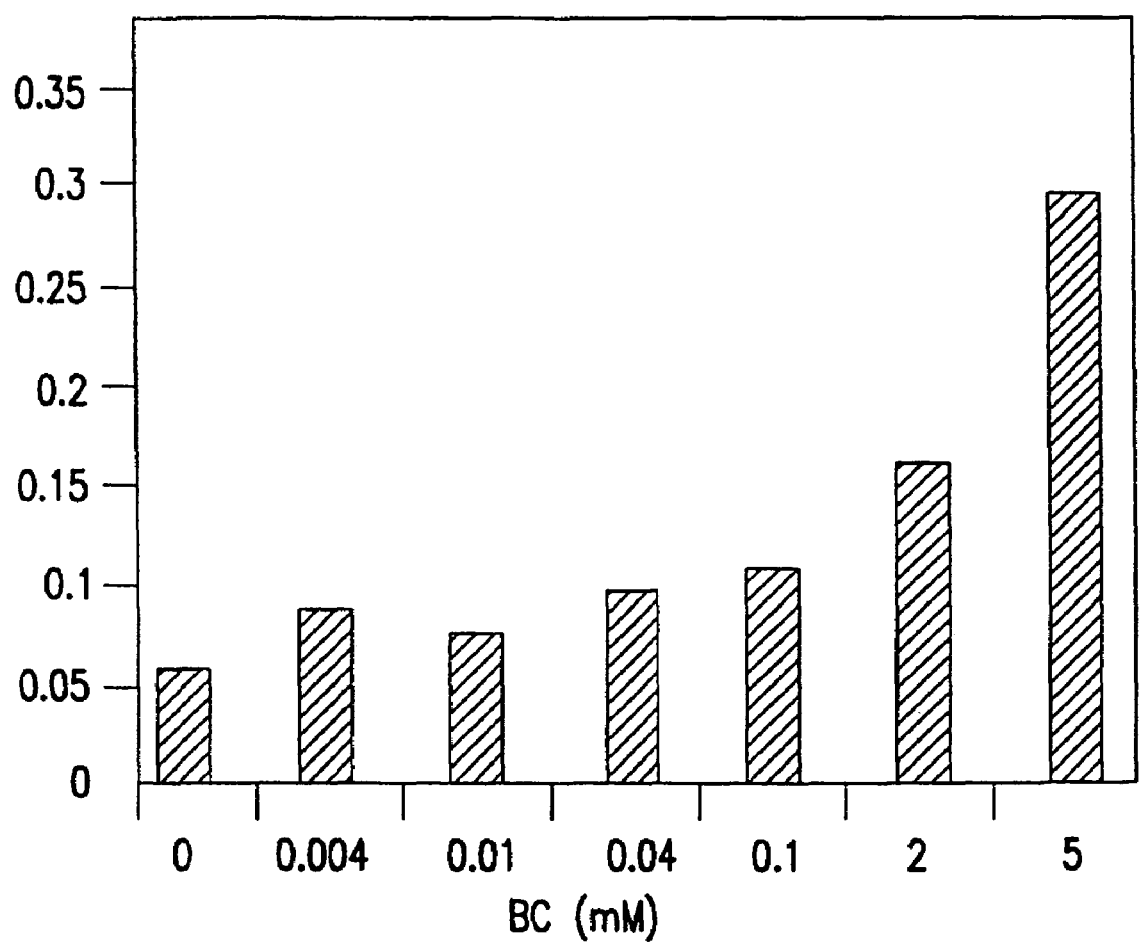

There is also a complex relationship between the dose of the chelator and the resultant resolubilization of Aβ (FIGS. 19A–C). For the same given sample, neither TPEN nor EGTA could increase the extraction of Aβ in a does-dependent manner. Rather, although concentrations of chelators could be very effective in the low micromolar range (e.g., TPEN 4 μM, FIG. 19A), higher concentrations induced a paradoxical loss of recovery. This kind of response was found in every case examined. The extraction of Aβ is abolished by adding exogenous zinc, but is enhanced by adding magnesium. Preliminary in vitro data indicate that whereas Mg has no effect on the precipitation of Aβ, its presence enhances the peptide's resolubilization following zinc-induced precipitation. Therefore, the "polyphasic" profile of chelator extraction of Aβ, with higher concentrations of TPEN and EGTA inducing a loss of recovery, may be explained by the chelation of Mg that is only expected to occur after the chelation of zinc when the relative abundance of Mg in the sample, and the relative dissociation constants of TPEN and EGTA are considered.

In contrast, bathocuproine (BC) exhibits a clear dose-dependent increase in Aβ extraction from human brain, probably due to its relatively high specificity for zinc, although an interaction with trace amounts of Cu$^+$ or other metals not yet assayed, cannot be excluded.

Western blot analysis of extracts using Aβ$_{1-42}$-specific monoclonals revealed the presence of abundant Aβ$_{1-42}$ species. It was observed that ≈20% of AD cases exhibit clear SDS-resistant Aβ dimers in the soluble extract after treatment with chelators. These dimers are reminiscent of the neurotoxic Aβ$_{1-42}$ dimers that were extracted by Roher and colleagues from AD-affected brain (Roher, A. E., et al., *Journal of Biological Chemistry* 271:20631–20635 (1996)). An estimation of the proportion of total precipitated Aβ in the sample was achieved by extracting the homogenate pellet following centrifugation, into formic acid, and then performing a western blot on the extract following neutralization. The proportion of pelletable Aβ that is released by chelation treatment varies considerably from case to case, from as little as 30% to as much as 80%. In the absence of a chelator, no more than ≈10% of the total pelletable Aβ is extracted by PBS alone.

One preliminary emerging trend is that samples with a greater proportion of diffuse or vascular Aβ deposit are more likely to have their pelletable Aβ resolubilized by chelation treatment. Also, extraction of the tissue homogenate overnight with agitation greatly increases the amount of Aβ extracted in the presence of chelators (compared to PBS alone), when compared to briefer periods of extraction indicating that the disassembly of Aβ deposits by chelation treatment is a time-dependent reaction and is unlikely to be due to inhibition of a protease. A study of brain cortical tissue from one amyloid-bearing APP transgenic mouse indicates that, like human brain, homogenization in the presence of a chelator enhances the extraction of pelletable Aβ.

Effects of various chelators on the extraction of Aβ into the supernatant as a percentage change from control extractions is summarized below in Table 2.

TABLE 2

Effects of Various Chelators Upon Extraction of Aβ.

| | Effect of Chelators (% change from control) | | | | | |
|---|---|---|---|---|---|---|
| | TPEN | | EGTA | | BATHOCUP | |
| | 0.1 mM | 2.0 mM | 0.1 mM | 2.0 mM | 0.1 mM | 2.0 mM |
| Mean (n = 6) | 182 | 241 | 207 | 46 | 301 | 400 |
| +/− SD | 79 | 81 | 115 | 48 | 190 | 181 |

Densitometry of Aβ western blots (FIGS. 19A–19C) was performed for a series of 6 AD brain samples homogenized in the presence of chelators as indicated. The mean (±SD) increases in signal, above the signal generated by PBS extraction alone, are indicated in Table 2. A significantly increased amount of chelator-induced Aβ resolubilization was achieved by a 16 hour extraction with agitation in subsequent studies.

Table 3 shows a comparison between pellets of post-centrifugation homogenates in the presence and absence of a chelator (TPEN).

TABLE 3

Residual Metals in Pellets of Post-Centrifugation Homogenates in the Presence and Absence of Chelator.

| METAL | Zn | Cu | Fe | Ca | Mg | Al |
|---|---|---|---|---|---|---|
| PBS alone mg/kg (SD) | 50.7 | 11.9 | 227 | 202 | 197 | 44 |
| | (12.0) | (3.5) | (69) | (69) | (94) | (111) |
| +TPEN mg/kg (SD) | 33.2* | 9.8 | 239 | (210) | 230 | 65 |
| | (9.8) | (3.1) | (76) | (89) | (94) | (108) |

Frontal cortex from AD (n=6) and healthy controls (n=4) was homogenized in the presence and absence of PBS±TPEN (0.1 mM). After ultracentrifugation of the homogenate, the pellets were extracted into concentrated HCl and measured for metal content by ion coupled plasma—atomic emission spectroscopy (ICP-AES).

Figure 20A:
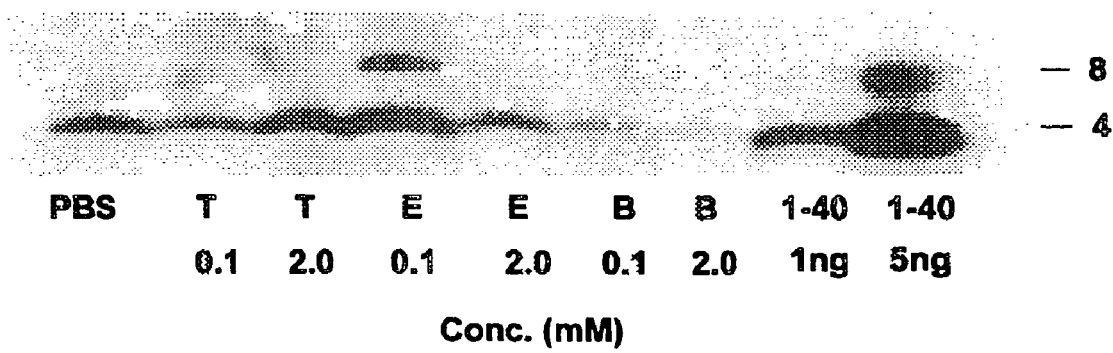
FIGS. 20A and 20B—FIG. 20A shows a western blot of chelation response in a typical AD brain.
Figure 20B:
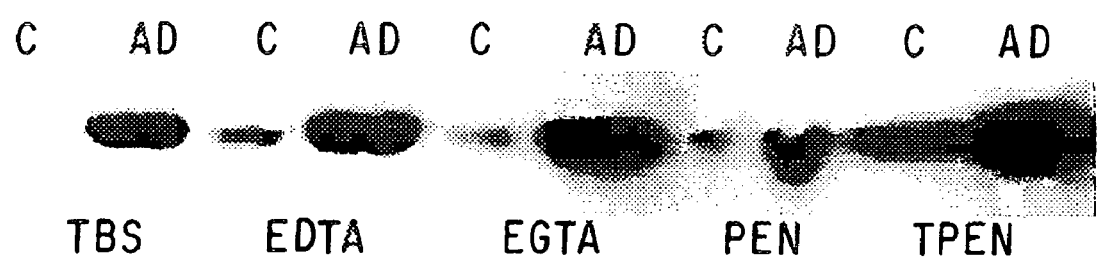

Using the same technique, zinc-mediated assembly of Aβ in normal brains was shown. FIGS. 20A and 20B show sedimentable Aβ deposits in healthy brain tissue. The effects of chelators in enhancing Aβ extraction from brain homogenates is also observed in normal tissue. FIG. 20A illustrates a western blot with anti-Aβ antibody of material extracted from a 27-year-old individual with no history of neurological disorder. T=TPEN, E=EGTA, B=bathocuproine. Bathocuproine is much less effective in extracting Aβ from control tissue than from AD tissue. These data are typical of 15 cases.

As expected, far less total Aβ is present in normal brain samples compared to AD brain samples, although the content of Aβ increases with age. It is possible that these findings in young adult brains represent the zinc-mediated initiation of amyloid formation in deposits that, in youth, are too diffuse to be detected by immunohistochemistry.

Figure 21:
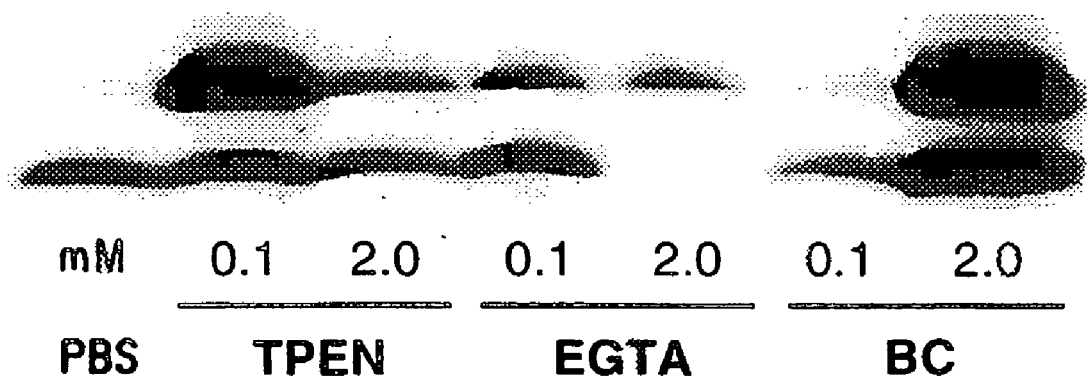
FIG. 21 shows an indicative blot from AD brain extract. The blot shows that chelation treatment results in disproportionate solubilization of $A\beta$ dimers, while PBS alone does not.

Roher and others have suggested that dimers of Aβ are the toxic component of amyloid. As shown in FIG. 21, dimers appear in response to chelation in disproportion to the monomeric signal (treatment with PBS alone does not generate soluble dimers). This su97ggests that Aβ deposits are being dismantled by the chelators into SDS-resistant dimeric structural units.

Figure 22:
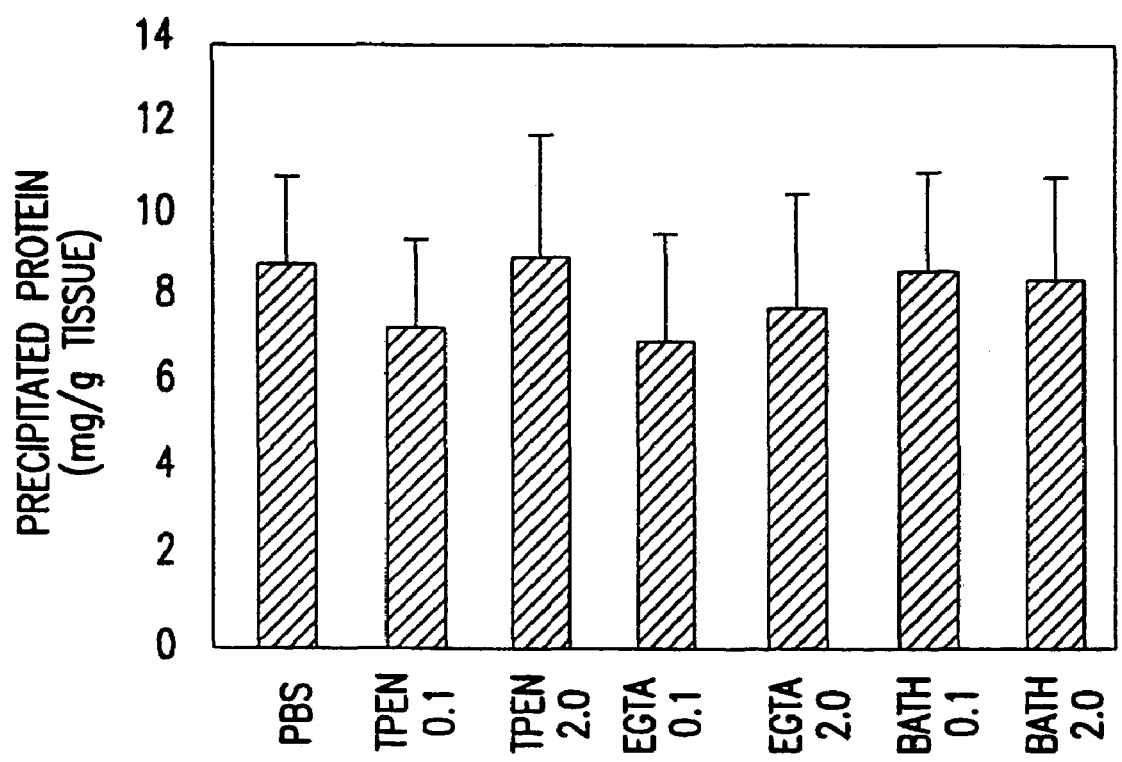
FIG. 22 shows that recovery of total soluble protein is not affected by the presence of chelators in the homogenization step.

FIG. 22 shows that the recovery of total soluble protein is not affected by the presence of chelators in the homogenization step. The proportionality of extracted subfractions, calculated based on total protein as determined by formic acid extraction, should not be prone to artifact based on chelator-specific affects.

Example 6

Differential Effects of Chelation of Cerebral Aβ Deposits in AD-Affected Subjects Versus Age-Matched Controls and the Effect of Magnesium Experiments involving extraction of cerebral tissue from AD-affected subjects and non-AD, age-matched controls by chelation indicate different resolubilization responses of amyloid deposits between the two sample groups with regard to extraction by specific chelators.

Higher concentrations of chelators with relatively broad specificity (e.g. EGTA) result in less resolubilization of Aβ deposits. Experiments show that chelation of magnesium negatively affects resolubilzation of Aβ deposits.

Materials and Methods

Cortical tissue was dissected from the frontal poles of frozen AD and age-matched normal brains for which histopathological and clinical documentation were provided. AD tissue was selected according to CERAD criteria (Mirra et al., *Neurology* 41:479–486 (1991)) with particular attention paid to the presence of neuritic plaques and neurofibrillary tangles. Histological examination of Aβ levels in normal specimens ranged from immunohistochemically undetectable to substantially present in the form of diffuse plaques.

Suitable quantities of gray matter from each subject were minced to serve as pools of homogenous tissue. Equal portions (0.5 g unless otherwise specified) were homogenized (Ika Ultaturax T-25, Janke and Kunkel, Staufen, Germany) for 3×30 second periods at full speed with a 30 second rest between runs in 3 ml of ice-cold phosphate-buffered saline (PBS pH 7.4) containing a cocktail of protease inhibitors (Biorad, Hercules, Calif.—Note: EDTA was not included in the protease inhibitor mixture) or in the presence of chelators or metal ions prepared in PBS. To obtain the soluble fraction, the homogenates were centrifuged at 100,000×g for 30 min (Beckman J180, Beckman instruments, Fullerton, Calif.) and the supernatant collected in 1 ml aliquots and stored on ice or immediately frozen at −70° C. In each experiment, all protein was precipitated from 1 ml of supernatant from each treatment group using 1:5 ice cold 10% trichloracetic acid and pelleted in a bench top microfuge (Heraeus, Osteroder, Germany) at 10,000×g. The remaining pellet was frozen at −70° C.

The efficiency of the precipitation was validated by applying the technique to a sample of whole human serum, diluted 1:10, to which had been added 2 μg of synthetic $A\beta_{1-40}$ or $A\beta_{1-42}$ (W. Keck Laboratory, Yale University New Haven, Conn.). Protein in the TCA pellet was estimated using the Pierce BCA kit (Pierce, Rockford, Ill.). The total Aβ load of unextracted cortex was obtained by dissolving 0.5 g of grey matter in 2 ml of 90% formic acid, followed by vacuum drying and neutralization with 30% ammonia.

Precipitated protein was subjected to SDS polyacrylamide gel electrophoresis (SDS-PAGE) on Novex pre-cast 10–20% Tris-Tricine gels followed by Western transfer onto 0.2 μm nitrocellulose membrane (Biorad, Hercules, Calif.). Aβ was detected using the WO2, G210 or G211 monoclonal antibodies (Ida, N. et al., *J. Biol. Chem.* 271:22908 (1996)) in combination with HRP-conjugated rabbit anti-mouse IgG (Dako, Denmark), and visualized using chemiluminescence (ECL, Amersham Life Science, Little Chalfont, Buckinghamshire, UK). Each gel included two or more lanes containing known quantities of synthetic Aβ which served as internal reference standards. Blot images were captured by a Relisys scanner with transparency adapter (Teco Information Systems, Taiwan, ROC) and densitometry conducted using the NIH Image 1.6 program (National Institutes for Health, USA., Modified for PC by Scion Corporation, Frederick, Md.), calibrated using a step diffusion chart. For quantitation of Aβ in brain extracts, the internal reference standards of synthetic Aβ were utilized to produce standard curves from which values were interpolated.

Figure 23:
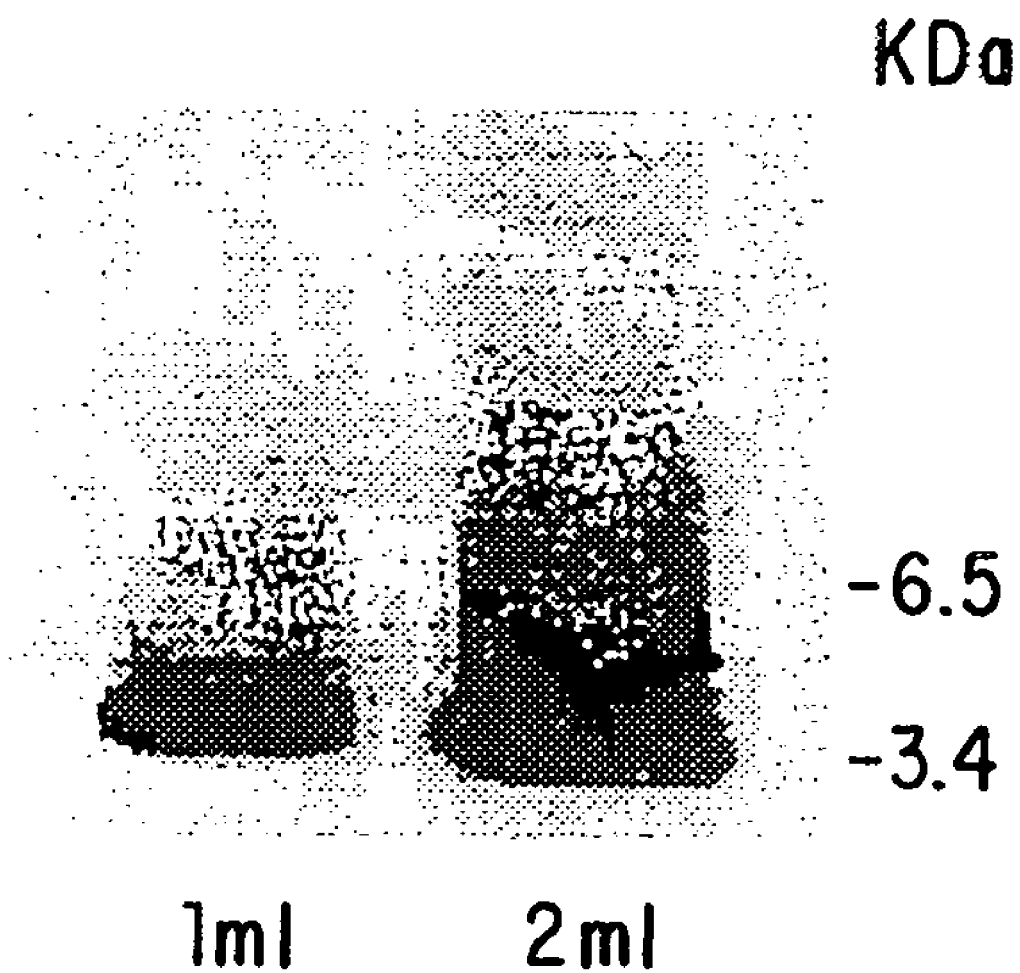
FIG. 23 shows that extraction volume affects Aβ solubilization.

In the experiments corresponding to the results shown in FIG. 23, duplicate 0.2 g samples of AD cortical tissue were homogenized and subjected to ultracentrifugation as described, but using either 1 ml or 2 ml of extraction buffer (PBS). Protein was precipitated from the entire supernatant and redissolved in 100 µl of sample buffer. Equal volumes of TCA-precipitated protein were subjected to Tris-Tricine SDS-PAGE and Aβ was visualized as described above.

Figure 24A:
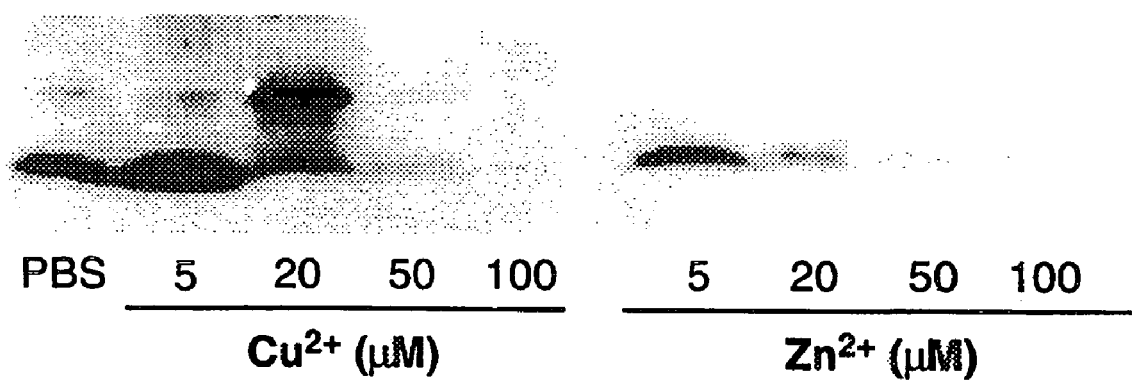
FIGS. 24A and 24B—FIG. 24A shows the effect of metals upon the solubility of brain-derived Aβ: copper and zinc can inhibit the solubilization of Aβ.

In the experiments corresponding to the results shown in FIG. 24A. 0.2 g specimens of frontal cortex from AD brain were homogenized in the presence of 2 ml of PBS or varying concentrations of $Cu^{2+}$ ($Cu(SO4)_2$) or $Zn^{2+}$ ($Zn(SO4)_2$). Aβ in the high speed supernatant was visualized as described above.

Figure 24B:
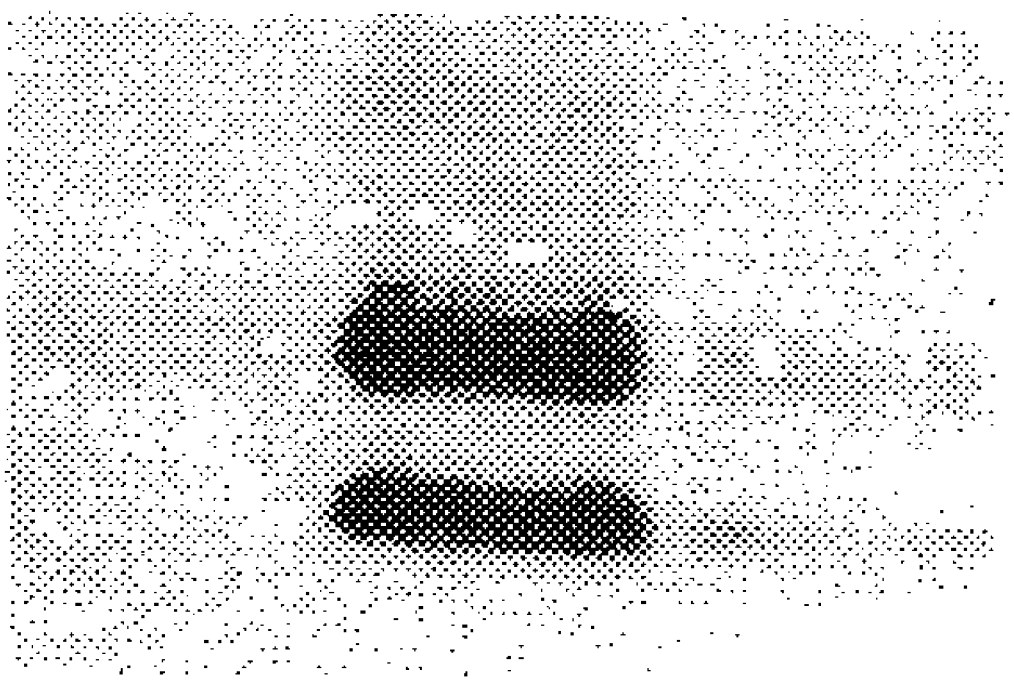

In the experiments corresponding to the results shown in FIG. 24B, 0.2 g specimens of frontal cortex from AD brain were homogenized in the presence of 2 ml or PBS or 2 mM EGTA. The homogenates were then spun at 100,000×g for 30 min and the supernatant discarded. The remaining (metal depleted) pellets were rehomogenized in a further 2 ml of either PBS alone, EGTA alone, 2 mM $Mg^{2+}$ ($MgCl_2.6H_2O$) in PBS or 2 mM $Ca^{2+}$ ($CaCl_2.2H_2O$) in PBS and the homogenate subjected to ultracentrifugation. Aβ in the soluble fraction was visualized as described above.

In the experiments corresponding to the results shown in FIGS. 25A and 25B, frontal cortex from AD (n=6) and age-matched, amyloid-positive (n=5) subjects were treated with PBS, TPEN, EGTA or BC (0.1 mM and 2 mM) and soluble Aβ assessed as described above.

In the experiments corresponding to the results shown in FIG. 26, representative AD (left panels) and aged-matched control specimens (right panels) were prepared as described in PBS or 5 mM BC. Identical gels were run and Western blots were probed with mAbs WO2 (raised against residues 5–16, recognizes $Aβ_{1-40}$ and $Aβ_{1-42}$), G210 (raised against residues 35–40, recognizes $Aβ_{1-40}$), or G211 (raised against residues 35–42, recognizes $Aβ_{1-42}$) (Ida, N. et al., *J. Biol. Chem.* 271:22908 (1996).

Results and Discussion

To further explore the involvement of metal ions in the deposition and architecture of amyloid deposits, the inventors extracted brain tissue from histologically-confirmed AD-affected subjects and from subjects that were age-matched to AD-affected subjects but were not clinically demented (age-matched controls, "AC") in the presence of a variety of chelating agents and metals. Chelators were selected which displayed high respective affinities for zinc and/or copper relative to more abundant metal ions such as calcium and magnesium. See Table 4 below.

TABLE 4

Stability constants of metal chelators

|      | Ca    | Cu                              | Mg   | Fe   | Zn   | Al   | Co    |
|------|-------|---------------------------------|------|------|------|------|-------|
| EGTA | 10.86 | 17.57                           | 5.28 | 11.8 | 12.6 | 13.9 | 12.35 |
| TPEN | 3     | 20.2                            | n/a  | 14.4 | 15.4 | n/a  | n/a   |
| BC   | n/a   | $Cu^{2+}$ 6.1<br>$Cu^{+}$ 19.1 | n/a  | n/a  | 14.1 | n/a  | 4.2   | logK10 where K=[Metal.Ligand]/[Metal][Ligand]. From: NIST database of critically selected stability constants for metal complexes Version 2.0 1995.

A series of titration curves were prepared to determine the chelator concentration at which maximal response was obtained. In these experiments, selected chelators were limited to EGTA, TPEN and BC. FIGS. 19A–C show interesting dose-dependent patterns of chelator solubilization of Aβ.

It was found that EGTA and TPEN elicited a significant enhancement in solubilization of Aβ in a pattern of response typified by peak values at or near 0.004 mM and 0.1 mM, and lower values at concentrations in between. Both chelators were increasingly ineffective at concentrations over 1 mM, and at 2 mM, EGTA virtually abolished the signal for Aβ. In contrast, BC elicited a typical concentration-dependent response with no decline in effectiveness in the low millmolar range even when extended to 20 mM. Total TCA-precipitated protein in the supernatant was assayed and found to be unaffected by either chelator kind or concentration.

Recent findings have demonstrated the presence of neurotoxic dimers in the soluble (Kuo, Y-M., et al., *J. Biol. Chem.* 271:4077–81 (1996)) and insoluble (Roher, A. E., et al., *Journal of Biological Chemistry* 271:20631–20635 (1996); Giulian, D. et al., *J. Neurosci.,* 16:6021–6037 (1996)) fractions of Aβ extracts of the brains of AD individuals. FIG. 21 shows that chelator-promoted solubilization of Aβ elicits SDS-resistant dimers. Under the preparation conditions used, SDS-resistant dimers were not generally observed in the extracts with PBS alone. Dimers were found to appear, however, in response to chelator-promoted solubilization of Aβ.

The signal for dimeric Aβ was frequently disproportionate to that of monomeric Aβ and the ratio varied with both the type and concentration of chelator used (FIG. 21). In contrast, when synthetic $Aβ_{1-40}$ was run under identical conditions, the monomer:dimer ratio reflected a predictable and reproducible concentration-dependent relationship. These data suggest that the dimers observed in extracts of human brain are predominantly an intermediate structural unit generated by the dissolution of amyloid, resulting in turn from the sequestration of metals by chelating agents.

FIG. 24A shows the effect of metals upon the solubility of brain-derived Aβ. Precipitation of Aβ was induced by adding either copper or zinc to unchelated extracts. The resulting signal for soluble Aβ was attenuated, the threshold concentration being between 20 and 50 µM for copper and between 5 and 20 µM for zinc. At concentrations greater than 100 µM solubility was abolished. Interestingly, at lower concentrations of copper there appears to be a transitional stage where Aβ is present in the dimeric form prior to complete aggregation, mirroring the intermediate stage dimers elicited by chelator-mediated solubilization.

In order to confirm that the chelators were effective at sequestering metals at the concentrations employed in these experiments, ICP-AES was used to determine the residual levels of several metals in the post-centrifugation pellets retained from the experiment described in FIGS. 19A–19C. Of the six metals tested, zinc levels were reduced by TPEN in a dose dependent manner, whereas EGTA affected calcium and magnesium, particularly at higher concentrations. See Table 5 below.

TABLE 5

Residual Metal Levels in Post-centrifugation (Extracted) Pellets

|  | Mg (mg/kg) | Al (mg/kg) | Ca (mg/kg) | Fe (mg/kg) | Zn (mg/kg) | Cu (mg/kg) |
| --- | --- | --- | --- | --- | --- | --- |
| PBS | 202 | 36 | 573 | 411 | 60 | 13 |
| TPEN (mM) | | | | | | |
| 0.004 | 147 | 22 | 322 | 317 | 28 | 10 |
| 0.001 | 192 | 34 | 490 | 512 | 42 | 12 |
| 0.04 | 201 | 22 | 956 | 322 | 22 | 10 |
| 0.1 | 200 | 60 | 708 | 389 | 21 | 12 |
| 2.0 | 200 | 148 | 419 | 376 | 19 | 11 |
| 5.0 | 205 | 16 | 377 | 307 | 17 | 10 |
| PBS | 223 | 52 | 1186 | 266 | 45 | 11 |
| EGTA (mM) | | | | | | |
| 0.004 | 228 | 73 | 795 | 247 | 53 | 11 |
| 0.001 | 237 | 43 | 862 | 281 | 49 | 12 |
| 0.04 | 247 | 104 | 1402 | 438 | 71 | 13 |
| 0.01 | 213 | 61 | 675 | 272 | 54 | 13 |
| 2.0 | 191 | 62 | 519 | 238 | 27 | 13 |
| 5.0 | 168 | 27 | 455 | 230 | 18 | 12 |
| BC (mM) | | | | | | |
| 0.004 | 234 | 33 | 489 | 231 | 47 | 12 |
| 0.001 | 225 | 88 | 1306 | 275 | 47 | 13 |
| 0.04 | 226 | 38 | 753 | 248 | 56 | 15 |
| 0.01 | 223 | 73 | 762 | 256 | 49 | 13 |
| 2.0 | 254 | 42 | 1602 | 271 | 49 | 14 |
| 5.0 | 238 | 38 | 912 | 249 | 53 | 15 |

Metal levels were measured in 10 AD specimens treated with 0.1 mM TPEN. See Table 6 below. The observed increase in extractable Aβ correlated with significant depletion in zinc in every case and to a lesser extent, copper, when compared with PBS-treated tissue. No other metal tested was significantly influenced by treatment at this concentration.

TABLE 6

Residual Metal Levels (Based on 10 AD Specimens)

|  | Zn | Cu | Fe | Ca | Mg | Al |
| --- | --- | --- | --- | --- | --- | --- |
| PBS (+/− SEM) | 50.7 | 11.9 | 227 | 202 | 197 | 44 |
|  | (4.9) | (1.5) | (28.8) | (28.3) | (39.1) | (46.2) |
| TPEN (+/− SEM) | 33.2 | 9.8 | 239 | 210 | 230 | 65 |
|  | (4.1) | (1.7) | (31.7) | (37.0) | (39.2) | (45.0) |

Given the precipitous decline in extractable Aβ observed when employing high concentrations of TPEN or EGTA (see FIGS. 19A and 19B), it was hypothesized that magnesium or calcium might also have a significant role in the Aβ solubility equilibrium. Magnesium or calcium added to the homogenization buffer produced no appreciable alteration in soluble Aβ. However, using an extract previously depleted of metals by high levels of EGTA, the addition of magnesium, and to a lesser extent calcium, led to resolubilization of the precipitated Aβ. FIG. 24B shows that Aβ solubility in metal-depleted tissue samples is restored by supplementing with magnesium.

Mindful of the high variability observed between individual subjects, 6 AD and 5 aged-matched control brains were chosen at random to determine if the observed phenomena were broadly applicable. These specimens were subjected to chelation treatment at selected concentrations of 0.1 or 2.0 mM or with PBS alone. FIG. 25A shows that patterns of chelator-promoted solubilization of Aβ differ in AD and aged, non-AD tissue. The chelator-promoted solubilization of Aβ from AD brains represented an increase of up to 7-fold over that seen with PBS alone; the mean increase for BC being around 4 fold, and that for TPEN around 2 fold. Treatment with EGTA at 2 mM always produced a diminution in Aβ signal below that observed for the PBS control (See FIG. 25B).

The effects observed with non-demented, aged-matched controls were similar with respect to EGTA and TPEN. However, it is noteworthy that the effect of BC was much reduced. In some cases (FIG. 25A, lower panel), BC treatment caused an attenuation in soluble Aβ suggesting that the amyloid deposits in AD-affected brain respond to this chelator in a different fashion than the deposits predominating in non-demented elderly brain.

For each subject in the experiments of FIGS. 25A and 25B, the extractable Aβ was derived and calculated as a proportion of the total pre-extraction Aβ load See Table 7 and 8 below.

TABLE 7

| AD-affected Tissue | | | | | | | | | |
| --- | --- | --- | --- | --- | --- | --- | --- | --- | --- |
| AD | 1 | 2 | 3 | 4 | 5 | 6 | X | +/− SEM | X C/PBS |
| Total Aβ (μg/g) | 10.8 | 77.0 | 80.3 | 6.0 | 14.4 | 16.8 | 43.0 | 14.1 | |
| PBS μg/g | 0.74 | 1.39 | 1.04 | 0.07 | 3.0 | 0.06 | 1.05 | 0.44 | |
| (% of total) | (0.1) | (1.8) | (1.3) | (1.1) | (2.1) | (0.4) | (1.2) | (0.3) | |
| TPEN 2 mM μg/g | 0.21 | 3.40 | 1.80 | 5.50 | 5.00 | 0.28 | 2.73 | 0.85 | 2.60 |
| (% of total) | (0.2) | (4.4) | (2.25) | (9.2) | (3.5) | (1.75) | (4.6) | (0.9) | |
| BC 2 mM μg/g | 0.31 | 5.54 | 3.62 | 6.05 | 6.03 | 0.54 | 4.10 | 0.86 | 3.90 |
| (% of total) | (0.3) | (7.2) | (4.5) | (10.0) | (4.2) | (3.4) | (5.4) | (1.2) | |

TABLE 8

Age-Matched Control Tissue

| AC | 1 | 2 | 3 | 4 | 5 | X | +/− SEM | X C/PBS |
|---|---|---|---|---|---|---|---|---|
| Total Aβ (μg/g) | 0.7 | 4.2 | 2.7 | 3.2 | 3.6 | 2.8 | 0.60 | |
| PBS μg/g | 0.17 | 0.13 | 0.18 | 0.10 | 0.66 | 0.25 | 0.10 | |
| (% of total) | (25.0) | (3.1) | (6.7) | (3.3) | (18.3) | (11.3) | (4.4) | |
| TPEN 2 mM μg/g | 0.22 | 0.38 | 0.26 | 0.09 | 1.06 | 0.40 | 0.17 | 1.6 |
| (% of total) | (32.0) | (9.0) | (9.7) | (3.0) | (29.5) | (16.7) | (5.1) | |
| BC 2 mM μg/g | 0.03 | 0.24 | 0.29 | 0.08 | 0.98 | 0.32 | 0.16 | 1.28 |
| (% of total) | (5) | (5.7) | (11.0) | (2.6) | (27.2) | (10.3) | (4.6) | |

Total Aβ for AD brains ranged from 6–80 μg/g wet weight tissue. The percentage of Aβ extractable (one extraction/centrifugation sequence) ranged from 0.33–10%. The corresponding values for aged-matched control brains were 0.68–4.2 μg/g total Aβ and 2.6–29.5% extractable.

In order to further investigate these different responses to chelators, triplicate blots of AD tissue and control tissue which displayed cerebrovascular and diffuse amyloid deposits were compared using antibodies specific for $A\beta_{1-40}$ and $A\beta_{1-42}$. FIG. 26 shows that chelation promotes the solubilization of $A\beta_{1-40}$ and $A\beta_{1-42}$ from AD and non-AD tissue. Using 3 different monoclonal antibodies, attempts to detect whether any particular species of Aβ were selectively affected by chelation were performed. Both $A\beta_{1-40}$ and $A\beta_{1-42}$ were liberated by chelation, however the dimeric form of $A\beta_{1-40}$ in both AD and control tissue predominated. As reported by Roher et al., Proc. Natl. Acad. Sci., 90:10836–10840 (1993) the predominant form of cerebrovascular amyloid is $A\beta_{1-42}$. Somewhat surprisingly, the dimeric form of this highly aggregating species is absent in the (control) tissue in which it is most favored.

It has recently been reported that the zinc-dependent Insulin Degrading Enzyme (IDE) has significant Aβ cleavage activity (Perez et al., Proc Soc. for Neuroscience 20: Abstract 321.13 (1997)). In the experiments presented here, the disassembly of amyloid is reflected in the intermediate dimeric species which result from conversion between soluble and insoluble forms. Thus, simple inhibition of catalytic enzyme activity cannot account for the observed increase in soluble Aβ. However, in the event that a proportion of the chelator-mediated augmentation of Aβ solubilization was due to inhibition of this enzyme, homogenisations were conducted both in the presence of 1 mM n-ethyl amimide (NEM), a potent inhibitor of IDE, and at 37° C. No enhancement of Aβ signal was observed above that of PBS alone for NEM, nor was there any diminution of signal after incubation at 37° C.

Discussion

Metal chelators offer a powerful tool for investigating the role of metals in the complex environment of the brain, however the strengths of these compounds may also define their limitations. The broad metal affinities of most chelators make them rather a blunt instrument. Attempts were made to sharpen the focus of the use of chelators by selecting chelators with a range of affinities for the metals of interest. These differences may be exploited by appropriate dilution, thereby favoring the binding of the relatively high affinity ligand (metal for which the chelator has the highest affinity).

The dilution profiles exhibited by EGTA and TPEN (FIGS. 19A and 19B) possibly reflect a series of equilibria between different metal ligands and the chelators, whereby the influence of low affinity, but abundant, metals is observed at high chelator concentrations and that of the high affinity, but more scarce, metals predominates at low concentrations of chelator. In the case of Aβ itself, this explanation is further complicated by the presence of low and high affinity binding sites for zinc (and copper) (Bush, A. I. et al., J. Biol. Chem., 269:12152–12158 (1994)).

The results shown in FIGS. 19A and 19B coupled with the hypothesis that lower affinity metals are removed at higher concentrations of chelators implies a role for lower affinity metals in meditation of Aβ solubility. Metals such as Mg and Ca may be increasingly removed at higher chelator concentrations. FIG. 24B shows that $Mg^{2+}$, and to a lesser extent, $Ca^{2+}$ restore solubility to metal depleted Aβ aggregate pellets. This indicates that these metals may function to mediate an Aβ solubility equilibrium in vivo.

Bathocuproine with its low affinity for metals other than $Cu^-$ is effective at solubilizing Aβ through a dilution range over 3 orders of magnitude, and interestingly, does not diminish in effectiveness at the highest levels tested. The particular affinity of BC for $Cu^+$ has been exploited to demonstrate that in the process of binding to APP, $Cu^{2+}$ is reduced to $Cu^+$ resulting in the liberation of potentially destructive free radicals (Multhaup, G., et al., Science 271: 1406–1409 (1996)). It has also been shown that Aβ has a similar propensity for reducing copper with consequent free radical generation (Huang, X., et al., J. Biol. Chem. 272: 26464–26470 (1997)).

Although the predicted reduction in copper in extraction pellets treated with BC has not been demonstrated, it is possible that the ratio of $Cu^{2+}$ to $Cu^+$ has been affected. At this stage, however, the means to evaluate the relative contributions of divalent and reduced forms to the total copper content of such extraction pellets are not available.

In addition to their primary metal binding characteristics, chelators are a class of compounds which vary in hydrophobicity and solubility. Their capacity to infiltrate the highly hydrophobic amyloid deposits may therefore be an important factor in the disassembly of aggregated Aβ. It is also possible that the chelators are also acting to liberate intracellular stores of Aβ in vesicular compartments as metal-bound aggregates. Preliminary data indicates that this may be the case with platelets.

The variability between subjects is consistent, reflecting the heterogeneity of the disease in its clinical and histopathological expression. Despite this, a consistent pattern of response to the actions of chelators by tissue from both AD and non-AD subjects is observed. This universality of the phenomenon of chelator-mediated solubilization is strongly suggestive that metals are also involved in the assembly of amyloid deposits in normal individuals, although the dissimilar patterns of response suggest that different mechanisms are operating in the disease and non-pathological states.

On the basis of the evidence presented here and the in vitro data, it is proposed that zinc functions in the healthy individual to promote the reversible aggregation of Aβ, counteracted by magnesium acting to maintain Aβ solubility. Further, the disease state is characterized by an unregulated interaction with copper resulting in the generation of free radicals.

A functional homoeostatic mechanism implies equilibrium between intracellular copper and zinc (and perhaps other metals) normally present in trace amounts, for which Aβ has strong affinity, and more abundant metals which bind less strongly to Aβ. Zinc is of particular interest because the anatomical distribution of zinc correlates with the cortical regions most susceptible to amyloid plaque formation (Assaf, S. Y. & Chung, S. H., Nature, 308:734–736 (1984)).

It has recently been demonstrated (Huang, X., et al., J. Biol. Chem. 272:26464–26470 (1997)) that zinc-promoted aggregation of synthetic Aβ is reversible by the application of EDTA. The tightly-regulated neurocortical zinc transport system might provide a physiological parallel for this chelator-mediated disaggregation by moving zinc quickly in and out of the intraneuronal spaces.

Copper, while binding less avidly to Aβ than zinc (Bush, A. I., et al. J. Biol. Chem. 269:12152–12158 (1994)) has greater potential to inflict damage via free radical generation, resulting polymers are SDS-resistant (see Example 7, below). Slight alterations in the transportation and/or metabolism of metals resulting from age-related deterioration of cellular processes may provide the environment for a rapid escalation of metal-mediated Aβ accretion which eventually overwhelms regulatory and clearance mechanisms. In describing a mechanism for Aβ homeostasis this model for amyloid deposition implies a possible physiological role for Aβ whereby aggregation and disaggregation may be effected through regulation or cortical metal levels and that the predominantly sporadic character of AD reflects individual differences in the brain milieu. Such a mechanism by no means rules out other genetic, environmental, inflammatory or other processes influencing the progression of the disease. Furthermore, in demonstrating the effectiveness of chelators in solubilising amyloid, it is suggested herein that suitable agents of this type are useful for therapeutic or prophylactic use in AD.

Example 7

Formation of SDS-Resistant Aβ Polymers

The cause for the permanent deposition of Aβ in states such as Alzheimer's Disease (AD) and Down's Syndrome (DS) are unknown, but the extraction of Aβ from the brains of AD and DS patients indicates that there are forms of Aβ that can be resolubilized in water and run as a monomer on SDS-PAGE (Kuo, Y-M., et al., J. Biol. Chem. 271:4077–4081 (1996)), and forms that manifest SDS-, urea- and formic acid-resistant polymers on PAGE (Masters, C. L. et al., Proc. Natl. Acad. Sci. USA 82:4245–4249(1985); Dyrks, T., et al., J. Biol. Chem. 267:18210–18217 (1992); Roher, A. E., et al., Journal of Biological Chemistry 271: 20631–20635 (1996). Thus, the extraction of SDS-resistant Aβ polymers from plaques implicates polymerization as a pathogenic mechanism that promotes the formation of AD amyloid.

The exact mechanism underlying the formation of SDS-resistant polymeric Aβ species remains unresolved. Recently, Huang, X., et al. have shown that Aβ reduces both $Cu^{2+}$ and $Fe^{3+}$ (Huang, X., et al., J. Biol. Chem. 272: 26464–26470 (1997)), providing a mechanism whereby a highly reactive species could promote the modification of proteins via an oxidative mechanism. Here, the inventors tested the ability of $Cu^{2+}$ and $Fe^{3+}$ to promote SDS-resistant Aβ polymerization.

Materials and Methods

Human $Aβ_{1-40}$ peptide was synthesized, purified and characterized as described above. Rat $Aβ_{1-40}$ was obtained from Quality Control Biochemicals, Inc. (Hopkinton, Mass.). Peptides were analyzed and stock solutions prepared as described above.

As above, electronic images captured using the Fluoro-S Image Analysis System (Bio-Rad, Hercules, Calif.) were analyzed using Multi-Analyst Software (Bio-Rad, Hercules, Calif.). This chemiluminescent image analysis system is linear over 2 orders of magnitude and has comparable sensitivity to film.

Human AD derived SDS-resistant polymers were solublized in formic acid, and then dialyzed with 5 changes of 100 mM ammonium bicarbonate, pH 7.5. The solublized peptide was then used for subsequent chelation experiments.

Results and Discussion

The generation of SDS-resistant Aβ polymers by metal ions was tested by incubating $Cu^{2+}$ (30 μM) or $Zn^{2+}$ (30 μM) at pH 6.6, 7.4 and 9.0 with $Aβ_{1-40}$. As shown in FIG. 9, Western blot analysis of samples incubated with $Cu^{2+}$ and run under SDS denaturing and β-mercaptoethanol reducing conditions revealed an increase in dimeric, trimeric and higher oligomeric Aβ species over time. The dimer and trimer had molecular weights of approximately 8.5 kD and 13.0 kD, respectively. Image analysis indicated 42% and 9% conversion of the monomer to dimer and trimer, respectively, in samples incubated at pH 7.4 after 5 d. The conversion of monomer to the dimer and trimer was 29% and 2%, respectively, at pH 6.6 after 5 d.

In contrast, changes in $[H^+]$ alone did not induce SDS-resistant $Aβ_{1-40}$ polymerization. Less than 4% of the peptide was converted to the SDS-resistant dimer after 5 d in samples incubated at pH 6.6, 7.4 or 9.0, most likely as a result of contaminating $Cu^{2+}$ in the buffer and Aβ solutions. $Cu^{2+}$ contamination of chelex-treated PBS was up to 0.5 μM as determined by ion coupled plasma-atomic emission spectroscopy (ICP-AES). Although $Zn^{2+}$ induces rapid aggregation of $Aβ_{1-40}$ (Bush, A. I. et al., J. Biol. Chem. 268:16109 (1993); Bush, A. I., et al., J. Biol. Chem. 269:12152 (1994); Bush, A. I., et al., Science 265:1464–1467 (1994); Bush, A. I., et al., Science 268:1921–1922 (1995); Atwood et al., submitted; Huang, X. et al., J. Biol. Chem. 272:26464–26470 (1997)), it did not induce SDS-resistant Aβ polymerization (FIG. 9) as previously reported (Bush, A. I., et al., Science 268:1921–1922 (1995)).

$Aβ_{1-42}$ is the predominant species found in amyloid plaques (Masters, C. L. et al., Proc. Natl. Acad. Sci. USA 82: 4245 (1985); Murphy, G. M., et al., Am. J. Pathol. 144: 1082–1088 (1994); Mak, K., et al., Brain Res. 667:138–142 (1994); Iwatsubo, T., et al., Ann. Neurol. 37:294–299 (1995); Mann et al., Ann. Neurol. 40:149–156 (1996)). Therefore, the ability of $Aβ_{1-40}$ and $Aβ_{1-42}$ to form SDS-resistant polymers was compared.

In contrast to $Cu^{2+}$-induced SDS-resistant $Aβ_{1-40}$ polymerization over days, SDS-resisitant $Aβ_{1-42}$ polymerization occurred within minutes in the presence of $Cu^{2+}$ (FIG. 27A). Unlike $Aβ_{1-40}$ where $Cu^{2+}$ induces the formation of a SDS-resistant dimeric species first, $Aβ_{1-42}$ initially forms an apparent trimer species in the presence of $Cu^{2+}$. Over time, dimeric and higher polymeric species also appear in $Aβ_{1-42}$ incubations with $Cu^{2+}$ at both pH 7.4 and 6.6. The greater $Cu^{2+}$ induced $A\beta_{1-42}$ polymerization observed at pH 6.6 compared with pH 7.4 in samples incubated for 30 min. was reversed after 5 d. At pH 6.6, both $A\beta_{1-40}$ and $A\beta_{1-42}$ exist in an aggregated form within minutes. Therefore, the formation of these polymeric species occurs within $A\beta$ aggregates and the formation of SDS-resistant $A\beta$ polymers is independent of aggregation state (see below). Similar results were obtained using the monoclonal antibody 4G8.

Since redox active Fe (Smith, M. A., et al., *Proc. Natl. Acad. Sci. USA* 94:9866 (1997)) and ferritin (Grudke-Iqbal, I., et al., *Acta Neuropathol.* 81:105 (1990)) are found in amyloid lesions, experiments were performed to determine if $Fe^{3+}$ could induce SDS-resistant polymerization of $A\beta_{1-40}$ and $A\beta_{1-42}$ (FIG. 27A). $Fe^{3+}$ did not induce $A\beta_{1-40}$ polymerization above background levels with either peptide. The small increase in polymeric $A\beta_{1-40}$ and $A\beta_{1-40}$ in samples with no metal ions reflects a small contaminating concentration of $Cu^{2+}$.

The formation of amyloid plaques is not a feature of aged rats (Johnstone, E. M., et al., *Mol. Brain Res.* 10:229 (1991); Shivers et al. (1988)). To test whether rat $A\beta_{1-40}$ would form SDS-resistant $A\beta$ polymers, rat $A\beta_{1-40}$ was incubated with $Cu^{2+}$ and $Fe^{3+}$ at pH 7.4 and 6.6 (FIG. 27B). Neither metal ion induced SDS-resistant $A\beta$ polymers (Huang, X. et al., *J. Biol. Chem.* 272:26464–26470 (1997)). The binding and reduction of $Cu^{2+}$ by rat $A\beta_{1-40}$ is markedly decreased compared to that of human $A\beta_{1-40}$ (Huang, X. et al., *J. Biol. Chem.* 272:26464–26470 (1997)). This result suggests that the generation of SDS-resistant $A\beta$ polymers is dependent upon the binding and reduction of $Cu^{2+}$ by $A\beta$.

Tests were performed to determine the concentration of $Cu^{2+}$ required to induce the formation of SDS-resistant $A\beta_{1-40}$ and $A\beta_{1-42}$ polymers. $A\beta_{1-40}$ and $A\beta_{1-42}$ were incubated with different $[Cu^{2+}]$ (0–30 μM) at pH 7.4 and 6.6 and the samples analyzed by Western blot and the signal quantitated using the Fluoro-S Image Analysis System (Bio-Rad, Hercules, Calif.) as previously described.

At pH 7.4, the increase in polymerization of $A\beta_{1-40}$ was barely detectable as $[Cu^{2+}]$ was increased from 0.5 to 1 μM, but under mildly acidic conditions (pH 6.6), SDS-resistant polymerization could be detected (over 3-fold increase in dimerization)(Table 9A).

TABLE 9A $Cu^{2+}$-Induced SDS-Resistant Polymers of $A\beta_{1-40}$

| $[Cu^{2+}]$ | Monomer | Dimer | Trimer | Tetramer | Pentamer |
|---|---|---|---|---|---|
| | | | pH 7.4 | | |
| 0 | 96.8 | 3.2 | <0.1 | 0 | 0 |
| 0.5 | 94.8 | 4.9 | 0.3 | 0 | 0 |
| 1 | 93.6 | 5.9 | 0.6 | 0 | 0 |
| 5 | 84.3 | 14.2 | 1.5 | 0 | 0 |
| 10 | 85.2 | 13.2 | 1.6 | 0 | 0 |
| 30 | 76.2 | 19.1 | 4.7 | 0 | 0 |
| | | | pH 6.6 | | |
| 0 | 97.9 | 2.1 | <0.1 | 0 | 0 |
| 0.5 | 97.6 | 2.2 | 0.2 | 0 | 0 |
| 1 | 92.6 | 7.3 | 0.1 | 0 | 0 |
| 5 | 90.1 | 9.8 | 0.1 | 0 | 0 |
| 10 | 79.4 | 16.1 | 4.5 | 0 | 0 |
| 30 | 74.5 | 13.2 | 12.2 | 0 | 0 |

A similar $C^{2+}$ concentration and pH dependent increase in SDS-resistant $A\beta_{1-42}$ polymers also was observed (Table 9B), but SDS-resistant polymerization occurred at much lower $[Cu^{2+}]$.

TABLE 9B $Cu^{2+}$-Induced SDS-resistant Polymers of $A\beta_{1-42}$

| $[Cu^{2+}]$ | Monomer | Dimer | Trimer | Tetramer | Pentamer |
|---|---|---|---|---|---|
| | | | pH 7.4 | | |
| 0 | 76.61 | 0 | 16.0 | 5.5 | 1.9 |
| 0.5 | 70.7 | 0 | 20.5 | 6.2 | 2.5 |
| 1 | 64.9 | 0 | 23.6 | 7.4 | 4.0 |
| 5 | 56.1 | 0 | 31.8 | 8.7 | 4.1 |
| 10 | 55.1 | 0 | 30.3 | 10.3 | 4.3 |
| 30 | 57.1 | 0 | 31.1 | 8.3 | 4.2 |
| | | | pH 6.6 | | |
| 0 | 61.0 | 0 | 27.3 | 8.6 | 3.8 |
| 0.5 | 52.1 | 0 | 33.8 | 12.0 | 3.0 |
| | | | pH 7.4 | | |
| 5 | 59.6 | 0 | 30.0 | 7.1 | 3.2 |
| 10 | 52.3 | 0 | 31.7 | 13.6 | 2.2 |

$A\beta_{1-40}$ polymerization was not detected with increasing $Fe^{3+}$ concentrations at any pH. Therefore, of the metal ions known to interact with $A\beta$, only $Cu^{2+}$, whose ability to aggregate and bind $Cu^{2+}$ under mildly acidic conditions is enhanced, is capable of inducing SDS-resistant $A\beta$ polymerization.

Oxygen radical mediated chemical attack has been correlated with an increase in protein and free carbonyls (Smith, C. D., et al., *Proc. Natl. Acad. Sci. USA* 88:10540 (1991); Hensley, K., et al., *J. Neurochem.* 65:2146 (1995); Smith, M. A., et al., *Nature* 382:120 (1996)) and peroxynitrite-mediated protein nitration (Good, P. F., et al., *Am. J Pathol.* 149:21 (1996); Smith, M. A., et al., Proc. Natl. Acad. Sci. USA 94:9866 (1997)).

$A\beta$ is capable of reducing $Cu^{2+}$ and $H_2O_2$ is produced in solutions containing $A\beta$ and $Cu^{2+}$ or $Fe^{3+}$ (Huang, X. et al., *J. Biol. Chem.* 272:26464–26470 (1997)). As shown above, the generation of SDS-resistant $A\beta$ polymers in the order $A\beta_{1-42} >> A\beta_{1-40} >>$ rat $A\beta_{1-40}$ in the presence of $Cu^{2+}$ correlates well with the generation of $Cu^+$ and reactive oxygen species (ROS; $OH^-$, $H_2O_2$ and $O_2^-$: Huang, X. et al., *J. Biol. Chem.* 272:26464–26470 (1997)) by each peptide.

The increased generation of SDS-resistant $A\beta$ polymers in the presence of $Cu^{2+}$ compared to $Fe^{3+}$ also was correlated with the generation of the reduced metal ions, respectively (Huang, X. et al., *J. Biol. Chem.* 272:26464–26470 (1997)). The increase in SDS-resistant $A\beta$ polymerization seen under mildly acidic conditions may be a result of the higher $[H^+]$ driving the production of $H_2O_2$ dismutated from $O_2^-$ with the subsequent generation of OH. via Fenton-like chemistry inducing a modification of $A\beta$ that results in SDS-resistant $A\beta$ polymers (see FIG. 12 showing a schematic of the proposed mechanism of $A\beta$-mediated reduced metal/ROS production).

To confirm whether ROS were involved in the generation of SDS-resistant polymers, experiments were performed to determine whether Cu in the presence or absence of $H_2O_2$ could promote $A\beta$ polymerization (FIG. 28A). A similar level of $A\beta_{1-42}$ polymerization was observed in the presence of $Cu^{2+}$ or $Cu^+$, indicating that the reduced metal ion alone was not capable of increasing $A\beta$ polymerization. Likewise, polymerization of $A\beta_{1-42}$ in the presence of $H_2O_2$ was low and equivalent to control levels. However, the addition of $Cu^{2+}$ or $Cu^+$ to Aβ in the presence of $H_2O_2$ induced a similar, marked increase in dimers, trimers and tetramers within 1 hour. After 1 day, higher molecular weight polymers (>18 kD) were generated (from the oligomers), with a subsequent reduction in the levels of monomer, dimer, trimer and tetramer only with the coincubation of $H_2O_2$ and $Cu^{2+}$.

Both the reduced and oxidized forms of Cu produced similar levels of polymerization in the presence of $H_2O_2$. In contrast, neither $Fe^{3+}$ nor $Fe^{2+}$ induced as much polymerization as $Cu^{2+}$ in the presence of $H_2O_2$ after 1 day incubation (FIGS. 28A and 28B). Since $Fe^{3+}$ is not reduced as efficiently as $Cu^{2+}$ by Aβ (Huang, X., et al., *J. Biol. Chem.* 272:26464–26470 (1997)), and $Cu^+$ is rapidly converted to $Cu^{2-}$ in solution, these results suggest that the reduction reaction is required for the polymerization reaction to proceed.

It was confirmed that the reduction of $Cu^{2+}$ was required for generating SDS-resistant Aβ polymerization by incubating $Aβ_{1-42}$ and $Cu^{2+}$ with and without bathocupoinedisulfonic acid (BC), a $Cu^+$ specific chelator (FIG. 28C). There was a marked decrease in polymerization, indicating that $Cu^+$ generation was crucial for the polymerization of Aβ. It is possible that the decreased polymerization may be due to chelation of $Cu^{2+}$ by BC, however given the low binding affinity of BC for $Cu^{2+}$ compared with Aβ, it seems likely that the chelation of $Cu^-$ by BC prevents it from inducing SDS-resistant Aβ polymerization. Therefore, Aβ may undergo a hydroxyl radical modification that promotes its assembly into SDS-resistant polymers.

If $H_2O_2$ is required for the polymerization reaction under physiological conditions, the removal of $H_2O_2$ and it's precursors $O_2$ and $O_2^-$ (Huang, X., et al., *J. Biol. Chem.* 272:26464–26470 (1997)) should decrease SDS-resistant polymerization. To confirm that $H_2O_2$ generated in the presence of Aβ and $Cu^{2+}$ required for the polymerization reaction, $Aβ_{1-42}$ was incubated with or without $Cu^{2+}$ in the presence of TCEP (FIG. 29A). TCEP significantly reduced the level of polymerization in samples with and without $Cu^{2+}$ over 3 days. This indicates that the generation of $H_2O_2$ is required for the polymerization of Aβ.

To confirm that the generation of $O_2^-$ was required for SDS-resistant Aβ polymerization, $Aβ_{1-42}$ was incubated with and without $Cu^{2+}$ at pH 7.4 and 6.6 under argon in order to decrease the reduction of molecular $O_2$ (FIG. 29B). Argon-purging of the solution markedly decreased $Aβ_{1-42}$ polymerization under each condition, indicating that the generation of ROS is required for the polymerization of Aβ.

Taken together, these results indicate that polymerization occurs as a result of Haber-Weiss chemistry where the continual reduction of $Cu^{2-}$ by Aβ provides a species for the reduction of molecular $O_2$ and the subsequent generation of $O_2^-$, $H_2O_2$ and $OH^-$. The binding and reduction of $Cu^{2+}$ by Aβ is supported by the finding that the incubation of $Fe^{3+}$, $H_2O_2$ and ascorbic acid with $Aβ_{1-40}$ (FIG. 29A) and $Aβ_{1-42}$ does not induce SDS-resistant polymerization equivalent to $Cu^{2+}$ with $H_2O_2$ alone. Since ascorbic acid effectively reduces $Fe^{3+}$, the reduction of a metal ion that is not bound to Aβ is insufficient to induce significant SDS-resistant polymerization.

The formation of SDS-resistant polymers of Aβ by this metal-catalyzed oxidative mechanism strongly suggested that a chemical modification to the peptide backbone allows the formation of the polymer species. To test if the SDS-resistant polymers were covalently linked, SDS-resistant polymers generated by incubating $Aβ_{1-42}$ with $Cu^{2+}$ at pH 7 4 and 6.6, or $Aβ_{1-42}$ with $Cu^{2+}$ plus $H_2O_2$ were subjected to treatment with urea (FIG. 30A) and guanidine HCl, chaotrophic agents known to disrupt H-bonding. Urea and guanidine HCl did not disrupt the SDS-resistant polymers at 4.5 M, and only slightly at 9M, suggesting that the SDS-resistant polymers were held together by high-affinity bonds, but not hydrogen bonding alone. HPLC-MS analyses, however, confirmed no covalent modification of the peptide and no evidence of covalent crosslinking.

Since covalent and/or hydrogen bonding were not involved in polymer formation, experiments were performed to detemine whether $Cu_{2+}$ coordination of the complex by ionic interactions was allowing for the formation of the SDS-resistant polymer species. To disrupt these ionic interactions, different chelating agents were added to a solution containing $Cu^{2+}$-induced $Aβ_{1-40}$ or $Aβ_{1-42}$ SDS-resistant polymers generated at pH 7.4 (FIGS. 30B and 30C; TETA, tetraethylenediamine; EDTA, ethylenediaminetetra acetic acid; DTPA, diethylenetriaminopenta acetic acid; CDTA, trans-1,2-diaminocyclohexanetetra acetic acid; NTA, nitrilotriacetic acid).

All chelators significantly reduced the amount of $Aβ_{1-40}$ or $Aβ_{1-42}$ SDS-resistant polymers. EDTA was less effective in destabilizing the polymers, possibly due to its larger molecular mass, and lower affinity for $Cu^{2+}$. EDTA reduced the amount of $Aβ_{1-40}$ polymers, but increased the amount of $Aβ_{1-40}$ polymers at pH 7.4. This may be due to the fact that EDTA can enhance the redox potential of Cu under certain conditions.

$Cu^{2+}$-induced SDS-resistant polymers generated at pH 6.6 were also disrupted with chelation treatment to a similar extent. These results suggest that the chelation of $Cu^{2+}$ away from Aβ results in the disruption of the polymer complex and the release of monomer species. Thus, there is an absolute requirement for metal ions in the stabilization of the SDS-resistant polymer complex.

The SDS-resistant polymers generated with $Cu^{2+}$ are similar to those extracted from post-mortem AD brains (Roher, A. E., et al., *Journal of Biological Chemistry* 271: 20631–20635 (1996)). To determine if these human oligomeric Aβ species could be disrupted by metal chelators, TETA and BC were incubated with Aβ oligomers extracted from human brain. FIG. 30E shows that both TETA and BC significantly increased the amount of monomer Aβ in samples treated with these chelators. Although the increase in the amount of monomer was small, these results suggest that human oligomeric Aβ species are partially held together with metal ions. Importantly, this result indicates the potential of chelation therapy as a means of reducing amyloidosis.

To examine whether conformational changes could disrupt the SDS-resistant polymers, solutions of SDS-resistant $Aβ_{1-42}$ polymers in the presence or absence of $Cu^{2+}$ were incubated with the α-helical promoting solvent system DMSO/HFIP, or under acidic conditions (pH 1) (FIG. 30D). These conditions reduced the amount of polymer compared to untreated controls at both pH 7.4 and 6.6, indicating that an alteration in the conformation of $Aβ_{1-42}$ to the α-helical conformation could disrupt the strong $Aβ$-$Cu^{2+}$ ionic interactions. This provides indirect evidence that the polymer structures are likely to be in the more thermodynamically favorable β-sheet conformation, such as those found in neuritic plaques.

SDS-resistant Aβ polymers, such as that found in the AD-affected brain, are likely to be more resilient to proteolytic degradation and may explain the permanent deposition of Aβ in amyloid plaques. Incubation of SDS-resistant Aβ polymers with proteinase K resulted in complete degradation of both monomer and oligomeric Aβ species. Since protease treatment is incapable of digesting hard core amyloid, covalent crosslinking of the peptide following its deposition may occur over time that prevents proteolytic digestion. This may explain the limited disruption of human SDS-resistant Aβ oligomers compared to the Cu-mediated SDS-resistant polymers generated in vitro.

Soluble $A\beta_{1-40}$ and $A\beta_{1-42}$ both exist in phosphate buffered saline as noncovalent dimers (Huang, X., et al., *J. Biol. Chem.* 272:26464–26470 (1997); and unpublished observations). Disruption of ionic and hydrogen bonding of Aβ in the soluble and aggregated forms (pH or $Zn^{2+}$) by the ionic detergent SDS results in the complete dissociation of Aβ into the monomer species as detected on SDS-PAGE (FIGS. 9, 32–34). The formation of SDS-resistant polymers of Aβ over time in the presence of $Cu^{2+}$ (FIGS. 9, 27A–27B, 28A–28C) suggests that conformational or structural alterations allow for the formation of a thermodynamically more stable complex.

Although no covalent crosslinking between peptides was detected, it is possible that a covalent modification(s) takes place within the peptide backbone that allows for a high affinity association to form between the peptide and $Cu^{2+}$. Thus, a chemical modification to the peptide may increase the affinity of the polymer for $Cu^{2+}$ and the formation of a stable complex. Alternatively, the requirement for molecular oxygen suggests that Cu may be coordinated by oxygen or ROS in the formation of SDS-resistant polymers.

The formation of SDS-resistant polymers was dependent upon the binding and reduction of $Cu^{2+}$. The binding of $Cu^{2+}$ to Aβ was confirmed by the detection of $Cu^{2+}$ in both the monomer and dimer following SDS-PAGE. The $[Cu^{2+}]$ of PVDF membrane containing the immobilized peptide species was measured by ICP-AES (unpublished observations; Huang, X., et al., *J. Biol. Chem.* 272:26464–26470 (1997)) and correlated with the generation of SDS-resistant polymers for each species.

$Cu^{2+}$ coordination between Aβ molecules was required in order to maintain the structure since chelation treatment disrupted the in vitro generated SDS-resistant polymer (FIGS. 30B–30E). Human SDS-resistant Aβ polymers also were disrupted with the $Cu^+$-specific chelator BC indicating Cu coordination in the stabilization of these structures (FIG. 30E). Together with the fact that Cu-specific chelators can extract more SDS-resistant Aβ polymers from AD brains in aqueous buffer (see Example 6), these results implicate $Cu^{2+}$ in the generation of SDS-resistant polymers in vivo.

$Fe^{3+}$ did not induce the formation of SDS-resistant polymers in vitro (FIGS. 27A) as previously reported except in the presence of excess $H_2O_2$ or ascorbic acid as previously reported (Dyrks, T., et al., *J. Biol. Chem.* 267:18210–18217 (1992); and data not shown). Dyrks, T., et al. did, however observe significant increases in SDS-resistant polymerization with metal-catalyzed oxidation systems (Fe-hemin, Fe-hemoglobin or Fe-EDTA) in the presence of $H_2O_2$. The $A\beta_{1-42}$ used in their experiments was likely to be Cu-bound as it was extracted from a wheat germ expression system and already was present as SDS-resistant oligomers. Thus, it is possible that Cu-bound Aβ used in these experiments contributed to the increased SDS-resistant polymerization observed in the Fe-catalyzed oxidation systems. Although $Fe^{3+}$ is reduced by Aβ (Huang, X., et al., *J. Biol. Chem.* 272:26464–26470 (1997)), it is unable to effectively coordinate the complex like Cu (FIG. 28B).

$Fe^{2+}$ is found in much higher concentrations in the brains of AD patients compared with age-matched controls (Ehmann, W. D., et al., *Neurotoxicol.* 7.197–206 (1986); Dedman, D. J., et al., *Biochem. J.* 287:509–514 (1992); Joshi, J. G. et al., *Environ. Health Perspect.* 102:207–213 (1994)). This is partly attributable to the increased ferritin rich microglia and oligodendrocytes that localize to amyloid plaques (Grudke-Iqbal, I., et al., *Acta Neuropathol.* 81:105 (1990); Conner, J. R., et al., *J. Neurosci. Res.* 31:75–83 (1992); Sadowki, M., et al., *Alzheimer's Res.* 1:71–76 (1995)).

Recently, redox active Fe was localized to amyloid lesions (Smith, M. A., et al., *Proc. Natl. Acad. Sci. USA* 94:9866 (1997)). While Fe is normally sequestered by metalloproteins, this localization of ferritin-rich cells around amyloid deposits, and the very high concentrations of iron in amyloid plaques (Conner, J. R., et al., *J. Neurosci. Res.* 31:75–83 (1992); Markesbery, W. R. and Ehmann, W. D., "Brain trace elements in Alzheimer's disease," in Terry, R. D., et al., eds., *Alzheimer Disease*, Raven Press, New York (1994), pp. 353–368) suggests that reduced Fe released from ferritin and transferrin under mildly acidic conditions could be available for Fenton chemistry and the formation of SDS-resistant polymers. However, even in the presence of a Fe-ROS generating system (ascorbic acid, $H_2O_2$ and Fe) the generation of SDS-resistant Aβ polymers in vitro was low (FIG. 29A) and may be explained by $Cu^{2+}$ contamination of the buffers.

Interestingly, diffuse plaques, which may represent the earliest stages of plaque formation, are relatively free of ferritin-rich cells (Ohgami, T., et al., *Acta Neuropathol* 81:242–247 (1991)). Therefore, the accretion of iron in amyloid plaques may be a secondary response to the neurodegeneration caused by the reduction of $Cu^{2+}$ and the generation of ROS by Aβ and the formation of neurotoxic SDS-resistant Aβ polymers.

Structural differences between $A\beta_{1-40}$ and $A\beta_{1-42}$ may allow for the formation of a thermodynamically stable dimer in the case of $A\beta_{1-40}$ and trimer in the case of $A\beta_{1-42}$ (FIGS. 27A, 30B and 30C). Irrespective of this, the increased generation of SDS-resistant polymers by $A\beta_{1-42}$ compared to $A\beta_{1-40}$ is most likely explained by the increased ability of $A\beta_{1-42}$ to reduce Cu and generate ROS. Since the addition of exogenous $H_2O_2$ to $A\beta_{1-42}$ increases the generation of dimeric SDS-resistant polymers of $A\beta_{1-42}$ (FIGS. 28A and 28B), this dimeric species may be an integral intermediate in the formation of the SDS-resistant Aβ trimers, and may explain why $A\beta_{1-40}$ polymerization occurs more slowly.

AD Pathology

The present invention indicates that the manipulation of the brain biometal environment with specific agents acting directly (e.g., chelators and antioxidants) or indirectly (e.g., by improving cerebral energy metabolism) provides a means for therapeutic intervention in the prevention and treatment of Alzheimer's disease.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

All patents and publications cited in the present specification are incorporated by reference herein in their entirety.

What is claimed is:

1. A method of treating amyloidosis in a subject, said method comprising administering to said subject an effective amount of (a) bathocuproine or a hydrophobic derivative thereof; and (b) one or more pharmaceutically acceptable carriers or diluents; for a time and under conditions to bring about said treatment; and wherein said bathocuproine or hydrophobic derivative thereof reduces, inhibits or otherwise interferes with amyloid beta peptide (Aβ)-mediated production of radical oxygen species.

2. The method of claim 1 further comprising administering to the subject an effective amount of indomethacin, or a pharmaceutically acceptable salt thereof.

3. A pharmaceutical composition for treatment of conditions caused by amyloidosis, amyloid beta peptide (Aβ)-mediated reactive oxygen species (ROS) formation, or both, comprising: (a) bathocuproine or a hydrophobic derivative thereof; (b) indomethacin or a hydrophobic derivative thereof; and (c) one or more pharmaceutically acceptable carriers or diluents.

4. A composition of matter comprising: (a) bathocuproine hydrophobic derivative thereof; and (b) indomethacin.

* * * * *